US010662215B2

United States Patent
Renslo et al.

(10) Patent No.: US 10,662,215 B2
(45) Date of Patent: *May 26, 2020

(54) CYCLIC PEROXIDES AS PRODRUGS FOR SELECTIVE DELIVERY OF AGENTS

(71) Applicant: THE REGENTS OF THE UNIVERSITY OF CALIFORNIA, Oakland, CA (US)

(72) Inventors: Adam R. Renslo, Oakland, CA (US); Erica M. W. Lauterwasser, Wachenheim (DE); Shaun D. Fontaine, Walnut Creek, CA (US); Benjamin B. Spangler, San Francisco, CA (US); James A. Wells, Burlingame, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/364,577

(22) Filed: Mar. 26, 2019

(65) Prior Publication Data

US 2019/0284224 A1    Sep. 19, 2019

Related U.S. Application Data

(63) Continuation of application No. 15/118,268, filed as application No. PCT/US2015/015948 on Feb. 13, 2015, now Pat. No. 10,287,312.

(Continued)

(51) Int. Cl.
*C07D 405/14* (2006.01)
*A61K 31/4709* (2006.01)
(Continued)

(52) U.S. Cl.
CPC ........... *C07H 19/16* (2013.01); *A61K 31/357* (2013.01); *A61K 31/404* (2013.01); *A61K 31/4025* (2013.01); *A61K 31/4192* (2013.01); *A61K 31/427* (2013.01); *A61K 31/435* (2013.01); *A61K 31/437* (2013.01); *A61K 31/444* (2013.01); *A61K 31/4709* (2013.01); *A61K 31/4745* (2013.01); *A61K 31/496* (2013.01); *A61K 31/4985* (2013.01); *A61K 31/513* (2013.01); *A61K 31/662* (2013.01); *A61K 31/7072* (2013.01); *A61K 31/7076* (2013.01); *A61K 31/7135* (2013.01); *A61K 47/64* (2017.08); *A61K 47/6803* (2017.08); *A61K 51/0459* (2013.01); *C07D 323/02* (2013.01); *C07D 405/12* (2013.01); *C07D 405/14* (2013.01); *C07D 407/12* (2013.01); *C07D 417/12* (2013.01); *C07D 417/14* (2013.01); *C07D 471/14* (2013.01); *C07D 487/04* (2013.01); *C07D 491/107* (2013.01); *C07D 491/113* (2013.01); *C07D 491/153* (2013.01); *C07D 493/04* (2013.01); *C07D 493/14* (2013.01); *C07D 519/04* (2013.01); *C07F 7/1804* (2013.01); *C07F 9/65517* (2013.01); *C07F 9/65586* (2013.01); *C07H 19/06* (2013.01); *C07H 19/167* (2013.01);
(Continued)

(58) Field of Classification Search
CPC ................ C07D 405/14; C07D 405/12; A61K 31/4709; A61K 31/403
USPC .................. 546/175; 548/427; 514/314, 411
See application file for complete search history.

(56) References Cited

U.S. PATENT DOCUMENTS

| 3,862,142 A | 1/1975 | Story et al. |
| 4,631,190 A | 12/1986 | Shen et al. |

(Continued)

FOREIGN PATENT DOCUMENTS

| JP | 2005-112799 A | 4/2005 |
| WO | WO-03/000676 A1 | 1/2003 |

(Continued)

OTHER PUBLICATIONS

Lauterwasser, E. M. W. et al.: Trioxolane-mediated delivery of Mefloquine limits brain exposure in a mouse model of malaria. ACS Med-Chem. Lett., vol. 6, pp. 1145-1149, 2015.*
Abdel-Magid, Ahmed F. et al., "Reductive Amination of Aldehydes and Ketones with Sodium Triacetoxyborohydride. Studies on Direct and Indirect Reductive Amination Procedures", Journal of Organic Chemistry 61:3849-3862, Jan. 1996.
Adam, Waldemar et al., "Titanium-Catalyzed Diastereoselective Epoxidations of Ene Diols and Allylic Alcohols with p-Hydroperoxy Alcohols as Novel Oxygen Donors", Journal of Organic Chemistry 62:3183-3189, Jan. 1997.

(Continued)

*Primary Examiner* — Charanjit Aulakh
(74) *Attorney, Agent, or Firm* — Mintz, Levin, Cohn, Ferris, Glovsky and Popeo, P.C.; Doris Lee

(57) ABSTRACT

Disclosed herein, inter alia, are prodrug compositions and methods of using the same for treatment and detection of disease. Specifically, disclosed herein is a compound of formula (I) having spiro-fused 1,2,4-trioxolane and piperidine rings, namely, 1,2,4-trioxa-8-azaspiro[4.5]decane. Also disclosed is a pharmaceutical composition containing the compound and a pharmaceutically acceptable carrier.

20 Claims, 1 Drawing Sheet

Related U.S. Application Data

(60) Provisional application No. 61/940,295, filed on Feb. 14, 2014.

(51) Int. Cl.

| | | |
|---|---|---|
| C07H 19/16 | (2006.01) | |
| C07F 7/18 | (2006.01) | |
| C07D 407/12 | (2006.01) | |
| C07D 323/02 | (2006.01) | |
| C07D 405/12 | (2006.01) | |
| C07D 417/12 | (2006.01) | |
| C07D 417/14 | (2006.01) | |
| C07D 471/14 | (2006.01) | |
| C07D 493/04 | (2006.01) | |
| C07D 519/04 | (2006.01) | |
| C07F 9/655 | (2006.01) | |
| C07H 19/06 | (2006.01) | |
| C07H 19/167 | (2006.01) | |
| A61K 47/64 | (2017.01) | |
| A61K 47/68 | (2017.01) | |
| C07F 9/6558 | (2006.01) | |
| A61K 31/357 | (2006.01) | |
| A61K 31/4025 | (2006.01) | |
| A61K 31/404 | (2006.01) | |
| A61K 31/4192 | (2006.01) | |
| A61K 31/427 | (2006.01) | |
| A61K 31/435 | (2006.01) | |
| A61K 31/437 | (2006.01) | |
| A61K 31/444 | (2006.01) | |
| A61K 31/4745 | (2006.01) | |
| A61K 31/496 | (2006.01) | |
| A61K 31/4985 | (2006.01) | |
| A61K 31/513 | (2006.01) | |
| A61K 31/662 | (2006.01) | |
| A61K 31/7072 | (2006.01) | |
| A61K 31/7076 | (2006.01) | |
| A61K 31/7135 | (2006.01) | |
| A61K 51/04 | (2006.01) | |
| C07D 487/04 | (2006.01) | |
| C07D 491/107 | (2006.01) | |
| C07D 491/113 | (2006.01) | |
| C07D 491/153 | (2006.01) | |
| C07D 493/14 | (2006.01) | |
| C07K 7/06 | (2006.01) | |

(52) U.S. Cl.
CPC ............ *C07K 7/06* (2013.01); *C07B 2200/05* (2013.01); *Y02A 50/411* (2018.01)

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 4,997,913 A | 3/1991 | Hellstrom et al. |
| 5,140,013 A | 8/1992 | Gaudreault et al. |
| 5,212,162 A | 5/1993 | Missel et al. |
| 5,306,809 A | 4/1994 | Boon et al. |
| 5,403,841 A | 4/1995 | Lang et al. |
| 5,578,637 A | 11/1996 | Lai et al. |
| 6,486,199 B1 | 11/2002 | Vennerstrom et al. |
| 6,825,230 B2 | 11/2004 | Vennerstrom et al. |
| 6,906,205 B2 | 6/2005 | Vennerstrom et al. |
| 7,371,778 B2 | 5/2008 | Vennerstrom et al. |
| 8,067,620 B2 | 11/2011 | Vennerstrom et al. |
| 8,618,096 B2 | 12/2013 | Renslo et al. |
| 10,287,312 B2 * | 5/2019 | Renslo ................. C07D 407/12 |
| 2004/0039008 A1 | 2/2004 | Vennerstrom et al. |
| 2004/0186168 A1 | 9/2004 | Vennerstrom et al. |
| 2005/0256184 A1 | 11/2005 | O'Neill et al. |
| 2005/0256185 A1 | 11/2005 | Vennerstrom et al. |
| 2007/0021423 A1 | 1/2007 | Cazelles et al. |
| 2008/0125411 A1 | 5/2008 | Vennerstrom et al. |
| 2008/0125441 A1 | 5/2008 | Vennerstrom et al. |
| 2016/0362439 A1 | 12/2016 | Renslo et al. |

FOREIGN PATENT DOCUMENTS

| | | |
|---|---|---|
| WO | WO-2005/110396 A2 | 11/2005 |
| WO | WO-2005/110396 A3 | 11/2005 |
| WO | WO-2009/058859 A2 | 5/2009 |
| WO | WO-2009/058859 A3 | 5/2009 |
| WO | WO-2009/091433 A2 | 7/2009 |
| WO | WO-2009/091433 A3 | 7/2009 |
| WO | WO-2010/011684 A2 | 1/2010 |
| WO | WO-2010/011684 A3 | 1/2010 |
| WO | WO-2012/059932 A1 | 5/2012 |

OTHER PUBLICATIONS

Arbuj, Sudhir S. et al., "Photochemical a-bromination of ketones using N-bromosuccinimide: a simple, mild and efficient method", Tetrahedron Letters 48:1411-1415, 2007.

Araujo, N.C. et al. (Apr. 1, 2009, e-published Feb. 8, 2009). "Semi-synthetic and synthetic 1,2,4-trioxaquines and 1,2,4-trioxolaquines: synthesis, preliminary SAR and comparison with acridine endoperoxide conjugates," *Bioorg Med Chem Lett* 19(7):2038-2043.

Barton, V. et al. (Jun. 10, 2010). "Rationale design of biotinylated antimalarial endoperoxide carbon centered radical prodrugs for applications in proteomics," *J Med Chem* 53(11):4555-4559.

Boeckman, R. J., "1,1,1-Triacetoxy-1,1-dihydro-1,2-benziodoxol-3(1H)-one" In *Encyclopedia of Reagents for Organic Synthesis*: L.A. Paquette, Ed; Wiley: Chichester, UK, 1995, 7:4982-4987.

Boswell, G., "Synthesis and Anti-tetrabenazine Activity of C-3 Analogues of Dimethyl-2-phenlymorpholines", Journal of Heterocyclic Chemistry 33(1):33-39, 1996.

Bouserja-El Garah, F. et al. (Oct. 13, 2011, e-published Sep. 19, 2011). "Comparison of the reactivity of antimalarial 1,2,4,5-tetraoxanes with 1,2,4-trioxolanes in the presence of ferrous iron salts, heme, and ferrous iron salts/phosphatidylcholine," *J Med Chem* 54(19):6443-6455.

Buckle, F.J. et al. (1949). "Toxic Fluorine Compounds containing the C-F Link. Part VI. Ω-Fluorocarboxylic Acids and Derivatives," *Journal of the Chemical Society* 1949:1471-1479.

Carabateas Philip M. et al., "1-Ethyl-1, 4-dihydro-oxo-7-(pyridinyl)-3-quinolinecarboxylic Acids. I. Synthesis of 3- and 4-(3-Aminophenyl)pyridine Intermediates", Journal of Heterocyclic Chemistry 21:1849-1856, 1984.

Creek, Darren J. et al., "Iron-Mediated Degradation Kinetics of Substituted Dispiro-1,2,4-trioxolane Antimalarials", Journal of Pharmaceutical Sciences 96(11):2945-2956, Nov. 2007.

Creek, D.J. et al. (Apr. 2008, e-published Feb. 11, 2008). "Relationship between antimalarial activity and heme alkylation for spiro- and dispiro-1,2,4-trioxolane antimalarials," *Antimicrob Agents Chemother* 52(4):1291-1296.

De Kimpe, Norbert et al., "Regiospecific Synthesis of a-Ketoacetals by Rearrangement of a-Bromo-a-Fluoroketones", Tetrahedron Letters 21:2257-2260, 1980.

Deu, E. et al. (Aug. 27, 2010). "Functional studies of Plasmodium falciparum dipeptidyl aminopeptidase I using small molecule inhibitors and active site probes," *Chem Biol* 17(8):808-819.

Disbrow, Gary L. et al., "Dihydroartemisinin Is Cytotoxic to Papillomavirus-Expressing Epithelial Cells In vitro and In vivo", Cancer Research 65:10854-10861, Dec. 2005.

Dong, Yuxiang et al., "Dispiro-1,2,4,5-tetraoxanes via Ozonolysis of Cycloalkanone 0-Methyl Oximes: A Comparison with the Peroxidation of Cycloalkanones in Acetonitrile-Sulfuric Acid Media", Journal of Organic Chemistry 63:8582-8585, 1988.

(56) References Cited

OTHER PUBLICATIONS

Dong, Y. et al. (Sep. 15, 2006, e-published Jun. 8, 2006). "Effect of functional group polarity on the antimalarial activity of spiro and dispiro-1,2,4-trioxolanes," *Bioorg Med Chem* 14(18):6368-6382.

Efferth, Thomas et al., "Enhancement of Cytotoxicity of Artemisinins toward Cancer Cells by Ferrous Iron", Free Radical Biology & Medicine 37(7):998-1009, 2004.

Efferth, Thomas, "Mechanistic perspectives for 1,2,4-trioxanes in anti-cancer therapy", Drug Resistance Updates 8:85-97, 2005.

Elliot, R.L. et al. (1994). "Relationship of serum and tumor levels of iron and iron-binding proteins to lymphocyte immunity against tumor antigen in breast cancer patients," *Breast Cancer Res Treat* 30(3):305-309.

Farmer, Luc J. et al., "Retinoic Acid Receptor Ligands Based on the 6-Cyclopropyl-2,4-hexadienoic Acid", Bioorganic & Medicinal Chemistry Letters 13:261-264, 2003.

Figueiredo, a.F. et al. (2011). "A Computational Study on Antimalarial Dispiro-1,2,4-Trioxolanes," *Journal of Computational and Theoretical Nanoscience* 8(9):1847-1856.

Fontaine, S.D. et al. (Nov. 7, 2014, e-published Oct. 21, 2014). "Efficient and stereocontrolled synthesis of 1,2,4-trioxolanes useful for ferrous iron-dependent drug delivery," *Org Lett* 16(21):5776-5779.

Gauthier, Jacques Y. et al., "The discovery of odanacatib (MK-0822), a selective inhibitor of cathepsin K", Bioorganic & Medicinal Chemistry Letters 18:923-928, 2008.

Grierson, D. et al., "Polonovski- and Pummerer-type Reactions and the Nef Reaction", Comprehensive Organic Synthesis 6: 924-937, 1991.

Griesbaum, Karl et al., "Diozonides from Coozonolyses of Suitable 0-Methyl Oximes and Ketones", Tetrahedron 53(15): 5463-5470, 1997.

Hareau, G. et al. (1999). "Synthesis of Optically Active 5-(tert-Butyldimethysiloxy)-2-cyclohexenone and Its 6-Substituted Derivatives as Useful Chiral Building Blocks for the Synthesis of Cyclohexane Rings. Syntheses of Carvone, Penienine, and Penihydrone," *J Am Chem Soc* 121:3640-3650.

Hartwig, C.L. et al. (Dec. 8, 2011, e-published Nov. 9, 2011). Investigating the antimalarial action of 1,2,4-trioxolanes with fluorescent chemical probes, *J Med Chem* 54(23):8207-8213.

Henriksena, B. et al. (2012). "Structural aspects of ozonides on lymphoma cell viability," *Journal of Chemical and Pharmaceutical Research* 4(4):2012-2020.

Hentze, M.W. et al. (Apr. 30, 2004). "Balancing acts: molecular control of mammalian iron metabolism," *Cell* 117(3):285-297.

Hilpert, H. et al. (2001). "Novel versatile approach to an enantiopure 19-nor, des-C,D Vitamin $D_3$ derivative," *Tetrahedron* 57:681-694.

Huttunen, Kristiina M. et al., "Novel Cyclic Phosphate Prodrug Approach for Cytochrome P450-activated Drugs Containing an Alcohol Functionality", Pharmaceutical Research 24:679-687, 2007.

International Preliminary Report on Patentability and Written Opinion dated Jan. 25, 2011 for International Application No. PCT/US2009/051304, 6 pages.

International Search Report dated Feb. 23, 2010 for International Application No. PCT/US2009/051304, 4 pages.

International Search Report and Written Opinion for International Application No. PCT/US2015/015948 dated Jul. 22, 2015, 11 pages.

Jin et al., Synthesis of 1,6,7-trioxa-spiro[4.5]decances. Tetrahedron Letters. 2005;46:5767-9. Abstract; scheme 1; scheme2.

Karmee, S.K. et al. (2011). "Kinetic resolution of 3-hydroxycyclohexanone using different lipases," *Tetrahedron:Asymm* 22:1736-1739.

Kerr, Bernadette et al., "Dispiro-1,2,4-Trioxanes as Precursors of Medium Ring Lactones: Thermolysis of Indan-2-spiro-3 4 1',2',4'-trioxane)-6'-spiro-1-cyclohexane", Journal of the Chemical Society, Chemical Communications 590-593, 1985.

Krow, Grant R., "The Baeyer-Villiger Reactin", Comprehensive Organic Synthesis 7:671-688, 1991.

Kucharzewski, M. et al. (Oct. 2003). "Iron concentrations in intestinal cancer tissue and in colon and rectum polyps," *Biol Trace Elem Res* 95(1):19-28.

Kuroda, Chiaki et al., "Intramolecular Cyclization of Allylsilanes in the Synthesis of Guaian-8,12-olide. Stereoselective Formation of trans- and cis-Fused Methylenelactones", Journal of the Chemical Society, Perkin Transactions' , 5:521-526, 1994.

Laurent, S.A.L. et al. (2008). "Synthesis of "Trioxaquantel" Derivatives as Potential New Antischistosomal Drugs," *Eur J Org Chem* pp. 895-913.

Madrid, Peter B. et al., "Incorporation of an Intramolecular Hydrogen-bonding Motif in the Side-Chain of 4-Aminoquinolines Enhances Activity against Drug-Resistant *P. falciparum*", J Med Chem. 49(15):4535-4543, 2006.

Mcconville, M. et al. (Jan. 7, 2014). "Selective trioxolane based bifunctional molecular linkers for covalent heme surface functionalization," *Chem Commun (Camb)* 50(2):186-188.

Moehrle,J.J. et al. (Feb. 2013). "First-in-man safety and pharmacokinetics of synthetic ozonide OZ439 demonstrates an improved exposure profile relative to other peroxide antimalarials," *Br J Clin Pharmacol* 75(2):524-537.

Odlo, K. et al. (May 1, 2008). "1,5-Disubstituted 1,2,3-triazoles as cis-restricted analogues of combretastatin A-4: Synthesis, molecular modeling and evaluation as cytotoxic agents and inhibitors of tubulin," *Bioorg Med Chem* 16(9):4829-4838.

Oliveira, R. et al. (Sep. 2013, e-published Jul 12, 2013). "An endoperoxide-based hybrid approach to deliver falcipain inhibitors inside malaria parasites," *Chem MedChem* 8(9):1528-1536.

O'Neill, P.M. et al. (Aug. 13, 2004). "Design and synthesis of endoperoxide antimalarial prodrug models," *Angew Chem Int Ed Engl* 43(32):4193-4197.

O'Neill, P.M. et al. (Sep. 2, 2004). "Application of thiol-olefin co-oxygenation methodology to a new synthesis of the 1,2,4-trioxane pharmacophore," *Org Lett* 6(18):3035-3038.

Padmanilayam, M. et al. (Nov. 1, 2006, e-published Aug. 22, 2006). "Antimalarial activity of N-alkyl amine, carboxamide, sulfonamide, and urea derivatives of a dispiro-1,2,4-trioxolane piperidine," *Bioorg Med Chem Lett* 16(21):5542-5545.

PubChem-CID-67435 (Create Date: Mar. 27, 2005) p. 3, Fig.

Robert, Anne et al., "The key role of heme to trigger the antimalarial activity of trixanes", Coordination Chemistry Reviews 249:1927-1936, 2005.

Rosenthal, Philip J. et al., "A Malarial Cysteine Proteinase Is Necessary for Hemoglobin Degradation by Plasmodium falciparum", Journal of Clinical Investigation 82:1560-1566, 1988.

Rosenthal, Philip J., "Proteases and hemoglobin degradation", Molecular Approaches to Malaria 311-326, 2005.

Singh, Narendra P. et al., "Selective toxicity of dihydroartemisinin and holotransferrin toward human breast cancer cells", Life Sciences 70:49-56, 2001.

Somoza, John R. et al., "Crystal Structure of Human Cathepsin V", Biochemistry 39(41):12543-12551, 2000.

Stocks, P.A. et al. (2007). "Evidence for a common non-heme chelatable-iron-dependent activation mechanism for semisynthetic and synthetic endoperoxide antimalarial drugs," *Angew Chem Int Ed Engl* 46(33):6278-6283.

Subramanyam, Vinayakam et al., "Synthesis and Reactions of 6-Hydroxyhydroperoxides", Journal of the Chemical Society, Chemical Communications 508-509, 1976.

Takagi, H. et al. (1999). "Synthesis and structure of tetraols with convergent and divergent arrays of hydroxyl groups," *J Chem Soc Perkin Trans* 1885-1892.

Tang, Yuanquing et al., "Synthesis of Tetrasubstituted Ozonides by the Griesbaum Coozonolysis Reaction: Diastereoselectivity and Functional Group Transformations by Post-Ozonolysis Reactions", Journal of Organic Chemistry 69:6470-6473, 2004.

Tang, Yuanquing et al., "Dispiro-1,2,4-trioxane Analogues of a Prototype Dispiro-1,2,4-trioxolane: Mechanistic Comparators for Artemisinin in the Context of Reaction Pathways with Iron(II)", Journal of Organic Chemistry 70(13):5103-5110, 2005.

Tang, Y. et al. (Mar. 1, 2007, e-published Dec. 15, 2006). "Weak base dispiro-1,2,4-trioxolanes: potent antimalarial ozonides," *Bioorg Med Chem Lett* 17(5):1260-1265.

(56) References Cited

OTHER PUBLICATIONS

Tang, Y. et al. (Jan. 2010, e-published Nov. 22, 2009). "The comparative antimalarial properties of weak base and neutral synthetic ozonides," *Bioorg Med Chem Lett* 20(2):563-566.

Tidwell, Thomas T., "Oxidation of Alcohols by Activated Dimethyl Sulfoxide and Related Reactions: An Update", Synthesis 857-870, 1990.

Yang, S. et al. (Dec. 13, 2002). "A new short synthesis of 3-substituted 5-amino-1-(chloromethyl)-1,2-dihydro-3H-benzo[e]indoles (amino-CBIs)," *J Org Chem* 67(25):8958-8961.

Zhao, Q. et al. (May 27, 2010). "Structure-activity relationship of an ozonide carboxylic acid (OZ78) against Fasciola hepatica," *J Med Chem* 53(10):4223-4233.

Zhou, L. et al. (Mar. 1, 2008, e-published Jan. 30, 2008). "Characterization of the two major CYP450 metabolites of ozonide (1,2,4-trioxolane) OZ277," *Bioorg Med Chem Lett* 18(5):1555-1558.

Aron, A.T. et al. (Nov. 28, 2017, e-published Nov. 14, 2017). "In vivo bioluminescence imaging of labile iron accumulation in a murine model of *Acinetobacter baumannii* infection," *PNAS USA* 114(48):12669-12674.

Blank, B.R. et al. (Aug. 9, 2019, e-published Jun. 11, 2019). "Targeting Mobilization of Ferrous Iron in *Pseudomonas aeruginosa* Infection with an Iron(II)-Caged LpxC Inhibitor," *ACS Infect Dis* 5(8):1366-1375.

Spangler, B. et al. (Dec. 2016, e-published Dec. 12, 2016). "A Novel Tumor-Activated Prodrug Strategy Targeting Ferrous Iron Is Effective in Multiple Preclinical Cancer Models," *J Med Chem* 59(24):11161-11170.

\* cited by examiner

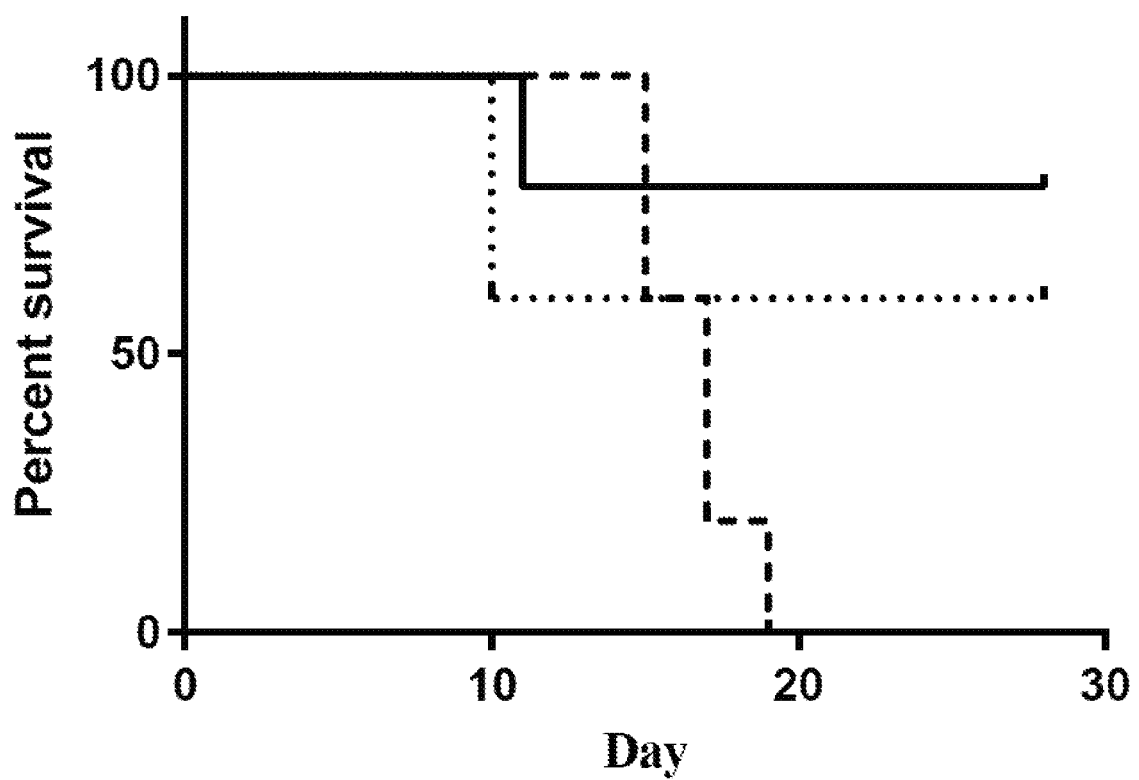

CYCLIC PEROXIDES AS PRODRUGS FOR SELECTIVE DELIVERY OF AGENTS

CROSS-REFERENCES TO RELATED APPLICATIONS

This application is a continuation of the U.S. patent application Ser. No. 15/118,268, filed Aug. 11, 2016, which is the national stage filing under USC 371 of international application PCT/US2015/015,948, filed Feb. 13, 2015, which claims the benefit of U.S. Provisional Patent Application No. 61/940,295, filed Feb. 14, 2014, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. AI094433, awarded by the National Institutes of Health. The government has certain rights in the invention.

BACKGROUND OF THE INVENTION

The majority of chemotherapeutic agents used to treat cancer exhibit serious toxicity, resulting in undesired side effects for patients and reducing efficacy by limiting the doses that can be safely administered. Similarly, many of the therapeutics used to treat infectious diseases, including parasitic diseases, confer undesirable side effects. It would be preferable if such agents could be administered in a prodrug form that masked the inherent toxicity of the agent from irrelevant, non-diseased tissues, and yet released the fully active drug species at the desired site of action. Such a technology would have the potential to increase the therapeutic window of a variety of drugs, possibly allowing them to be used safely at a more efficacious dose, and with reduced incidence of undesired side-effects for the patient.

In normal cells and tissues, iron remains sequestered in forms that are non-toxic to the cell, bound to the iron carrying protein transferrin for example, or bound as heme within hemoglobin. Diseased tissues and cells, on the other hand, can contain higher than normal concentrations of iron. Many neoplastic cells for example over-express the transferrin receptor to increase their uptake of iron. Increased iron uptake has been proposed to explain the increased toxicity that iron-dependent endoperoxides like artemisinin exhibit towards cancer cell lines as compared to normal cells (Efferth, T. *Drug Resistance Updates*, 2005, 8:85-97). In one study, the expression level of the transferrin receptor was shown to correlate with the cytotoxicity of an artemisinin derivative towards HeLa cells (see for example Disbrow, G. L., et al *Cancer Research*, 2005, 65, 10854-10861). Artemisinin and its derivatives are believed to exert their cytotoxic effect via reaction with $Fe^{II}$ and the resulting generation of reactive oxygen and carbon centered radical species. The cytotoxicity of artemisinin derivatives towards leukemia, astrocytoma, and breast cancer cell lines can be potentiated by the addition of exogenous $Fe^{II}$ salts or transferrin (Efferth, T. et al *Free Radical Biology & Medicine*, 2004, 37, 998-1009; Singh, N. P. et al *Life Sciences*, 2001, 70, 49-56). U.S. Pat. No. 5,578,637 describes the use of an endoperoxide moiety (i.e., an artemisinin) to kill cancer cells under conditions that enhance intracellular iron concentrations. None of these prior works teach or suggest how higher than normal concentrations of iron in such cells could be exploited for selective delivery of a drug species via an iron-sensitive prodrug moiety.

The blood-scavenging parasites responsible for diseases such as malaria and schistosomiasis also possess biological compartments rich in ferrous iron. In malaria parasites, unbound heme is generated in the parasite digestive vacuole where hemoglobin is degraded by a number of proteases (See Rosenthal, P. J. in *Protease and hemoglobin degradation*. Molecular Approaches to Malaria, 2005: p. 311-326). Hence, while the concentration of unbound, ferrous iron is vanishingly small in human plasma ($\sim 10^{-16}$M), significant quantities of ferrous iron are present within malaria parasites (see Robert, A. et al *Coordination Chemistry Reviews*, 2005, 249, p. 1927-1936). The antimalarial drug artemisinin and its related synthetic derivatives are thought to confer their antiparasitic effect via reaction with ferrous iron and the resulting generation of reactive oxygen and carbon centered radical species. An excess of iron, and ferrous iron in particular, is therefore a distinguishing characteristic of many neoplastic cells and pathogenic parasites.

Among synthetic endoperoxide ring systems, the iron reactivity of 1,2,4-trioxolanes has been extensively studied in vitro using model systems (see Creek, D. J. et al, *J. Pharm. Sci.* 2007, 96, 2945-2956).

The use of prodrugs to confer improved properties such as increased bioavailability or aqueous solubility is a well established concept in the art of pharmaceutical research. These standard approaches rely on the action of serum esterases or phosphatases to remove the blocking pro moiety and thereby liberate the drug species. The attachment of a cytotoxic agent to a targeting moiety such as a protein or antibody via an acid-labile linker moiety is another known prodrug approach, intended to deliver a drug moiety to a specific cell or tissue. See U.S. Pat. No. 5,306,809. Acid labile linker moieties have also been used to attach drug species to biopolymers or antibodies where the intention is that the lower pH of the diseased tissue serves to trigger release of the drug moiety. See U.S. Pat. Nos. 4,631,190; 4,997,913; 5,140,013. Antibody-drug conjugates (ADC) are currently being developed for the more selective delivery of therapeutic agents, especially in cancer. Typically a potent drug is conjugated to an antibody that recognizes antigen on a particular cell type of interest. The ADC is internalized via receptor mediated endocytosis and the free drug is released, often via an acid labile linker or a reductively labile (disulfide) linker. ADCs are complex and not always as selective as desired because the targeted antigen can be expressed in normal cells. Insufficiently stable linkers can also result in spurious drug release from ADCs. Disclosed herein, inter alia, are solutions to these and other problems in the art.

BRIEF SUMMARY OF THE INVENTION

In an aspect is provided a compound, or a pharmaceutically acceptable salt thereof, having the formula:

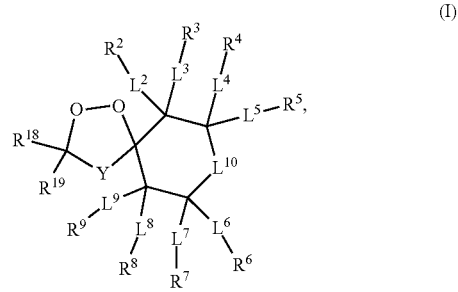

(I)

wherein $L^2$, $L^3$, $L^4$, $L^5$, $L^6$, $L^7$, $L^8$, $L^9$, $L^{11}$, and $L^{12}$ are independently a bond, $-N(R^{17})-L^{13}-L^{14}-$, $-N(R^{17})C(O)O-L^{13}-L^{14}-$, $-O-L^{13}-L^{14}-$, $-S-L^{13}-L^{14}-$, $-OC(O)-L^{13}-L^{14}-$, $-OC(O)N(R^{17})-L^{13}-L^{14}-$, $-OC(O)O-L^{13}-L^{14}-$, $-OSO_2-L^{13}-L^{14}-$, $-C(O)N(R^{17})-L^{13}-L^{14}-$, $-N(R^{17})C(O)-L^{13}-L^{14}-$, $-S(O)_2N(R^{17})-L^{13}-L^{14}-$, $-N(R^{17})S(O)_2-L^{13}-L^{14}-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{10}$ is $-N(-L^{11}-R^{11})-$ or $-C((-L^{11}-R^{11})(-L^{12}-R^{12}))-$; each $L^{13}$ and $L^{14}$ are independently selected from a bond, $-N(R^{17})-$, $-N(R^{17})C(O)O-$, $-O-$, $-S-$, $-OC(O)-$, $-OC(O)N(R^{17})-$, $-OC(O)O-$, $-OSO_2-$, $-C(O)N(R^{17})-$, $-N(R^{17})C(O)-$, $-S(O)_2N(R^{17})-$, $-N(R^{17})S(O)_2-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^2$, $R^3$, $R^4$, $R^5$, $R^6$, $R^7$, $R^8$, $R^9$, $R^{11}$, and $R^{12}$, are independently hydrogen, oxo, halogen, $-CX_3$, $-CN$, $-SO_2Cl$, $-SO_nR^{16}$, $-SO_vNR^{13}R^{14}$, $-NHNH_2$, $-ONR^{13}R^{14}$, $-NHC=(O)NHNH_2$, $-NHC=(O)NR^{13}R^{14}$, $-N(O)_m$, $-NR^{13}R^{14}$, $-C(O)R^{15}$, $-C(O)-OR^{15}$, $-C(O)NR^{13}R^{14}$, $-OR^{16}$, $-NR^{13}SO_2R^{16}$, $-NR^{13}C=(O)R^{15}$, $-NR^{13}C(O)-OR^{15}$, $-NR^{13}OR^{15}$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, a detectable moiety, or a drug moiety; $R^5$ and $R^{11}$ substituents may be joined to form a substituted or unsubstituted cycloalkyl, substituted or unsubstituted heterocycloalkyl, substituted or unsubstituted aryl, or substituted or unsubstituted heteroaryl; $R^6$ and $R^{11}$ substituents may be joined to form a substituted or unsubstituted cycloalkyl, substituted or unsubstituted heterocycloalkyl, substituted or unsubstituted aryl, or substituted or unsubstituted heteroaryl; $R^2$ and $R^3$, $R^4$ and $R^5$, $R^6$ and $R^7$, $R^8$ and $R^9$, or $R^{11}$ and $R^{12}$ may be joined to form a substituted or unsubstituted cycloalkyl, substituted or unsubstituted heterocycloalkyl, substituted or unsubstituted aryl, or substituted or unsubstituted heteroaryl; each $R^{13}$, $R^{14}$, $R^{15}$, $R^{16}$, and $R^{17}$ are independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ and $R^{14}$ substituents bonded to the same atom may be joined to form a substituted or unsubstituted heterocycloalkyl or substituted or unsubstituted heteroaryl; $R^{18}$ and $R^{19}$ are independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, detectable moiety, siderophore moiety, or a drug moiety; $R^{18}$ and $R^{19}$ may be joined to form a substituted or unsubstituted cycloalkyl, substituted or unsubstituted heterocycloalkyl, protein moiety, detectable moiety, siderophore moiety, or drug moiety; m and v are independently 1 or 2; n is independently an integer from 0 to 2; Y is $-O-$, $-S-$, $-OO-$, $-CH_2O-$, or $-OCH_2-$; and X is independently $-Cl$, $-Br$, $-I$, or $-F$.

In an aspect is provided a pharmaceutical composition including a pharmaceutically acceptable excipient and a compound described herein (including in an aspect, embodiment, table, example, or claim), or pharmaceutically acceptable salt thereof.

In an aspect is provided a method of treating a disease in a patient in need of such treatment, said method including administering a therapeutically effective amount of a compound described herein (including in an aspect, embodiment, table, example, or claim), or a pharmaceutically acceptable salt thereof, to the patient.

In an aspect is provided a method of identifying a patient having a disease associated with a cell or organism having an increased $Fe^{II}$ level compared to a standard control, the method including administering an effective amount of a compound described herein (including in an aspect, embodiment, table, example, or claim), or a pharmaceutically acceptable salt thereof, to the patient.

BRIEF DESCRIPTION OF THE DRAWINGS

FIG. 1. In vivo efficacy of Example 23 (9.5 mg/kg/day, solid line) as compared to chloroquine (33 mg/kg/day, dashed line) and arterolane tosylate (13.6 mg/kg/day, dotted line) in *P. berghei* infected mice. All compounds were administered to *P. berghei* infected mice by oral gavage once a day for three days at the indicated daily dose.

DETAILED DESCRIPTION OF THE INVENTION

Described herein are novel prodrugs capable of the selective release of an agent (e.g. drug, detectable agent, protein) to biological compartments containing unbound forms of ferrous iron, pharmaceutical compositions thereof, methods for their use, and methods for preparing these prodrugs. Described herein is the use of the prodrugs in the treatment of parasitic and neoplastic disease, or any condition where the targeting of cells or biological compartments with higher than normal concentrations of a reductant (e.g. ferrous iron) is of benefit (e.g. diagnostic or therapeutic). Examples of the prodrug moieties described herein include a heterocyclic ring system containing a peroxide bond (e.g. a 1,2,4-trioxane or 1,2,4-trioxolane ring system). The agent (e.g. drug, detectable agent, protein) may be directly embedded in the structure of the prodrug, or it may be attached via a self-immolating linker. Upon exposure to ferrous iron, or other biologically relevant reductants, the peroxide containing heterocyclic undergoes a fragmentation reaction, releasing the agent (e.g. drug, detectable agent, protein), or alternatively unveiling a carbonyl function in the linker, which then undergoes a spontaneous elimination reaction to release the tethered agent (e.g. drug, detectable agent, protein). The agent (e.g. drug, detectable agent, protein) can be conjugated to the prodrug via a variety of chemical functionality, including but not limited to a carbonyl, ester, ether, carbamate, carbonate, amine, or thioether.

A. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocyloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S($O)_2$R', —S($O)_2$NR'R", —NRS$O_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C($O)_2$R', —NR—C(NR'R"R'")=NR"", —NR—C(NR'R")=NR'", —S(O)R', —S($O)_2$R', —S($O)_2$NR'R", —NRS$O_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, proteins, drugs, detectable agents, therapeutic agents) in a prodrug form. Prodrugs of the compounds described herein are those compounds that readily undergo chemical changes under select physiological conditions (e.g. increased $Fe^{II}$ concentration relative to normal physiological levels, increased reductant levels relative to normal physiological levels) to provide the final agents (e.g. compounds, proteins, drugs, detectable agents, therapeutic agents). Additionally, prodrugs can be converted to agents (e.g. compounds, proteins, drugs, detectable agents, therapeutic agents) by chemical or biochemical methods in an ex vivo environment. Prodrugs described herein include compounds that readily undergo chemical changes under select physiological conditions (e.g. increased $Fe^{II}$ concentration relative to normal physiological levels, increased reductant levels relative to normal physiological levels) to provide agents (e.g. compounds, proteins, drugs, detectable agents, therapeutic agents) to a biological system (e.g. in a subject, in an infected cell, in a cancer cell, in the extracellular space near an infected cell, in the extracellular space near a cancer cell from the moieties (e.g. moiety of a protein, drug, detectable agent) attached to the prodrug moiety and included in the prodrug (e.g. compound of formula I, including embodiments, compound described herein, examples)).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds. A protein moiety is a radical of a protein.

The term "peptidyl" and "peptidyl moiety" means a monovalent peptide.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. An oligomer comprising amino acid mimetics is a peptidomimetic. A peptidomimetic moiety is a monovalent peptidomimetic.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)). In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions. In some embodiments, there may be 1, 2, 3, 4, 5, 6, 7, 8, 9, 10, 15, 20, 25, 30, 35, or 40 conservative substitutions.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An antibody moiety is a radical of an antibody. Non-limiting examples of antibodies (or functional fragments thereof or antigen-binding fragments thereof, derived from such antibodies) that may be included in the compounds described herein include 3F8, 8H9, Abagovomab, Abciximab, Abrilumab, Actoxumab, Adalimumab, Adecatumumab, Aducanumab, Afelimomab, Afutuzumab, Alacizumab pegol, ALD518, Alemtuzumab, Alirocumab, Altumomab pentetate, Amatuximab, Anatumomab mafenatox, Anifrolumab, Anrukinzumab (IMA-638), Apolizumab, Arcitumomab, Aselizumab, Atinumab, Atlizumab (tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, CC49, cBR96-doxorubicin immunoconjugate, Cedelizumab, Certolizumab pegol, Cetuximab, Ch.14.18, Citatuzumab bogatox, Cixutumumab, Clazakizumab, Clenoliximab, Clivatuzumab tetraxetan, Conatumumab, Concizumab, Crenezumab, CR6261, Dacetuzumab, Daclizumab, Dalotuzumab, Daratumumab, Demcizumab, Denosumab, Detumomab, Dinutuximab, Diridavumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elotuzumab, Elsilimomab, Emibetuzumab, Enavatuzumab, Enfortumab vedotin, Enlimomab pegol, Enokizumab, Enoticumab, Ensituximab, Epitumomab cituxetan, Epratuzumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, IMAB362, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Lifastuzumab vedotin, Ligelizumab, Lintuzumab, Lirilumab, Lodelcizumab, Lorvotuzumab mertansine, Lucatumumab, Lulizumab pegol, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Obiltoxaximab, Ocaratuzumab, Ocrelizumab, Odulimomab, Ofatumumab, Olaratumab, Olokizumab, Omalizumab, Onartuzumab, Ontuxizumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Patecilizumab, Patritumab, Pembrolizumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teplizumab, Teprotumumab, TGN1412, Ticilimumab (tremelimumab), Tildrakizumab, Tigatuzumab, TNX-650, Tocilizumab (atlizumab), Toralizumab, Tositumomab, Tovetumab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vantictumab, Vapaliximab, Varlilumab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab, and Zolimomab aritox.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments (e.g., antigen-binding fragments) include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

A "label" or a "detectable agent" is a composition detectable by spectroscopic, photochemical, biochemical, immunochemical, chemical, magnetic resonance imaging, or other physical means. For example, useful detectable agents include $^{32}$P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), fluorodeoxyglucose nucleotide or nucleoside (e.g. fluorine-18 labeled A, C, G, or T), gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable agents also include any of the above compositions encapsulated in nanoparticles, particles, aggregates, coated with additional compositions, derivatized for binding to a targeting agent (e.g. antibody or antigen binding fragment). A detectable moiety is a radical of a detectable agent.

The terms "fluorophore" or "fluorescent agent" are used interchangeably and refer to a composition (e.g. compound) that can absorb light at one or more wavelengths and re-emit light at one or more longer wavelengths, relative to the one or more wavelengths of absorbed light. Examples of fluorophores that may be included in the compositions described herein include fluorescent proteins, xanthene derivatives (e.g. fluorescein, rhodamine, Oregon green, eosin, or Texas red), cyanine and derivatives (e.g. cyanine, indocarbocyanine, oxacarbocyanine, thiacarbocyanine or merocyanine), napthalene derivatives (e.g. dansyl or prodan derivatives), coumarin and derivatives, oxadiazole derivatives (e.g. pyridyloxazole, nitrobenzoxadiazole or benzoxadiazole), anthracene derivatives (e.g. anthraquinones, DRAQ5, DRAQ7, or CyTRAK Orange), pyrene derivatives (e.g. cascade blue and derivatives), oxazine derivatives (e.g. Nile red, Nile blue, cresyl violet, oxazine 170), acridine derivatives (e.g. proflavin, acridine orange, acridine yellow), arylmethine derivatives (e.g. auramine, crystal violet, malachite green), tetrapyrrole derivatives (e.g. porphin, phthalocyanine, bilirubin), CF Dye™, DRAQ™, CyTRAK™, BODIPY™, Alexa Fluor™, DyLight Fluor™, Atto™, Tracy™, FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™, Phycobilisomes™, APC™, APCXL™, RPE™, and/or BPE™. A fluorescent moiety is a radical of a fluorescent agent.

The term "drug" is used in accordance with its common meaning and refers to a substance which has a physiological effect (e.g. beneficial effect, is useful for treating a subject) when introduced into or to a subject (e.g. in or on the body of a subject or patient). A drug moiety is a radical of a drug.

The term "siderophore" is used in accordance with its common meaning and refers to a high-affinity iron chelating compound that may be secreted by a microorganism (e.g., bacteria, fungi, grasses). Non-limiting examples of siderophores include catecholates (e.g., phenolates), hydroxamates, carboxylates (e.g., derivatives of citric acid), ferrichrome, desferrioxamine B (deferoxamine), desferrioxamine E, fusarinine C, ornibactin, rhodotorulic acid, enterobactin, bacillibactin, vibriobactin, azotobactin, pyoverdine, yersiniabactin, aerobactin, simochelin, alcaligin, mycobactin, staphyloferrin A, and petrobactin. In embodiments, a siderophore may chelate a non-iron metal (e.g., aluminum, gallium, chromium, copper, zinc, lead, manganese, cadmium vanadium indium, plutonium, or uranium). A siderophore moiety is a radical of a siderophore. Additional non-limiting examples of a siderophore include Achromobactin, Acinetoferrin, Aerobactin, Aeruginic, Agrobactin, Agrobactin A, Albomycin 271, Alcaligin 230, Alterobactin A, Alterobactin B, Aminochelin 262, Amonabactin P693, Amonabactin P750, Amonabactin T732, Amonabactin T789, Amphibactin B, Amphibactin C, Amphibactin D, Amphibactin E, Amphibactin F, Amphibactin G, Amphibactin H, Amphibactin I, Amycolachrome 235, Anachelin 1, Anachelin 2, Anguibactin 247, Aquachelin A, Aquachelin B, Aquachelin C, 2, Aquachelin D, Arthrobactin 199, Asperchrome A, Asperchrome B1, Asperchrome B2, Asperchrome B3, Asperchrome C, Asperchrome D1, Asperchrome D2, Asperchrome D3, Asperchrome E, Asperchrome F1, Asperchrome F2, Asperchrome F3, Aspergillic acid, Avenic acid, Azotobactin 236, Azotobactin D, Azotobactin 87, Azotochelin 236, Azoverdin 174, Bacillibactin 85, Basidiochrome 46, Bisucaberin 232, Carboxymycobactin 107, Carboxymycobactin 1, Carboxymycobactin 2, Carboxymycobactin 3, Carboxymycobactin 4, Cepabactin 266, Chrysobactin 261, Citrate 260, Coelichelin 72, 3, Coprogen 51, Coprogen B, Corynebactin 84, Deoxydistichonic acid, 2'-Deoxymugineic acid, Deoxyschizokinen 251, Des(diserylglycyl)-ferrirhodin 45, Desacetylcoprogen 52, Desferrioxamine A1, Desferrioxamine A2, Desferrioxamine B, Desferrioxamine D1, Desferrioxamine D2, Desferrioxamine E, Desferrioxamine Et1 21A, Desferrioxamine Et2 21B, Desferrioxamine Et3 21C, Desferrioxamine G1, Desferrioxamine G2A, Desferrioxamine G2B, Desferrioxamine G2C, Desferrioxamine H, Desferrioxamine P1, Desferrioxamine T1, Desferrioxamine T2, Desferrioxamine T3, Desferrioxamine T7, Desferrioxamine T8, Desferrioxamine Te1 21D, Desferrioxamine Te2 21E Desferrioxamine Te3 21F, Desferrioxamine X1, Desferrioxamine X2, 4, Desferrioxamine X3, Desferrioxamine X4, Desferrithiocin, 2,3-Dihydroxybenzoylserine, Dimerum acid, Dimethylcoprogen, Dimethylneocoprogen I, Dimethyltriornicin, Distichonic acid, Enantio Rhizoferrin, Enantio-Pyochelin, Enterobactin, Enterochelin, Exochelin MN, Exochelin MS, Ferrichrome, Ferrichrome A, Ferrichrome C, Ferrichrysin, Ferricrocin, Ferrimycin A, Ferrirhodin, Ferrirubin, Ferrocin A, Fluvibactin, Formobactin, Fusarinine A, Fusarinine B, Fusarinine C, Heterobactin A, Heterobactin B, Hydroxycopropen, Hydroxyisoneocoprogen I, 3-Hydroxymugineic acid, 5, Hydroxy-neocoprogen I, Isoneocoprogen I, Isopyoverdin BTP1, Isopyoverdin 6.7, Isopyoverdin 7.13, Isopyoverdin 90-33, Isopyoverdin 90-44, Isopyoverdin 10.7, Isotriornicin, Itoic acid, Loihichelin A, Loihichelin B, Loihichelin C, Loihichelin D, Loihichelin E, Loihichelin F, Maduraferrin, Malonichrome, Marinobactin A, Marinobactin B, Marinobactin C, Marinobactin D1, Marinobactin D2, Marinobactin E, Micacocidin, Mugineic acid, Mycobactin A, Mycobactin Av, Mycobactin F, Mycobactin H, Mycobactin J, Mycobactin M, Mycobactin N, 6, Mycobactin NA, Mycobactin P, Mycobactin R, Mycobactin S, Mycobactin T, Myxochelin, Nannochelin A, Nannochelin B, Nannochelin C, Neocoprogen I, Neocoprogen II, Neurosporin, Nocobactin, Nocobactin NA, Ochrobactin A, Ochrobactin B, Ochrobactin C, Ornibactin-C4, Ornibactin-C6, Ornibactin-C8, Ornicorrugatin, palmitoylcoprogen, Parabactin, Parabactin A, Petrobactin, Petrobactin disulphonate, Petrobactin sulphonate, Pistillarin, Protochelin, Pseudoalterobactin A, Pseudoalterobactin B, Pseudobactin 112, Pseudobactin 589A, 7, Putrebactin, Pyochelin, Pyoverdin A214, Pyoverdin BTP2, Pyoverdin C, Pyoverdin CHAO, Pyoverdin D-TR133, Pyoverdin E, Pyoverdin G R Pyoverdin GM, Pyoverdin I-III, Pyoverdin P19, Pyoverdin Pau, Pyoverdin PL8, Pyoverdin PVD, Pyoverdin R', Pyoverdin Thai, Pyoverdin TII, Pyoverdin 1, Pyoverdin 11370, Pyoverdin 13525, Pyoverdin 1547, Pyoverdin 17400, Pyoverdin 18-1, Pyoverdin 19310, Pyoverdin 2192, Pyoverdin 2392, Pyoverdin 2461, Pyoverdin 2798, Pyoverdin 51W, Pyoverdin 9AW, Pyoverdin 90-51, Pyoverdin 95-275, Pyoverdin 96-312, Pyoverdin 96-318, Pyoverdin, Pyoverdin 6.1, Pyoverdin 6.2, Pyoverdin 6.3, Pyoverdin 6.4, Pyoverdin 6.5, Pyoverdin 6.6, Pyoverdin 6.8, Pyoverdin 7.1, Pyoverdin 7.2, Pyoverdin 7.3, Pyoverdin 7.4, Pyoverdin 7.5, Pyoverdin 7.6, Pyoverdin 7.7, Pyoverdin 7.8, Pyoverdin 7.9, Pyoverdin 7.10, Pyoverdin 7.11, Pyoverdin 7.12, Pyoverdin 7.14, Pyoverdin 7.15, Pyoverdin 7.16, Pyoverdin 7.17, Pyoverdin 7.18, Pyoverdin 7.19, Pyoverdin 8.1, Pyoverdin 8.2, Pyoverdin 8.3, Pyoverdin 8.4, Pyoverdin 8.5, Pyoverdin 8.6, Pyoverdin 8.7, Pyoverdin 8.8, Pyoverdin 8.9, Pyoverdin 9.1, Pyoverdin 9.2, Pyoverdin 9.3, Pyoverdin 9.4, Pyoverdin 9.5, Pyoverdin 9.6, Pyoverdin 9.7, Pyoverdin 9.8, Pyoverdin 9.9, Pyoverdin 9.10, Pyoverdin 9.11, Pyoverdin 9.12, Pyoverdin 10.1, Pyoverdin 10.2, Pyoverdin 10.3, Pyoverdin 10.4, Pyoverdin 10.5, Pyoverdin 10.6, Pyoverdin 10.8, Pyoverdin 10.9, Pyoverdin 10.10, Pyoverdin 11.1, Pyoverdin 11.2, Pyoverdin 12, Pyoverdin 12.1, Pyoverdin 12.2, Pyridoxatin, Quinolobactin, Rhizobactin, 10, Rhizobactin, Rhizoferrin, Rhizoferrin analogues 88A-88E, Rhodotrulic acid, Salmochelin S1, Salmochelin S2, Salmochelin S4, Salmochelin SX, Salmycin A, Schizokinen, Serratiochelin, Siderochelin A, Snychobactin A, Snychobactin B, Snychobactin C, Staphyloferrin A, Staphyloferrin B, Tetraglycine ferrichrome, Thiazostatin, Triacetylfusarinine, Triornicin, Vibriobactin, Vibrioferrin, Vicibactin, Vulnibactin, and Yersiniabactin.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of an injury, pathology, condition, or disease. For example, certain methods herein treat infectious diseases (e.g., malaria, bacterial diseases, viral diseases, parasitic diseases). For example certain methods herein treat infectious diseases (e.g., malaria, bacterial diseases, viral diseases, parasitic diseases) by decreasing a symptom of the infectious disease (e.g., malaria, bacterial diseases, viral diseases, parasitic diseases). For example certain methods herein treat infectious diseases (e.g., malaria, bacterial diseases, viral diseases, parasitic diseases) by decreasing the level or viability or amount of the infectious agent (e.g., bacterium, virus, parasite).

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease (e.g. cancer) is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with an infectious organism may be treated with an agent (e.g. compound as described herein) effective for decreasing the amount of the infectious organism.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is an anti-infective agent. In embodiments, a modulator is an anti-malarial agent.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. In embodiments, an anti-cancer agent is an agent with antineoplastic properties that has not (e.g., yet) been approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivaties, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

A "bioconjugate linker" is a covalent linker moiety that results from bioconjugate chemistry as generally known in the art. See for example, *Bioconjugate Techniques*, Second Edition, Greg T. Hermanson. Exemplary bioconjugate linkers can be found in Table 2 linking an adamantyl moiety (Ring A) to a variety of biomolecules, such as an antibody or peptide (e.g. modified peptide such as peptide including folate or a folate derivative).

In embodiments, a linker is formed by a conjugation or bioconjugation reaction combining a first reactant moiety covalently bonded to an agent (e.g., including $R^1$, a protein moiety, antibody moiety, siderophore moiety, detectable moiety, or drug moiety) and a second reactant moiety covalently bonded to a linker of a compound described herein (e.g., compound of formula I, Ia, Ib), for example a linker selected from $L^1$, $L^2$, $L^3$, $L^4$, $L^5$, $L^6$, $L^7$, $L^8$, $L^9$, $L^{11}$, $L^{12}$, $L^{13}$, and $L^{14}$. In such embodiments, the compound formed by such conjugation or bioconjugation reaction (including compounds as described herein) may be referred to as a conjugate.

Conjugates described herein may be synthesized using bioconjugate or conjugate chemistry. Conjugate chemistry includes coupling two molecules together to form an adduct. Conjugation may be a covalent modification. Currently favored classes of conjugate chemistry reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982, all of which are incorporated by reference in their entirety for all purposes. In embodiments, the bioconjugation reaction is a click chemistry reaction (Angewandte Chemie International Edition 40 (11): 2004-2021). In embodiments, the bioconjugation reaction is a Huisgen cyclization of azides. In embodiments, the bioconjugation reaction is a copper catalyzed Huisgen cyclization of azides. In embodiments, the bioconjugation reaction is a click chemistry reaction that does not require copper.

Useful reactive functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;
(f) sulfonyl halide groups for subsequent reaction with amines, for example, to form sulfonamides;
(g) thiol groups, which can be converted to disulfides, reacted with acyl halides, or bonded to metals such as gold;
(h) amine or sulfhydryl groups, which can be, for example, acylated, alkylated or oxidized;
(i) alkenes, which can undergo, for example, cycloadditions, acylation, Michael addition, etc;
(j) epoxides, which can react with, for example, amines and hydroxyl compounds;
(k) phosphoramidites and other standard functional groups useful in nucleic acid synthesis;
(l) metal silicon oxide bonding; and
(m) metal bonding to reactive phosphorus groups (e.g. phosphines) to form, for example, phosphate diester bonds.
(n) azides coupled to alkynes using copper catalyzed or non-copper catalyzed cycloaddition click chemistry.

The reactive functional groups can be chosen such that they do not participate in, or interfere with, the chemical stability of the conjugate described herein. Alternatively, a reactive functional group can be protected from participating in the crosslinking reaction by the presence of a protecting group.

"Chemotherapeutic" or "chemotherapeutic agent" is used in accordance with its plain ordinary meaning and refers to a chemical composition or compound having antineoplastic properties or the ability to inhibit the growth or proliferation of cells.

The terms "anti-infective agent" or "anti-infectious agent" or "anti-infective drug" or "anti-infective" are interchangeable and are used in accordance with their plain ordinary meaning and refer to a composition (e.g. compound, drug, antagonist, inhibitor, modulator) having anti-infectious agent properties or the ability to inhibit the growth or proliferation of an infectious agent (e.g. parasite (e.g. protozoa), bacterium, virus, fungus, or microorganism) or treat a symptom of a disease caused by an infectious agent. In some embodiments, an anti-infective agent is an agent approved by the FDA or similar regulatory agency of a country other than the USA, for treating infection by an infectious agent or a disease associated with an infectious agent. In embodiments, an anti-infective agent is an agent with anti-infectious agent properties that has not (e.g., yet) been approved by the FDA or similar regulatory agency of a country other than the USA, for treating infection by an infectious agent or a disease associated with an infectious agent. Examples of anti-infective agents include, but are not limited to, anti-viral agents, anti-bacterial agents, antibiotics, anti-parasitic (e.g. anti-protozoan) agents, anti-malarial agents, and anti-fungal agents.

The terms "anti-bacterial agent" or "anti-bacterial drug" or "anti-bacterial" or "antibiotic" are interchangeable and are used in accordance with their plain ordinary meaning and refer to a composition (e.g. compound, drug, antagonist, inhibitor, modulator) having anti-bacterial properties or the ability to inhibit the growth or proliferation of bacteria (e.g., bacteria that infect humans). In some embodiments, an anti-bacterial agent is an agent approved by the FDA or similar regulatory agency of a country other than the USA, for treating a bacterial infection. In embodiments, an anti-bacterial agent is an agent with the ability to inhibit the growth or proliferation of bacteria that has not (e.g., yet) been approved by the FDA or similar regulatory agency of a country other than the USA, for treating a bacterial infection. Examples of anti-bacterial agents include, but are not limited to, Penicillins (e.g., penicillins, antistaphylococcal penicillins, aminopenicillins, antipseudomonal penicillins), cephalosporins, polymyxins, rifamycins, lipiarmycins, quinolones, sulfonamides. macrolides, lincosamides, tetracyclines, aminoglycosides, cyclic lipopeptides (e.g., daptomycin, sufactin, echinocandins, caspofungin), glycylcyclines (e.g., tigecycline), oxazolidinones (e.g., linezolid, posizolid, tedizolid, radezolid, cycloserine), lipiarmycins (e.g., fidaxomicin), mecillinams, and carbapenems. An anti-bacterial moiety is a radical of an anti-bacterial. Non-limiting examples of an anti-bacterial agent include Amikacin, Gentamicin, Kanamycin, Neomycin, Netilmicin, Tobramycin, Paromomycin, Streptomycin, Spectinomycin, Geldanamycin, Herbimycin, Rifaximin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline fosamil, Ceftobiprole, Teicoplanin, Vancomycin, Telavancin, Dalbavancin, Oritavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, Amoxicillin/clavulanate, Ampicillin/sulbactam, Piperacillin/tazobactam, Ticarcillin/clavulanate, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole) (TMP-SMX), Sulfonamidochrysoidine, Demeclocycline, Doxycycline, Minocycline, Oxytetracycline, Tetracycline, Clofazimine, Dapsone, Capreomycin, Cycloserine, Ethambutol, Ethionamide, Isoniazid, Pyrazinamide, Rifampicin (Rifampin), Rifabutin, Rifapentine, Streptomycin, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, and Trimethoprim.

The terms "anti-malarial agent" or "anti-malarial drug" or "anti-malarial" are interchangeable and are used in accordance with their plain ordinary meaning and refer to a composition (e.g. compound, drug, antagonist, inhibitor, modulator) having anti-malarial properties or the ability to inhibit the growth or proliferation of *Plasmodium* that infect humans (e.g. *P. vivax, P. ovale, P. malariae P. falciparum, P. knowlesi, P. brasilianum, P. cynomolgi, P. cynomolgi bastianellii, P. inui, P. rhodiani, P. schweitzi, P. semiovale*, or *P. simium*). In embodiments, an anti-malarial agent treats infection with *P. vivax, P. ovale, P. malariae*, and/or *P. falciparum*. In embodiments, an anti-malarial agent treats infection with *P. vivax*. In embodiments, an anti-malarial agent treats infection with *P. ovale*. In embodiments, an anti-malarial agent treats infection with *P. malariae*. In embodiments, an anti-malarial agent treats infection with *P. falciparum*. In some embodiments, an anti-malarial agent is an agent approved by the FDA or similar regulatory agency of a country other than the USA, for treating malaria. In embodiments, an anti-malarial agent is an agent with the ability to inhibit the growth or proliferation of *Plasmodium* that infect humans that has not (e.g., yet) been approved by the FDA or similar regulatory agency of a country other than the USA, for treating malaria. Examples of anti-malarial agents include, but are not limited to, amodiaquine, atovaquone, chloroquine, clardribine, clindamycin, cytarabine, daunorubicin, docetaxel, doxorubicin, doxycycline, etoposide, fansidar, fludarabine, halofantrine, idarubicin, imiquimod, irinotecan, mefloquine, methotrexate, mitomycin, oxamniquine, paclitaxel, plicamycin, primaquine, proquanil, pyrimethamine, quinidine, quinine, topotecan, vinblastine, vincristine, KA609, KAF 156, tafenoquine, and pyronaridine. An anti-malarial moiety is a radical of an anti-malarial.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of an increased amount of $Fe^{II}$ relative to normal $Fe^{II}$ amounts in a subject (e.g. human). In some embodiments, the disease is a disease having the symptom of an increased amount of a reductant (e.g. biological reductant, $Fe^{II}$) relative to normal reductant (e.g. biological reductant, $Fe^{II}$) amounts in a subject (e.g. human). In embodiments, the disease is an infectious disease. In embodiments, the disease is a bacterial disease. In embodiments, the disease is a parasitic disease. In embodiments, the disease is a viral disease. In embodiments, the disease is malaria. In embodiments, the disease is drug-resistant malaria. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In some embodiments, the disease is a disease related to (e.g. caused by) an infectious agent (e.g. bacteria) Examples of diseases, disorders, or conditions include, but are not limited to, infectious diseases, bacterial infectious diseases, nosocomial infections, nosocomial bacterial infections, ventilator associated pneumonias, bacterial blood stream infections, Cutaneous anthrax, Pulmonary anthrax, Gastrointestinal anthrax, Whooping cough, bacterial pneumonia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), Tuberculosis, Mycoplasma pneumonia, Gonorrhea, Ophthalmia neonatorum, Septic arthritis, Meningococcal disease, Waterhouse-Friderichsen syndrome, Pseudomonas infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections: Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, sepsis, Iraq war infection caused by *Acinetobacter baumannii* (i.e. Iraq war-related *Acinetobacter baumannii* infection), skin diseases or conditions, acne, acne vulgaris, keratosis pilaris, acne rosacea, harlequin ichthyosis, xeroderma pigmentosum, keratoses, eczema, rosacea, necrotizing fasciitis, tuberculosis, hospital-acquired pneumonia, gastroenteritis, or bacteremia.

As used herein, the term "infectious disease" refers to a disease or condition related to the presence of an organism (the agent or infectious agent) within or contacting the subject or patient. Examples include a bacterium, fungus, virus, or other microorganism. A "bacterial infectious disease" or "bacterial disease" is an infectious disease wherein the organism is a bacterium. A "viral infectious disease" or "viral disease" is an infectious disease wherein the organism is a virus. An "antibiotic resistant bacterial infectious disease" or "antibiotic resistant bacterial disease" is an infectious disease wherein the organism is a bacterium resistant to one or more antibiotics effective in treating a disease caused by the non-antibiotic resistant strains of the bacterium. A "penicillin resistant bacterial infectious disease" or "penicillin resistant bacterial disease" is an antibiotic resistant bacterial infectious disease wherein the disease is not treated as effectively by a penicillin or penicillin-related compounds as a similar disease caused by a bacterial strain that is not penicillin resistant. A "cephalosporin resistant bacterial infectious disease" or "cephalosporin resistant bacterial disease" is an antibiotic resistant bacterial infectious disease wherein the disease is not treated as effectively by a cephalosporin or cephalosporin-related compounds as a similar disease caused by a bacterial strain that is not cephalosporin resistant. A "beta-lactam antibiotic resistant bacterial infectious disease" or "beta-lactam antibiotic resistant bacterial disease" is a an antibiotic resistant bacterial infectious disease wherein the disease is not treated as effectively by beta-lactam containing antibiotics as a similar disease caused by a bacterial strain that is not beta-lactam antibiotic resistant. Examples of infectious diseases that may be treated with a compound or method described herein include nosocomial infections, bacteremia, Cutaneous anthrax, Pulmonary anthrax, Gastrointestinal anthrax, Whooping cough, bacterial pneumonia, bacteremia, Lyme disease, Brucellosis, Acute enteritis, Community-acquired respiratory infection, Nongonococcal urethritis (NGU), Lymphogranuloma venereum (LGV), Trachoma, Inclusion conjunctivitis of the newborn (ICN), Psittacosis, Botulism, Pseudomembranous colitis, Gas gangrene, Acute food poisoning, Anaerobic cellulitis, Tetanus, Diphtheria, Nosocomial infections, Urinary tract infections (UTI), Diarrhea, Meningitis in infants, Traveller's diarrhea, Diarrhea in infants, Hemorrhagic colitis, Hemolytic-uremic syndrome, Tularemia, Bacterial meningitis, Upper respiratory tract infections, Pneumonia, bronchitis, Peptic ulcer, gastric carcinoma, gastric B-cell lymphoma, Legionnaire's Disease, Pontiac fever, Leptospirosis, Listeriosis, Leprosy (Hansen's disease), Tuberculosis, Mycoplasma pneumonia, Gonorrhea, Ophthalmia neonatorum, Septic arthritis, Meningococcal disease, Waterhouse-Friderichsen syndrome, Pseudomonas infection, Bacteremia, endocarditis, Rocky mountain spotted fever, Typhoid fever type salmonellosis (dysentery, colitis), Salmonellosis, gastroenteritis, enterocolitis, Bacillary dysentery/Shigellosis, Coagulase-positive staphylococcal infections: Impetigo, Acute infective endocarditis, Septicemia, Necrotizing pneumonia, Toxinoses, Toxic shock syndrome, Staphylococcal food poisoning, Cystitis, Meningitis, septicemia, Endometritis, Opportunistic infections, Acute bacterial pneumonia, Otitis media, sinusitis, Streptococcal pharyngitis, Scarlet fever, Rheumatic fever, erysipelas, Puerperal fever, Necrotizing fasciitis, Syphilis, Congenital syphilis, Cholera, Plague, Bubonic plague, Pneumonic plague, Iraq war infection caused by *Acinetobacter baumannii* (i.e. Iraq war-related *Acinetobacter baumannii* infection), necrotizing fasciitis, tuberculosis, hospital-acquired pneumonia, gastroenteritis, or sepsis.

"Infectious agent" refers to an organism that is associated with (in or contacting) patients with an infectious disease but not in patients without the infectious disease and wherein contacting a patient without the infectious disease with the organism results in the patient having the infectious disease. In some embodiments, the infectious agent associated with a disease that may be treated by the compounds and/or methods described herein is a bacterium. In some embodiments, the bacteria is of a genera selected from *Stenotrophomonas, Clostridium, Acinetobacter, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio, Klebsiella, Enterobacter, Citrobacter*, or *Yersinia*. In some embodiments, the bacteria is selected from *Stenotrophomonas maltophilia, Clostridium difficile, Bacillus anthracis, Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli,* Enterotoxigenic *Escherichia coli* (ETEC), Enteropathogenic *E. coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Klebsiella pneumoniae, Enterobacter cloacae, Citrobacter freundii, Acinetobacter baumannii,* or *Yersinia pestis*. In some embodiments, the bacteria is gram negative. In some embodiments, the bacteria is gram positive.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, anti-infective, anti-bacterial, anti-parasitic, anti-malarial). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent, protein). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer, an infectious disease, or malaria). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer, an infectious disease, or malaria), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

B. Compounds

In an aspect is provided a compound, or a pharmaceutically acceptable salt thereof, having the formula:

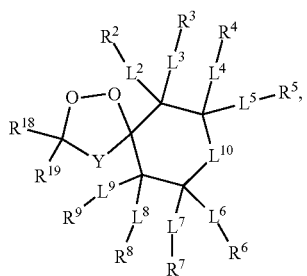

(I)

wherein $L^2$, $L^3$, $L^4$, $L^5$, $L^6$, $L^7$, $L^8$, $L^9$, $L^{11}$, and $L^{12}$ are independently a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, —N($R^{17}$)S(O)$_2$-$L^{13}$-$L^{14}$-, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, or a bioconjugate linker (e.g. where $R^2$, $R^3$, $R^4$, $R^5$, $R^6$, $R^7$, $R^8$, $R^9$, $R^{11}$, and $R^{12}$ is, for example a biomolecule such as a protein moiety (e.g antibody moiety, peptide moiety, modified peptide moiety such as peptide moiety including folate). $L^{10}$ is —N(-$L^{11}$-$R^{11}$)— or —C((-$L^{11}$-$R^{11}$)(-$L^{12}$-$R^{12}$))—. Each $L^{13}$ and $L^{14}$ are independently selected from a bond, —N($R^{17}$)—, —N($R^{17}$)C(O)O—, —O—, —S—, —OC(O)—, —OC(O)N($R^{17}$)—, —OC(O)O—, —OSO$_2$—, —C(O)N($R^{17}$)—, —N($R^{17}$)C(O)—, —S(O)$_2$N($R^{17}$)—, —N($R^{17}$)S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker (e.g. where $R^2$, $R^3$, $R^4$, $R^5$, $R^6$, $R^7$, $R^8$, $R^9$, $R^{11}$, and $R^{12}$ is, for example a biomolecule such as a protein moiety (e.g antibody, peptide, modified peptide such as peptide including folate). $R^2$, $R^3$, $R^4$, $R^5$, $R^6$, $R^7$, $R^8$, $R^9$, $R^{11}$, and $R^{12}$, are independently hydrogen, oxo, halogen, —CX$_3$, —CN, —SO$_2$Cl, —SO$_n$$R^{16}$, —SO$_v$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_m$, —NR$^{13}$R$^{14}$, —C(O)R$^{15}$, —C(O)—OR$^{15}$, —C(O)NR$^{13}$R$^{14}$, —OR$^{16}$, —NR$^{13}$SO$_2$R$^{16}$, —NR$^{13}$C=(O)R$^{15}$, —NR$^{13}$C(O)—OR$^{15}$, —NR$^{13}$OR$^{15}$, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, a detectable moiety, or a drug moiety; $R^5$ and $R^{11}$ substituents may be joined to form a substituted or unsubstituted cycloalkyl, substituted or unsubstituted heterocycloalkyl, substituted or unsubstituted aryl, or substituted or unsubstituted heteroaryl; $R^6$ and $R^{11}$ substituents may be joined to form a substituted or unsubstituted cycloalkyl, substituted or unsubstituted heterocycloalkyl, substituted or unsubstituted aryl, or substituted or unsubstituted heteroaryl; $R^2$ and $R^3$, $R^4$ and $R^5$, $R^6$ and $R^7$, $R^8$ and $R^9$, or $R^{11}$ and $R^{12}$ may be joined to form a substituted or unsubstituted cycloalkyl, substituted or unsubstituted heterocycloalkyl, substituted or unsubstituted aryl, or substituted or unsubstituted heteroaryl. Each $R^{13}$, $R^{14}$, $R^{15}$, $R^{16}$, and $R^{17}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$ and $R^{14}$ substituents bonded to the same atom may be joined to form a substituted or unsubstituted heterocycloalkyl or substituted or unsubstituted heteroaryl. $R^{18}$ and $R^{19}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, detectable moiety, siderophore moiety, or a drug moiety; $R^{18}$ and $R^{19}$ may be joined to form a substituted or unsubstituted cycloalkyl, substituted or unsubstituted heterocycloalkyl, protein moiety, detectable moiety, or drug moiety. The symbols m and v are independently 1 or 2. The symbol n is independently an integer from 0 to 2. Y is —O—, —S—, —OO—, —CH$_2$O—, or —OCH$_2$—. X is independently —Cl, —Br, —I, or —F.

The compounds described herein (e.g. formulae I, Ia, Ib, and embodiments thereof) are prodrugs. The term "compound" when referring to a compound of the invention and the term "prodrug" when referring to a prodrug of the invention (e.g. compound including a drug moiety or those compounds including a detectable moiety, protein moiety, or other moiety in place of a drug moiety or in addition to a drug moiety) are interchangeable. In embodiments, the compounds described herein (e.g. formula I and/or embodiments thereof) are prodrugs, wherein the prodrug moiety is the component of the compound that is not a drug moiety/detectable moiety/protein moiety and is released from the drug moiety/detectable moiety/protein moiety upon degradation of the prodrug in the presence of a high level of reductant (e.g. biological reductant, Fe$^{II}$). In embodiments, degradation of the prodrug in the presence of a high level of reductant (e.g. biological reductant, Fe$^{II}$) includes opening of the peroxide containing ring (e.g. trioxolane) in the prodrug moiety and release of an active drug/detectable agent/protein (e.g. where the monovalent moiety is cleaved to form a compound with full valency). A person having ordinary skill in the art would understand that the drug/detectable agent/protein and drug moiety/detectable moiety/protein moiety include only those compounds compatible with the chemistry provided herein for connecting the drug moiety/detectable moiety/protein moiety to the prodrug moiety and for release of the drug/detectable agent/protein from the compound (prodrug) by the presence of a high level of reductant (e.g. biological reductant, $Fe^{II}$). In embodiments, degradation of the prodrug to release an active agent (e.g., drug, protein, detectable agent, active compound) may result in an active agent including a linker or portion of the peroxide containing ring in the active agent. In such compounds, the resulting active agent includes a higher level of activity compared to the level of activity of the intact prodrug.

In embodiments, a drug moiety is i) a radical composition that upon release (cleavage of the bond connecting the drug moiety to the prodrug moiety) from a compound (i.e. prodrugs) described herein, forms a drug (e.g. therapeutic agent); and ii) is connected to the prodrug moiety by a bond to an N atom of the drug moiety. In embodiments, a drug moiety is i) a radical composition that upon release (cleavage of the bond connecting the drug moiety to the prodrug moiety) from a compound (i.e. prodrugs) described herein, forms a drug (e.g. therapeutic agent); and ii) is connected to the prodrug moiety by a bond to an O atom of the drug moiety. In embodiments, a drug moiety is i) a radical composition that upon release (cleavage of the bond connecting the drug moiety to the prodrug moiety) from a compound (i.e. prodrugs) described herein, forms a drug (e.g. therapeutic agent); and ii) is connected to the prodrug moiety by a bond to an S atom of the drug moiety. In embodiments, a drug moiety is i) a radical composition that upon release (cleavage of the bond connecting the drug moiety to the prodrug moiety) from a compound (i.e. prodrugs) described herein, forms a drug (e.g. therapeutic agent); and ii) is connected to the prodrug moiety by a bond to a —OC(O)-(remainder of drug moiety) of the drug moiety. In embodiments, the drug moiety is an anti-cancer agent moiety (e.g., described herein). In embodiments, the drug moiety is an anti-infective agent moiety (e.g., described herein). In embodiments, the drug moiety is an anti-malaria agent moiety (e.g., described herein). In embodiments, the drug moiety is an anti-bacterial agent moiety (e.g., described herein). In embodiments, the drug moiety is an antibiotic moiety (e.g., described herein). In embodiments, the drug moiety is an anti-parasitic agent moiety (e.g., described herein).

In embodiments, a detectable moiety is i) a radical composition that upon release (cleavage of the bond connecting the detectable moiety to the prodrug moiety) from a compound (i.e. prodrugs) described herein, forms a detectable agent (e.g. fluorescent agent); and ii) is connected to the prodrug moiety by a bond to an N atom of the detectable moiety. In embodiments, a detectable moiety is i) a radical composition that upon release (cleavage of the bond connecting the detectable moiety to the prodrug moiety) from a compound (i.e. prodrugs) described herein, forms a detectable agent (e.g. fluorescent agent); and ii) is connected to the prodrug moiety by a bond to an O atom of the detectable moiety. In embodiments, a detectable moiety is i) a radical composition that upon release (cleavage of the bond connecting the detectable moiety to the prodrug moiety) from a compound (i.e. prodrugs) described herein, forms a detectable agent (e.g. fluorescent agent); and ii) is connected to the prodrug moiety by a bond to an S atom of the detectable moiety. In embodiments, a drug moiety is i) a radical composition that upon release (cleavage of the bond connecting the drug moiety to the prodrug moiety) from a compound (i.e. prodrugs) described herein, forms a drug (e.g. therapeutic agent); and ii) is connected to the prodrug moiety by a bond to a —OC(O)-(remainder of detectable moiety) of the detectable moiety.

In embodiments, a protein moiety is i) a radical composition that upon release (cleavage of the bond connecting the protein moiety to the prodrug moiety) from a compound (i.e. prodrugs) described herein, forms a protein (e.g antibody); and ii) is connected to the prodrug moiety by a bond to an N atom of the protein moiety. In embodiments, a protein moiety is i) a radical composition that upon release (cleavage of the bond connecting the protein moiety to the prodrug moiety) from a compound (i.e. prodrugs) described herein, forms a protein (e.g antibody); and ii) is connected to the prodrug moiety by a bond to an O atom of the protein moiety. In embodiments, a protein moiety is i) a radical composition that upon release (cleavage of the bond connecting the protein moiety to the prodrug moiety) from a compound (i.e. prodrugs) described herein, forms a protein (e.g antibody); and ii) is connected to the prodrug moiety by a bond to an S atom of the protein moiety. In embodiments, a drug moiety is i) a radical composition that upon release (cleavage of the bond connecting the drug moiety to the prodrug moiety) from a compound (i.e. prodrugs) described herein, forms a drug (e.g. therapeutic agent); and ii) is connected to the prodrug moiety by a bond to a —OC(O)-(remainder of protein moiety) of the protein moiety.

In embodiments, Y is —O—. In embodiments, Y is —S—. In embodiments, Y is —OO—. In embodiments, Y is —$CH_2O$—. In embodiments, Y is —$OCH_2$—. In embodiments, $R^{17}$ is independently hydrogen. In embodiments, $L^{10}$ is —N(-$L^{11}$-$R^{11}$)—. In embodiments, $L^{10}$ is —C((-$L^{11}$-$R^{11}$)(-$L^{12}$-$R^{12}$))—. In embodiments, m is independently 1. In embodiments, m is independently 2. In embodiments, v is independently 1. In embodiments, v is independently 2. In embodiments, n is independently 0. In embodiments, n is independently 1. In embodiments, n is independently 2. In embodiments, X is independently —Cl. In embodiments, X is independently —Br. In embodiments, X is independently —I. In embodiments, X is independently —F. In embodiments, $R^2$ and $R^3$, $R^4$ and $R^5$, $R^6$ and $R^7$, $R^8$ and $R^9$, or $R^{11}$ and $R^{12}$ may be joined to form a substituted or unsubstituted cycloalkyl or substituted or unsubstituted heterocycloalkyl.

In embodiments, $R^4$ is a protein moiety. In embodiments, $R^4$ is a drug moiety. In embodiments, $R^4$ is a detectable moiety. In embodiments, $R^5$ is a protein moiety. In embodiments, $R^5$ is a drug moiety. In embodiments, $R^5$ is a detectable moiety. In embodiments, $R^6$ is a protein moiety. In embodiments, $R^6$ is a drug moiety. In embodiments, $R^6$ is a detectable moiety. In embodiments, $R^7$ is a protein moiety. In embodiments, $R^7$ is a drug moiety. In embodiments, $R^7$ is a detectable moiety. In embodiments, $R^{11}$ is a protein moiety. In embodiments, $R^{11}$ is a drug moiety. In embodiments, $R^{11}$ is a detectable moiety. In embodiments, $R^{12}$ is a protein moiety. In embodiments, $R^{12}$ is a drug moiety. In embodiments, $R^{12}$ is a detectable moiety. In embodiments, $R^2$ is a protein moiety. In embodiments, $R^2$ is a drug moiety. In embodiments, $R^2$ is a detectable moiety. In embodiments, $R^3$ is a protein moiety. In embodiments, $R^3$ is a drug moiety. In embodiments, $R^3$ is a detectable moiety. In embodiments, $R^8$ is a protein moiety. In embodiments, $R^8$ is a drug moiety. In embodiments, $R^8$ is a detectable moiety. In embodiments, $R^9$ is a protein moiety. In embodiments, $R^9$ is a drug moiety. In embodiments, $R^9$ is a detectable moiety. In embodiments, $R^2$ is an antibody moiety. In embodiments, $R^3$ is an antibody moiety. In embodiments, $R^4$ is an antibody moiety. In embodiments, $R^5$ is an antibody moiety. In embodiments, $R^6$ is an antibody moiety. In embodiments, $R^7$ is an antibody moiety. In embodiments, $R^8$ is an antibody moiety. In embodiments, $R^9$ is an antibody moiety. In embodiments, $R^{11}$ is an antibody moiety. In embodiments, $R^{12}$ is an antibody moiety. In embodiments, $R^2$ is a siderophore moiety. In embodiments, $R^3$ is a siderophore moiety. In embodiments, $R^4$ is a siderophore moiety. In embodiments, $R^5$ is a siderophore moiety. In embodiments, $R^6$ is a siderophore moiety. In embodiments, $R^7$ is a siderophore moiety. In embodiments, $R^8$ is a siderophore moiety. In embodiments, $R^9$ is a siderophore moiety. In embodiments, $R^{11}$ is a siderophore moiety. In embodiments, $R^{12}$ is a siderophore moiety.

In embodiments, a compound described herein (prodrug described herein) including a drug moiety is less active than the corresponding free drug. In embodiments, a compound described herein does not have the activity of the free drug. In embodiments, a compound described herein has less than 0.9 times the activity of the free drug (e.g. less than 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001 times the activity of the free drug). Drug moieties that form part of the prodrugs described herein may obtain functionality due to chemical changes in the prodrugs that occur under physiological conditions.

In embodiments, a compound described herein (prodrug described herein) including a detectable moiety is less detectable than the corresponding free detectable agent. In embodiments, a prodrug compound including a detectable moiety described herein cannot be detected using an identical method capable of detecting the free detectable agent. In embodiments, a prodrug compound including a detectable moiety described herein is less than 0.9 times as detectable as the free detectable moiety (e.g. less than 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001 times as detectable as the free detectable moiety using the same method (e.g. assay)). In embodiments, a prodrug compound including a detectable moiety described herein is at least 0.9 times as detectable as the free detectable moiety (e.g. at least 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001 times as detectable as the free detectable moiety using the same method (e.g. assay)). In embodiments, a compound described herein can be detected with the same sensitivity as the free detectable agent using an identical method of detection.

In embodiments, a compound described herein includes one drug moiety. In embodiments, a compound described herein includes a plurality of optionally different drug moieties. In embodiments, a compound described herein includes one detectable moiety. In embodiments, a compound described herein includes a plurality of optionally different detectable moieties. In embodiments, a compound described herein includes one protein moiety. In embodiments, a compound described herein includes a plurality of optionally different protein moieties. In embodiments, a compound described herein includes at least one drug moiety and at least one detectable moiety. In embodiments, a compound described herein includes at least one drug moiety and at least one protein moiety. In embodiments, a compound described herein includes at least one protein moiety and at least one detectable moiety. In embodiments, a compound described herein includes at least one protein moiety, at least one drug moiety, and at least one detectable moiety. In embodiments, a compound described herein includes one antibody moiety. In embodiments, a compound described herein includes a plurality of optionally different antibody moieties. In embodiments, a compound described herein includes one siderophore moiety. In embodiments, a compound described herein includes a plurality of optionally different siderophore moieties.

In embodiments $L^2$ is a bond. In embodiments $L^2$ is —OC(O)—. In embodiments $L^2$ is —OC(O)NH-Ph-CH$_2$—. In embodiments $L^2$ is —OC(O)NH-Ph-CH$_2$—OC(O)—. In embodiments $L^2$ is —NH-Ph-CH$_2$—. In embodiments $L^2$ is —NH-Ph-CH$_2$—OC(O)—. In embodiments $L^2$ is —O-Ph-CH$_2$—. In embodiments $L^2$ is —O-Ph-CH$_2$—OC(O)—. In embodiment, $R^2$ is a protein moiety. In embodiment, $R^2$ is a protein moiety bonded to $L^2$ through an N of the protein moiety. In embodiment, $R^2$ is a protein moiety bonded to $L^2$ through an O of the protein moiety. In embodiment, $R^2$ is a protein moiety bonded to $L^2$ through an S of the protein moiety. In embodiment, $R^2$ is a protein moiety bonded to $L^2$ through an O of a —OC(O)— of the protein moiety. In embodiment, $R^2$ is a detectable moiety. In embodiment, $R^2$ is a detectable moiety bonded to $L^2$ through an N of the detectable moiety. In embodiment, $R^2$ is a detectable moiety bonded to $L^2$ through an O of the detectable moiety. In embodiment, $R^2$ is a detectable moiety bonded to $L^2$ through an S of the detectable moiety. In embodiment, $R^2$ is a detectable moiety bonded to $L^2$ through an O of a —OC(O)— of the detectable moiety. In embodiment, $R^2$ is a drug moiety. In embodiment, $R^2$ is a drug moiety bonded to $L^2$ through an N of the drug moiety. In embodiment, $R^2$ is a drug moiety bonded to $L^2$ through an O of the drug moiety. In embodiment, $R^2$ is a drug moiety bonded to $L^2$ through an S of the drug moiety. In embodiment, $R^2$ is a drug moiety bonded to $L^2$ through an O of a —OC(O)— of the drug moiety.

In embodiments $L^3$ is a bond. In embodiments $L^3$ is —OC(O)—. In embodiments $L^3$ is —OC(O)NH-Ph-CH$_2$—. In embodiments $L^3$ is —OC(O)NH-Ph-CH$_2$—OC(O)—. In embodiments $L^3$ is —NH-Ph-CH$_2$—. In embodiments $L^3$ is —NH-Ph-CH$_2$—OC(O)—. In embodiments $L^3$ is —O-Ph-CH$_2$-. In embodiments $L^3$ is —O-Ph-CH$_2$—OC(O)—. In embodiment, $R^3$ is a protein moiety. In embodiment, $R^3$ is a protein moiety bonded to $L^3$ through an N of the protein moiety. In embodiment, $R^3$ is a protein moiety bonded to $L^3$ through an O of the protein moiety. In embodiment, $R^3$ is a protein moiety bonded to $L^3$ through an S of the protein moiety. In embodiment, $R^3$ is a protein moiety bonded to $L^3$ through an O of a —OC(O)— of the protein moiety. In embodiment, $R^3$ is a detectable moiety. In embodiment, $R^3$ is a detectable moiety bonded to $L^3$ through an N of the detectable moiety. In embodiment, $R^3$ is a detectable moiety bonded to $L^3$ through an O of the detectable moiety. In embodiment, $R^3$ is a detectable moiety bonded to $L^3$ through an S of the detectable moiety. In embodiment, $R^3$ is a detectable moiety bonded to $L^3$ through an O of a —OC(O)— of the detectable moiety. In embodiment, $R^3$ is a drug moiety. In embodiment, $R^3$ is a drug moiety bonded to $L^3$ through an N of the drug moiety. In embodiment, $R^3$ is a drug moiety bonded to $L^3$ through an O of the drug moiety. In embodiment, $R^3$ is a drug moiety bonded to $L^3$ through an S of the drug moiety. In embodiment, $R^3$ is a drug moiety bonded to $L^3$ through an O of a —OC(O)— of the drug moiety. In embodiments, $L^3$ is a substituted or unsubstituted $C_1$-$C_{20}$ alkylene. In embodiments, $L^3$ is a substituted or unsubstituted 2 to 20 membered heteroalkylene. In embodiments, $L^3$ is a substituted or unsubstituted $C_3$-$C_{20}$ cycloalkylene. In embodiments, $L^3$ is a substituted or unsubstituted 3 to 20 membered heterocycloalkylene. In embodiments, $L^3$ is a substituted or unsubstituted $C_6$-$C_{20}$ arylene. In embodiments, $L^3$ is a substituted or unsubstituted 5 to 20 membered heteroarylene. In embodiments, $L^3$ is a substituted $C_1$-$C_{20}$ alkylene. In embodiments, $L^3$ is a substituted 2 to 20 membered heteroalkylene. In embodiments, $L^3$ is a substituted $C_3$-$C_{20}$ cycloalkylene. In embodiments, $L^3$ is a substituted 3 to 20 membered heterocycloalkylene. In embodiments, $L^3$ is a substituted $C_6$-$C_{20}$ arylene. In embodiments, $L^3$ is a substituted 5 to 20 membered heteroarylene. In embodiments, $L^3$ is an unsubstituted $C_1$-$C_{20}$ alkylene. In embodiments, $L^3$ is an unsubstituted 2 to 20 membered heteroalkylene. In embodiments, $L^3$ is an unsubstituted $C_3$-$C_{20}$ cycloalkylene. In embodiments, $L^3$ is an unsubstituted 3 to 20 membered heterocycloalkylene. In embodiments, $L^3$ is an unsubstituted $C_6$-$C_{20}$ arylene. In embodiments, $L^3$ is an unsubstituted 5 to 20 membered heteroarylene. In embodiments, $L^3$ is a substituted or unsubstituted $C_1$-$C_{14}$ alkylene. In embodiments, $L^3$ is a substituted or unsubstituted 2 to 14 membered heteroalkylene. In embodiments, $L^3$ is a substituted or unsubstituted $C_3$-$C_{14}$ cycloalkylene. In embodiments, $L^3$ is a substituted or unsubstituted 3 to 14 membered heterocycloalkylene. In embodiments, $L^3$ is a substituted or unsubstituted $C_6$-$C_{14}$ arylene. In embodiments, $L^3$ is a substituted or unsubstituted 5 to 14 membered heteroarylene. In embodiments, $L^3$ is a substituted $C_1$-$C_{14}$ alkylene. In embodiments, $L^3$ is a substituted 2 to 14 membered heteroalkylene. In embodiments, $L^3$ is a substituted $C_3$-$C_{14}$ cycloalkylene. In embodiments, $L^3$ is a substituted 3 to 14 membered heterocycloalkylene. In embodiments, $L^3$ is a substituted $C_6$-$C_{14}$ arylene. In embodiments, $L^3$ is a substituted 5 to 14 membered heteroarylene. In embodiments, $L^3$ is an unsubstituted $C_1$-$C_{14}$ alkylene. In embodiments, $L^3$ is an unsubstituted 2 to 14 membered heteroalkylene. In embodiments, $L^3$ is an unsubstituted $C_3$-$C_{14}$ cycloalkylene. In embodiments, $L^3$ is an unsubstituted 3 to 14 membered heterocycloalkylene. In embodiments, $L^3$ is an unsubstituted $C_6$-$C_{14}$ arylene. In embodiments, $L^3$ is an unsubstituted 5 to 14 membered heteroarylene. In embodiments, $L^3$ is a substituted or unsubstituted $C_1$-$C_8$ alkylene. In embodiments, $L^3$ is a substituted or unsubstituted 2 to 8 membered heteroalkylene. In embodiments, $L^3$ is a substituted or unsubstituted $C_3$-$C_8$ cycloalkylene. In embodiments, $L^3$ is a substituted or unsubstituted 3 to 8 membered heterocycloalkylene. In embodiments, $L^3$ is a substituted or unsubstituted $C_6$-$C_{10}$ arylene. In embodiments, $L^3$ is a substituted or unsubstituted 5 to 10 membered heteroarylene. In embodiments, $L^3$ is a substituted $C_1$-$C_8$ alkylene. In embodiments, $L^3$ is a substituted 2 to 8 membered heteroalkylene. In embodiments, $L^3$ is a substituted $C_3$-$C_8$ cycloalkylene. In embodiments, $L^3$ is a substituted 3 to 8 membered heterocycloalkylene. In embodiments, $L^3$ is a substituted $C_6$-$C_{10}$ arylene. In embodiments, $L^3$ is a substituted 5 to 10 membered heteroarylene. In embodiments, $L^3$ is an unsubstituted $C_1$-$C_8$ alkylene. In embodiments, $L^3$ is an unsubstituted 2 to 8 membered heteroalkylene. In embodiments, $L^3$ is an unsubstituted $C_3$-$C_8$ cycloalkylene. In embodiments, $L^3$ is an unsubstituted 3 to 8 membered heterocycloalkylene. In embodiments, $L^3$ is an unsubstituted $C_6$-$C_{10}$ arylene. In embodiments, $L^3$ is an unsubstituted 5 to 10 membered heteroarylene.

In embodiments $L^4$ is a bond. In embodiments $L^4$ is —OC(O)—. In embodiments $L^4$ is —OC(O)NH-Ph-$CH_2$—. In embodiments $L^4$ is —OC(O)NH-Ph-$CH_2$—OC(O)—. In embodiments $L^4$ is —NH-Ph-$CH_2$—. In embodiments $L^4$ is —NH-Ph-$CH_2$—OC(O)—. In embodiments $L^4$ is —O-Ph-$CH_2$—. In embodiments $L^4$ is —O-Ph-$CH_2$—OC(O)—. In embodiment, $R^4$ is a protein moiety. In embodiment, $R^4$ is a protein moiety bonded to $L^4$ through an N of the protein moiety. In embodiment, $R^4$ is a protein moiety bonded to $L^4$ through an O of the protein moiety. In embodiment, $R^4$ is a protein moiety bonded to $L^4$ through an S of the protein moiety. In embodiment, $R^4$ is a protein moiety bonded to $L^4$ through an O of a —OC(O)— of the protein moiety. In embodiment, $R^4$ is a detectable moiety. In embodiment, $R^4$ is a detectable moiety bonded to $L^4$ through an N of the detectable moiety. In embodiment, $R^4$ is a detectable moiety bonded to $L^4$ through an O of the detectable moiety. In embodiment, $R^4$ is a detectable moiety bonded to $L^4$ through an S of the detectable moiety. In embodiment, $R^4$ is a detectable moiety bonded to $L^4$ through an O of a —OC(O)— of the detectable moiety. In embodiment, $R^4$ is a drug moiety. In embodiment, $R^4$ is a drug moiety bonded to $L^4$ through an N of the drug moiety. In embodiment, $R^4$ is a drug moiety bonded to $L^4$ through an O of the drug moiety. In embodiment, $R^4$ is a drug moiety bonded to $L^4$ through an S of the drug moiety. In embodiment, $R^4$ is a drug moiety bonded to $L^4$ through an O of a —OC(O)— of the drug moiety.

In embodiments $L^5$ is a bond. In embodiments $L^5$ is —OC(O)—. In embodiments $L^5$ is —OC(O)NH-Ph-$CH_2$—. In embodiments $L^5$ is —OC(O)NH-Ph-$CH_2$—OC(O)—. In embodiments $L^5$ is —NH-Ph-$CH_2$—. In embodiments $L^5$ is —NH-Ph-$CH_2$—OC(O)—. In embodiments $L^5$ is —O-Ph-$CH_2$—. In embodiments $L^5$ is —O-Ph-$CH_2$—OC(O)—. In embodiment, $R^5$ is a protein moiety. In embodiment, $R^5$ is a protein moiety bonded to $L^5$ through an N of the protein moiety. In embodiment, $R^5$ is a protein moiety bonded to $L^5$ through an O of the protein moiety. In embodiment, $R^5$ is a protein moiety bonded to $L^5$ through an S of the protein moiety. In embodiment, $R^5$ is a protein moiety bonded to $L^5$ through an O of a —OC(O)— of the protein moiety. In embodiment, $R^5$ is a detectable moiety. In embodiment, $R^5$ is a detectable moiety bonded to $L^5$ through an N of the detectable moiety. In embodiment, $R^5$ is a detectable moiety bonded to $L^5$ through an O of the detectable moiety. In embodiment, $R^5$ is a detectable moiety bonded to $L^5$ through an S of the detectable moiety. In embodiment, $R^5$ is a detectable moiety bonded to $L^5$ through an O of a —OC(O)— of the detectable moiety. In embodiment, $R^5$ is a drug moiety. In embodiment, $R^5$ is a drug moiety bonded to $L^5$ through an N of the drug moiety. In embodiment, $R^5$ is a drug moiety bonded to $L^5$ through an O of the drug moiety. In embodiment, $R^5$ is a drug moiety bonded to $L^5$ through an S of the drug moiety. In embodiment, $R^5$ is a drug moiety bonded to $L^5$ through an O of a —OC(O)— of the drug moiety. In embodiments, $R^5$ is

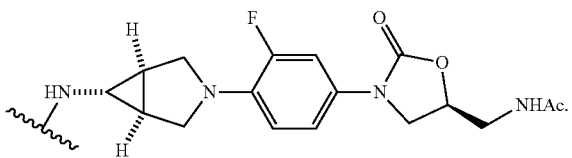 [SMILES: *N[C@H]1[C@@H]2CN(c3ccc(N4C[C@H](CNC(C)=O)OC4=O)cc3F)C[C@@H]21]

In embodiments, $R^5$ is

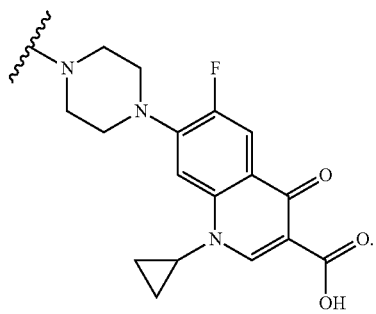 [SMILES: *N1CCN(c2cc3c(cc2F)c(=O)c(C(=O)O)cn3C2CC2)CC1]

In embodiments, $R^5$ is

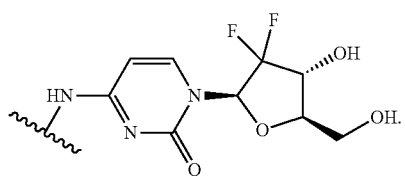 [SMILES: *Nc1ccn([C@@H]2O[C@H](CO)[C@@H](O)C2(F)F)c(=O)n1]

In embodiments, $R^5$ is

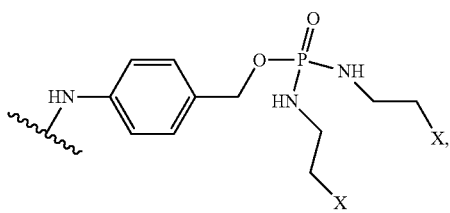

X is halide (e.g., Cl or Br). In embodiments, $R^5$ is

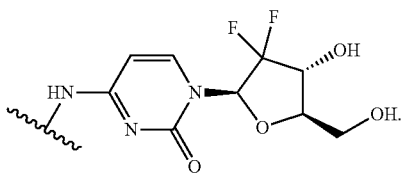 [SMILES: *Nc1ccn([C@@H]2O[C@H](CO)[C@@H](O)C2(F)F)c(=O)n1]

In embodiments, $L^5$ is a substituted or unsubstituted $C_1$-$C_{20}$ alkylene. In embodiments, $L^5$ is a substituted or unsubstituted 2 to 20 membered heteroalkylene. In embodiments, $L^5$ is a substituted or unsubstituted $C_3$-$C_{20}$ cycloalkylene. In embodiments, $L^5$ is a substituted or unsubstituted 3 to 20 membered heterocycloalkylene. In embodiments, $L^5$ is a substituted or unsubstituted $C_6$-$C_{20}$ arylene. In embodiments, $L^5$ is a substituted or unsubstituted 5 to 20 membered heteroarylene. In embodiments, $L^5$ is a substituted $C_1$-$C_{20}$ alkylene. In embodiments, $L^5$ is a substituted 2 to 20 membered heteroalkylene. In embodiments, $L^5$ is a substituted $C_3$-$C_{20}$ cycloalkylene. In embodiments, $L^5$ is a substituted 3 to 20 membered heterocycloalkylene. In embodiments, $L^5$ is a substituted $C_6$-$C_{20}$ arylene. In embodiments, $L^5$ is a substituted 5 to 20 membered heteroarylene. In embodiments, $L^5$ is an unsubstituted $C_1$-$C_{20}$ alkylene. In embodiments, $L^5$ is an unsubstituted 2 to 20 membered heteroalkylene. In embodiments, $L^5$ is an unsubstituted $C_3$-$C_{20}$ cycloalkylene. In embodiments, $L^5$ is an unsubstituted 3 to 20 membered heterocycloalkylene. In embodiments, $L^5$ is an unsubstituted $C_6$-$C_{20}$ arylene. In embodiments, $L^5$ is an unsubstituted 5 to 20 membered heteroarylene. In embodiments, $L^5$ is a substituted or unsubstituted $C_1$-$C_{14}$ alkylene. In embodiments, $L^5$ is a substituted or unsubstituted 2 to 14 membered heteroalkylene. In embodiments, $L^5$ is a substituted or unsubstituted $C_3$-$C_{14}$ cycloalkylene. In embodiments, $L^5$ is a substituted or unsubstituted 3 to 14 membered heterocycloalkylene. In embodiments, $L^5$ is a substituted or unsubstituted $C_6$-$C_{14}$ arylene. In embodiments, $L^5$ is a substituted or unsubstituted 5 to 14 membered heteroarylene. In embodiments, $L^5$ is a substituted $C_1$-$C_{14}$ alkylene. In embodiments, $L^5$ is a substituted 2 to 14 membered heteroalkylene. In embodiments, $L^5$ is a substituted $C_3$-$C_{14}$ cycloalkylene. In embodiments, $L^5$ is a substituted 3 to 14 membered heterocycloalkylene. In embodiments, $L^5$ is a substituted $C_6$-$C_{14}$ arylene. In embodiments, $L^5$ is a substituted 5 to 14 membered heteroarylene. In embodiments, $L^5$ is an unsubstituted $C_1$-$C_{14}$ alkylene. In embodiments, $L^5$ is an unsubstituted 2 to 14 membered heteroalkylene. In embodiments, $L^5$ is an unsubstituted $C_3$-$C_{14}$ cycloalkylene. In embodiments, $L^5$ is an unsubstituted 3 to 14 membered heterocycloalkylene. In embodiments, $L^5$ is an unsubstituted $C_6$-$C_{14}$ arylene. In embodiments, $L^5$ is an unsubstituted 5 to 14 membered heteroarylene. In embodiments, $L^5$ is a substituted or unsubstituted $C_1$-$C_8$ alkylene. In embodiments, $L^5$ is a substituted or unsubstituted 2 to 8 membered heteroalkylene. In embodiments, $L^5$ is a substituted or unsubstituted $C_3$-$C_8$ cycloalkylene. In embodiments, $L^5$ is a substituted or unsubstituted 3 to 8 membered heterocycloalkylene. In embodiments, $L^5$ is a substituted or unsubstituted $C_6$-$C_{10}$ arylene. In embodiments, $L^5$ is a substituted or unsubstituted 5 to 10 membered heteroarylene. In embodiments, $L^5$ is a substituted $C_1$-$C_8$ alkylene. In embodiments, $L^5$ is a substituted 2 to 8 membered heteroalkylene. In embodiments, $L^5$ is a substituted $C_3$-$C_8$ cycloalkylene. In embodiments, $L^5$ is a substituted 3 to 8 membered heterocycloalkylene. In embodiments, $L^5$ is a substituted $C_6$-$C_{10}$ arylene. In embodiments, $L^5$ is a substituted 5 to 10 membered heteroarylene. In embodiments, $L^5$ is an unsubstituted $C_1$-$C_8$ alkylene. In embodiments, $L^5$ is an unsubstituted 2 to 8 membered heteroalkylene. In embodiments, $L^5$ is an unsubstituted $C_3$-$C_8$ cycloalkylene. In embodiments, $L^5$ is an unsubstituted 3 to 8 membered heterocycloalkylene. In embodiments, $L^5$ is an unsubstituted $C_6$-$C_{10}$ arylene. In embodiments, $L^5$ is an unsubstituted 5 to 10 membered heteroarylene.

In embodiments $L^6$ is a bond. In embodiments $L^6$ is —OC(O)—. In embodiments $L^6$ is —OC(O)NH-Ph-CH$_2$—. In embodiments $L^6$ is —OC(O)NH-Ph-CH$_2$—OC(O)—. In embodiments $L^6$ is —NH-Ph-CH$_2$—. In embodiments $L^6$ is —NH-Ph-CH$_2$—OC(O)—. In embodiments $L^6$ is —O-Ph-CH$_2$—. In embodiments $L^6$ is —O-Ph-CH$_2$—OC(O)—. In embodiment, $R^6$ is a protein moiety. In embodiment, $R^6$ is a protein moiety bonded to $L^6$ through an N of the protein moiety. In embodiment, $R^6$ is a protein moiety bonded to $L^6$ through an O of the protein moiety. In embodiment, $R^6$ is a protein moiety bonded to $L^6$ through an S of the protein moiety. In embodiment, $R^6$ is a protein moiety bonded to $L^6$ through an O of a —OC(O)— of the protein moiety. In embodiment, $R^6$ is a detectable moiety. In embodiment, $R^6$ is a detectable moiety bonded to $L^6$ through an N of the detectable moiety. In embodiment, $R^6$ is a detectable moiety bonded to $L^6$ through an O of the detectable moiety. In embodiment, $R^6$ is a detectable moiety bonded to $L^6$ through an S of the detectable moiety. In embodiment, $R^6$ is a detectable moiety bonded to $L^6$ through an O of a —OC(O)— of the detectable moiety. In embodiment, $R^6$ is a drug moiety. In embodiment, $R^6$ is a drug moiety bonded to $L^6$ through an N of the drug moiety. In embodiment, $R^6$ is a drug moiety bonded to $L^6$ through an O of the drug moiety. In embodiment, $R^6$ is a drug moiety bonded to $L^6$ through an S of the drug moiety. In embodiment, $R^6$ is a drug moiety bonded to $L^6$ through an O of a —OC(O)— of the drug moiety.

In embodiments $L^7$ is a bond. In embodiments $L^7$ is —OC(O)—. In embodiments $L^7$ is —OC(O)NH-Ph-CH$_2$—. In embodiments $L^7$ is —OC(O)NH-Ph-CH$_2$—OC(O)—. In embodiments $L^7$ is —NH-Ph-CH$_2$—. In embodiments $L^7$ is —NH-Ph-CH$_2$—OC(O)—. In embodiments $L^7$ is —O-Ph-CH$_2$—. In embodiments $L^7$ is —O-Ph-CH$_2$—OC(O)—. In embodiment, $R^7$ is a protein moiety. In embodiment, $R^7$ is a protein moiety bonded to $L^7$ through an N of the protein moiety. In embodiment, $R^7$ is a protein moiety bonded to $L^7$ through an O of the protein moiety. In embodiment, $R^7$ is a protein moiety bonded to $L^7$ through an S of the protein moiety. In embodiment, $R^7$ is a protein moiety bonded to $L^7$ through an O of a —OC(O)— of the protein moiety. In embodiment, $R^7$ is a detectable moiety. In embodiment, $R^7$ is a detectable moiety bonded to $L^7$ through an N of the detectable moiety. In embodiment, $R^7$ is a detectable moiety bonded to $L^7$ through an O of the detectable moiety. In embodiment, $R^7$ is a detectable moiety bonded to $L^7$ through an S of the detectable moiety. In embodiment, $R^7$ is a detectable moiety bonded to $L^7$ through an O of a —OC(O)— of the detectable moiety. In embodiment, $R^7$ is a drug moiety. In embodiment, $R^7$ is a drug moiety bonded to $L^7$ through an N of the drug moiety. In embodiment, $R^7$ is a drug moiety bonded to $L^7$ through an O of the drug moiety. In embodiment, $R^7$ is a drug moiety bonded to $L^7$ through an S of the drug moiety. In embodiment, $R^7$ is a drug moiety bonded to $L^7$ through an O of a —OC(O)— of the drug moiety. In embodiments, $R^7$ is

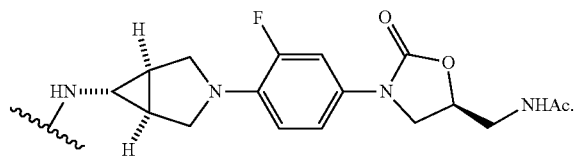

In embodiments, $R^7$ is

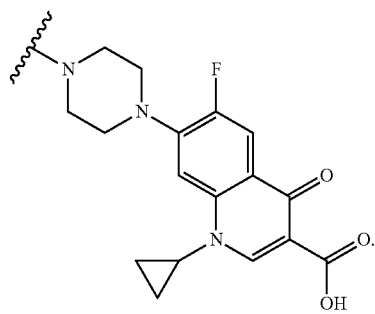 [SMILES: *N1CCN(c2cc3c(cc2F)c(=O)c(C(=O)O)cn3C2CC2)CC1]

In embodiments, $R^7$ is

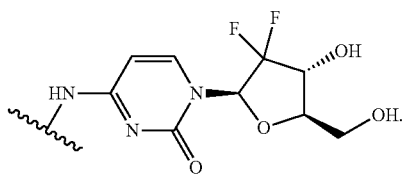 [SMILES: *Nc1ccn([C@@H]2O[C@H](CO)[C@@H](O)C2(F)F)c(=O)n1]

In embodiments, $R^7$ is

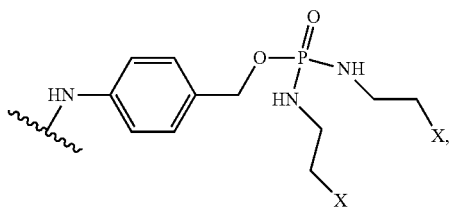

X is halide (e.g., Cl or Br). In embodiments, $R^7$ is

In embodiments, $L^7$ is a substituted or unsubstituted $C_1$-$C_{20}$ alkylene. In embodiments, $L^7$ is a substituted or unsubstituted 2 to 20 membered heteroalkylene. In embodiments, $L^7$ is a substituted or unsubstituted $C_3$-$C_{20}$ cycloalkylene. In embodiments, $L^7$ is a substituted or unsubstituted 3 to 20 membered heterocycloalkylene. In embodiments, $L^7$ is a substituted or unsubstituted $C_6$-$C_{20}$ arylene. In embodiments, $L^7$ is a substituted or unsubstituted 5 to 20 membered heteroarylene. In embodiments, $L^7$ is a substituted $C_1$-$C_{20}$ alkylene. In embodiments, $L^7$ is a substituted 2 to 20 membered heteroalkylene. In embodiments, $L^7$ is a substituted $C_3$-$C_{20}$ cycloalkylene. In embodiments, $L^7$ is a substituted 3 to 20 membered heterocycloalkylene. In embodiments, $L^7$ is a substituted $C_6$-$C_{20}$ arylene. In embodiments, $L^7$ is a substituted 5 to 20 membered heteroarylene. In embodiments, $L^7$ is an unsubstituted $C_1$-$C_{20}$ alkylene. In embodiments, $L^7$ is an unsubstituted 2 to 20 membered heteroalkylene. In embodiments, $L^7$ is an unsubstituted $C_3$-$C_{20}$ cycloalkylene. In embodiments, $L^7$ is an unsubstituted 3 to 20 membered heterocycloalkylene. In embodiments, $L^7$ is an unsubstituted $C_6$-$C_{20}$ arylene. In embodiments, $L^7$ is an unsubstituted 5 to 20 membered heteroarylene. In embodiments, $L^7$ is a substituted or unsubstituted $C_1$-$C_{14}$ alkylene. In embodiments, $L^7$ is a substituted or unsubstituted 2 to 14 membered heteroalkylene. In embodiments, $L^7$ is a substituted or unsubstituted $C_3$-$C_{14}$ cycloalkylene. In embodiments, $L^7$ is a substituted or unsubstituted 3 to 14 membered heterocycloalkylene. In embodiments, $L^7$ is a substituted or unsubstituted $C_6$-$C_{14}$ arylene. In embodiments, $L^7$ is a substituted or unsubstituted 5 to 14 membered heteroarylene. In embodiments, $L^7$ is a substituted $C_1$-$C_{14}$ alkylene. In embodiments, $L^7$ is a substituted 2 to 14 membered heteroalkylene. In embodiments, $L^7$ is a substituted $C_3$-$C_{14}$ cycloalkylene. In embodiments, $L^7$ is a substituted 3 to 14 membered heterocycloalkylene. In embodiments, $L^7$ is a substituted $C_6$-$C_{14}$ arylene. In embodiments, $L^7$ is a substituted 5 to 14 membered heteroarylene. In embodiments, $L^7$ is an unsubstituted $C_1$-$C_{14}$ alkylene. In embodiments, $L^7$ is an unsubstituted 2 to 14 membered heteroalkylene. In embodiments, $L^7$ is an unsubstituted $C_3$-$C_{14}$ cycloalkylene. In embodiments, $L^7$ is an unsubstituted 3 to 14 membered heterocycloalkylene. In embodiments, $L^7$ is an unsubstituted $C_6$-$C_{14}$ arylene. In embodiments, $L^7$ is an unsubstituted 5 to 14 membered heteroarylene. In embodiments, $L^7$ is a substituted or unsubstituted $C_1$-$C_8$ alkylene. In embodiments, $L^7$ is a substituted or unsubstituted 2 to 8 membered heteroalkylene. In embodiments, $L^7$ is a substituted or unsubstituted $C_3$-$C_8$ cycloalkylene. In embodiments, $L^7$ is a substituted or unsubstituted 3 to 8 membered heterocycloalkylene. In embodiments, $L^7$ is a substituted or unsubstituted $C_6$-$C_{10}$ arylene. In embodiments, $L^7$ is a substituted or unsubstituted 5 to 10 membered heteroarylene. In embodiments, $L^7$ is a substituted $C_1$-$C_8$ alkylene. In embodiments, $L^7$ is a substituted 2 to 8 membered heteroalkylene. In embodiments, $L^7$ is a substituted $C_3$-$C_8$ cycloalkylene. In embodiments, $L^7$ is a substituted 3 to 8 membered heterocycloalkylene. In embodiments, $L^7$ is a substituted $C_6$-$C_{10}$ arylene. In embodiments, $L^7$ is a substituted 5 to 10 membered heteroarylene. In embodiments, $L^7$ is an unsubstituted $C_1$-$C_8$ alkylene. In embodiments, $L^7$ is an unsubstituted 2 to 8 membered heteroalkylene. In embodiments, $L^7$ is an unsubstituted $C_3$-$C_8$ cycloalkylene. In embodiments, $L^7$ is an unsubstituted 3 to 8 membered heterocycloalkylene. In embodiments, $L^7$ is an unsubstituted $C_6$-$C_{10}$ arylene. In embodiments, $L^7$ is an unsubstituted 5 to 10 membered heteroarylene.

In embodiments $L^8$ is a bond. In embodiments $L^8$ is —OC(O)—. In embodiments $L^8$ is —OC(O)NH-Ph-CH$_2$—. In embodiments $L^8$ is —OC(O)NH-Ph-CH$_2$—OC(O)—. In embodiments $L^8$ is —NH-Ph-CH$_2$—. In embodiments $L^8$ is —NH-Ph-CH$_2$—OC(O)—. In embodiments $L^8$ is —O-Ph-CH$_2$—. In embodiments $L^8$ is —O-Ph-CH$_2$—OC(O)—. In embodiment, $R^8$ is a protein moiety. In embodiment, $R^8$ is a protein moiety bonded to $L^8$ through an N of the protein moiety. In embodiment, $R^8$ is a protein moiety bonded to $L^8$ through an O of the protein moiety. In embodiment, $R^8$ is a protein moiety bonded to $L^8$ through an S of the protein moiety. In embodiment, $R^8$ is a protein moiety bonded to $L^8$ through an O of a —OC(O)— of the protein moiety. In embodiment, $R^8$ is a detectable moiety. In embodiment, $R^8$ is a detectable moiety bonded to $L^8$ through an N of the detectable moiety. In embodiment, $R^8$ is a detectable moiety bonded to $L^8$ through an O of the detectable moiety. In embodiment, $R^8$ is a detectable moiety bonded to $L^8$ through an S of the detectable moiety. In embodiment, $R^8$ is a detectable moiety bonded to $L^8$ through an O of a —OC(O)— of the detectable moiety. In embodiment, $R^8$ is a drug moiety. In embodiment, $R^8$ is a drug moiety bonded to $L^8$ through an N of the drug moiety. In embodiment, $R^8$ is a drug moiety bonded to $L^8$ through an O of the drug moiety. In embodiment, $R^8$ is a drug moiety bonded to $L^8$ through an S of the drug moiety. In embodiment, $R^8$ is a drug moiety bonded to $L^8$ through an O of a —OC(O)— of the drug moiety.

In embodiments $L^9$ is a bond. In embodiments $L^9$ is —OC(O)—. In embodiments $L^9$ is —OC(O)NH-Ph-CH$_2$—. In embodiments $L^9$ is —OC(O)NH-Ph-CH$_2$—OC(O)—. In embodiments $L^9$ is —NH-Ph-CH$_2$—. In embodiments $L^9$ is —NH-Ph-CH$_2$—OC(O)—. In embodiments $L^9$ is —O-Ph-CH$_2$—. In embodiments $L^9$ is —O-Ph-CH$_2$—OC(O)—. In embodiment, $R^9$ is a protein moiety. In embodiment, $R^9$ is a protein moiety bonded to $L^9$ through an N of the protein moiety. In embodiment, $R^9$ is a protein moiety bonded to $L^9$ through an O of the protein moiety. In embodiment, $R^9$ is a protein moiety bonded to $L^9$ through an S of the protein moiety. In embodiment, $R^9$ is a protein moiety bonded to $L^9$ through an O of a —OC(O)— of the protein moiety. In embodiment, $R^9$ is a detectable moiety. In embodiment, $R^9$ is a detectable moiety bonded to $L^9$ through an N of the detectable moiety. In embodiment, $R^9$ is a detectable moiety bonded to $L^9$ through an O of the detectable moiety. In embodiment, $R^9$ is a detectable moiety bonded to $L^9$ through an S of the detectable moiety. In embodiment, $R^9$ is a detectable moiety bonded to $L^9$ through an O of a —OC(O)— of the detectable moiety. In embodiment, $R^9$ is a drug moiety. In embodiment, $R^9$ is a drug moiety bonded to $L^9$ through an N of the drug moiety. In embodiment, $R^9$ is a drug moiety bonded to $L^9$ through an O of the drug moiety. In embodiment, $R^9$ is a drug moiety bonded to $L^9$ through an S of the drug moiety. In embodiment, $R^9$ is a drug moiety bonded to $L^9$ through an O of a —OC(O)— of the drug moiety. In embodiments, $L^9$ is a substituted or unsubstituted $C_1$-$C_{20}$ alkylene. In embodiments, $L^9$ is a substituted or unsubstituted 2 to 20 membered heteroalkylene. In embodiments, $L^9$ is a substituted or unsubstituted $C_3$-$C_{20}$ cycloalkylene. In embodiments, $L^9$ is a substituted or unsubstituted 3 to 20 membered heterocycloalkylene. In embodiments, $L^9$ is a substituted or unsubstituted $C_6$-$C_{20}$ arylene. In embodiments, $L^9$ is a substituted or unsubstituted 5 to 20 membered heteroarylene. In embodiments, $L^9$ is a substituted $C_1$-$C_{20}$ alkylene. In embodiments, $L^9$ is a substituted 2 to 20 membered heteroalkylene. In embodiments, $L^9$ is a substituted $C_3$-$C_{20}$ cycloalkylene. In embodiments, $L^9$ is a substituted 3 to 20 membered heterocycloalkylene. In embodiments, $L^9$ is a substituted $C_6$-$C_{20}$ arylene. In embodiments, $L^9$ is a substituted 5 to 20 membered heteroarylene. In embodiments, $L^9$ is an unsubstituted $C_1$-$C_{20}$ alkylene. In embodiments, $L^9$ is an unsubstituted 2 to 20 membered heteroalkylene. In embodiments, $L^9$ is an unsubstituted $C_3$-$C_{20}$ cycloalkylene. In embodiments, $L^9$ is an unsubstituted 3 to 20 membered heterocycloalkylene. In embodiments, $L^9$ is an unsubstituted $C_6$-$C_{20}$ arylene. In embodiments, $L^9$ is an unsubstituted 5 to 20 membered heteroarylene. In embodiments, $L^9$ is a substituted or unsubstituted $C_1$-$C_{14}$ alkylene. In embodiments, $L^9$ is a substituted or unsubstituted 2 to 14 membered heteroalkylene. In embodiments, $L^9$ is a substituted or unsubstituted $C_3$-$C_{14}$ cycloalkylene. In embodiments, $L^9$ is a substituted or unsubstituted 3 to 14 membered heterocycloalkylene. In embodiments, $L^9$ is a substituted or unsubstituted $C_6$-$C_{14}$ arylene. In embodiments, $L^9$ is a substituted or unsubstituted 5 to 14 membered heteroarylene. In embodiments, $L^9$ is a substituted $C_1$-$C_{14}$ alkylene. In embodiments, $L^9$ is a substituted 2 to 14 membered heteroalkylene. In embodiments, $L^9$ is a substituted $C_3$-$C_{14}$ cycloalkylene. In embodiments, $L^9$ is a substituted 3 to 14 membered heterocycloalkylene. In embodiments, $L^9$ is a substituted $C_6$-$C_{14}$ arylene. In embodiments, $L^9$ is a substituted 5 to 14 membered heteroarylene. In embodiments, $L^9$ is an unsubstituted $C_1$-$C_{14}$ alkylene. In embodiments, $L^9$ is an unsubstituted 2 to 14 membered heteroalkylene. In embodiments, $L^9$ is an unsubstituted $C_3$-$C_{14}$ cycloalkylene. In embodiments, $L^9$ is an unsubstituted 3 to 14 membered heterocycloalkylene. In embodiments, $L^9$ is an unsubstituted $C_6$-$C_{14}$ arylene. In embodiments, $L^9$ is an unsubstituted 5 to 14 membered heteroarylene. In embodiments, $L^9$ is a substituted or unsubstituted $C_1$-$C_8$ alkylene. In embodiments, $L^9$ is a substituted or unsubstituted 2 to 8 membered heteroalkylene. In embodiments, $L^9$ is a substituted or unsubstituted $C_3$-$C_8$ cycloalkylene. In embodiments, $L^9$ is a substituted or unsubstituted 3 to 8 membered heterocycloalkylene. In embodiments, $L^9$ is a substituted or unsubstituted $C_6$-$C_{10}$ arylene. In embodiments, $L^9$ is a substituted or unsubstituted 5 to 10 membered heteroarylene. In embodiments, $L^9$ is a substituted $C_1$-$C_8$ alkylene. In embodiments, $L^9$ is a substituted 2 to 8 membered heteroalkylene. In embodiments, $L^9$ is a substituted $C_3$-$C_8$ cycloalkylene. In embodiments, $L^9$ is a substituted 3 to 8 membered heterocycloalkylene. In embodiments, $L^9$ is a substituted $C_6$-$C_{10}$ arylene. In embodiments, $L^9$ is a substituted 5 to 10 membered heteroarylene. In embodiments, $L^9$ is an unsubstituted $C_1$-$C_8$ alkylene. In embodiments, $L^9$ is an unsubstituted 2 to 8 membered heteroalkylene. In embodiments, $L^9$ is an unsubstituted $C_3$-$C_8$ cycloalkylene. In embodiments, $L^9$ is an unsubstituted 3 to 8 membered heterocycloalkylene. In embodiments, $L^9$ is an unsubstituted $C_6$-$C_{10}$ arylene. In embodiments, $L^9$ is an unsubstituted 5 to 10 membered heteroarylene.

In embodiments $L^{11}$ is a bond. In embodiments $L^{11}$ is —OC(O)—. In embodiments $L^{11}$ is —OC(O)NH-Ph-CH$_2$—. In embodiments $L^{11}$ is —OC(O)NH-Ph-CH$_2$—OC(O)—. In embodiments $L^{11}$ is —NH-Ph-CH$_2$—. In embodiments $L^{11}$ is —NH-Ph-CH$_2$—OC(O)—. In embodiments $L^{11}$ is —O-Ph-CH$_2$—. In embodiments $L^{11}$ is —O-Ph-CH$_2$—OC(O)—. In embodiment, $R^{11}$ is a protein moiety. In embodiment, $R^{11}$ is a protein moiety bonded to $L^{11}$ through an N of the protein moiety. In embodiment, $R^{11}$ is a protein moiety bonded to $L^{11}$ through an O of the protein moiety. In embodiment, $R^{11}$ is a protein moiety bonded to $L^{11}$ through an S of the protein moiety. In embodiment, $R^{11}$ is a protein moiety bonded to $L^{11}$ through an O of a —OC(O)— of the protein moiety. In embodiment, $R^{11}$ is a detectable moiety. In embodiment, $R^{11}$ is a detectable moiety bonded to $L^{11}$ through an N of the detectable moiety. In embodiment, $R^{11}$ is a detectable moiety bonded to $L^{11}$ through an O of the detectable moiety. In embodiment, $R^{11}$ is a detectable moiety bonded to $L^{11}$ through an S of the detectable moiety. In embodiment, $R^{11}$ is a detectable moiety bonded to $L^{11}$ through an O of a —OC(O)— of the detectable moiety. In embodiment, $R^{11}$ is a drug moiety. In embodiment, $R^{11}$ is a drug moiety bonded to $L^{11}$ through an N of the drug moiety. In embodiment, $R^{11}$ is a drug moiety bonded to $L^{11}$ through an O of the drug moiety. In embodiment, $R^{11}$ is a drug moiety bonded to $L^{11}$ through an S of the drug moiety. In embodiment, $R^{11}$ is a drug moiety bonded to $L^{11}$ through an O of a —OC(O)— of the drug moiety. In embodiments, $R^{11}$ is

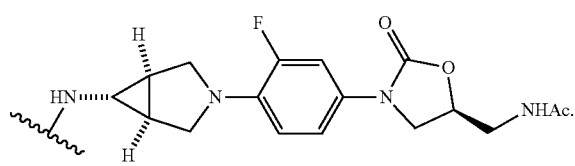 [SMILES: *N[C@H]1[C@@H]2CN(c3ccc(N4C[C@H](CNC(C)=O)OC4=O)cc3F)C[C@@H]21]

In embodiments, $R^{11}$

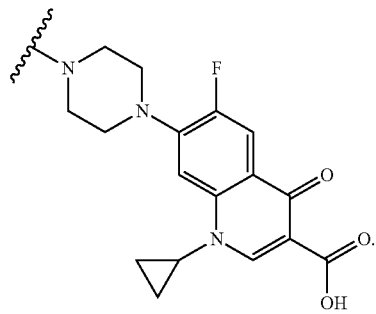 [SMILES: *N1CCN(c2cc3c(cc2F)c(=O)c(C(=O)O)cn3C2CC2)CC1]

In embodiments, $R^{11}$ is

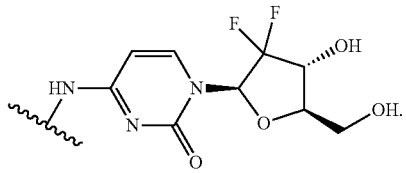 [SMILES: *Nc1ccn([C@@H]2O[C@H](CO)[C@@H](O)C2(F)F)c(=O)n1]

In embodiments, $R^{11}$ is

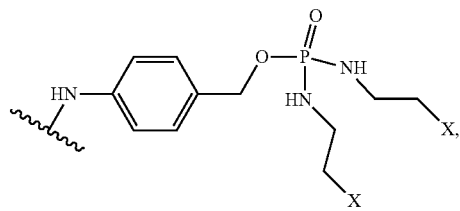

X is halide (e.g., Cl or Br). In embodiments, $R^{11}$ is

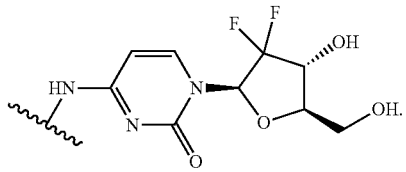 [SMILES: *Nc1ccn([C@@H]2O[C@H](CO)[C@@H](O)C2(F)F)c(=O)n1]

In embodiments, $L^1$ is a substituted or unsubstituted $C_1$-$C_{20}$ alkylene. In embodiments, $L^{11}$ is a substituted or unsubstituted 2 to 20 membered heteroalkylene. In embodiments, $L^{11}$ is a substituted or unsubstituted $C_3$-$C_{20}$ cycloalkylene. In embodiments, $L^{11}$ is a substituted or unsubstituted 3 to 20 membered heterocycloalkylene. In embodiments, $L^{11}$ is a substituted or unsubstituted $C_6$-$C_{20}$ arylene. In embodiments, $L^{11}$ is a substituted or unsubstituted 5 to 20 membered heteroarylene. In embodiments, $L^{11}$ is a substituted $C_1$-$C_{20}$ alkylene. In embodiments, $L^{11}$ is a substituted 2 to 20 membered heteroalkylene. In embodiments, $L^{11}$ is a substituted $C_3$-$C_{20}$ cycloalkylene. In embodiments, $L^{11}$ is a substituted 3 to 20 membered heterocycloalkylene. In embodiments, $L^{11}$ is a substituted $C_6$-$C_{20}$ arylene. In embodiments, $L^{11}$ is a substituted 5 to 20 membered heteroarylene. In embodiments, $L^{11}$ is an unsubstituted $C_1$-$C_{20}$ alkylene. In embodiments, $L^{11}$ is an unsubstituted 2 to 20 membered heteroalkylene. In embodiments, $L^{11}$ is an unsubstituted $C_3$-$C_{20}$ cycloalkylene. In embodiments, $L^{11}$ is an unsubstituted 3 to 20 membered heterocycloalkylene. In embodiments, $L^{11}$ is an unsubstituted $C_6$-$C_{20}$ arylene. In embodiments, $L^{11}$ is an unsubstituted 5 to 20 membered heteroarylene. In embodiments, $L^1$ is a substituted or unsubstituted $C_1$-$C_{14}$ alkylene. In embodiments, $L^{11}$ is a substituted or unsubstituted 2 to 14 membered heteroalkylene. In embodiments, $L^{11}$ is a substituted or unsubstituted $C_3$-$C_{14}$ cycloalkylene. In embodiments, $L^{11}$ is a substituted or unsubstituted 3 to 14 membered heterocycloalkylene. In embodiments, $L^{11}$ is a substituted or unsubstituted $C_6$-$C_{14}$ arylene. In embodiments, $L^{11}$ is a substituted or unsubstituted 5 to 14 membered heteroarylene. In embodiments, $L^{11}$ is a substituted $C_1$-$C_{14}$ alkylene. In embodiments, $L^{11}$ is a substituted 2 to 14 membered heteroalkylene. In embodiments, $L^{11}$ is a substituted $C_3$-$C_{14}$ cycloalkylene. In embodiments, $L^{11}$ is a substituted 3 to 14 membered heterocycloalkylene. In embodiments, $L^{11}$ is a substituted $C_6$-$C_{14}$ arylene. In embodiments, $L^{11}$ is a substituted 5 to 14 membered heteroarylene. In embodiments, $L^{11}$ is an unsubstituted $C_1$-$C_{14}$ alkylene. In embodiments, $L^{11}$ is an unsubstituted 2 to 14 membered heteroalkylene. In embodiments, $L^{11}$ is an unsubstituted $C_3$-$C_{14}$ cycloalkylene. In embodiments, $L^{11}$ is an unsubstituted 3 to 14 membered heterocycloalkylene. In embodiments, $L^{11}$ is an unsubstituted $C_6$-$C_{14}$ arylene. In embodiments, $L^1$ is an unsubstituted 5 to 14 membered heteroarylene. In embodiments, $L^1$ is a substituted or unsubstituted $C_1$-$C_8$ alkylene. In embodiments, $L^{11}$ is a substituted or unsubstituted 2 to 8 membered heteroalkylene. In embodiments, $L^{11}$ is a substituted or unsubstituted $C_3$-$C_8$ cycloalkylene. In embodiments, $L^{11}$ is a substituted or unsubstituted 3 to 8 membered heterocycloalkylene. In embodiments, $L^{11}$ is a substituted or unsubstituted $C_6$-$C_{10}$ arylene. In embodiments, $L^{11}$ is a substituted or unsubstituted 5 to 10 membered heteroarylene. In embodiments, $L^{11}$ is a substituted $C_1$-$C_8$ alkylene. In embodiments, $L^{11}$ is a substituted 2 to 8 membered heteroalkylene. In embodiments, $L^{11}$ is a substituted $C_3$-$C_8$ cycloalkylene. In embodiments, $L^{11}$ is a substituted 3 to 8 membered heterocycloalkylene. In embodiments, $L^{11}$ is a substituted $C_6$-$C_{10}$ arylene. In embodiments, $L^{11}$ is a substituted 5 to 10 membered heteroarylene. In embodiments, $L^{11}$ is an unsubstituted $C_1$-$C_8$ alkylene. In embodiments, $L^{11}$ is an unsubstituted 2 to 8 membered heteroalkylene. In embodiments, $L^{11}$ is an unsubstituted $C_3$-$C_8$ cycloalkylene. In embodiments, $L^{11}$ is an unsubstituted 3 to 8 membered heterocycloalkylene. In embodiments, $L^{11}$ is an unsubstituted $C_6$-$C_{10}$ arylene. In embodiments, $L^{11}$ is an unsubstituted 5 to 10 membered heteroarylene.

In embodiments $L^{12}$ is a bond. In embodiments $L^{12}$ is —OC(O)—. In embodiments $L^{12}$ is —OC(O)NH-Ph-CH$_2$—. In embodiments $L^{12}$ is —OC(O)NH-Ph-CH$_2$—OC(O)—. In embodiments $L^{12}$ is —NH-Ph-CH$_2$—. In embodiments $L^{12}$ is —NH-Ph-CH$_2$—OC(O)—. In embodiments $L^{12}$ is —O-Ph-CH$_2$—. In embodiments $L^{12}$ is —O-Ph-CH$_2$—OC(O)—. In embodiment, $R^{12}$ is a protein moiety. In embodiment, $R^{12}$ is a protein moiety bonded to $L^{12}$ through an N of the protein moiety. In embodiment, $R^{12}$ is a protein moiety bonded to $L^{12}$ through an O of the protein moiety. In embodiment, $R^{12}$ is a protein moiety bonded to $L^{12}$ through an S of the protein moiety. In embodiment, $R^{12}$ is a protein moiety bonded to $L^{12}$ through an O of a —OC(O)— of the protein moiety. In embodiment, $R^{12}$ is a detectable moiety. In embodiment, $R^{12}$ is a detectable moiety bonded to $L^{12}$ through an N of the detectable moiety. In embodiment, $R^{12}$ is a detectable moiety bonded to $L^{12}$ through an O of the detectable moiety. In embodiment, $R^{12}$ is a detectable moiety bonded to $L^{12}$ through an S of the detectable moiety. In embodiment, $R^{12}$ is a detectable moiety bonded to $L^{12}$ through an O of a —OC(O)— of the detectable moiety. In embodiment, $R^{12}$ is a drug moiety. In embodiment, $R^{12}$ is a drug moiety bonded to $L^{12}$ through an N of the drug moiety. In embodiment, $R^{12}$ is a drug moiety bonded to $L^{12}$ through an O of the drug moiety. In embodiment, $R^{12}$ is a drug moiety bonded to $L^{12}$ through an S of the drug moiety. In embodiment, $R^{12}$ is a drug moiety bonded to $L^{12}$ through an O of a —OC(O)— of the drug moiety. In embodiments, $L^{12}$ is a substituted or unsubstituted $C_1$-$C_{20}$ alkylene. In embodiments, $L^{12}$ is a substituted or unsubstituted 2 to 20 membered heteroalkylene. In embodiments, $L^{12}$ is a substituted or unsubstituted $C_3$-$C_{20}$ cycloalkylene. In embodiments, $L^{12}$ is a substituted or unsubstituted 3 to 20 membered heterocycloalkylene. In embodiments, $L^{12}$ is a substituted or unsubstituted $C_6$-$C_{20}$ arylene. In embodiments, $L^{12}$ is a substituted or unsubstituted 5 to 20 membered heteroarylene. In embodiments, $L^{12}$ is a substituted $C_1$-$C_{20}$ alkylene. In embodiments, $L^{12}$ is a substituted 2 to 20 membered heteroalkylene. In embodiments, $L^{12}$ is a substituted $C_3$-$C_{20}$ cycloalkylene. In embodiments, $L^{12}$ is a substituted 3 to 20 membered heterocycloalkylene. In embodiments, $L^{12}$ is a substituted $C_6$-$C_{20}$ arylene. In embodiments, $L^{12}$ is a substituted 5 to 20 membered heteroarylene. In embodiments, $L^{12}$ is an unsubstituted $C_1$-$C_{20}$ alkylene. In embodiments, $L^{12}$ is an unsubstituted 2 to 20 membered heteroalkylene. In embodiments, $L^{12}$ is an unsubstituted $C_3$-$C_{20}$ cycloalkylene. In embodiments, $L^{12}$ is an unsubstituted 3 to 20 membered heterocycloalkylene. In embodiments, $L^{12}$ is an unsubstituted $C_6$-$C_{20}$ arylene. In embodiments, $L^{12}$ is an unsubstituted 5 to 20 membered heteroarylene. In embodiments, $L^{12}$ is a substituted or unsubstituted $C_1$-$C_{14}$ alkylene. In embodiments, $L^{12}$ is a substituted or unsubstituted 2 to 14 membered heteroalkylene. In embodiments, $L^{12}$ is a substituted or unsubstituted $C_3$-$C_{14}$ cycloalkylene. In embodiments, $L^{12}$ is a substituted or unsubstituted 3 to 14 membered heterocycloalkylene. In embodiments, $L^{12}$ is a substituted or unsubstituted $C_6$-$C_{14}$ arylene. In embodiments, $L^{12}$ is a substituted or unsubstituted 5 to 14 membered heteroarylene. In embodiments, $L^{12}$ is a substituted $C_1$-$C_{14}$ alkylene. In embodiments, $L^{12}$ is a substituted 2 to 14 membered heteroalkylene. In embodiments, $L^{12}$ is a substituted $C_3$-$C_{14}$ cycloalkylene. In embodiments, $L^{12}$ is a substituted 3 to 14 membered heterocycloalkylene. In embodiments, $L^{12}$ is a substituted $C_6$-$C_{14}$ arylene. In embodiments, $L^{12}$ is a substituted 5 to 14 membered heteroarylene. In embodiments, $L^{12}$ is an unsubstituted $C_1$-$C_{14}$ alkylene. In embodiments, $L^{12}$ is an unsubstituted 2 to 14 membered heteroalkylene. In embodiments, $L^{12}$ is an unsubstituted $C_3$-$C_{14}$ cycloalkylene. In embodiments, $L^{12}$ is an unsubstituted 3 to 14 membered heterocycloalkylene. In embodiments, $L^{12}$ is an unsubstituted $C_6$-$C_{14}$ arylene. In embodiments, $L^{12}$ is an unsubstituted 5 to 14 membered heteroarylene. In embodiments, $L^{12}$ is a substituted or unsubstituted $C_1$-$C_8$ alkylene. In embodiments, $L^{12}$ is a substituted or unsubstituted 2 to 8 membered heteroalkylene. In embodiments, $L^{12}$ is a substituted or unsubstituted $C_3$-$C_8$ cycloalkylene. In embodiments, $L^{12}$ is a substituted or unsubstituted 3 to 8 membered heterocycloalkylene. In embodiments, $L^{12}$ is a substituted or unsubstituted $C_6$-$C_{10}$ arylene. In embodiments, $L^{12}$ is a substituted or unsubstituted 5 to 10 membered heteroarylene. In embodiments, $L^{12}$ is a substituted $C_1$-$C_8$ alkylene. In embodiments, $L^{12}$ is a substituted 2 to 8 membered heteroalkylene. In embodiments, $L^{12}$ is a substituted $C_3$-$C_8$ cycloalkylene. In embodiments, $L^{12}$ is a substituted 3 to 8 membered heterocycloalkylene. In embodiments, $L^{12}$ is a substituted $C_6$-$C_{10}$ arylene. In embodiments, $L^{12}$ is a substituted 5 to 10 membered heteroarylene. In embodiments, $L^{12}$ is an unsubstituted $C_1$-$C_8$ alkylene. In embodiments, $L^{12}$ is an unsubstituted 2 to 8 membered heteroalkylene. In embodiments, $L^{12}$ is an unsubstituted $C_3$-$C_8$ cycloalkylene. In embodiments, $L^{12}$ is an unsubstituted 3 to 8 membered heterocycloalkylene. In embodiments, $L^{12}$ is an unsubstituted $C_6$-$C_{10}$ arylene. In embodiments, $L^{12}$ is an unsubstituted 5 to 10 membered heteroarylene.

As described above, each $L^2$, $L^3$, $L^4$, $L^5$, $L^6$, $L^7$, $L^8$, $L^9$, $L^{11}$, and $L^{12}$ may be different. Where each of $L^2$, $L^3$, $L^4$, $L^5$, $L^6$, $L^7$, $L^8$, $L^9$, $L^{11}$, and $L^{12}$ are different, $L^{13}$ may be referred to as $L^{132}$, $L^{133}$, $L^{134}$, $L^{135}$, $L^{136}$, $L^{137}$, $L^{138}$, $L^{139}$, $L^{1311}$, and $L^{1312}$ to refer to $L^{13}$ substituents that correlate to $L^2$, $L^3$, $L^4$, $L^5$, $L^6$, $L^7$, $L^8$, $L^9$, $L^{11}$, and $L^{12}$, respectively. Likewise, where each of $L^2$, $L^3$, $L^4$, $L^5$, $L^6$, $L^7$, $L^8$, $L^9$, $L^{11}$, and $L^{12}$ are different, $L^{14}$ may be referred to as $L^{142}$, $L^{143}$, $L^{144}$, $L^{145}$, $L^{146}$, $L^{147}$, $L^{148}$, $L^{149}$, $L^{1411}$, and $L^{1412}$ to refer to $L^{14}$ substituents that correlate to $L^2$, $L^3$, $L^4$, $L^5$, $L^6$, $L^7$, $L^8$, $L^9$, $L^{11}$, and $L^{12}$, respectively. Likewise, where each of $L^2$, $L^3$, $L^4$, $L^5$, $L^6$, $L^7$, $L^8$, $L^9$, $L^{11}$, and $L^{12}$ are different, $R^{17}$ may be referred to as $R^{172}$, $R^{173}$, $R^{174}$, $R^{175}$, $R^{176}$, $R^{177}$, $R^{178}$, $R^{179}$, $R^{1711}$, and $R^{1712}$ to refer to $R^{17}$ substituents that correlate to $L^2$, $L^3$, $L^4$, $L^5$, $L^6$, $L^7$, $L^8$, $L^9$, $L^{11}$, and $L^{12}$, respectively. For example, in embodiments, $L^2$ is a bond, —N($R^{172}$)-$L^{132}$-$L^{142}$-, —N($R^{172}$)C(O)O-$L^{132}$-$L^{142}$-, —O-$L^{132}$-$L^{142}$-, —S-$L^{132}$-$L^{142}$-, —OC(O)-$L^{132}$-$L^{142}$-, —O C(O)N($R^{172}$)-$L^{132}$-$L^{142}$-, —OC(O)O-$L^{132}$-$L^{142}$-, —OSO$_2$-$L^{132}$-$L^{142}$, —C(O)N($R^{172}$)-$L^{132}$-$L^{142}$-, —N($R^{172}$)C(O)-$L^{132}$-$L^{142}$-, —S(O)$_2$N($R^{172}$)-$L^{132}$-$L^{142}$-, —N($R^{172}$)S(O)$_2$-$L^{132}$-$L^{142}$-, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. Likewise, embodiments, $L^{12}$ is a bond, —N($R^{1712}$)-$L^{1312}$-$L^{1412}$-, —N($R^{1712}$)C(O)O-$L^{1312}$-$L^{1412}$-, —O-$L^{1312}$-$L^{1412}$-, —S-$L^{1312}$-$L^{1412}$-, —OC(O)-$L^{1312}$-$L^{1412}$, —OC(O)N($R^{1712}$)-$L^{1312}$-$L^{1412}$-, —OC(O)O-$L^{1312}$-$L^{1412}$-, —OSO$_2$-$L^{1312}$-$L^{1412}$-, —C(O)N($R^{1712}$)-$L^{132}$-$L^{1412}$-, —N($R^{1712}$)C(O)-$L^{1312}$-$L^{1412}$-, —S(O)$_2$N($R^{1712}$)-$L^{1321}$-$L^{1412}$-, —N($R^{1712}$)S(O)$_2$-$L^{1312}$-$L^{1412}$-, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, each $L^{13}$ is independently selected from a bond or substituted or unsubstituted arylene. In embodiments, each $L^{13}$ is independently selected from a bond or substituted or unsubstituted phenylene. In embodiments, each $L^{14}$ is independently selected from a bond, substituted or unsubstituted alkylene, or substituted or unsubstituted heteroalkylene. In embodiments, each $L^{14}$ is independently selected from a bond, —(CH$_2$)$_w$—, or —(CH$_2$)$_w$—OC(O)—; and w is an integer between 1 and 4. In embodiments, each -$L^{13}$-$L^{14}$- is independently selected from a bond, -Ph-(CH$_2$)$_w$—, or -Ph-(CH$_2$)$_w$—OC(O)—; and w is an integer between 1 and 4. In embodiments, -$L^{13}$-$L^{14}$- is a bond. In embodiments, -$L^{13}$-$L^{14}$- is -Ph-(CH$_2$)$_w$—. In embodiments, -$L^{13}$-$L^{14}$- is -Ph-(CH$_2$)$_w$—OC(O)—. In embodiments, w is 1. In embodiments, w is 2. In embodiments, w is 3. In embodiments, w is 4. In embodiments, -$L^{13}$-$L^{14}$- is independently -Ph-CH$_2$—, or -Ph-CH$_2$—OC(O)—. In embodiments, one or more linkers (e.g. $L^1$, $L^2$, $L^3$, $L^5$, $L^6$, $L^7$, $L^8$, $L^9$, $L^{11}$, and/or $L^{12}$) connected to an R group including a drug moiety, protein moiety, or detectable moiety is —OC(O)NH-Ph-CH$_2$—, —OC(O)NH-Ph-CH$_2$—OC(O)—, —NH-Ph-CH$_2$—, —NH-Ph-CH$_2$—OC(O)—, —O-Ph-CH$_2$—, or —O-Ph-CH$_2$—OC(O)— (collectively "extended linkers"). In embodiments, $L^{13}$ is independently a bond. In embodiments, $L^{13}$ is independently an unsubstituted arylene. In embodiments, $L^{13}$ is independently a substituted arylene. In embodiments, $L^{14}$ is independently a bond. In embodiments, $L^{14}$ is independently an unsubstituted methylene. In embodiments, $L^{14}$ is independently an unsubstituted ethylene. In embodiments, $L^{14}$ is independently an unsubstituted propylene. In embodiments, $L^{14}$ is independently an unsubstituted butylene. In embodiments, each $L^{14}$ is independently a —(CH$_2$)—. In embodiments, each $L^{14}$ is independently a —(CH$_2$)$_2$—. In embodiments, each $L^{14}$ is independently a —(CH$_2$)$_3$—. In embodiments, each $L^{14}$ is independently a —(CH$_2$)$_4$—. In embodiments, each $L^{14}$ is independently a —(CH$_2$)—OC(O)—. In embodiments, each $L^{14}$ is independently a —(CH$_2$)$_2$—OC(O)—. In embodiments, each $L^{14}$ is independently a —(CH$_2$)$_3$—OC(O)—. In embodiments, each $L^{14}$ is independently a —(CH$_2$)$_4$—OC(O)—.

In embodiments, $L^{13}$ is —NHC(O)—(CH$_2$)$_W$—NHC(O)O—(CH$_2$)$_{Y1}$—. In embodiments, $L^{13}$ is —NHC(O)—(CH$_2$)$_W$—C(O)NH—(CH$_2$)$_{Y1}$—. In embodiments, $L^{13}$ is —NHC(O)—(CH$_2$)$_W$—C(O)—. In embodiments, $L^{13}$ is —NHC(O)—(CH$_2$)$_W$—NH—. In embodiments, $L^{13}$ is —NHC(O)—(CH$_2$)$_W$—NHC(O)—. In embodiments, $L^{13}$ is —NHC(O)—(CH$_2$)$_W$—C(O)NH—. In embodiments, $L^{13}$ is —NHC(O)—(CH$_2$)$_W$—NHC(O)O—. In embodiments, $L^{13}$ is —NHC(O)—(CH$_2$)$_W$—(OCH$_2$CH$_2$)$_{T1}$—C(O)NH—(CH$_2$)$_{Y1}$—. In embodiments, $L^{13}$ is —NHC(O)—(CH$_2$)$_W$—(OCH$_2$CH$_2$)$_{T1}$—C(O)NH—(CH$_2$)$_{Y1}$—C(O)—. In embodiments, $L^{13}$ is a substituted or unsubstituted $C_1$-$C_{20}$ alkylene. In embodiments, $L^{13}$ is a substituted or unsubstituted 2 to 20 membered heteroalkylene. In embodiments, $L^{13}$ is a substituted or unsubstituted $C_3$-$C_{20}$ cycloalkylene. In embodiments, $L^{13}$ is a substituted or unsubstituted 3 to 20 membered heterocycloalkylene. In embodiments, $L^{13}$ is a substituted or unsubstituted $C_6$-$C_{20}$ arylene. In embodiments, $L^{13}$ is a substituted or unsubstituted 5 to 20 membered heteroarylene. In embodiments, $L^{13}$ is a substituted $C_1$-$C_{20}$ alkylene. In embodiments, $L^{13}$ is a substituted 2 to 20 membered heteroalkylene. In embodiments, $L^{13}$ is a substituted $C_3$-$C_{20}$ cycloalkylene. In embodiments, $L^{13}$ is a substituted 3 to 20 membered heterocycloalkylene. In embodiments, $L^{13}$ is a substituted $C_6$-$C_{20}$ arylene. In embodiments, $L^{13}$ is a substituted 5 to 20 membered heteroarylene. In embodiments, $L^{13}$ is an unsubstituted $C_1$-$C_{20}$ alkylene. In embodiments, $L^{13}$ is an unsubstituted 2 to 20 membered heteroalkylene. In embodiments, $L^{13}$ is an unsubstituted $C_3$-$C_{20}$ cycloalkylene. In embodiments, $L^{13}$ is an unsubstituted 3 to 20 membered heterocycloalkylene. In embodiments, $L^{13}$ is an unsubstituted $C_6$-$C_{20}$ arylene. In embodiments, $L^{13}$ is an unsubstituted 5 to 20 membered heteroarylene. In embodiments, $L^{13}$ is a substituted or unsubstituted $C_1$-$C_{14}$ alkylene. In embodiments, $L^{13}$ is a substituted or unsubstituted 2 to 14 membered heteroalkylene. In embodiments, $L^{13}$ is a substituted or unsubstituted $C_3$-$C_{14}$ cycloalkylene. In embodiments, $L^{13}$ is a substituted or unsubstituted 3 to 14 membered heterocycloalkylene. In embodiments, $L^{13}$ is a substituted or unsubstituted $C_6$-$C_{14}$ arylene. In embodiments, $L^{13}$ is a substituted or unsubstituted 5 to 14 membered heteroarylene. In embodiments, $L^{13}$ is a substituted $C_1$-$C_{14}$ alkylene. In embodiments, $L^{13}$ is a substituted 2 to 14 membered heteroalkylene. In embodiments, $L^{13}$ is a substituted $C_3$-$C_{14}$ cycloalkylene. In embodiments, $L^{13}$ is a substituted 3 to 14 membered heterocycloalkylene. In embodiments, $L^{13}$ is a substituted $C_6$-$C_{14}$ arylene. In embodiments, $L^{13}$ is a substituted 5 to 14 membered heteroarylene. In embodiments, $L^{13}$ is an unsubstituted $C_1$-$C_{14}$ alkylene. In embodiments, $L^{13}$ is an unsubstituted 2 to 14 membered heteroalkylene. In embodiments, $L^{13}$ is an unsubstituted $C_3$-$C_{14}$ cycloalkylene. In embodiments, $L^{13}$ is an unsubstituted 3 to 14 membered heterocycloalkylene. In embodiments, $L^{13}$ is an unsubstituted $C_6$-$C_{14}$ arylene. In embodiments, $L^{13}$ is an unsubstituted 5 to 14 membered heteroarylene. In embodiments, $L^{13}$ is a substituted or unsubstituted $C_1$-$C_8$ alkylene. In embodiments, $L^{13}$ is a substituted or unsubstituted 2 to 8 membered heteroalkylene. In embodiments, $L^{13}$ is a substituted or unsubstituted $C_3$-$C_8$ cycloalkylene. In embodiments, $L^{13}$ is a substituted or unsubstituted 3 to 8 membered heterocycloalkylene. In embodiments, $L^{13}$ is a substituted or unsubstituted $C_6$-$C_{10}$ arylene. In embodiments, $L^{13}$ is a substituted or unsubstituted 5 to 10 membered heteroarylene. In embodiments, $L^{13}$ is a substituted $C_1$-$C_8$ alkylene. In embodiments, $L^{13}$ is a substituted 2 to 8 membered heteroalkylene. In embodiments, $L^{13}$ is a substituted $C_3$-$C_8$ cycloalkylene. In embodiments, $L^{13}$ is a substituted 3 to 8 membered heterocycloalkylene. In embodiments, $L^{13}$ is a substituted $C_6$-$C_{10}$ arylene. In embodiments, $L^{13}$ is a substituted 5 to 10 membered heteroarylene. In embodiments, $L^{13}$ is an unsubstituted $C_1$-$C_8$ alkylene. In embodiments, $L^{13}$ is an unsubstituted 2 to 8 membered heteroalkylene. In embodiments, $L^{13}$ is an unsubstituted $C_3$-$C_8$ cycloalkylene. In embodiments, $L^{13}$ is an unsubstituted 3 to 8 membered heterocycloalkylene. In embodiments, $L^{13}$ is an unsubstituted $C_6$-$C_{10}$ arylene. In embodiments, $L^{13}$ is an unsubstituted 5 to 10 membered heteroarylene. In embodiments, $L^{13}$ includes a substituted or unsubstituted cyclooctynyl. In embodiments, $L^{13}$ includes a substituted cyclooctenyl. In embodiments, $L^{13}$ includes a product of a click chemistry reaction. In embodiments, $L^{13}$ includes a product of a click chemistry reaction including the product of the reaction of a cyclooctyne and an azide.

In embodiments, $L^{14}$ is

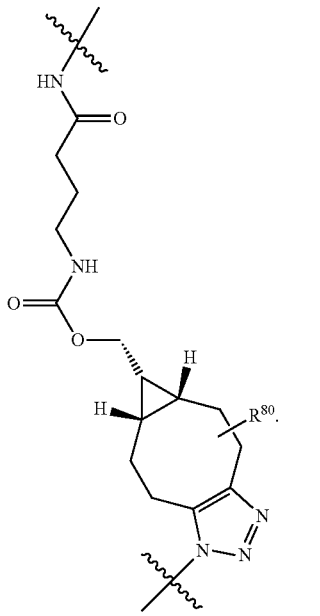

In embodiments, $L^{14}$ is

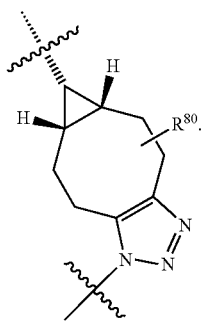

In embodiments, $L^1$ is

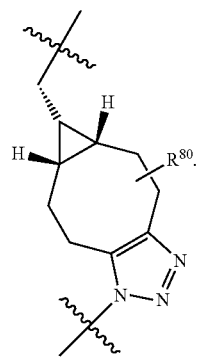

In embodiments, $L^{14}$ is

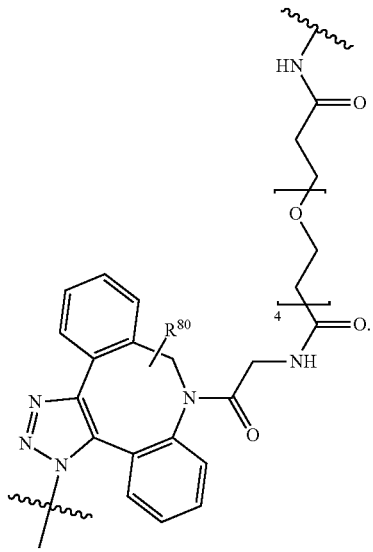

In embodiments, $L^{14}$ is
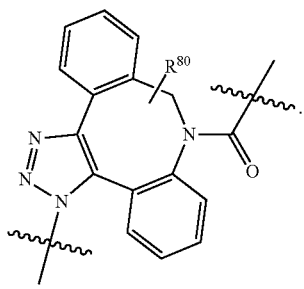
In embodiments, $L^{14}$ is
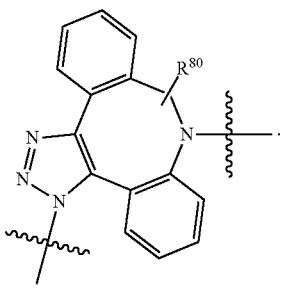
In embodiments, $L^{14}$ is
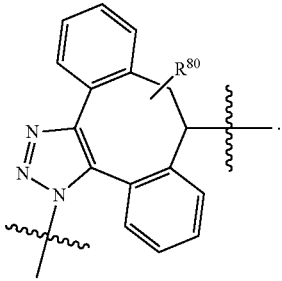
In embodiments, $L^{14}$ is
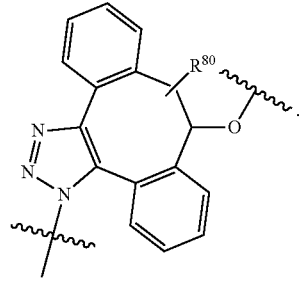
In embodiments, $L^{14}$ is
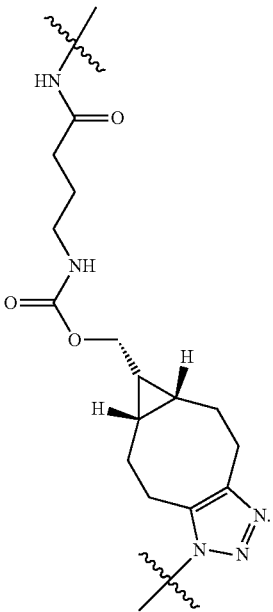
In embodiments, $L^{14}$ is
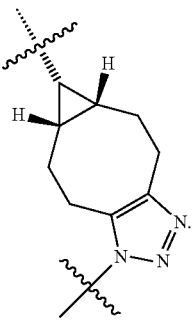
In embodiments, $L^{14}$ is
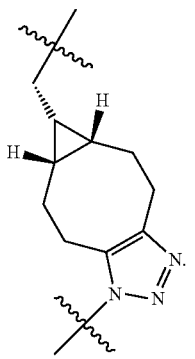

In embodiments, $L^{14}$ is

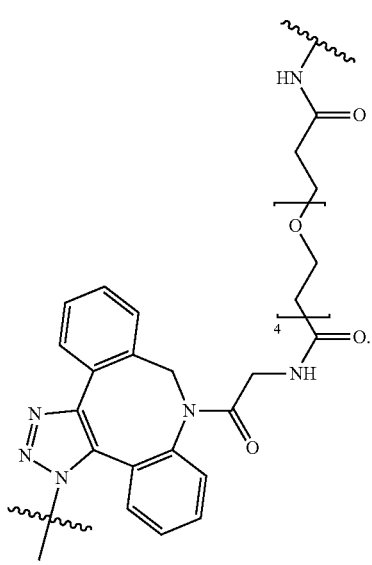

In embodiments, $L^{14}$ is

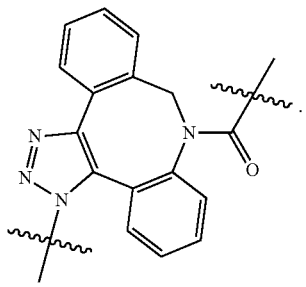 [SMILES: *C(=O)N1Cc2ccccc2-c2nnn(*)c2-c2ccccc21]

In embodiments $L^{14}$ is

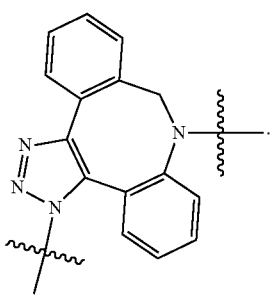 [SMILES: *N1Cc2ccccc2-c2nnn(*)c2-c2ccccc21]

In embodiments, $L^{14}$ is

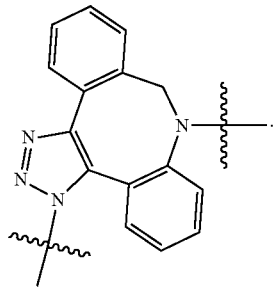 [SMILES: *N1Cc2ccccc2-c2nnn(*)c2-c2ccccc21]

In embodiments, $L^{14}$ is

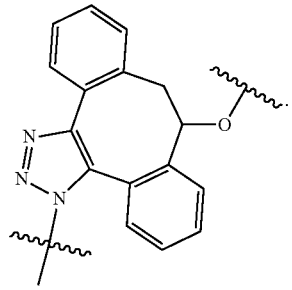 [SMILES: *OC1Cc2ccccc2-c2nnn(*)c2-c2ccccc21]

In embodiments, $L^{14}$ is —NHC(O)—$(CH_2)_{W1}$—NHC(O)O—$(CH_2)_{Y1}$—. In embodiments, $L^{14}$ is —NHC(O)—$(CH_2)_{W1}$—C(O)NH—$(CH_2)_{Y1}$—. In embodiments, $L^{14}$ is —NHC(O)—$(CH_2)_{W1}$—C(O)—. In embodiments, $L^{14}$ is —NHC(O)—$(CH_2)_{W1}$—NH—. In embodiments, $L^{14}$ is —NHC(O)—$(CH_2)_{W1}$—NHC(O)—. In embodiments, $L^{14}$ is —NHC(O)—$(CH_2)_{W1}$—C(O)NH—. In embodiments, $L^{14}$ is —NHC(O)—$(CH_2)_{W1}$—NHC(O)O—. In embodiments, $L^{14}$ is —NHC(O)—$(CH_2)_{W1}$—$(OCH_2CH_2)_{T1}$—C(O)NH—$(CH_2)_{Y1}$—. In embodiments, $L^{14}$ is —NHC(O)—$(CH_2)_{W1}$—$(OCH_2CH_2)_{T1}$—C(O)NH—$(CH_2)_{Y1}$—C(O)—. In embodiments, $L^{14}$ is a substituted or unsubstituted $C_1$-$C_{20}$ alkylene. In embodiments, $L^{14}$ is a substituted or unsubstituted 2 to 20 membered heteroalkylene. In embodiments, $L^{14}$ is a substituted or unsubstituted $C_3$-$C_{20}$ cycloalkylene. In embodiments, $L^{14}$ is a substituted or unsubstituted 3 to 20 membered heterocycloalkylene. In embodiments, $L^{14}$ is a substituted or unsubstituted $C_6$-$C_{20}$ arylene. In embodiments, $L^{14}$ is a substituted or unsubstituted 5 to 20 membered heteroarylene. In embodiments, $L^{14}$ is a substituted $C_1$-$C_{20}$ alkylene. In embodiments, $L^{14}$ is a substituted 2 to 20 membered heteroalkylene. In embodiments, $L^{14}$ is a substituted $C_3$-$C_{20}$ cycloalkylene. In embodiments, $L^{14}$ is a substituted 3 to 20 membered heterocycloalkylene. In embodiments, $L^{14}$ is a substituted $C_6$-$C_{20}$ arylene. In embodiments, $L^{14}$ is a substituted 5 to 20 membered heteroarylene. In embodiments, $L^{14}$ is an unsubstituted $C_1$-$C_{20}$ alkylene. In embodiments, $L^{14}$ is an unsubstituted 2 to 20 membered heteroalkylene. In embodiments, $L^{14}$ is an unsubstituted $C_3$-$C_{20}$ cycloalkylene. In embodiments, $L^{14}$ is an unsubstituted 3 to 20 membered heterocycloalkylene. In embodiments, $L^{14}$ is an unsubstituted $C_6$-$C_{20}$ arylene. In embodiments, $L^{14}$ is an unsubstituted 5 to 20 membered heteroarylene. In embodiments, $L^{14}$ is a substituted or unsubstituted $C_1$-$C_{14}$ alkylene. In embodiments, $L^{14}$ is a substituted or unsubstituted 2 to 14 membered heteroalkylene. In embodiments, $L^{14}$ is a substituted or unsubstituted $C_3$-$C_{14}$ cycloalkylene. In embodiments, $L^{14}$ is a substituted or unsubstituted 3 to 14 membered heterocycloalkylene. In embodiments, $L^{14}$ is a substituted or unsubstituted $C_6$-$C_{14}$ arylene. In embodiments, $L^{14}$ is a substituted or unsubstituted 5 to 14 membered heteroarylene. In embodiments, $L^{14}$ is a substituted $C_1$-$C_{14}$ alkylene. In embodiments, $L^{14}$ is a substituted 2 to 14 membered heteroalkylene. In embodiments, $L^{14}$ is a substituted $C_3$-$C_{14}$ cycloalkylene. In embodiments, $L^{14}$ is a substituted 3 to 14 membered heterocycloalkylene. In embodiments, $L^{14}$ is a substituted $C_6$-$C_{14}$ arylene. In embodiments, $L^{14}$ is a substituted 5 to 14 membered heteroarylene. In embodiments, $L^{14}$ is an unsubstituted $C_1$-$C_{14}$ alkylene. In embodiments, $L^{14}$ is an unsubstituted 2 to 14 membered heteroalkylene. In embodiments, $L^{14}$ is an unsubstituted $C_3$-$C_{14}$ cycloalkylene. In embodiments, $L^{14}$ is an unsubstituted 3 to 14 membered heterocycloalkylene. In embodiments, $L^{14}$ is an unsubstituted $C_6$-$C_{14}$ arylene. In embodiments, $L^{14}$ is an unsubstituted 5 to 14 membered heteroarylene. In embodiments, $L^{14}$ is a substituted or unsubstituted $C_1$-$C_8$ alkylene. In embodiments, $L^{14}$ is a substituted or unsubstituted 2 to 8 membered heteroalkylene. In embodiments, $L^{14}$ is a substituted or unsubstituted $C_3$-$C_8$ cycloalkylene. In embodiments, $L^{14}$ is a substituted or unsubstituted 3 to 8 membered heterocycloalkylene. In embodiments, $L^{14}$ is a substituted or unsubstituted $C_6$-$C_{10}$ arylene. In embodiments, $L^{14}$ is a substituted or unsubstituted 5 to 10 membered heteroarylene. In embodiments, $L^{14}$ is a substituted $C_1$-$C_8$ alkylene. In embodiments, $L^{14}$ is a substituted 2 to 8 membered heteroalkylene. In embodiments, $L^{14}$ is a substituted $C_3$-$C_8$ cycloalkylene. In embodiments, $L^{14}$ is a substituted 3 to 8 membered heterocycloalkylene. In embodiments, $L^{14}$ is a substituted $C_6$-$C_{10}$ arylene. In embodiments, $L^{14}$ is a substituted 5 to 10 membered heteroarylene. In embodiments, $L^{14}$ is an unsubstituted $C_1$-$C_8$ alkylene. In embodiments, $L^{14}$ is an unsubstituted 2 to 8 membered heteroalkylene. In embodiments, $L^{14}$ is an unsubstituted $C_3$-$C_8$ cycloalkylene. In embodiments, $L^{14}$ is an unsubstituted 3 to 8 membered heterocycloalkylene. In embodiments, $L^{14}$ is an unsubstituted $C_6$-$C_{10}$ arylene. In embodiments, $L^{14}$ is an unsubstituted 5 to 10 membered heteroarylene. In embodiments, $L^{14}$ includes a substituted or unsubstituted cyclooctynyl. In embodiments, $L^{14}$ includes a substituted cyclooctenyl. In embodiments, $L^{14}$ includes a product of a click chemistry reaction. In embodiments, $L^{14}$ includes a product of a click chemistry reaction including the product of the reaction of a cyclooctyne and an azide.

W is an integer between 0 and 10. W may be an integer between 1 and 10. W may be 0. W may be 1. W may be 2. W may be 3. W may be 4. W may be 5. W may be 6. W may be 7. W may be 8. W may be 9. W may be 10. Y1 is an integer between 0 and 10. Y1 may be an integer between 1 and 10. Y1 may be 10. Y1 may be 1. Y1 may be 2. Y1 may be 3. Y1 may be 4. Y1 may be 5. Y1 may be 6. Y1 may be 7. Y1 may be 8. Y1 may be 9. Y1 may be 10. T1 is an integer between 0 and 10. T1 may be an integer between 1 and 10. T1 may be 0. T1 may be 1. T1 may be 2. T1 may be 3. T1 may be 4. T1 may be 5. T1 may be 6. T1 may be 7. T1 may be 8. T1 may be 9. T1 may be 10.

In embodiments, $R^2$ is hydrogen. In embodiments, $R^3$ is hydrogen. In embodiments, $R^4$ is hydrogen. In embodiments, $R^5$ is hydrogen. In embodiments, $R^6$ is hydrogen. In embodiments, $R^7$ is hydrogen. In embodiments, $R^8$ is hydrogen. In embodiments, $R^9$ is hydrogen. In embodiments, $R^{11}$ is hydrogen. In embodiments, $R^{12}$ is hydrogen. In embodiments, $R^2$ is unsubstituted $C_1$-$C_4$ alkyl. In embodiments, $R^3$ is unsubstituted $C_1$-$C_4$ alkyl. In embodiments, $R^4$ is unsubstituted $C_1$-$C_4$ alkyl. In embodiments, $R^5$ is unsubstituted $C_1$-$C_4$ alkyl. In embodiments, $R^6$ is unsubstituted $C_1$-$C_4$ alkyl. In embodiments, $R^7$ is unsubstituted $C_1$-$C_4$ alkyl. In embodiments, $R^8$ is unsubstituted $C_1$-$C_4$ alkyl. In embodiments, $R^9$ is unsubstituted $C_1$-$C_4$ alkyl. In embodiments, $R^1$ is unsubstituted $C_1$-$C_4$ alkyl. In embodiments, $R^{12}$ is unsubstituted $C_1$-$C_4$ alkyl. In embodiments, $R^2$ is $C_2$-$C_4$ alkynyl. In embodiments, $R^3$ is $C_2$-$C_4$ alkynyl. In embodiments, $R^4$ is $C_2$-$C_4$ alkynyl. In embodiments, $R^5$ is $C_2$-$C_4$ alkynyl. In embodiments, $R^6$ is $C_2$-$C_4$ alkynyl. In embodiments, $R^7$ is $C_2$-$C_4$ alkynyl. In embodiments, $R^8$ is $C_2$-$C_4$ alkynyl. In embodiments, $R^9$ is $C_2$-$C_4$ alkynyl. In embodiments, $R^{11}$ is $C_2$-$C_4$ alkynyl. In embodiments, $R^{12}$ is $C_2$-$C_4$ alkynyl.

$R^2$ may be

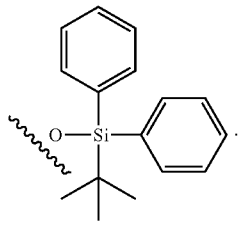

$R^3$ may be

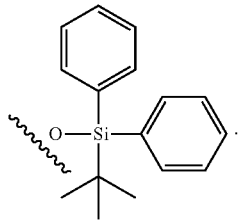

$R^4$ may be

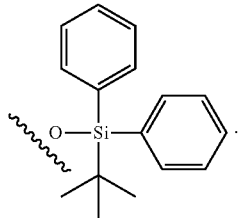

$R^5$ may be

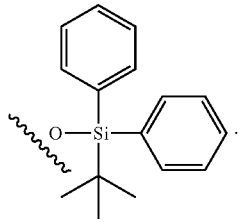

R⁶ may be

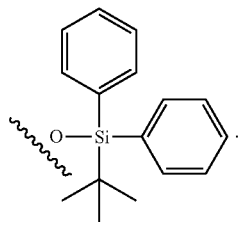

R⁷ may be

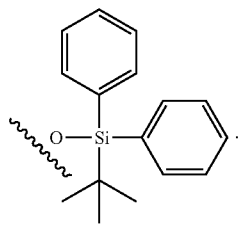

R⁸ may be

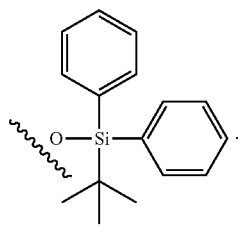

R⁹ may be

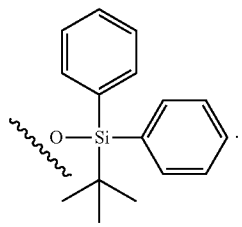

R¹¹ may be

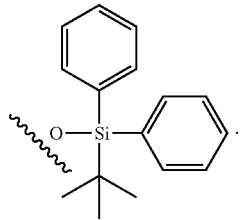

R¹² may be

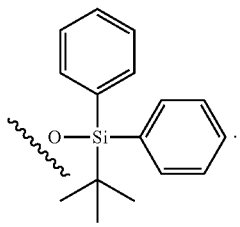

In embodiments, the compound has the formula:

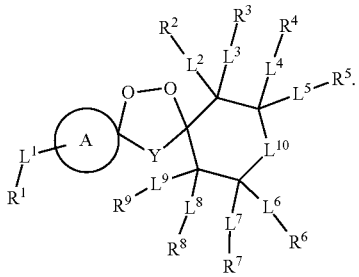

(Ia)

$L^2$, $L^3$, $L^4$, $L^5$, $L^6$, $L^7$, $L^8$, $L^9$, $L^{10}$, $L^{13}$, $L^{14}$, $R^2$, $R^3R^4$, $R^5$, $R^6$, $R^7$, $R^8$, $R^9$, $R^{17}$, and Y are as described herein (e.g. in an aspect, embodiment, example, table, figure, or claim). Ring A is a substituted or unsubstituted cycloalkylene or substituted or unsubstituted heterocycloalkylene. Where ring A is "unsubstituted," Ring A retains the -$L^1$-$R^1$ substituent, but is otherwise not substituted. Likewise, where ring A is "substituted," Ring A includes one or more substituents (e.g. substituent group, size-limited substituent, or lower substituent group as defined above) in addition to the -$L^1$-$R^1$ substituent. $R^1$ is independently a hydrogen, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)—OH, —NHOH, —OCF₃, —OCHF₂, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, a detectable moiety, a siderophore moiety, a folate moiety, or a drug moiety. $L^1$ is independently a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO₂-$L^{13}$-$L^{14}$-, —C(O)N($R^{17}$)-$L^{13}$-$L^{14}$-, —N($R^{17}$)C(O)-$L^{13}$-$L^{14}$-, —S(O)₂N($R^{17}$)-$L^{13}$-$L^{14}$-, —N($R^{17}$)S(O)₂-$L^{13}$-$L^{14}$-, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a bioconjugate linker (e.g. where $R^1$ is, for example a biomolecule such as a protein moiety (e.g antibody moiety, peptide moiety, modified peptide moiety such as peptide moiety including folate).

As described above, each $L^1$, $L^2$, $L^3$, $L^4$, $L^5$, $L^6$, $L^7$, $L^8$, $L^9$, $L^{11}$, and $L^{12}$ may be different. Where each of $L^1$, $L^2$, $L^3$, $L^4$, $L^5$, $L^6$, $L^7$, $L^8$, $L^9$, $L^{11}$, and $L^{12}$ are different, $L^{13}$ may be referred to as $L^{131}$, $L^{132}$, $L^{133}$, $L^{134}$, $L^{135}$, $L^{136}$, $L^{137}$, $L^{138}$, $L^{139}$, $L^{1311}$, and $L^{1312}$ to refer to $L^{13}$ substituents that correlate to $L^1$, $L^2$, $L^3$, $L^4$, $L^5$, $L^6$, $L^7$, $L^8$, $L^9$, $L^{11}$, and $L^{12}$, respectively. Likewise, where each of $L^1$, $L^2$, $L^3$, $L^4$, $L^5$, $L^6$, $L^7$, $L^8$, $L^9$, $L^{11}$, and $L^{12}$ are different, $L^{14}$ may be referred to as $L^{141}$, $L^{142}$, $L^{143}$, $L^{144}$, $L^{145}$, $L^{146}$, $L^{147}$, $L^{148}$, $L^{149}$, $L^{1411}$, and $L^{1412}$ to refer to $L^{14}$ substituents that correlate to $L^1$, $L^2$, $L^3$, $L^4$, $L^5$, $L^6$, $L^7$, $L^8$, $L^9$, $L^{11}$, and $L^{12}$, respectively. Likewise, where each of $L^1$, $L^2$, $L^3$, $L^4$, $L^5$, $L^6$, $L^7$, $L^8$, $L^9$, $L^{11}$, and $L^{12}$ are different, $R^{17}$ may be referred to as $R^{171}$, $R^{172}$, $R^{173}$, $R^{174}$, $R^{175}$, $R^{176}$, $R^{177}$, $R^{178}$, $R^{179}$, $R^{1711}$, and $R^{1712}$ to refer to $R^{17}$ substituents that correlate to $L^1$, $L^2$, $L^3$, $L^4$, $L^5$, $L^6$, $L^7$, $L^8$, $L^9$, $L^{11}$, and $L^{12}$, respectively. For example, in embodiments, $L^1$ is a bond, —N($R^{171}$)-$L^{131}$-$L^{141}$-, —N($R^{171}$)C(O)O-$L^{131}$-$L^{141}$-, —O-$L^{131}$-$L^{141}$-, —S-$L^{131}$-$L^{141}$-, —OC(O)-$L^{131}$-$L^{141}$-, —O C(O)N($R^{171}$)-$L^{131}$-$L^{141}$-, —OC(O)O-$L^{131}$-$L^{141}$-, —OSO$_2$-$L^{131}$-$L^{141}$-, —C(O)N($R^{171}$)-$L^{131}$-$L^{141}$-, —N($R^{171}$)C(O)-$L^{131}$-$L^{141}$-, —S(O)$_2$N($R^{171}$)-$L^{131}$-$L^{141}$-, —N($R^{171}$)S(O)$_2$-$L^{131}$-$L^{141}$-, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, ring A is a substituted or unsubstituted divalent radical of adamantane. In embodiments, ring A is a substituted or unsubstituted adamantylene. In embodiments, ring A is an unsubstituted adamantylene. In embodiments, ring A is a substituted or unsubstituted cycloalkylene. In embodiments, ring A is a substituted or unsubstituted $C_3$-$C_{20}$ cycloalkylene. In embodiments, ring A is a substituted or unsubstituted $C_3$-$C_{18}$ cycloalkylene. In embodiments, ring A is a substituted or unsubstituted $C_3$-$C_{16}$ cycloalkylene. In embodiments, ring A is a substituted or unsubstituted $C_3$-$C_{14}$ cycloalkylene. In embodiments, ring A is a substituted or unsubstituted $C_3$-$C_{12}$ cycloalkylene. In embodiments, ring A is a substituted or unsubstituted $C_3$-$C_{10}$ cycloalkylene. In embodiments, ring A is a substituted or unsubstituted $C_6$-$C_{10}$ cycloalkylene. In embodiments, ring A is a substituted or unsubstituted $C_8$-$C_{10}$ cycloalkylene. In embodiments, ring A is a substituted or unsubstituted 3 to 20 membered heterocycloalkylene. In embodiments, ring A is a substituted or unsubstituted 3 to 18 membered heterocycloalkylene. In embodiments, ring A is a substituted or unsubstituted 3 to 16 membered heterocycloalkylene. In embodiments, ring A is a substituted or unsubstituted 3 to 14 membered heterocycloalkylene. In embodiments, ring A is a substituted or unsubstituted 3 to 12 membered heterocycloalkylene. In embodiments, ring A is a substituted or unsubstituted 3 to 10 membered heterocycloalkylene. In embodiments, ring A is a substituted or unsubstituted 6 to 10 membered heterocycloalkylene. In embodiments, ring A is a substituted or unsubstituted 8 to 10 membered heterocycloalkylene.

In embodiments, -$L^1$-$R^1$ is —H. In embodiments, $R^1$ is hydrogen. In embodiments, $R^1$ is a protein moiety. In embodiments, $R^1$ is an antibody moiety. In embodiments, $R^1$ is a drug moiety. In embodiments, $R^1$ is a detectable moiety. In embodiments, $R^1$ is a fluorescent moiety. In embodiments, $R^1$ is a siderophore moiety. In embodiments, $R^1$ is a folate moiety. In embodiments, $R^1$ is an antibody moiety. In embodiments $L^1$ is a bond. In embodiments $L^1$ is —OC(O)—. In embodiments $L^1$ is —OC(O)NH-Ph-CH$_2$—. In embodiments $L^1$ is —OC(O)NH-Ph-CH$_2$—OC(O)—. In embodiments $L^1$ is —NH-Ph-CH$_2$—. In embodiments $L^1$ is —NH-Ph-CH$_2$—OC(O)—. In embodiments $L^1$ is —O-Ph-CH$_2$—. In embodiments $L^1$ is —O-Ph-CH$_2$—OC(O)—. In embodiments, $L^1$ is

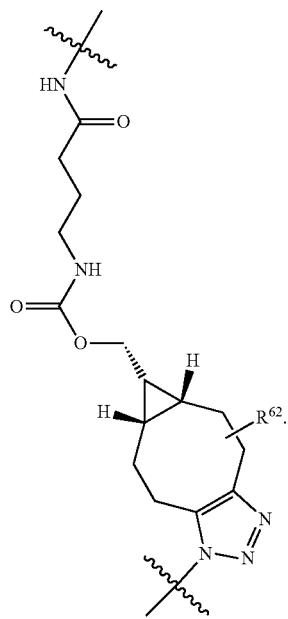

In embodiments, $L^1$ is

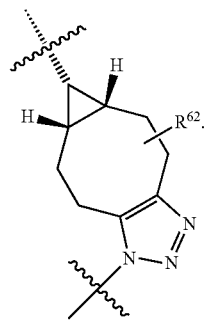

In embodiments, $L^1$ is

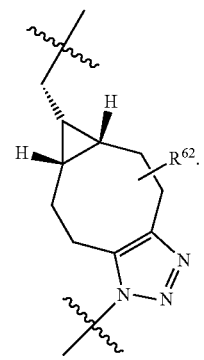

In embodiments, L¹ is
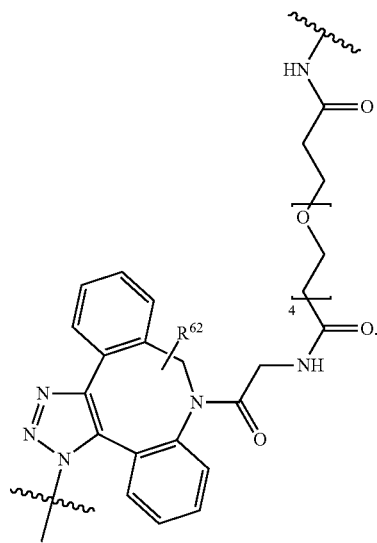
In embodiments, L¹ is
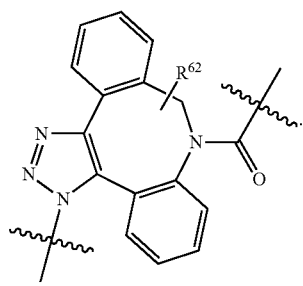
In embodiments, L¹ is
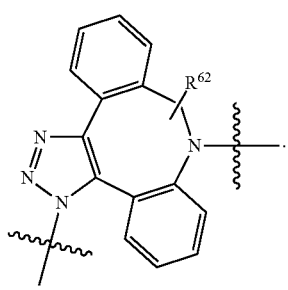
In embodiments, L¹ is
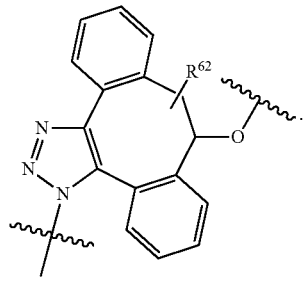
In embodiments, L¹ is
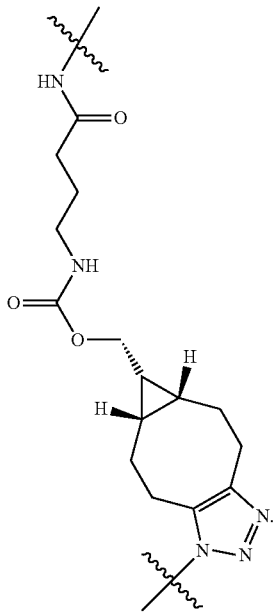
In embodiments, L¹ is
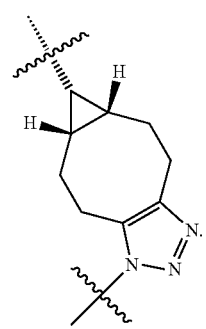

In embodiments, $L^1$ is

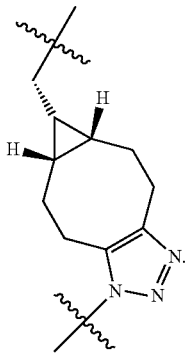

In embodiments, $L^1$ is

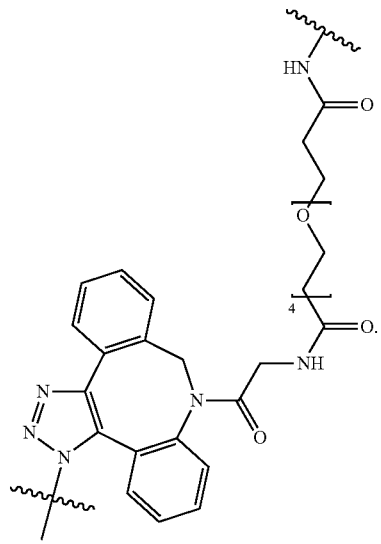

In embodiments, $L^1$ is

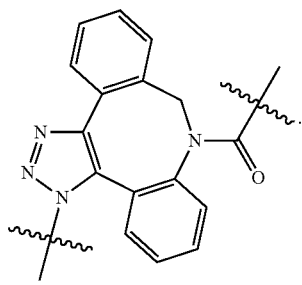 [SMILES: *C(=O)N1Cc2ccccc2-c2nnn(*)c2-c2ccccc21]

In embodiments, $L^1$ is

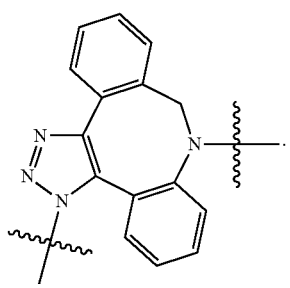 [SMILES: *N1Cc2ccccc2-c2nnn(*)c2-c2ccccc21]

In embodiments, $L^1$ is

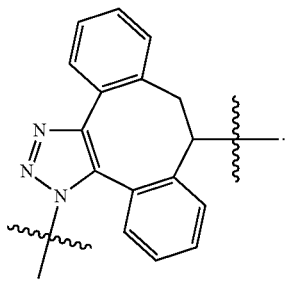 [SMILES: *C1Cc2ccccc2-c2nnn(*)c2-c2ccccc21]

In embodiments, $L^1$ is

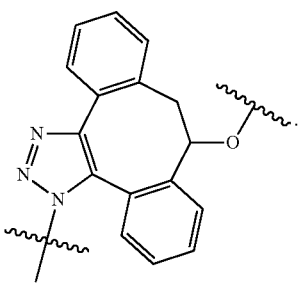 [SMILES: *OC1Cc2ccccc2-c2nnn(*)c2-c2ccccc21]

In embodiments, $L^1$ is —NHC(O)—(CH$_2$)$_W$—NHC(O)O—(CH$_2$)$_{Y1}$—. In embodiments, $L^1$ is —NHC(O)—(CH$_2$)$_W$—C(O)NH—(CH$_2$)$_{Y1}$—. In embodiments, $L^1$ is —NHC(O)—(CH$_2$)$_W$—C(O)—. In embodiments, $L^1$ is —NHC(O)—(CH$_2$)$_W$—NH—. In embodiments, $L^1$ is —NHC(O)—(CH$_2$)$_W$—NHC(O)—. In embodiments, $L^1$ is —NHC(O)—(CH$_2$)$_W$—C(O)NH—. In embodiments, $L^1$ is —NHC(O)—(CH$_2$)$_W$—NHC(O)O—. In embodiments, $L^1$ is —NHC(O)—(CH$_2$)$_W$—(OCH$_2$CH$_2$)$_{T1}$—C(O)NH—(CH$_2$)$_{Y1}$—. In embodiments, $L^1$ is —NHC(O)—(CH$_2$)$_W$—(OCH$_2$CH$_2$)$_{T1}$—C(O)NH—(CH$_2$)$_{Y1}$—C(O)—. In embodiments, $L^1$ is a substituted or unsubstituted $C_1$-$C_{20}$ alkylene. In embodiments, $L^1$ is a substituted or unsubstituted 2 to 20 membered heteroalkylene. In embodiments, $L^1$ is a substituted or unsubstituted $C_3$-$C_{20}$ cycloalkylene. In embodiments, $L^1$ is a substituted or unsubstituted 3 to 20 membered heterocycloalkylene. In embodiments, $L^1$ is a substituted or unsubstituted $C_6$-$C_{20}$ arylene. In embodiments, $L^1$ is a substituted or unsubstituted 5 to 20 membered heteroarylene. In embodiments, $L^1$ is a substituted $C_1$-$C_{20}$ alkylene. In embodiments, $L^1$ is a substituted 2 to 20 membered heteroalkylene. In embodiments, $L^1$ is a substituted $C_3$-$C_{20}$ cycloalkylene. In embodiments, $L^1$ is a substituted 3 to 20 membered heterocycloalkylene. In embodiments, $L^1$ is a substituted $C_6$-$C_{20}$ arylene. In embodiments, $L^1$ is a substituted 5 to 20 membered heteroarylene. In embodiments, $L^1$ is an unsubstituted $C_1$-$C_{20}$ alkylene. In embodiments, $L^1$ is an unsubstituted 2 to 20 membered heteroalkylene. In embodiments, $L^1$ is an unsubstituted $C_3$-$C_{20}$ cycloalkylene. In embodiments, $L^1$ is an unsubstituted 3 to 20 membered heterocycloalkylene. In embodiments, $L^1$ is an unsubstituted $C_6$-$C_{20}$ arylene. In embodiments, $L^1$ is an unsubstituted 5 to 20 membered heteroarylene. In embodiments, $L^1$ is a substituted or unsubstituted $C_1$-$C_{14}$ alkylene. In embodiments, $L^1$ is a substituted or unsubstituted 2 to 14 membered heteroalkylene. In embodiments, $L^1$ is a substituted or unsubstituted $C_3$-$C_{14}$ cycloalkylene. In embodiments, $L^1$ is a substituted or unsubstituted 3 to 14 membered heterocycloalkylene. In embodiments, $L^1$ is a substituted or unsubstituted $C_6$-$C_{14}$ arylene. In embodiments, $L^1$ is a substituted or unsubstituted 5 to 14 membered heteroarylene. In embodiments, $L^1$ is a substituted $C_1$-$C_{14}$ alkylene. In embodiments, $L^1$ is a substituted 2 to 14 membered heteroalkylene. In embodiments, $L^1$ is a substituted $C_3$-$C_{14}$ cycloalkylene. In embodiments, $L^1$ is a substituted 3 to 14 membered heterocycloalkylene. In embodiments, $L^1$ is a substituted $C_6$-$C_{14}$ arylene. In embodiments, $L^1$ is a substituted 5 to 14 membered heteroarylene. In embodiments, $L^1$ is an unsubstituted $C_1$-$C_{14}$ alkylene. In embodiments, $L^1$ is an unsubstituted 2 to 14 membered heteroalkylene. In embodiments, $L^1$ is an unsubstituted $C_3$-$C_{14}$ cycloalkylene. In embodiments, $L^1$ is an unsubstituted 3 to 14 membered heterocycloalkylene. In embodiments, $L^1$ is an unsubstituted $C_6$-$C_{14}$ arylene. In embodiments, $L^1$ is an unsubstituted 5 to 14 membered heteroarylene. In embodiments, $L^1$ is a substituted or unsubstituted $C_1$-$C_8$ alkylene. In embodiments, $L^1$ is a substituted or unsubstituted 2 to 8 membered heteroalkylene. In embodiments, $L^1$ is a substituted or unsubstituted $C_3$-$C_8$ cycloalkylene. In embodiments, $L^1$ is a substituted or unsubstituted 3 to 8 membered heterocycloalkylene. In embodiments, $L^1$ is a substituted or unsubstituted $C_6$-$C_{10}$ arylene. In embodiments, $L^1$ is a substituted or unsubstituted 5 to 10 membered heteroarylene. In embodiments, $L^1$ is a substituted $C_1$-$C_8$ alkylene. In embodiments, $L^1$ is a substituted 2 to 8 membered heteroalkylene. In embodiments, $L^1$ is a substituted $C_3$-$C_8$ cycloalkylene. In embodiments, $L^1$ is a substituted 3 to 8 membered heterocycloalkylene. In embodiments, $L^1$ is a substituted $C_6$-$C_{10}$ arylene. In embodiments, $L^1$ is a substituted 5 to 10 membered heteroarylene. In embodiments, $L^1$ is an unsubstituted $C_1$-$C_8$ alkylene. In embodiments, $L^1$ is an unsubstituted 2 to 8 membered heteroalkylene. In embodiments, $L^1$ is an unsubstituted $C_3$-$C_8$ cycloalkylene. In embodiments, $L^1$ is an unsubstituted 3 to 8 membered heterocycloalkylene. In embodiments, $L^1$ is an unsubstituted $C_6$-$C_{10}$ arylene. In embodiments, $L^1$ is an unsubstituted 5 to 10 membered heteroarylene. In embodiments, $L^1$ includes a substituted or unsubstituted cyclooctynyl. In embodiments, $L^1$ includes a substituted cyclooctenyl. In embodiments, $L^1$ includes a product of a click chemistry reaction. In embodiments, $L^1$ includes a product of a click chemistry reaction including the product of the reaction of a cyclooctyne and an azide. In embodiments, $L^1$ is

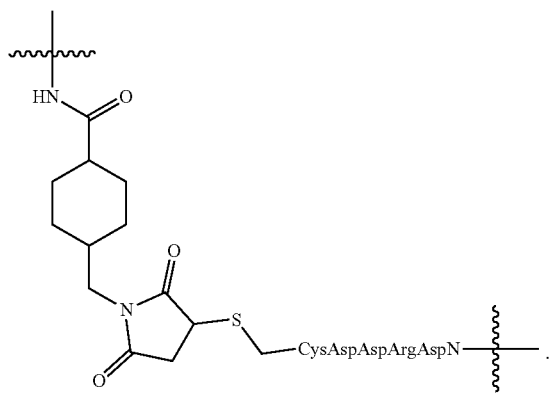

In embodiments, $L^1$ includes

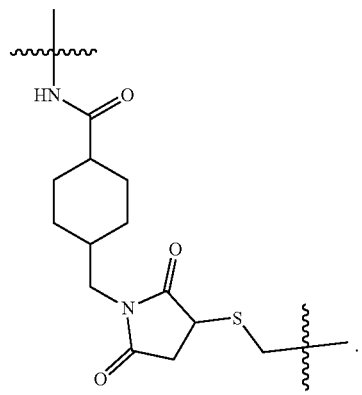 [SMILES: *CSC1CC(=O)N(CC2CCC(C(=O)N*)CC2)C1=O]

W is an integer between 0 and 10. W may be an integer between 1 and 10. W may be 0. W may be 1. W may be 2. W may be 3. W may be 4. W may be 5. W may be 6. W may be 7. W may be 8. W may be 9. W may be 10. Y1 is an integer between 0 and 10. Y1 may be an integer between 1 and 10. Y1 may be 0. Y1 may be 1. Y1 may be 2. Y1 may be 3. Y1 may be 4. Y1 may be 5. Y1 may be 6. Y1 may be 7. Y1 may be 8. Y1 may be 9. Y1 may be 10. T1 is an integer between 0 and 10. T1 may be an integer between 1 and 10. T1 may be 0. T1 may be 1. T1 may be 2. T1 may be 3. T1 may be 4. T1 may be 5. T1 may be 6. T1 may be 7. T1 may be 8. T1 may be 9. T1 may be 10.

In embodiment, $R^1$ is a protein moiety bonded to $L^1$ through an N of the protein moiety. In embodiment, $R^1$ is a protein moiety bonded to $L^1$ through an O of the protein moiety. In embodiment, $R^1$ is a protein moiety bonded to $L^1$ through an S of the protein moiety. In embodiment, $R^1$ is a protein moiety bonded to $L^1$ through an O of a —OC(O)— of the protein moiety. In embodiment, $R^1$ is a detectable moiety. In embodiment, $R^1$ is a detectable moiety bonded to $L^1$ through an N of the detectable moiety. In embodiment, $R^1$ is a detectable moiety bonded to $L^1$ through an O of the detectable moiety. In embodiment, $R^1$ is a detectable moiety bonded to $L^1$ through an S of the detectable moiety. In embodiment, $R^1$ is a detectable moiety bonded to $L^1$ through an O of a —OC(O)— of the detectable moiety. In embodiment, $R^1$ is a drug moiety. In embodiment, $R^1$ is a drug moiety bonded to $L^1$ through an N of the drug moiety. In embodiment, $R^1$ is a drug moiety bonded to $L^1$ through an O of the drug moiety. In embodiment, $R^1$ is a drug moiety bonded to $L^1$ through an S of the drug moiety. In embodiment, $R^1$ is a drug moiety bonded to $L^1$ through an O of a —OC(O)— of the drug moiety. In embodiments, $R^1$ is unsubstituted $C_1$-$C_4$ alkyl. In embodiments, $R^1$ is unsubstituted $C_2$-$C_4$ alkynyl. In embodiment, $R^1$ is a siderophore moiety. In embodiment, $R^1$ is a siderophore moiety bonded to $L^1$ through an N of the siderophore moiety. In embodiment, $R^1$ is a siderophore moiety bonded to $L^1$ through an O of the siderophore moiety. In embodiment, $R^1$ is a siderophore moiety bonded to $L^1$ through an S of the siderophore moiety. In embodiment, $R^1$ is a siderophore moiety bonded to $L^1$ through an O of a —OC(O)— of the siderophore moiety. In embodiments, $R^1$ is a ligand for a receptor. In embodiments, $R^1$ is a receptor. In embodiments, $R^1$ is a chelator (e.g., metal chelator, iron chelator). In embodiments, $R^1$ is independently a hydrogen, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O) $NH_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, a detectable moiety, or a drug moiety. In embodiments, R$^1$ is

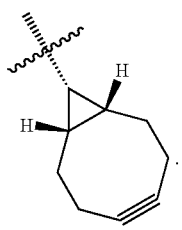

In embodiments R$^1$ is

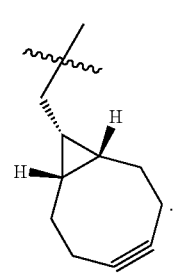 [SMILES: *C[C@H]1[C@H]2CCC#CCC[C@@H]12]

In embodiments, R$^1$ is

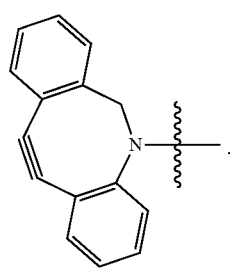 [SMILES: *N1Cc2ccccc2C#Cc2ccccc21]

In embodiments, R$^1$ is

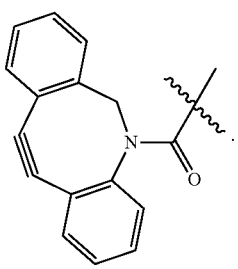 [SMILES: *C(=O)N1Cc2ccccc2C#Cc2ccccc21]

In embodiments, R$^1$ is

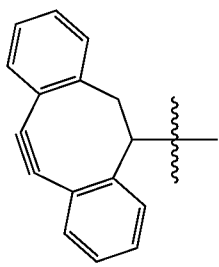

In embodiments, R$^1$ is

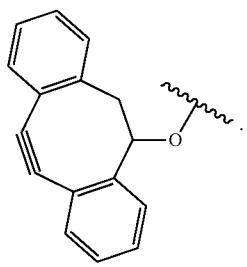 [SMILES: *OC1Cc2ccccc2C#Cc2ccccc21]

In embodiments, R$^1$ is H

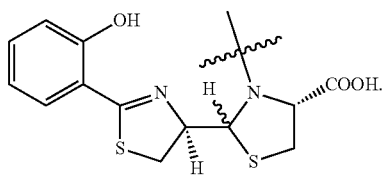 [SMILES: *N1C([C@H]2CSC(c3ccccc3O)=N2)SC[C@H]1C(=O)O]

In embodiments, R$^1$ is

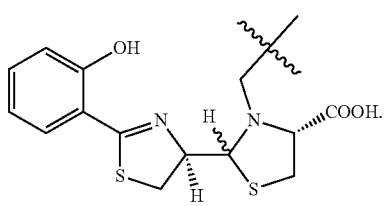 [SMILES: *CN1C([C@H]2CSC(c3ccccc3O)=N2)SC[C@H]1C(=O)O]

In embodiments, R$^1$ is

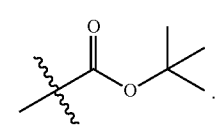 [SMILES: *C(=O)OC(C)(C)C]

$R^1$ may be

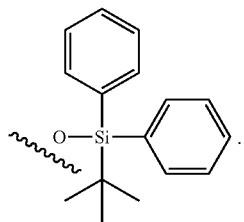

In embodiments, $R^1$ is folate. In embodiments, $R^1$ is a folate moiety. In embodiments, $R^1$ is a folate derivative. In embodiments, $R^1$ is a folate derivative moiety. In embodiments, $R^1$ is a siderophore. In embodiments, $R^1$ is a siderophore moiety.

In embodiments, the compound has the formula:

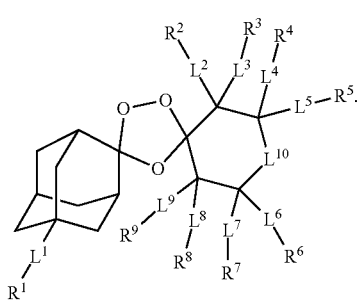

(Ib)

$L^1$, $L^2$, $L^3$, $L^4$, $L^5$, $L^6$, $L^7$, $L^8$, $L^9$, $L^{10}$, $L^{13}$, $L^{14}$, $R^1$, $R^2$, $R^3$, $R^4$, $R^5$, $R^6$, $R^7$, $R^8$, $R^9$, and $R^{17}$ are as described herein (e.g. in an aspect, embodiment, example, table, figure, or claim).

In embodiments, $L^2$, $L^3$, $L^5$, $L^6$, $L^7$, $L^8$, $L^9$, $L^{11}$, and $L^{12}$ are each a bond; $R^2$, $R^3$, $R^5$, $R^6$, $R^7$, $R^8$, $R^9$, $R^{11}$, and $R^{12}$ are each hydrogen; $L^{10}$ is —$CH_2$—; $L^4$ is a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, —N($R^{17}$)S(O)$_2$-$L^{13}$-$L^{14}$-; and $R^4$ is a protein moiety, drug moiety, or a detectable moiety. In embodiments $L^4$ is a bond, —OC(O)—, —OC(O)NH-Ph-$CH_2$—, —OC(O)NH-Ph-$CH_2$—OC(O)—, —NH-Ph-$CH_2$—, —NH-Ph-$CH_2$—OC(O)—, —O-Ph-$CH_2$—, or —O-Ph-$CH_2$—OC(O)—. In embodiment, $R^4$ is independently a protein moiety. In embodiment, $R^4$ is independently a drug moiety. In embodiment, $R^4$ is independently a detectable moiety.

In embodiments, $L^2$, $L^3$, $L^5$, $L^7$, $L^8$, $L^9$, $L^{11}$, and $L^{12}$ are each a bond; $R^2$, $R^3$, $R^5$, $R^7$, $R^8$, $R^9$, $R^{11}$, and $R^{12}$ are each hydrogen; $L^4$ and $L^6$ are independently a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, or —N($R^{17}$)S(O)$_2$-$L^{13}$-$L^{14}$-; and $R^4$ and $R^6$ are each independently a drug moiety, protein moiety, or detectable moiety. In embodiments $L^4$ is a bond, —OC(O)—, —OC(O)NH-Ph-$CH_2$—, —OC(O)NH-Ph-$CH_2$—OC(O)—, —NH-Ph-$CH_2$—, —NH-Ph-$CH_2$—OC(O)—, —O-Ph-$CH_2$—, or —O-Ph-$CH_2$—OC(O)—. In embodiment, $R^4$ is independently a protein moiety. In embodiment, $R^4$ is independently a drug moiety. In embodiment, $R^4$ is independently a detectable moiety. In embodiments $L^6$ is a bond, —OC(O)—, —OC(O)NH-Ph-$CH_2$—, —OC(O)NH-Ph-$CH_2$—OC(O)—, —NH-Ph-$CH_2$—, —NH-Ph-$CH_2$—OC(O)—, —O-Ph-$CH_2$—, or —O-Ph-$CH_2$—OC(O)—. In embodiment, $R^6$ is independently a protein moiety. In embodiment, $R^6$ is independently a drug moiety. In embodiment, $R^6$ is independently a detectable moiety.

In embodiments, $L^2$, $L^3$, $L^4$, $L^5$, $L^6$, $L^7$, $L^8$, $L^9$, and $L^{12}$ are each a bond; $R^2$, $R^3$, $R^4$, $R^5$, $R^6$, $R^7$, $R^8$, $R^9$, and $R^{12}$ are each hydrogen; $L^{10}$ is —N(-$L^{11}$-$R^{11}$)—; $L^{11}$ is a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, —N($R^{17}$)S(O)$_2$-$L^{13}$-$L^{14}$-; and $R^{11}$ is a drug moiety, protein moiety, or detectable moiety. In embodiments $L^{11}$ is a bond, —OC(O)—, —OC(O)NH-Ph-$CH_2$—, —OC(O)NH-Ph-$CH_2$—OC(O)—, —NH-Ph-$CH_2$—, —NH-Ph-$CH_2$—OC(O)—, —O-Ph-$CH_2$—, or —O-Ph-$CH_2$—OC(O)—. In embodiment, $R^{11}$ is independently a protein moiety. In embodiment, $R^{11}$ is independently a drug moiety. In embodiment, $R^{11}$ is independently a detectable moiety.

In embodiments, $L^2$, $L^3$, $L^5$, $L^6$, $L^7$, $L^8$, $L^9$, $L^{11}$, and $L^{12}$ are each a bond; $R^2$, $R^3$, $R^5$, $R^7$, $R^8$, $R^9$, and $R^{12}$ are each hydrogen; $L^{10}$ is —CH(—$R^{11}$)—; $R^6$ and $R^{11}$ are joined to form a substituted or unsubstituted cycloalkyl, substituted or unsubstituted heterocycloalkyl, substituted or unsubstituted aryl, or substituted or unsubstituted heteroaryl; $L^4$ is a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, or —N($R^{17}$)S(O)$_2$-$L^{13}$-$L^{14}$-; and $R^4$ is a drug moiety, protein moiety, or detectable moiety. In embodiments, $R^6$ and $R^{11}$ are joined to form an unsubstituted aryl (it is understood that the unsubstituted aryl is a fused ring that does not include additional substituents beyond the fused ring). In embodiments, $R^6$ and $R^1$ are joined to form an unsubstituted phenyl. In embodiments $L^4$ is a bond, —OC(O)—, —OC(O)NH-Ph-$CH_2$—, —OC(O)NH-Ph-$CH_2$—OC(O)—, —NH-Ph-$CH_2$—, —NH-Ph-$CH_2$—OC(O)—, —O-Ph-$CH_2$—, or —O-Ph-$CH_2$—OC(O)—. In embodiment, $R^4$ is independently a protein moiety. In embodiment, $R^4$ is independently a drug moiety. In embodiment, $R^4$ is independently a detectable moiety.

In embodiments, $L^2$, $L^3$, $L^4$, $L^6$, $L^7$, $L^8$, $L^9$, $L^{11}$, and $L^{12}$ are each a bond; $R^2$, $R^3$, $R^4$, $R^6$, $R^7$, $R^8$, $R^9$, $R^{11}$, and $R^{12}$ are each hydrogen; $L^{10}$ is —$CH_2$—; $L^5$ is a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, —N($R^{17}$)S(O)$_2$-$L^{13}$-$L^{14}$-; and $R^5$ is a protein moiety, drug moiety, or a detectable moiety. In embodiments $L^5$ is a bond, —OC(O)—, —OC(O)NH-Ph-$CH_2$—, —OC(O)NH-Ph-$CH_2$—OC(O)—, —NH-Ph-$CH_2$—, —NH-Ph-$CH_2$—OC(O)—, —O-Ph-$CH_2$—, or —O-Ph-$CH_2$—OC(O)—. In embodiment, $R^5$ is independently a protein moiety. In embodiment, $R^5$ is independently a drug moiety. In embodiment, $R^5$ is independently a detectable moiety.

In embodiments, $L^2$, $L^3$, $L^4$, $L^6$, $L^8$, $L^9$, $L^{11}$, and $L^{12}$ are each a bond; $R^2$, $R^3$, $R^4$, $R^6$, $R^8$, $R^9$, $R^{11}$, and $R^{12}$ are each hydrogen; $L^5$ and $L^7$ are independently a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N $(R^{17})$-$L^{13}$-$L^{14}$-, —N($R^{17}$)C(O)-$L^{13}$-$L^{14}$-, —S(O)$_2$N($R^{17}$)-$L^{13}$-$L^{14}$-, or —N($R^{17}$)S(O)$_2$-$L^{13}$-$L^{14}$-; and $R^5$ and $R^7$ are each independently a drug moiety, protein moiety, or detectable moiety. In embodiments $L^5$ is a bond, —OC(O)—, —OC(O)NH-Ph-CH$_2$—, —OC(O)NH-Ph-CH$_2$—OC(O)—, —NH-Ph-CH$_2$—, —NH-Ph-CH$_2$—OC(O)—, —O-Ph-CH$_2$—, or —O-Ph-CH$_2$—OC(O)—. In embodiment, $R^5$ is independently a protein moiety. In embodiment, $R^5$ is independently a drug moiety. In embodiment, $R^5$ is independently a detectable moiety. In embodiments $L^7$ is a bond, —OC(O)—, —OC(O)NH-Ph-CH$_2$—, —OC(O)NH-Ph-CH$_2$—OC(O)—, —NH-Ph-CH$_2$—, —NH-Ph-CH$_2$—OC(O)—, —O-Ph-CH$_2$—, or —O-Ph-CH$_2$—OC(O)—. In embodiment, $R^7$ is independently a protein moiety. In embodiment, $R^7$ is independently a drug moiety. In embodiment, $R^7$ is independently a detectable moiety.

In embodiments, $L^2$, $L^3$, $L^4$, $L^5$, $L^6$, $L^7$, $L^8$, $L^9$, and $L^{12}$ are each a bond; $R^2$, $R^3$, $R^4$, $R^5$, $R^6$, $R^7$, $R^8$, $R^9$, and $R^{12}$ are each hydrogen; $L^{10}$ is —N(-$L^{11}$-$R^{11}$)—; $L^{11}$ is a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{11}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, —N($R^{17}$)S(O)$_2$-$L^{13}$-$L^{14}$-; and $R^{11}$ is a drug moiety, protein moiety, or detectable moiety. In embodiments $L^{11}$ is a bond, —OC(O)—, —OC(O)NH-Ph-CH$_2$—, —OC(O)NH-Ph-CH$_2$—OC(O)—, —NH-Ph-CH$_2$—, —NH-Ph-CH$_2$—OC(O)—, —O-Ph-CH$_2$—, or —O-Ph-CH$_2$—OC(O)—. In embodiment, $R^{11}$ is independently a protein moiety. In embodiment, $R^{11}$ is independently a drug moiety. In embodiment, $R^{11}$ is independently a detectable moiety.

In embodiments, $L^2$, $L^3$, $L^4$, $L^6$, $L^7$, $L^8$, $L^9$, $L^{11}$, and $L^{12}$ are each a bond; $R^2$, $R^3$, $R^4$, $R^6$, $R^8$, $R^9$, and $R^{12}$ are each hydrogen; $L^{10}$ is —CH(—$R^{11}$)—; $R^7$ and $R^{11}$ are joined to form a substituted or unsubstituted cycloalkyl, substituted or unsubstituted heterocycloalkyl, substituted or unsubstituted aryl, or substituted or unsubstituted heteroaryl; $L^5$ is a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, or —N($R^{17}$)S(O)$_2$-$L^{13}$-$L^{14}$-; and $R^5$ is a drug moiety, protein moiety, or detectable moiety. In embodiments, $R^7$ and $R^{11}$ are joined to form an unsubstituted aryl (it is understood that the unsubstituted aryl is a fused ring that does not include additional substituents beyond the fused ring). In embodiments, $R^7$ and $R^{11}$ are joined to form an unsubstituted phenyl. In embodiments $L^5$ is a bond, —OC(O)—, —OC(O)NH-Ph-CH$_2$—, —OC(O)NH-Ph-CH$_2$—OC(O)—, —NH-Ph-CH$_2$—, —NH-Ph-CH$_2$—OC(O)—, —O-Ph-CH$_2$—, or —O-Ph-CH$_2$—OC(O)—. In embodiment, $R^5$ is independently a protein moiety. In embodiment, $R^5$ is independently a drug moiety. In embodiment, $R^5$ is independently a detectable moiety.

In embodiments, the drug moiety is independently a monovalent radical of an anti-infective agent. In embodiments, the anti-infective agent is an anti-parasitic drug. In embodiments, the anti-infective agent is an anti-bacterial drug. In embodiments, the anti-infective agent is an anti-malarial drug. In embodiments, the drug moiety is independently a monovalent radical of an anti-cancer agent. In embodiments, the detectable moiety is independently a monovalent radical of a fluorophore. In embodiments, the protein moiety is independently a monovalent radical of an antibody. In embodiments, the drug moiety is a monovalent radical of an anti-cancer agent described herein having an N, O, S, or OC(O) group capable of binding the prodrug moiety (e.g. component of the compounds described herein not including a drug moiety, detectable moiety, or protein moiety). In embodiments, the drug moiety is a monovalent radical of an anti-infective agent described herein having an N, O, S, or OC(O) group capable of binding the prodrug moiety (e.g. component of the compounds described herein not including a drug moiety, detectable moiety, or protein moiety).

In embodiments, the drug moiety is a moiety of a pyrrolo benzodiazepine (e.g. tomaymycin), carboplatin, CC-1065, CC-1065 analog (e.g. amino-CBIs), nitrogen mustard (such as chlorambucil or melphalan), phosphoroamidate mustard, combretastatin, combretastatin analog, puromycin, centanamycin, gemcitabine, dolastatin, dolastatin analog (including auristatin (e.g. monomethyl auristatin E), anthracycline antibiotic (such as doxorubicin, daunorubicin), a duocarmycin, duocarmycin analog, enediynes (such as neocarzinostatin or calicheamicins), leptomycin derivaties, maytansinoid, maytansinoid analog (e.g. mertansine), methotrexate, mitomycin C, a taxoid, a vinca alkaloid (such as vinblastine or vincristine), epothilones, camptothecin, camptothecin analog, topotecan, or irinotecan.

In embodiments, the drug moiety is a moiety of amodiaquine, atovaquone, chloroquine, clardribine, clindamycin, cytarabine, daunorubicin, docetaxel, doxorubicin, doxycycline, etoposide, fansidar, fludarabine, halofantrine, idarubicin, imiquimod, irinotecan, mefloquine, methotrexate, mitomycin, oxamniquine, paclitaxel, plicamycin, primaquine, proquanil, pyrimethamine, quinidine, quinine, topotecan, vinblastine, vincristine, KA609, KAF 156, tafenoquine, or pyronaridine. In embodiments, the drug moiety is a moiety of an anti-bacterial agent described herein. In embodiments, the drug moiety is a moiety of an anti-cancer agent described herein. In embodiments, the drug moiety is a moiety of an antibody or antigen-binding fragment thereof described herein. In embodiments, the drug moiety is a moiety of an anti-malarial agent described herein.

In some embodiments, the agent moiety (e.g. drug moiety, detectable moiety, protein moiety) that forms part of the prodrug is chemically changed under physiological conditions to form an agent (e.g. drug, detectable agent, protein) selected from an anti-cancer agent or anti-infective agent (e.g. antibiotic, anti-parasitic agent, anti-viral agent), detectable agent (e.g. fluorescent agent), or protein (e.g. antibody). Examples of agents include amodiaquine, mefloquine, chloroquine, primaquine, imiquimod, oxamniquine, doxycycline, clindamycin, quinine, quinidine, halofantrine, artesunate, fansidar, atovaquone, pyrimethamine, proguanil, vinblastine, vincristine, daunorubicin, docetaxel, paclitaxel, irinotecan, etoposide, doxorubicin, idarubicin, mitomycin, plicamycin, topotecan, clardribine, cytarabine, fludarabine, and methotrexate. In some embodiments, the agent (e.g. drug, detectable agent, protein) moiety that forms part of the prodrug is a moiety as described herein.

In embodiments, the detectable moiety is a moiety of a fluorescent protein, a xanthene derivative (e.g. fluorescein, rhodamine, Oregon green, eosin, or Texas red), cyanine, a cyanine derivative (e.g. cyanine, indocarbocyanine, oxacarbocyanine, thiacarbocyanine or merocyanine), a napththalene derivative (e.g. dansyl or prodan or derivatives), coumarin, a coumarin derivative, an oxadiazole derivative (e.g. pyridyloxazole, nitrobenzoxadiazole or benzoxadiazole), an anthracene derivative (e.g. anthraquinones, DRAQ5, DRAQ7, or CyTRAK Orange), a pyrene derivative (e.g. cascade blue and derivatives), an oxazine derivative (e.g. Nile red, Nile blue, cresyl violet, oxazine 170), an acridine derivative (e.g. proflavin, acridine orange, acridine yellow), am arylmethine derivative (e.g. auramine, crystal violet, malachite green), tetrapyrrole derivative (e.g. porphin, phthalocyanine, bilirubin), CF Dye™, DRAQ™, CyTRAK™, BODIPY™, an Alexa Fluor™, DyLight Fluor™, Atto™, Tracy™, FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™, Phycobilisomes™, APC™, APCXL™, RPE™, or BPE™. In embodiments, the detectable moiety is a monovalent radical of a detectable agent described herein having an N, O, S, or OC(O) group capable of binding the prodrug moiety (e.g. component of the compounds described herein not including a drug moiety, detectable moiety, or protein moiety). In embodiments, the detectable moiety is a moiety described herein.

In embodiments, the protein moiety is an antibody moiety. In embodiments the antibody moiety is a moiety of bevacizumab, cetuximab, denosumab, ipilimumab, panitumumab, trastuzumab, or catumaxomab. In embodiments, the protein moiety is a monovalent radical of a protein described herein having an N, O, S, or OC(O) group capable of binding the prodrug moiety (e.g. component of the compounds described herein not including a drug moiety, detectable moiety, or protein moiety). In embodiments, the protein moiety is a moiety of an antibody, or an antigen-binding fragment thereof, described herein.

In embodiments, -$L^{11}$-$R^{11}$ and -$L^{12}$-$R^{12}$ are hydrogen. In embodiments, -$L^{11}$-$R^{11}$ is hydrogen. In embodiments, -$L^{12}$-$R^{12}$ is hydrogen.

In embodiments, the compound is not a compound including: $R^{11}$ and $R^{12}$ do not independently include a drug moiety, protein moiety, or detectable moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound including: $R^{11}$ and $R^{12}$ are not independently a drug moiety, protein moiety, or detectable moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound including: $R^{11}$ and $R^{12}$ do not independently include a drug moiety, protein moiety, or detectable moiety; $R^{18}$ and $R^{19}$ are joined to form a substituted or unsubstituted cycloalkyl, substituted or unsubstituted heterocycloalkyl, protein moiety, detectable moiety, or drug moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound including: $R^{11}$ and $R^{12}$ are not independently a drug moiety, protein moiety, or detectable moiety; $R^{18}$ and $R^{19}$ are joined to form a substituted or unsubstituted cycloalkyl, substituted or unsubstituted heterocycloalkyl, protein moiety, detectable moiety, or drug moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound including: $R^{11}$ and $R^{12}$ do not independently include a drug moiety, protein moiety, or detectable moiety; $R^{18}$ and $R^{19}$ are joined to form an unsubstituted adamantyl; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound including: $R^{11}$ and $R^{12}$ are not independently a drug moiety, protein moiety, or detectable moiety; $R^{18}$ and $R^{19}$ are joined to form an unsubstituted adamantyl; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen.

In embodiments, the compound is not a compound wherein $R^{11}$ and $R^{12}$ do not independently include a drug moiety, protein moiety, or detectable moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound wherein $R^{11}$ and $R^{12}$ are not independently a drug moiety, protein moiety, or detectable moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound wherein $R^{11}$ and $R^{12}$ do not independently include a drug moiety, protein moiety, or detectable moiety; $R^{18}$ and $R^{19}$ are joined to form a substituted or unsubstituted cycloalkyl, substituted or unsubstituted heterocycloalkyl, protein moiety, detectable moiety, or drug moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound wherein $R^{11}$ and $R^{12}$ are not independently a drug moiety, protein moiety, or detectable moiety; $R^{18}$ and $R^{19}$ are joined to form a substituted or unsubstituted cycloalkyl, substituted or unsubstituted heterocycloalkyl, protein moiety, detectable moiety, or drug moiety; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound wherein $R^{11}$ and $R^{12}$ do not independently include a drug moiety, protein moiety, or detectable moiety; $R^{18}$ and $R^{19}$ are joined to form an unsubstituted adamantyl; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound wherein $R^{11}$ and $R^{12}$ are not independently a drug moiety, protein moiety, or detectable moiety; $R^{18}$ and $R^{19}$ are joined to form an unsubstituted adamantyl; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound wherein $R^{11}$ and $R^{12}$ do not independently include a drug moiety, protein moiety, or detectable moiety; $R^{18}$ and $R^{19}$ are joined to form a substituted adamantyl; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen. In embodiments, the compound is not a compound wherein $R^{11}$ and $R^{12}$ are not independently a drug moiety, protein moiety, or detectable moiety; $R^{18}$ and $R^{19}$ are joined to form a substituted adamantyl; $L^2$, $L^3$, $L^4$, $L^5$, $L^6$, $L^7$, $L^8$, and $L^9$ are bonds; and $R^2$, $R^3$, $R^4$, $R^5$, $R^6$, $R^7$, $R^8$, and $R^9$ are hydrogen.

In embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ are independently oxo, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, —C(O)$CH_3$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

Each $R^{20}$ is independently oxo, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —S $O_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCH_3$, —$OCF_3$, —$OCHF_2$, —C(O)$CH_3$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

Each $R^{21}$ is independently oxo, halogen, —$CF_3$, —$CCl_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —C(O)CH$_3$, R$^{22}$-substituted or unsubstituted alkyl, R$^{22}$-substituted or unsubstituted heteroalkyl, R$^{22}$-substituted or unsubstituted cycloalkyl, R$^{22}$-substituted or unsubstituted heterocycloalkyl, R$^{22}$-substituted or unsubstituted aryl, or R$^{22}$-substituted or unsubstituted heteroaryl.

Each R$^{22}$ is independently oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —C(O)CH$_3$, unsubstituted alkyl, unsubstituted heteroalkyl, unsubstituted cycloalkyl, unsubstituted heterocycloalkyl, unsubstituted aryl, or unsubstituted heteroaryl.

In embodiments, L$^1$, L$^2$, L$^3$, L$^4$, L$^5$, L$^6$, L$^7$, L$^8$, L$^9$, L$^{10}$, L$^{11}$, L$^{12}$, L$^{13}$, and L$^{14}$ are independently R$^{23}$-substituted or unsubstituted alkylene, R$^{23}$-substituted or unsubstituted heteroalkylene, R$^{23}$-substituted or unsubstituted cycloalkylene, R$^{23}$-substituted or unsubstituted heterocycloalkylene, R$^{23}$-substituted or unsubstituted arylene, or R$^{23}$-substituted or unsubstituted heteroarylene.

Each R$^{23}$ is independently oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —C(O)CH$_3$, R$^{24}$-substituted or unsubstituted alkyl, R$^{24}$-substituted or unsubstituted heteroalkyl, R$^{24}$-substituted or unsubstituted cycloalkyl, R$^{24}$-substituted or unsubstituted heterocycloalkyl, R$^{24}$-substituted or unsubstituted aryl, or R$^{24}$-substituted or unsubstituted heteroaryl.

Each R$^{24}$ is independently oxo, halogen —CF$_2$, —CCl$_3$, —CN, —OH, —NH$_2$, —COOH, —CONH$_2$, —NO$_2$, —SH, —SO$_2$Cl, —SO$_3$H, —SO$_4$H, —S O$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —C(O)CH$_3$, R$^{25}$-substituted or unsubstituted alkyl, R$^{25}$-substituted or unsubstituted heteroalkyl, R$^{25}$-substituted or unsubstituted cycloalkyl, R$^{25}$-substituted or unsubstituted heterocycloalkyl, R$^{25}$-substituted or unsubstituted aryl, or R$^{25}$-substituted or unsubstituted heteroaryl.

Each R$^{25}$ is independently oxo, halogen, —CF$_3$, —CCl$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCH$_3$, —OCF$_3$, —OCHF$_2$, —C(O)CH$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the compound is a compound described herein, including in an example or table. In embodiments, L$^1$, L$^1$, L$^3$, L$^4$, L$^5$, L$^6$, L$^7$, L$^8$, L$^9$, L$^{10}$, L$^{11}$, L$^{12}$, L$^{13}$, L$^{14}$, R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$ and/or R$^{25}$ are L$^1$, L$^2$, L$^3$, L$^4$, L$^5$, L$^6$, L$^7$, L$^8$, L$^9$, L$^{10}$, L$^{11}$, L$^{12}$, L$^{13}$, L$^{14}$, R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, and/or R$^{25}$ in an example (e.g. in a compound of table 1, table 2).

In some embodiments, a compound as described herein may include multiple instances of L$^{13}$, L$^{14}$, R$^{13}$, R$^{14}$, R$^{15}$, R$^{16}$, R$^{17}$, R$^{20}$, R$^{21}$, R$^{22}$, R$^{23}$, R$^{24}$, R$^{25}$, X, protein moiety, drug moiety, detectable moiety and/or other variables. In such embodiments, each variable may optional be different and be appropriately labeled to distinguish each group for greater clarity. For example, where each L$^{13}$, L$^{14}$, R$^{13}$, R$^{14}$, R$^{15}$, R$^{16}$, R$^{17}$, R$^{20}$, R$^{21}$, R$^{22}$, R$^{23}$, R$^{24}$, R$^{25}$, X, protein moiety, drug moiety, and/or detectable moiety is different, they may be referred to, for example, as L$^{13.1}$, L$^{13.2}$, L$^{13.3}$, L$^{13.4}$, L$^{13.5}$, L$^{13.6}$, L$^{13.7}$, L$^{13.8}$, L$^{13.9}$, L$^{13.10}$, L$^{13.11}$, L$^{13.12}$, L$^{13.13}$, L$^{13.14}$, L$^{13.15}$, L$^{13.16}$, L$^{13.17}$, L$^{13.18}$, L$^{13.19}$, L$^{13.20}$, L$^{13.21}$, L$^{13.22}$, L$^{13.23}$, L$^{13.24}$, L$^{13.25}$, L$^{13.26}$, L$^{13.27}$, L$^{13.28}$, L$^{13.29}$, L$^{13.30}$, L$^{13.31}$, L$^{13.32}$, L$^{13.33}$, L$^{13.34}$, L$^{13.35}$, L$^{13.36}$, L$^{13.37}$, L$^{13.38}$, L$^{13.39}$, L$^{13.40}$, L$^{13.41}$, L$^{13.42}$, L$^{14.1}$, L$^{14.2}$, L$^{14.3}$, L$^{14.4}$, L$^{14.5}$, L$^{14.6}$, L$^{14.7}$, L$^{14.8}$, L$^{14.9}$, L$^{14.10}$, L$^{14.11}$, L$^{14.12}$, L$^{14.13}$, L$^{14.14}$, L$^{14.15}$, L$^{14.16}$, L$^{14.17}$, L$^{14.18}$, L$^{14.19}$, L$^{14.20}$, L$^{14.21}$, L$^{14.22}$, L$^{14.23}$, L$^{14.24}$, L$^{14.25}$, L$^{14.26}$, L$^{14.27}$, L$^{14.28}$, L$^{14.29}$, L$^{14.30}$, L$^{14.31}$, L$^{14.32}$, L$^{14.33}$, L$^{14.34}$, L$^{14.35}$, L$^{14.36}$, L$^{14.37}$, L$^{14.38}$, L$^{14.39}$, L$^{14.40}$, L$^{14.41}$, L$^{14.42}$, R$^{13.1}$, R$^{13.2}$, R$^{13.3}$, R$^{13.4}$, R$^{13.5}$, R$^{13.6}$, R$^{13.7}$, R$^{13.8}$, R$^{13.9}$, R$^{13.10}$, R$^{13.11}$, R$^{13.12}$, R$^{13.13}$, R$^{13.14}$, R$^{13.15}$, R$^{13.16}$, R$^{13.17}$, R$^{13.18}$, R$^{13.19}$, R$^{13.20}$, R$^{13.21}$, R$^{13.22}$, R$^{13.23}$, R$^{13.24}$, R$^{13.25}$, R$^{13.26}$, R$^{13.27}$, R$^{13.28}$, R$^{13.29}$, R$^{13.30}$, R$^{13.31}$, R$^{13.32}$, R$^{13.33}$, R$^{13.34}$, R$^{13.35}$, R$^{13.36}$, R$^{13.37}$, R$^{13.38}$, R$^{13.39}$, R$^{13.40}$, R$^{13.41}$, R$^{13.42}$, R$^{14.1}$, R$^{14.2}$, R$^{14.3}$, R$^{14.4}$, R$^{14.5}$, R$^{14.6}$, R$^{14.7}$, R$^{14.8}$, R$^{14.9}$, R$^{14.10}$, R$^{14.11}$, R$^{14.12}$, R$^{14.13}$, R$^{14.14}$, R$^{14.15}$, R$^{14.16}$, R$^{14.17}$, R$^{14.18}$, R$^{14.19}$, R$^{14.20}$, R$^{14.21}$, R$^{14.22}$, R$^{14.23}$, R$^{14.24}$, R$^{14.25}$, R$^{14.26}$, R$^{14.27}$, R$^{14.28}$, R$^{14.29}$, R$^{14.30}$, R$^{14.31}$, R$^{14.32}$, R$^{14.33}$, R$^{14.34}$, R$^{14.35}$, R$^{14.36}$, R$^{14.37}$, R$^{14.38}$, R$^{14.39}$, R$^{14.40}$, R$^{14.41}$, R$^{14.42}$, R$^{15.1}$, R$^{15.2}$, R$^{15.3}$, R$^{15.4}$, R$^{15.5}$, R$^{15.6}$, R$^{15.7}$, R$^{15.8}$, R$^{15.9}$, R$^{15.10}$, R$^{15.11}$, R$^{15.12}$, R$^{15.13}$, R$^{15.14}$, R$^{15.15}$, R$^{15.16}$, R$^{15.17}$, R$^{15.18}$, R$^{15.19}$, R$^{15.20}$, R$^{15.21}$, R$^{15.22}$, R$^{15.23}$, R$^{15.24}$, R$^{15.25}$, R$^{15.26}$, R$^{15.27}$, R$^{15.28}$, R$^{15.29}$, R$^{15.30}$, R$^{15.31}$, R$^{15.32}$, R$^{15.33}$, R$^{15.34}$, R$^{15.35}$, R$^{15.36}$, R$^{15.37}$, R$^{15.38}$, R$^{15.39}$, R$^{15.40}$, R$^{15.41}$, R$^{15.42}$, R$^{16.1}$, R$^{16.2}$, R$^{16.3}$, R$^{16.4}$, R$^{16.5}$, R$^{16.6}$, R$^{16.7}$, R$^{16.8}$, R$^{16.9}$, R$^{16.10}$, R$^{16.11}$, R$^{16.12}$, R$^{16.13}$, R$^{16.14}$, R$^{16.15}$, R$^{16.16}$, R$^{16.17}$, R$^{16.18}$, R$^{16.19}$, R$^{16.20}$, R$^{16.21}$, R$^{16.22}$, R$^{16.23}$, R$^{16.24}$, R$^{16.25}$, R$^{16.26}$, R$^{16.27}$, R$^{16.28}$, R$^{16.29}$, R$^{16.30}$, R$^{16.31}$, R$^{16.32}$, R$^{16.33}$, R$^{16.34}$, R$^{16.35}$, R$^{16.36}$, R$^{16.37}$, R$^{16.38}$, R$^{16.39}$, R$^{16.40}$, R$^{16.41}$, R$^{16.42}$, R$^{17.1}$, R$^{17.2}$, R$^{17.3}$, R$^{17.4}$, R$^{17.5}$, R$^{17.6}$, R$^{17.7}$, R$^{17.8}$, R$^{17.9}$, R$^{17.10}$, R$^{17.11}$, R$^{17.12}$, R$^{17.13}$, R$^{17.14}$, R$^{17.15}$, R$^{17.16}$, R$^{17.17}$, R$^{17.18}$, R$^{17.19}$, R$^{17.20}$, R$^{17.21}$, R$^{17.22}$, R$^{17.23}$, R$^{17.24}$, R$^{17.25}$, R$^{17.26}$, R$^{17.27}$, R$^{17.28}$, R$^{17.29}$, R$^{17.30}$, R$^{17.31}$, R$^{17.32}$, R$^{17.33}$, R$^{17.34}$, R$^{17.35}$, R$^{17.36}$, R$^{17.37}$, R$^{17.38}$, R$^{17.39}$, R$^{17.40}$, R$^{17.41}$, R$^{17.42}$, R$^{20.1}$, R$^{20.2}$, R$^{20.3}$, R$^{20.4}$, R$^{20.5}$, R$^{20.6}$, R$^{20.7}$, R$^{20.8}$, R$^{20.9}$, R$^{20.10}$, R$^{20.11}$, R$^{20.12}$, R$^{20.13}$, R$^{20.14}$, R$^{20.15}$, R$^{20.16}$, R$^{20.17}$, R$^{20.18}$, R$^{20.19}$, R$^{20.20}$, R$^{20.21}$, R$^{20.22}$, R$^{20.23}$, R$^{20.24}$, R$^{20.25}$, R$^{20.26}$, R$^{20.27}$, R$^{20.28}$, R$^{20.29}$, R$^{20.30}$, R$^{20.31}$, R$^{20.32}$, R$^{20.33}$, R$^{20.34}$, R$^{20.35}$, R$^{20.36}$, R$^{20.37}$, R$^{20.38}$, R$^{20.39}$, R$^{20.40}$, R$^{20.41}$, R$^{20.42}$, R$^{21.1}$, R$^{21.2}$, R$^{21.3}$, R$^{21.4}$, R$^{21.5}$, R$^{21.6}$, R$^{21.7}$, R$^{21.8}$, R$^{21.9}$, R$^{21.10}$, R$^{21.11}$, R$^{21.12}$, R$^{21.13}$, R$^{21.14}$, R$^{21.15}$, R$^{21.16}$, R$^{21.17}$, R$^{21.18}$, R$^{21.19}$, R$^{21.20}$, R$^{21.21}$, R$^{21.22}$, R$^{21.23}$, R$^{21.24}$, R$^{21.25}$, R$^{21.26}$, R$^{21.27}$, R$^{21.28}$, R$^{21.29}$, R$^{21.30}$, R$^{21.31}$, R$^{21.32}$, R$^{21.33}$, R$^{21.34}$, R$^{21.35}$, R$^{21.36}$, R$^{21.37}$, R$^{21.38}$, R$^{21.39}$, R$^{21.40}$, R$^{21.41}$, R$^{21.42}$, R$^{22.1}$, R$^{22.2}$, R$^{22.3}$, R$^{22.4}$, R$^{22.5}$, R$^{22.6}$, R$^{22.7}$, R$^{22.8}$, R$^{22.9}$, R$^{22.10}$, R$^{22.11}$, R$^{22.12}$, R$^{22.13}$, R$^{22.14}$, R$^{22.15}$, R$^{22.16}$, R$^{22.17}$, R$^{22.18}$, R$^{22.19}$, R$^{22.20}$, R$^{22.21}$, R$^{22.22}$, R$^{22.23}$, R$^{22.24}$, R$^{22.25}$, R$^{22.26}$, R$^{22.27}$, R$^{22.28}$, R$^{22.29}$, R$^{22.30}$, R$^{22.31}$, R$^{22.32}$, R$^{22.33}$, R$^{22.34}$, R$^{22.35}$, R$^{22.36}$, R$^{22.37}$, R$^{22.38}$, R$^{22.39}$, R$^{22.40}$, R$^{22.41}$, R$^{22.42}$, X$^{0.1}$, X$^{0.2}$, X$^{0.3}$, X$^{0.4}$, X$^{0.5}$, X$^{0.6}$, X$^{0.7}$, X$^{0.8}$, X$^{0.9}$, X$^{0.10}$, X$^{0.11}$, X$^{0.12}$, X$^{0.13}$, X$^{0.14}$, X$^{0.15}$, X$^{0.16}$, X$^{0.17}$, X$^{0.18}$, X$^{0.19}$, X$^{0.20}$, X$^{0.21}$, X$^{0.22}$, X$^{0.23}$, X$^{0.24}$, X$^{0.25}$, X$^{0.26}$, X$^{0.27}$, X$^{0.28}$, X$^{0.29}$, X$^{0.30}$, X$^{0.31}$, X$^{0.32}$, X$^{0.33}$, X$^{0.34}$, X$^{0.35}$, X$^{0.36}$, X$^{0.37}$, X$^{0.38}$, X$^{0.39}$, X$^{0.40}$, X$^{0.41}$, X$^{0.42}$, protein moiety$^1$, protein moiety$^2$, protein moiety$^3$, protein moiety$^4$, protein moiety$^5$, protein moiety$^6$, protein moiety$^7$, protein moiety$^8$, protein moiety$^9$, protein moiety$^{10}$, protein moiety$^{11}$, protein moiety$^{12}$, protein moiety$^{13}$, protein moiety$^{14}$, protein moiety$^{15}$, protein moiety$^{16}$, protein moiety$^{17}$, protein moiety$^{18}$, protein moiety$^{19}$, protein moiety$^{20}$, protein moiety$^{21}$, protein moiety$^{22}$, protein moiety$^{23}$, protein moiety$^{24}$, protein moiety$^{25}$, protein moiety$^{26}$, protein moiety$^{27}$, protein moiety$^{28}$, protein moiety$^{29}$, protein moiety$^{30}$, protein moiety$^{31}$, protein moiety$^{32}$, protein moiety$^{33}$, protein moiety$^{34}$, protein moiety$^{35}$ m protein moiety$^{36}$, protein moiety$^{37}$, protein moiety$^{38}$, protein moiety$^{39}$, protein moiety$^{40}$, protein moiety$^{41}$, protein moiety$^{42}$, drug moiety$^{1}$, drug moiety$^{2}$, drug moiety$^{3}$, drug moiety$^{4}$, drug moiety$^{5}$, drug moiety$^{6}$, drug moiety$^{7}$, drug moiety$^{8}$, drug moiety$^{9}$, drug moiety$^{10}$, drug moiety$^{11}$, drug moiety$^{12}$, drug moiety$^{13}$, drug moiety$^{14}$, protein moiety$^{15}$, drug moiety$^{16}$, drug moiety$^{17}$, drug moiety$^{18}$, drug moiety$^{19}$, drug moiety$^{20}$, drug moiety$^{21}$, drug moiety$^{22}$, drug moiety$^{23}$, drug moiety$^{24}$, drug moiety$^{25}$, drug moiety$^{26}$, drug moiety$^{27}$, drug moiety$^{28}$, drug moiety$^{29}$, drug moiety$^{30}$, drug moiety$^{31}$, drug moiety$^{32}$, drug moiety$^{33}$, drug moiety$^{34}$, drug moiety$^{35}$, drug moiety$^{36}$, drug moiety$^{37}$, drug moiety$^{38}$, drug moiety$^{39}$, drug moiety$^{40}$, drug moiety$^{41}$, drug moiety$^{42}$, detectable moiety$^{1}$, detectable moiety$^{2}$, detectable moiety$^{3}$, detectable moiety$^{4}$, detectable moiety$^{5}$, detectable moiety$^{6}$, detectable moiety$^{7}$, detectable moiety$^{8}$, detectable moiety$^{9}$, detectable moiety$^{10}$, detectable moiety$^{11}$, detectable moiety$^{12}$, detectable moiety$^{13}$, detectable, detectable moiety$^{14}$, detectable moiety$^{15}$, detectable moiety$^{16}$, detectable moiety$^{17}$, detectable moiety$^{18}$, detectable moiety$^{19}$, detectable moiety$^{20}$, detectable moiety$^{21}$, detectable moiety$^{22}$, detectable moiety$^{23}$, detectable moiety$^{24}$, detectable moiety$^{25}$, detectable moiety$^{26}$, detectable moiety$^{27}$, detectable moiety$^{28}$, detectable moiety$^{29}$, detectable moiety$^{30}$, detectable moiety$^{31}$, detectable moiety$^{32}$, detectable moiety$^{33}$, detectable moiety$^{34}$, detectable moiety$^{35}$, detectable moiety$^{36}$, detectable moiety$^{37}$, detectable moiety$^{38}$, detectable moiety$^{39}$, detectable moiety$^{40}$, detectable moiety$^{41}$, detectable moiety$^{42}$, respectively, wherein the definition of $L^{13}$ is assumed by $L^{13.1}$, $L^{13.2}$, $L^{13.3}$, $L^{13.4}$, $L^{13.5}$, $L^{13.6}$, $L^{13.7}$, $L^{13.8}$, $L^{13.9}$, $L^{13.10}$, $L^{13.11}$, $L^{13.12}$, $L^{13.13}$, $L^{13.14}$, $L^{13.15}$, $L^{13.16}$, $L^{13.17}$, $L^{13.18}$, $L^{13.19}$, $L^{13.20}$, $L^{13.21}$, $L^{13.22}$, $L^{13.23}$, $L^{13.24}$, $L^{13.25}$, $L^{13.26}$, $L^{13.27}$, $L^{13.28}$, $L^{13.29}$, $L^{13.30}$, $L^{13.31}$, $L^{13.32}$, $L^{13.33}$, $L^{13.34}$, $L^{13.35}$, $L^{13.36}$, $L^{13.37}$, $L^{13.38}$, $L^{13.39}$, $L^{13.40}$, $L^{13.41}$, $L^{13.42}$, the definition of $L^{14}$ is assumed by $L^{14.1}$, $L^{14.2}$, $L^{14.3}$, $L^{14.4}$, $L^{14.5}$, $L^{14.6}$, $L^{14.7}$, $L^{14.8}$, $L^{14.9}$, $L^{14.10}$, $L^{14.11}$, $L^{14.12}$, $L^{14.13}$, $L^{14.14}$, $L^{14.15}$, $L^{14.16}$, $L^{14.17}$, $L^{14.18}$, $L^{14.19}$, $L^{14.20}$, $L^{14.21}$, $L^{14.22}$, $L^{14.23}$, $L^{14.24}$, $L^{14.25}$, $L^{14.26}$, $L^{14.27}$, $L^{14.28}$, $L^{14.29}$, $L^{14.30}$, $L^{14.31}$, $L^{14.32}$, $L^{14.33}$, $L^{14.34}$, $L^{14.35}$, $L^{14.36}$, $L^{14.37}$, $L^{14.38}$, $L^{14.39}$, $L^{14.40}$, $L^{14.41}$, $L^{14.42}$, the definition of $R^{13}$ is assumed by $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$, the definition of $R^{14}$ is assumed by $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$, the definition of $R^{15}$ is assumed by $R^{15.1}$, $R^{15.2}$, $R^{15.3}$, $R^{15.4}$, $R^{15.5}$, $R^{15.6}$, $R^{15.7}$, $R^{15.8}$, $R^{15.9}$, $R^{15.10}$, $R^{15.11}$, $R^{15.12}$, $R^{15.13}$, $R^{15.14}$, $R^{15.15}$, $R^{15.16}$, $R^{15.17}$, $R^{15.18}$, $R^{15.19}$, $R^{15.20}$, $R^{15.21}$, $R^{15.22}$, $R^{15.23}$, $R^{15.24}$, $R^{15.25}$, $R^{15.26}$, $R^{15.27}$, $R^{15.28}$, $R^{15.29}$, $R^{15.30}$, $R^{15.31}$, $R^{15.32}$, $R^{15.33}$, $R^{15.34}$, $R^{15.35}$, $R^{15.36}$, $R^{15.37}$, $R^{15.38}$, $R^{15.39}$, $R^{15.40}$, $R^{15.41}$, $R^{15.42}$, the definition of $R^{16}$ is assumed by $R^{16.1}$, $R^{16.2}$, $R^{16.3}$, $R^{16.4}$, $R^{16.5}$, $R^{16.6}$, $R^{16.7}$, $R^{16.8}$, $R^{16.9}$, $R^{16.10}$, $R^{16.11}$, $R^{16.12}$, $R^{16.13}$, $R^{16.14}$, $R^{16.15}$, $R^{16.16}$, $R^{16.17}$, $R^{16.18}$, $R^{16.19}$, $R^{16.20}$, $R^{16.21}$, $R^{16.22}$, $R^{16.23}$, $R^{16.24}$, $R^{16.25}$, $R^{16.26}$, $R^{16.27}$, $R^{16.28}$, $R^{16.29}$, $R^{16.30}$, $R^{16.31}$, $R^{16.32}$, $R^{16.33}$, $R^{16.34}$, $R^{16.35}$, $R^{16.36}$, $R^{16.37}$, $R^{16.38}$, $R^{16.39}$, $R^{16.40}$, $R^{16.41}$, $R^{16.42}$, the definition of $R^{17}$ is assumed by $R^{17.1}$, $R^{17.2}$, $R^{17.3}$, $R^{17.4}$, $R^{17.5}$, $R^{17.6}$, $R^{17.7}$, $R^{17.8}$, $R^{17.9}$, $R^{17.10}$, $R^{17.11}$, $R^{17.12}$, $R^{17.13}$, $R^{17.14}$, $R^{17.15}$, $R^{17.16}$, $R^{17.17}$, $R^{17.18}$, $R^{17.19}$, $R^{17.20}$, $R^{17.21}$, $R^{17.22}$, $R^{17.23}$, $R^{17.24}$, $R^{17.25}$, $R^{17.26}$, $R^{17.27}$, $R^{17.28}$, $R^{17.29}$, $R^{17.30}$, $R^{17.31}$, $R^{17.32}$, $R^{17.33}$, $R^{17.34}$, $R^{17.35}$, $R^{17.36}$, $R^{17.37}$, $R^{17.38}$, $R^{17.39}$, $R^{17.40}$, $R^{17.41}$, $R^{17.42}$, the definition of $R^{20}$ is assumed by $R^{20.1}$, $R^{20.2}$, $R^{20.3}$, $R^{20.4}$, $R^{20.5}$, $R^{20.6}$, $R^{20.7}$, $R^{20.8}$, $R^{20.9}$, $R^{20.10}$, $R^{20.11}$, $R^{20.12}$, $R^{20.13}$, $R^{20.14}$, $R^{20.15}$, $R^{20.16}$, $R^{20.17}$, $R^{20.18}$, $R^{20.19}$, $R^{20.20}$, $R^{20.21}$, $R^{20.22}$, $R^{20.23}$, $R^{20.24}$, $R^{20.25}$, $R^{20.26}$, $R^{20.27}$, $R^{20.28}$, $R^{20.29}$, $R^{20.30}$, $R^{20.31}$, $R^{20.32}$, $R^{20.33}$, $R^{20.34}$, $R^{2.35}$, $R^{20.36}$, $R^{20.37}$, $R^{20.38}$, $R^{20.39}$, $R^{20.40}$, $R^{20.41}$, $R^{20.42}$, the definition of $R^{21}$ is assumed by $R^{21.1}$, $R^{21.2}$, $R^{21.3}$, $R^{21.4}$, $R^{21.5}$, $R^{21.6}$, $R^{21.7}$, $R^{21.8}$, $R^{21.9}$, $R^{21.10}$, $R^{21.11}$, $R^{21.12}$, $R^{21.13}$, $R^{21.14}$, $R^{21.15}$, $R^{21.16}$, $R^{21.17}$, $R^{21.18}$, $R^{21.19}$, $R^{21.20}$, $R^{21.21}$, $R^{21.22}$, $R^{21.23}$, $R^{21.24}$, $R^{21.25}$, $R^{21.26}$, $R^{21.27}$, $R^{21.28}$, $R^{21.29}$, $R^{21.30}$, $R^{21.31}$, $R^{21.32}$, $R^{21.33}$, $R^{21.34}$, $R^{21.35}$, $R^{21.36}$, $R^{21.37}$, $R^{21.38}$, $R^{21.39}$, $R^{21.40}$, $R^{21.41}$, $R^{21.42}$, the definition of $R^{22}$ is assumed by $R^{22.1}$, $R^{22.2}$, $R^{22.3}$, $R^{22.4}$, $R^{22.5}$, $R^{22.6}$, $R^{22.7}$, $R^{22.8}$, $R^{22.9}$, $R^{22.10}$, $R^{22.11}$, $R^{22.12}$, $R^{22.13}$, $R^{22.14}$, $R^{22.15}$, $R^{22.16}$, $R^{22.17}$, $R^{22.18}$, $R^{22.19}$, $R^{22.20}$, $R^{22.21}$, $R^{22.22}$, $R^{22.23}$, $R^{22.24}$, $R^{22.25}$, $R^{22.26}$, $R^{22.27}$, $R^{22.28}$, $R^{22.29}$, $R^{22.30}$, $R^{22.31}$, $R^{22.32}$, $R^{22.33}$, $R^{22.34}$, $R^{22.35}$, $R^{22.36}$, $R^{22.37}$, $R^{22.38}$, $R^{22.39}$, $R^{22.40}$, $R^{22.41}$, $R^{22.42}$, the definition of $R^{23}$ is assumed by $R^{23.1}$, $R^{23.2}$, $R^{23.3}$, $R^{23.4}$, $R^{23.5}$, $R^{23.6}$, $R^{23.7}$, $R^{23.8}$, $R^{23.9}$, $R^{23.10}$, $R^{23.11}$, $R^{23.12}$, $R^{23.13}$, $R^{23.14}$, $R^{23.15}$, $R^{23.16}$, $R^{23.17}$, $R^{23.18}$, $R^{23.19}$, $R^{23.20}$, $R^{23.21}$, $R^{23.22}$, $R^{23.23}$, $R^{23.24}$, $R^{23.25}$, $R^{23.26}$, $R^{23.27}$, $R^{23.28}$, $R^{23.29}$, $R^{23.30}$, $R^{23.31}$, $R^{23.32}$, $R^{23.33}$, $R^{23.34}$, $R^{23.35}$, $R^{23.36}$, $R^{23.37}$, $R^{23.38}$, $R^{23.39}$, $R^{23.40}$, $R^{23.41}$, $R^{23.42}$, the definition of $R^{24}$ is assumed by $R^{24.1}$, $R^{24.2}$, $R^{24.3}$, $R^{24.4}$, $R^{24.5}$, $R^{24.6}$, $R^{24.7}$, $R^{24.8}$, $R^{24.9}$, $R^{24.10}$, $R^{24.11}$, $R^{24.12}$, $R^{24.13}$, $R^{24.14}$, $R^{24.15}$, $R^{24.16}$, $R^{24.17}$, $R^{24.18}$, $R^{24.19}$, $R^{24.20}$, $R^{24.21}$, $R^{24.22}$, $R^{24.23}$, $R^{24.24}$, $R^{24.25}$, $R^{24.26}$, $R^{24.27}$, $R^{24.28}$, $R^{24.29}$, $R^{24.30}$, $R^{24.31}$, $R^{24.32}$, $R^{24.33}$, $R^{24.34}$, $R^{24.35}$, $R^{24.36}$, $R^{24.37}$, $R^{24.38}$, $R^{24.39}$, $R^{24.40}$, $R^{24.41}$, $R^{24.42}$, the definition of $R^{25}$ is assumed by $R^{25.1}$, $R^{25.2}$, $R^{25.3}$, $R^{25.4}$, $R^{25.5}$, $R^{25.6}$, $R^{25.7}$, $R^{25.8}$, $R^{25.9}$, $R^{25.10}$, $R^{25.11}$, $R^{25.12}$, $R^{25.13}$, $R^{25.14}$, $R^{25.15}$, $R^{25.16}$, $R^{25.17}$, $R^{25.18}$, $R^{25.19}$, $R^{25.20}$, $R^{25.21}$, $R^{25.22}$, $R^{25.23}$, $R^{25.24}$, $R^{25.25}$, $R^{25.26}$, $R^{25.27}$, $R^{25.28}$, $R^{25.29}$, $R^{25.30}$, $R^{25.31}$, $R^{25.32}$, $R^{25.33}$, $R^{25.34}$, $R^{25.35}$, $R^{25.36}$, $R^{25.37}$, $R^{25.38}$, $R^{25.39}$, $R^{25.40}$, $R^{25.41}$, $R^{25.42}$, the definition of X is assumed by $X^{0.1}$, $X^{0.2}$, $X^{0.3}$, $X^{0.4}$, $X^{0.5}$, $X^{0.6}$, $X^{0.7}$, $X^{0.8}$, $X^{0.9}$, $X^{0.10}$, $X^{0.11}$, $X^{0.12}$, $X^{0.13}$, $X^{0.14}$, $X^{0.15}$, $X^{0.16}$, $X^{0.17}$, $X^{0.18}$, $X^{0.19}$, $X^{0.20}$, $X^{0.21}$, $X^{0.22}$, $X^{0.23}$, $X^{0.24}$, $X^{0.25}$, $X^{0.26}$, $X^{0.27}$, $X^{0.28}$, $X^{0.29}$, $X^{0.30}$, $X^{0.31}$, $X^{0.32}$, $X^{0.33}$, $X^{0.34}$, $X^{0.35}$, $X^{0.36}$, $X^{0.37}$, $X^{0.38}$, $X^{0.39}$, $X^{0.40}$, $X^{0.41}$, $X^{0.42}$, the definition of protein moiety is assumed by protein moiety$^{1}$, protein moiety$^{2}$, protein moiety$^{3}$, protein moiety$^{4}$, protein moiety$^{5}$, protein moiety$^{6}$, protein moiety$^{7}$, protein moiety$^{8}$, protein moiety$^{9}$, protein moiety$^{10}$, protein moiety$^{11}$, protein moiety$^{12}$, protein moiety$^{13}$, protein moiety$^{14}$, protein moiety$^{15}$, protein moiety$^{16}$, protein moiety$^{17}$, protein moiety$^{18}$, protein moiety$^{19}$, protein moiety$^{20}$, protein moiety$^{21}$, protein moiety$^{22}$, protein moiety$^{23}$, protein moiety$^{24}$, protein moiety$^{25}$, protein moiety$^{26}$, protein moiety$^{27}$, protein moiety$^{28}$, protein moiety$^{29}$, protein moiety$^{30}$, protein moiety$^{31}$, protein moiety$^{32}$, protein moiety$^{33}$, protein moiety$^{34}$, protein moiety$^{35}$, protein moiety$^{36}$, protein moiety$^{37}$, protein moiety$^{38}$, protein moiety$^{39}$, protein moiety$^{40}$, protein moiety$^{41}$, protein moiety$^{42}$, the definition of drug moiety is assumed by drug moiety$^{1}$, drug moiety$^{2}$, drug moiety$^{3}$, drug moiety$^{4}$, drug moiety$^{5}$, drug moiety$^{6}$, drug moiety$^{7}$, drug moiety$^{8}$, drug moiety$^{9}$, drug moiety$^{10}$, drug moiety$^{11}$, drug moiety$^{12}$, drug moiety$^{13}$, drug moiety$^{14}$, drug moiety$^{15}$, drug moiety$^{16}$, drug moiety$^{17}$, drug moiety$^{18}$, drug moiety$^{19}$, drug moiety$^{20}$, drug moiety$^{21}$, drug moiety$^{22}$, drug moiety$^{23}$, drug moiety$^{24}$, drug moiety$^{25}$, drug moiety$^{26}$, drug moiety$^{27}$, drug moiety$^{28}$, drug moiety$^{29}$, drug moiety$^{30}$, drug moiety$^{31}$, drug moiety$^{32}$, drug moiety$^{33}$, drug moiety$^{34}$, drug moiety$^{35}$, drug moiety$^{36}$, drug moiety$^{37}$, drug moiety$^{38}$, drug moiety$^{39}$, drug moiety$^{40}$, drug moiety$^{41}$, drug moiety$^{42}$, the definition of detectable moiety is assumed by detectable moiety$^{1}$, detectable moiety$^{2}$, detectable moiety$^{3}$, detectable moiety$^{4}$, detectable moiety$^{5}$, detectable moiety$^{6}$, detectable moiety$^{7}$, detectable moiety$^{8}$, detectable moiety$^{9}$, detectable moiety$^{10}$, detectable moiety$^{11}$, detectable moiety$^{12}$, detectable moiety$^{13}$, detectable moiety$^{14}$, detectable moiety$^{15}$, detectable moiety$^{16}$, detectable moiety$^{17}$, detectable moiety$^{18}$, detectable moiety$^{19}$, detectable moiety$^{20}$, detectable moiety$^{21}$, detectable moiety$^{22}$, detectable moiety$^{23}$, detectable moiety$^{24}$, detectable moiety$^{25}$, detectable moiety$^{26}$, detectable moiety$^{27}$, detectable moiety$^{28}$, detectable moiety$^{29}$, detectable moiety$^{30}$, detectable moiety$^{31}$, detectable moiety$^{32}$, detectable moiety$^{33}$, detectable moiety$^{34}$, detectable moiety$^{35}$, detectable moiety$^{36}$, detectable moiety$^{37}$, detectable moiety$^{38}$, detectable moiety$^{39}$, detectable moiety$^{40}$, detectable moiety$^{41}$, detectable moiety$^{42}$.

The variables used within the definition of $L^{13}$, $L^{14}$, $R^{13}$, $R^{14}$, $R^{15}$, $R^{16}$, $R^{17}$, $R^{20}$, $R^{21}$, $R^{22}$, $R^{23}$, $R^{24}$, $R^{25}$, X, protein moiety, drug moiety, detectable moiety, and/or other variables that appear at multiple instances and are different may similarly be appropriately labeled to distinguish each group for greater clarity.

In embodiments, $R^{1}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^{26}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$ substituted or unsubstituted heterocycloalkyl, $R^{27}$-substituted or unsubstituted aryl, or $R^{27}$-substituted or unsubstituted heteroaryl.

$R^{27}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In embodiments, $R^{5}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{29}$-substituted or unsubstituted alkylene, $R^{29}$-substituted or unsubstituted heteroalkylene, $R^{29}$-substituted or unsubstituted cycloalkylene, $R^{29}$ substituted or unsubstituted heterocycloalkylene, $R^{29}$-substituted or unsubstituted arylene, or $R^{29}$-substituted or unsubstituted heteroarylene.

$R^{29}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl.

$R^{30}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In embodiments, $R^{7}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{32}$-substituted or unsubstituted alkylene, $R^{32}$-substituted or unsubstituted heteroalkylene, $R^{32}$-substituted or unsubstituted cycloalkylene, $R^{32}$-substituted or unsubstituted heterocycloalkylene, $R^{32}$-substituted or unsubstituted arylene, or $R^{32}$-substituted or unsubstituted heteroarylene.

$R^{32}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$ substituted or unsubstituted heterocycloalkyl, $R^{33}$-substituted or unsubstituted aryl, or $R^{33}$-substituted or unsubstituted heteroaryl.

$R^{33}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In embodiments, $R^{11}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{35}$-substituted or unsubstituted alkylene, $R^{35}$-substituted or unsubstituted heteroalkylene, $R^{35}$-substituted or unsubstituted cycloalkylene, $R^{35}$-substituted or unsubstituted heterocycloalkylene, $R^{35}$-substituted or unsubstituted arylene, or $R^{35}$-substituted or unsubstituted heteroarylene.

$R^{35}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{36}$-substituted or unsubstituted alkyl, R$^{36}$-substituted or unsubstituted heteroalkyl, R$^{36}$-substituted or unsubstituted cycloalkyl, R$^{36}$ substituted or unsubstituted heterocycloalkyl, R$^{36}$-substituted or unsubstituted aryl, or R$^{36}$-substituted or unsubstituted heteroaryl.

R$^{36}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{37}$-substituted or unsubstituted alkyl, R$^{37}$-substituted or unsubstituted heteroalkyl, R$^{37}$-substituted or unsubstituted cycloalkyl, R$^{37}$-substituted or unsubstituted heterocycloalkyl, R$^{37}$-substituted or unsubstituted aryl, or R$^{37}$-substituted or unsubstituted heteroaryl.

In embodiments, R$^{12}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{38}$-substituted or unsubstituted alkyl, R$^{38}$-substituted or unsubstituted heteroalkyl, R$^{38}$-substituted or unsubstituted cycloalkyl, R$^{38}$-substituted or unsubstituted heterocycloalkyl, R$^{38}$-substituted or unsubstituted aryl, or R$^{38}$-substituted or unsubstituted heteroaryl.

R$^{38}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, —S(O)$_2$CHCH$_2$, —NHS(O)$_2$CHCH$_2$, R$^{39}$-substituted or unsubstituted alkyl, R$^{39}$-substituted or unsubstituted heteroalkyl, R$^{39}$-substituted or unsubstituted cycloalkyl, R$^{39}$ substituted or unsubstituted heterocycloalkyl, R$^{39}$-substituted or unsubstituted aryl, or R$^{39}$-substituted or unsubstituted heteroaryl.

R$^{39}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, —S(O)$_2$CHCH$_2$, —NHS(O)$_2$CHCH$_2$, R$^{40}$-substituted or unsubstituted alkyl, R$^{40}$-substituted or unsubstituted heteroalkyl, R$^{40}$-substituted or unsubstituted cycloalkyl, R$^{40}$-substituted or unsubstituted heterocycloalkyl, R$^{40}$-substituted or unsubstituted aryl, or R$^{40}$-substituted or unsubstituted heteroaryl.

In embodiments, R$^{13}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl.

R$^{41}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, —S(O)$_2$CHCH$_2$, —NHS(O)$_2$CHCH$_2$, R$^{42}$-substituted or unsubstituted alkyl, R$^{42}$-substituted or unsubstituted heteroalkyl, R$^{42}$-substituted or unsubstituted cycloalkyl, R$^{42}$ substituted or unsubstituted heterocycloalkyl, R$^{42}$-substituted or unsubstituted aryl, or R$^{42}$-substituted or unsubstituted heteroaryl.

R$^{42}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, —S(O)$_2$CHCH$_2$, —NHS(O)$_2$CHCH$_2$, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, R$^{43}$-substituted or unsubstituted aryl, or R$^{43}$-substituted or unsubstituted heteroaryl.

In embodiments, R$^{14}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{44}$-substituted or unsubstituted alkyl, R$^{44}$-substituted or unsubstituted heteroalkyl, R$^{44}$-substituted or unsubstituted cycloalkyl, R$^{44}$-substituted or unsubstituted heterocycloalkyl, R$^{44}$-substituted or unsubstituted aryl, or R$^{44}$-substituted or unsubstituted heteroaryl.

R$^{44}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{45}$-substituted or unsubstituted alkyl, R$^{45}$-substituted or unsubstituted heteroalkyl, R$^{45}$-substituted or unsubstituted cycloalkyl, R$^{45}$ substituted or unsubstituted heterocycloalkyl, R$^{45}$-substituted or unsubstituted aryl, or R$^{45}$-substituted or unsubstituted heteroaryl.

R$^{45}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl.

In embodiments, R$^{15}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl.

R$^{47}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(=O)NHNH$_2$, —NHC(=O) NH$_2$, —NHSO$_2$H, —NHC(=O)H, —NHC(O)—OH, —NHOH, —OCF$_3$, —OCHF$_2$, R$^{48}$-substituted or unsubstituted alkyl, R$^{48}$-substituted or unsubstituted heteroalkyl, R$^{48}$-substituted or unsubstituted cycloalkyl, R$^{48}$ substituted or unsubstituted heterocycloalkyl, R$^{48}$-substituted or unsubstituted aryl, or R$^{48}$-substituted or unsubstituted heteroaryl.

R$^{48}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{49}$-substituted or unsubstituted alkyl, R$^{49}$-substituted or unsubstituted heteroalkyl, R$^{49}$-substituted or unsubstituted cycloalkyl, R$^{49}$-substituted or unsubstituted heterocycloalkyl, R$^{49}$-substituted or unsubstituted aryl, or R$^{49}$-substituted or unsubstituted heteroaryl.

In embodiments, R$^{16}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{50}$-substituted or unsubstituted alkyl, R$^{50}$-substituted or unsubstituted heteroalkyl, R$^{50}$-substituted or unsubstituted cycloalkyl, R$^{50}$-substituted or unsubstituted heterocycloalkyl, R$^{50}$-substituted or unsubstituted aryl, or R$^{50}$-substituted or unsubstituted heteroaryl.

R$^{50}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{51}$-substituted or unsubstituted alkyl, R$^{51}$-substituted or unsubstituted heteroalkyl, R$^{51}$-substituted or unsubstituted cycloalkyl, R$^{51}$ substituted or unsubstituted heterocycloalkyl, R$^{51}$-substituted or unsubstituted aryl, or R$^{51}$-substituted or unsubstituted heteroaryl.

R$^{51}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{52}$-substituted or unsubstituted alkyl, R$^{52}$-substituted or unsubstituted heteroalkyl, R$^{52}$-substituted or unsubstituted cycloalkyl, R$^{52}$-substituted or unsubstituted heterocycloalkyl, R$^{52}$-substituted or unsubstituted aryl, or R$^{52}$-substituted or unsubstituted heteroaryl.

In embodiments, R$^{17}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{53}$-substituted or unsubstituted alkyl, R$^{53}$-substituted or unsubstituted heteroalkyl, R$^{53}$-substituted or unsubstituted cycloalkyl, R$^{53}$-substituted or unsubstituted heterocycloalkyl, R$^{53}$-substituted or unsubstituted aryl, or R$^{53}$-substituted or unsubstituted heteroaryl.

R$^{53}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{54}$-substituted or unsubstituted alkyl, R$^{54}$-substituted or unsubstituted heteroalkyl, R$^{54}$-substituted or unsubstituted cycloalkyl, R$^{54}$ substituted or unsubstituted heterocycloalkyl, R$^{54}$-substituted or unsubstituted aryl, or R$^{54}$-substituted or unsubstituted heteroaryl.

R$^{54}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{55}$-substituted or unsubstituted alkyl, R$^{55}$-substituted or unsubstituted heteroalkyl, R$^{55}$-substituted or unsubstituted cycloalkyl, R$^{55}$-substituted or unsubstituted heterocycloalkyl, R$^{55}$-substituted or unsubstituted aryl, or R$^{55}$-substituted or unsubstituted heteroaryl.

In embodiments, R$^{18}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{56}$-substituted or unsubstituted alkyl, R$^{56}$-substituted or unsubstituted heteroalkyl, R$^{56}$-substituted or unsubstituted cycloalkyl, R$^{56}$-substituted or unsubstituted heterocycloalkyl, R$^{56}$-substituted or unsubstituted aryl, or R$^{56}$-substituted or unsubstituted heteroaryl.

R$^{56}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{57}$-substituted or unsubstituted alkyl, R$^{57}$-substituted or unsubstituted heteroalkyl, R$^{57}$-substituted or unsubstituted cycloalkyl, R$^{57}$ substituted or unsubstituted heterocycloalkyl, R$^{57}$-substituted or unsubstituted aryl, or R$^{57}$-substituted or unsubstituted heteroaryl.

R$^{57}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{58}$-substituted or unsubstituted alkyl, R$^{58}$-substituted or unsubstituted heteroalkyl, R$^{58}$-substituted or unsubstituted cycloalkyl, R$^{58}$-substituted or unsubstituted heterocycloalkyl, R$^{58}$-substituted or unsubstituted aryl, or R$^{58}$-substituted or unsubstituted heteroaryl.

In embodiments, R$^{19}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{59}$-substituted or unsubstituted alkyl, R$^{59}$-substituted or unsubstituted heteroalkyl, R$^{59}$-substituted or unsubstituted cycloalkyl, R$^{59}$-substituted or unsubstituted heterocycloalkyl, R$^{59}$-substituted or unsubstituted aryl, or R$^{59}$-substituted or unsubstituted heteroaryl.

R$^{59}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{60}$-substituted or unsubstituted alkyl, R$^{60}$-substituted or unsubstituted heteroalkyl, R$^{60}$-substituted or unsubstituted cycloalkyl, R$^{60}$-substituted or unsubstituted heterocycloalkyl, R$^{60}$-substituted or unsubstituted aryl, or R$^{60}$-substituted or unsubstituted heteroaryl.

R$^{60}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{61}$-substituted or unsubstituted alkyl, R$^{61}$-substituted or unsubstituted heteroalkyl, R$^{61}$-substituted or unsubstituted cycloalkyl, R$^{61}$-substituted or unsubstituted heterocycloalkyl, R$^{61}$-substituted or unsubstituted aryl, or R$^{61}$-substituted or unsubstituted heteroaryl.

In embodiments, L$^1$ is independently a bond, —N(R$^{17}$)-L$^{13}$-L$^{14}$-, —N(R$^{17}$)C(O)-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R$^{17}$)-L$^{13}$-L$^{14}$-, —OC(O)O-L$^{13}$-L$^{14}$-, —OSO$_2$-L$^{13}$-L$^{14}$-, —C(O)N (R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, —N(R$^{17}$)S(O)$_2$-L$^{13}$-L$^{14}$-, R$^{62}$-substituted or unsubstituted alkylene, R$^{62}$-substituted or unsubstituted heteroalkylene, R$^{62}$-substituted or unsubstituted cycloalkylene, R$^{62}$-substituted or unsubstituted heterocycloalkylene, R$^{62}$-substituted or unsubstituted arylene, or R$^{62}$-substituted or unsubstituted heteroarylene. L$^1$ may be a bond. L$^1$ may be —N(R$^{171}$)-L$^{131}$-L$^{141}$-. L$^1$ may be —N(R$^{171}$)C(O)O-L$^{131}$-L$^{141}$-. L$^1$ may be —O-L$^{131}$-L$^{141}$-. L$^1$ may be —S-L$^{131}$-L$^{141}$-. L$^1$ may be —OC(O)-L$^{131}$-L$^{141}$-. L$^1$ may be —OC(O)N(R$^{171}$)-L$^{131}$-L$^{141}$-. L$^1$ may be —OC(O)O-L$^{131}$-L$^{141}$-. L$^1$ may be —OSO$_2$-L$^{131}$-L$^{141}$-. L$^1$ may be —C(O)N(R$^{171}$)-L$^{131}$-L$^{141}$-. L$^1$ may be —N(R$^{171}$)C(O)-L$^{131}$-L$^{141}$-. L$^1$ may be —S(O)$_2$N(R$^{171}$)-L$^{131}$-L$^{141}$-. L$^1$ may be —N(R$^{171}$)S(O)$_2$-L$^{131}$-L$^{141}$-. L$^1$ may be —C(O)O-L$^{131}$-L$^{141}$-. L$^1$ may be —SO$_2$-L$^{131}$-L$^{141}$-. L$^1$ may be —N(H)—. L$^1$ may be —N(H)C(O)O—. L$^1$ may be —O—. L$^1$ may be —S—. L$^1$ may be —OC(O)—. L$^1$ may be —OC(O)N(H)—. L$^1$ may be —OC(O)O—. L$^1$ may be —OSO$_2$—. L$^1$ may be —C(O)N(H)—. L$^1$ may be —N(H)C(O)—. L$^1$ may be —S(O)$_2$N(H)—. L$^1$ may be —N(H)S(O)$_2$—. L$^1$ may be —C(O)O—. L$^1$ may be —SO$_2$—.

R$^{62}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{63}$-substituted or unsubstituted alkyl, R$^{63}$-substituted or unsubstituted heteroalkyl, R$^{63}$-substituted or unsubstituted cycloalkyl, R$^{63}$-substituted or unsubstituted heterocycloalkyl, R$^{63}$-substituted or unsubstituted aryl, or R$^{63}$-substituted or unsubstituted heteroaryl.

R$^{63}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{64}$-substituted or unsubstituted alkyl, R$^{64}$-substituted or unsubstituted heteroalkyl, R$^{64}$-substituted or unsubstituted cycloalkyl, R$^{64}$-substituted or unsubstituted heterocycloalkyl, R$^{64}$-substituted or unsubstituted aryl, or R$^{64}$-substituted or unsubstituted heteroaryl.

In embodiments, L$^5$ is independently a bond, —N(R$^{17}$)-L$^{13}$-L$^{14}$-, —N(R$^{17}$)C(O)O-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R$^{17}$)-L$^{13}$-L$^{14}$-, —OC(O)O-L$^{13}$-L$^{14}$-, —OSO$_2$-L$^{13}$-L$^{14}$-, —C(O)N(R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, —N(R$^{17}$)S(O)$_2$-L$^{13}$-L$^{14}$-, R$^{65}$-substituted or unsubstituted alkylene, R$^{65}$-substituted or unsubstituted heteroalkylene, R$^{65}$-substituted or unsubstituted cycloalkylene, R$^{65}$ substituted or unsubstituted heterocycloalkylene, R$^{65}$-substituted or unsubstituted arylene, or R$^{65}$-substituted or unsubstituted heteroarylene. L$^5$ may be a bond. L$^5$ may be —N(R$^{175}$)-L$^{135}$-L$^{145}$-. L$^5$ may be —N(R$^{175}$)C(O)O-L$^{135}$-L$^{145}$-. L$^5$ may be —O-L$^{135}$-L$^{145}$-. L$^5$ may be —S-L$^{135}$-L$^{145}$-. L$^5$ may be —OC(O)-L$^{135}$-L$^{145}$-. L$^5$ may be —OC(O)N(R$^{175}$)-L$^{135}$-L$^{145}$-. L$^5$ may be —OC(O)O-L$^{135}$-L$^{145}$-. L$^5$ may be —OSO$_2$-L$^{135}$-L$^{145}$-. L$^5$ may be —C(O)N(R$^{175}$)-L$^{135}$-L$^{145}$-. L$^5$ may be —N(R$^{175}$)C(O)-L$^{135}$-L$^{145}$-. L$^5$ may be —S(O)$_2$N(R$^{175}$)-L$^{135}$-L$^{145}$-. L$^5$ may be —N(R$^{175}$)S(O)$_2$-L$^{135}$-L$^{145}$-. L$^5$ may be —C(O)O-L$^{135}$-L$^{145}$-. L$^5$ may be —SO$_2$-L$^{135}$-L$^{145}$-. L$^5$ may be —N(H)—. L$^5$ may be —N(H)C(O)O—. L$^5$ may be —O—. L$^5$ may be —S—. L$^5$ may be —OC(O)—. L$^5$ may be —OC(O)N(H)—. L$^5$ may be —OC(O)O—. L$^5$ may be —OSO$_2$—. L$^5$ may be —C(O)N(H)—. L$^5$ may be —N(H)C(O)—. L$^5$ may be —S(O)$_2$N(H)—. L$^5$ may be —N(H)S(O)$_2$—. L$^5$ may be —C(O)O—. L$^5$ may be —SO$_2$—.

R$^{65}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_7$NH$_7$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{66}$-substituted or unsubstituted alkyl, R$^{66}$-substituted or unsubstituted heteroalkyl, R$^{66}$-substituted or unsubstituted cycloalkyl, R$^{66}$-substituted or unsubstituted heterocycloalkyl, R$^{66}$-substituted or unsubstituted aryl, or R$^{66}$-substituted or unsubstituted heteroaryl.

R$^{66}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{67}$-substituted or unsubstituted alkyl, R$^{67}$-substituted or unsubstituted heteroalkyl, R$^{67}$-substituted or unsubstituted cycloalkyl, R$^{67}$-substituted or unsubstituted heterocycloalkyl, R$^{67}$-substituted or unsubstituted aryl, or R$^{67}$-substituted or unsubstituted heteroaryl.

In embodiments, L$^7$ is independently a bond, —N(R$^{17}$)-L$^{13}$-L$^{14}$-, —N(R$^{17}$)C(O)O-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R$^{17}$)-L$^{13}$-L$^{14}$-, —OC(O)O-L$^{13}$-L$^{14}$-, —OSO$_2$-L$^{13}$-L$^{14}$-, —C(O)N(R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, —N(R$^{17}$)S(O)$_2$-L$^{13}$-L$^{14}$-, R$^{68}$-substituted or unsubstituted alkylene, R$^{68}$-substituted or unsubstituted heteroalkylene, R$^{68}$-substituted or unsubstituted cycloalkylene, R$^{68}$ substituted or unsubstituted heterocycloalkylene, R$^{68}$-substituted or unsubstituted arylene, or R$^{68}$-substituted or unsubstituted heteroarylene. L$^7$ may be a bond. L$^7$ may be —N(R$^{177}$)-L$^{137}$-L$^{147}$-. L$^7$ may be —N(R$^{177}$)C(O)O-L$^{137}$-L$^{147}$-. L$^7$ may be —O-L$^{137}$-L$^{147}$-. L$^7$ may be —S-L$^{137}$-L$^{147}$-. L$^7$ may be —OC(O)-L$^{137}$-L$^{147}$-. L$^7$ may be —OC(O)N(R$^{177}$)-L$^{137}$-L$^{147}$-. L$^7$ may be —OC(O)O-L$^{137}$-L$^{147}$-. L$^7$ may be —OSO$_2$-L$^{137}$-L$^{147}$-. L$^7$ may be —C(O)N(R$^{177}$)-L$^{137}$-L$^{147}$-. L$^7$ may be —N(R$^{177}$)C(O)-L$^{137}$-L$^{147}$-. L$^7$ may be —S(O)$_2$N(R$^{177}$)-L$^{137}$-L$^{147}$-. L$^7$ may be —N(R$^{177}$)S(O)$_2$-L$^{137}$-L$^{147}$-. L$^7$ may be —C(O)O-L$^{137}$-L$^{147}$-. L$^7$ may be —SO$_2$-L$^{137}$-L$^{147}$-. L$^7$ may be —N(H)—. L$^7$ may be —N(H)C(O)O—. L$^7$ may be —O—. L$^7$ may be —S—. L$^7$ may be —OC(O)—. L$^7$ may be —OC(O)N(H)—. L$^7$ may be —OC(O)O—. L$^7$ may be —OSO$_2$—. L$^7$ may be —C(O)N(H)—. L$^7$ may be —N(H)C(O)—. L$^7$ may be —S(O)$_2$N(H)—. L$^7$ may be —N(H)S(O)$_2$—. L$^7$ may be —C(O)O—. L$^7$ may be —SO$_2$—.

R$^{68}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{69}$-substituted or unsubstituted alkyl, R$^{69}$-substituted or unsubstituted heteroalkyl, R$^{69}$-substituted or unsubstituted cycloalkyl, R$^{69}$-substituted or unsubstituted heterocycloalkyl, R$^{69}$-substituted or unsubstituted aryl, or R$^{69}$-substituted or unsubstituted heteroaryl.

R$^{69}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{70}$-substituted or unsubstituted alkyl, R$^{70}$-substituted or unsubstituted heteroalkyl, R$^{70}$-substituted or unsubstituted cycloalkyl, R$^{70}$-substituted or unsubstituted heterocycloalkyl, $R^{70}$-substituted or unsubstituted aryl, or $R^{70}$-substituted or unsubstituted heteroaryl.

In embodiments, $L^{11}$ is independently a bond, $-N(R^{17})-$, $-N(R^{17})C(O)O-L^{13}-L^{14}-$, $-O-L^{13}-L^{14}-$, $-S-L^{13}-L^{14}-$, $-OC(O)-L^{13}-L^{14}-$, $-OC(O)N(R^{17})-L^{13}-L^{14}-$, $-OC(O)O-L^{13}-L^{14}-$, $-OSO_2-L^{13}-L^{14}-$, $-C(O)N(R^{17})-L^{13}-L^{14}-$, $-N(R^{17})C(O)-L^{13}-L^{14}-$, $-S(O)_2N(R^{17})-L^{13}-L^{14}-$, $-N(R^{17})S(O)_2-L^{13}-L^{14}-$, $R^{71}$-substituted or unsubstituted alkylene, $R^{71}$-substituted or unsubstituted heteroalkylene, $R^{71}$-substituted or unsubstituted cycloalkylene, $R^{71}$-substituted or unsubstituted heterocycloalkylene, $R^{71}$-substituted or unsubstituted arylene, or $R^{71}$-substituted or unsubstituted heteroarylene. $L^{11}$ may be a bond. $L^{11}$ may be $-N(R^{1711})-L^{1311}-L^{1411}-$. $L^{11}$ may be $-N(R^{171})C(O)O-L^{1311}-L^{1411}-$. $L^{11}$ may be $-O-L^{1311}-L^{1411}-$. $L^{11}$ may be $-S-L^{1311}-L^{1411}-$. $L^{11}$ may be $-OC(O)-L^{1311}-L^{1411}-$. $L^{11}$ may be $-OC(O)N(R^{1711})-L^{131}-L^{1411}-$. $L^{11}$ may be $-OC(O)O-L^{1311}-L^{1411}-$. $L^{11}$ may be $-OSO_2-L^{1311}-L^{1411}-$. $L^{11}$ may be $-C(O)N(R^{1711})-L^{1311}-L^{1411}-$. $L^{11}$ may be $-N(R^{1711})C(O)-L^{1311}-L^{1411}-$. $L^{11}$ may be $-S(O)_2N(R^{1711})-L^{1311}-L^{1411}-$. $L^{11}$ may be $-N(R^{1711})S(O)_2-L^{1311}-L^{1411}-$. $L^{11}$ may be $-C(O)O-L^{1311}-L^{1411}-$. $L^{11}$ may be $-SO_2-L^{1311}-L^{1411}-$. $L^{11}$ may be $-N(H)-$. $L^{11}$ may be $-N(H)C(O)O-$. $L^{11}$ may be $-O-$. $L^{11}$ may be $-S-$. $L^{11}$ may be $-OC(O)-$. $L^{11}$ may be $-OC(O)N(H)-$. $L^{11}$ may be $-OC(O)O-$. $L^{11}$ may be $-OSO_2-$. $L^{11}$ may be $-C(O)N(H)-$. $L^{11}$ may be $-N(H)C(O)-$. $L^{11}$ may be $-S(O)_2N(H)-$. $L^{11}$ may be $-N(H)S(O)_2-$. $L^{11}$ may be $-C(O)O-$. $L^{11}$ may be $-SO_2-$.

$R^{71}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{72}$-substituted or unsubstituted alkyl, $R^{72}$-substituted or unsubstituted heteroalkyl, $R^{72}$-substituted or unsubstituted cycloalkyl, $R^{72}$-substituted or unsubstituted heterocycloalkyl, $R^{72}$-substituted or unsubstituted aryl, or $R^{72}$-substituted or unsubstituted heteroaryl.

$R^{72}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl.

In embodiments, $L^{12}$ is independently a bond, $-N(R^{17})-$, $-N(R^{17})C(O)O-L^{13}-L^{14}-$, $-O-L^{13}-L^{14}-$, $-S-L^{13}-L^{14}-$, $-OC(O)-L^{13}-L^{14}-$, $-OC(O)N(R^{17})-L^{13}-L^{14}-$, $-OC(O)O-L^{13}-L^{14}-$, $-OSO_2-L^{13}-L^{14}-$, $-C(O)N(R^{17})-L^{13}-L^{14}-$, $-N(R^{17})C(O)-L^{13}-L^{14}-$, $-S(O)_2N(R^{17})-L^{13}-L^{14}-$, $-N(R^{17})S(O)_2-L^{13}-L^{14}-$, $R^{74}$-substituted or unsubstituted alkylene, $R^{74}$-substituted or unsubstituted heteroalkylene, $R^{74}$-substituted or unsubstituted cycloalkylene, $R^{74}$-substituted or unsubstituted heterocycloalkylene, $R^{74}$-substituted or unsubstituted arylene, or $R^{74}$-substituted or unsubstituted heteroarylene. $L^{12}$ may be a bond. $L^{12}$ may be $-N(R^{1712})-L^{1312}-L^{1412}-$. $L^{12}$ may be $-N(R^{1712})C(O)O-L^{1312}-L^{1412}-$. $L^{12}$ may be $-O-L^{1312}-L^{1412}-$. $L^{12}$ may be $-S-L^{1312}-L^{1412}-$. $L^{12}$ may be $-OC(O)-L^{1312}-L^{1412}-$. $L^{12}$ may be $-OC(O)N(R^{1712})-L^{1312}-L^{1412}-$. $L^{12}$ may be $-OC(O)O-L^{1312}-L^{1412}-$. $L^{12}$ may be $-OSO_2-L^{1312}-L^{1412}-$. $L^{12}$ may be $-C(O)N(R^{1712})-L^{1312}-L^{1412}-$. $L^{12}$ may be $-N(R^{1712})C(O)-L^{1312}-L^{1412}-$. $L^{12}$ may be $-S(O)_2N(R^{1712})-L^{1312}-L^{1412}-$. $L^{12}$ may be $-N(R^{1712})S(O)_2-L^{1312}-L^{1412}-$. $L^{12}$ may be $-C(O)O-L^{1312}-L^{1412}-$. $L^{12}$ may be $-SO_2-L^{131}-L^{1412}-$. $L^{12}$ may be $-N(H)-$. $L^{12}$ may be $-N(H)C(O)O-$. $L^{12}$ may be $-O-$. $L^{12}$ may be $-S-$. $L^{12}$ may be $-OC(O)-$. $L^{12}$ may be $-OC(O)N(H)-$. $L^{12}$ may be $-OC(O)O-$. $L^{12}$ may be $-OSO_2-$. $L^{12}$ may be $-C(O)N(H)-$. $L^{12}$ may be $-N(H)C(O)-$. $L^{12}$ may be $-S(O)_2N(H)-$. $L^{12}$ may be $-N(H)S(O)_2-$. $L^{12}$ may be $-C(O)O-$. $L^{12}$ may be $-SO_2-$.

$R^{74}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{75}$-substituted or unsubstituted alkyl, $R^{75}$-substituted or unsubstituted heteroalkyl, $R^{75}$-substituted or unsubstituted cycloalkyl, $R^{75}$-substituted or unsubstituted heterocycloalkyl, $R^{75}$-substituted or unsubstituted aryl, or $R^{75}$-substituted or unsubstituted heteroaryl.

$R^{75}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{76}$-substituted or unsubstituted alkyl, $R^{76}$-substituted or unsubstituted heteroalkyl, $R^{76}$-substituted or unsubstituted cycloalkyl, $R^{76}$-substituted or unsubstituted heterocycloalkyl, $R^{76}$-substituted or unsubstituted aryl, or $R^{76}$-substituted or unsubstituted heteroaryl.

In embodiments, $L^{13}$ is independently a bond, $-N(R^{17})-$, $-N(R^{17})C(O)O-$, $-O-$, $-S-$, $-OC(O)-$, $-OC(O)N(R^{17})-$, $-OC(O)O-$, $-OSO_2-$, $-C(O)N(R^{17})-$, $-N(R^{17})C(O)-$, $-S(O)_2N(R^{17})-$, $-N(R^{17})S(O)_2-$, $R^{77}$-substituted or unsubstituted alkylene, $R^{77}$-substituted or unsubstituted heteroalkylene, $R^{77}$-substituted or unsubstituted cycloalkylene, $R^{77}$-substituted or unsubstituted heterocycloalkylene, $R^{77}$-substituted or unsubstituted arylene, or $R^{77}$ substituted or unsubstituted heteroarylene. $L^{13}$ may be a bond. $L^{13}$ may be $-N(H)-$. $L^{13}$ may be $-N(H)C(O)O-$. $L^{13}$ may be $-O-$. $L^{13}$ may be $-S-$. $L^{13}$ may be $-OC(O)-$. $L^{13}$ may be $-OC(O)N(H)-$. $L^{13}$ may be $-OC(O)O-$. $L^{13}$ may be $-OSO_2-$. $L^{13}$ may be $-C(O)N(H)-$. $L^{13}$ may be $-N(H)C(O)-$. $L^{13}$ may be $-S(O)_2N(H)-$. $L^{13}$ may be $-N(H)S(O)_2-$. $L^{13}$ may be $-C(O)O-$. $L^{13}$ may be $-SO_2-$.

$R^{77}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{78}$-substituted or unsubstituted alkyl, $R^{78}$-substituted or unsubstituted heteroalkyl, $R^{78}$-substituted or unsubstituted cycloalkyl, $R^{78}$-substituted or unsubstituted heterocycloalkyl, $R^{78}$-substituted or unsubstituted aryl, or $R^{78}$-substituted or unsubstituted heteroaryl.

$R^{78}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, $R^{79}$-substituted or unsubstituted alkyl, $R^{79}$-substituted or unsubstituted heteroalkyl, $R^{79}$-substituted or unsubstituted cycloalkyl, $R^{79}$-substituted or unsubstituted heterocycloalkyl, $R^{79}$-substituted or unsubstituted aryl, or $R^{79}$-substituted or unsubstituted heteroaryl.

In embodiments, $L^{14}$ is independently a bond, $-N(R^{17})-$, $-N(R^{17})C(O)O-$, $-O-$, $-S-$, $-OC$ (O)—, —OC(O)N($R^{17}$)—, —OC(O)O—, —OSO$_2$—, —C(O)N($R^{17}$)—, —N($R^{17}$)C(O)—, —S(O)$_2$N($R^{17}$)—, —N($R^{17}$)S(O)$_2$—, $R^{80}$-substituted or unsubstituted alkylene, $R^{80}$-substituted or unsubstituted heteroalkylene, $R^{50}$-substituted or unsubstituted cycloalkylene, $R^{80}$-substituted or unsubstituted heterocycloalkylene, $R^{50}$-substituted or unsubstituted arylene, or $R^{80}$-substituted or unsubstituted heteroarylene. $L^{14}$ may be a bond. $L^{14}$ may be —N(H)—. $L^{14}$ may be —N(H)C(O)O—. $L^{14}$ may be —O—. $L^{14}$ may be —S—. $L^{14}$ may be —OC(O)—. $L^{14}$ may be —OC(O)N(H)—. $L^{14}$ may be —OC(O)O—. $L^{14}$ may be —OSO$_2$—. $L^{14}$ may be —C(O)N(H)—. $L^{14}$ may be —N(H)C(O)—. $L^{14}$ may be —S(O)$_2$N(H)—. $L^{14}$ may be —N(H)S(O)$_2$—. $L^{14}$ may be —C(O)O—. $L^{14}$ may be —SO$_2$—.

$R^{80}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{81}$-substituted or unsubstituted alkyl, $R^{81}$-substituted or unsubstituted heteroalkyl, $R^{81}$-substituted or unsubstituted cycloalkyl, $R^{81}$-substituted or unsubstituted heterocycloalkyl, $R^{81}$-substituted or unsubstituted aryl, or $R^{81}$-substituted or unsubstituted heteroaryl.

$R^{81}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{82}$-substituted or unsubstituted alkyl, $R^{82}$-substituted or unsubstituted heteroalkyl, $R^{82}$-substituted or unsubstituted cycloalkyl, $R^{82}$-substituted or unsubstituted heterocycloalkyl, $R^{82}$-substituted or unsubstituted aryl, or $R^{82}$-substituted or unsubstituted heteroaryl.

$R^{28}$, $R^{31}$, $R^{34}$, $R^{37}$, $R^{40}$, $R^{43}$, $R^{46}$, $R^{49}$, $R^{52}$, $R^{55}$, $R^{58}$, $R^{61}$, $R^{64}$, $R^{67}$, $R^{70}$, $R^{73}$, $R^{76}$, $R^{79}$, and $R^{82}$, are independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the compound is in a pharmaceutically acceptable salt. In embodiments, the compound is not in a pharmaceutically acceptable salt. In embodiments, the compound is co-administered with a second agent (e.g. therapeutic agent). In embodiments, the second agent is administered in a therapeutically effective amount. In embodiments, the second agent is an agent for treating an infectious disease. In embodiments, the second agent is an agent for treating a parasitic disease. In embodiments, the second agent is an agent for treating malaria. In embodiments, the second agent is an agent for treating cancer. In embodiments, the second agent is an agent for treating solid tumors. In embodiments, the second agent is an agent for treating hematological cancers. In embodiments, the second agent is an agent for treating diseases characterized by an increased level of iron relative to a control (e.g. subject without the disease or sample from a subject without the disease). In embodiments, the second agent is an agent for treating diseases characterized by an increased level of a reductant (e.g. biological reductant, iron) relative to a control (e.g. subject without the disease or sample from a subject without the disease).

Non-limiting examples of prodrug formulae described herein are shown below, wherein (-X-AGENT) represent R groups as described herein (e.g. $R^4$, $R^5$, $R^6$, $R^7$, $R^{11}$, or $R^{12}$). In embodiments, each (-X-AGENT) is independently a drug moiety, detectable moiety, or protein moiety. In embodiments, the compound is a compound described herein or a compound having the formula of a compound described herein, including in the examples section below and in the tables contained therein, for example

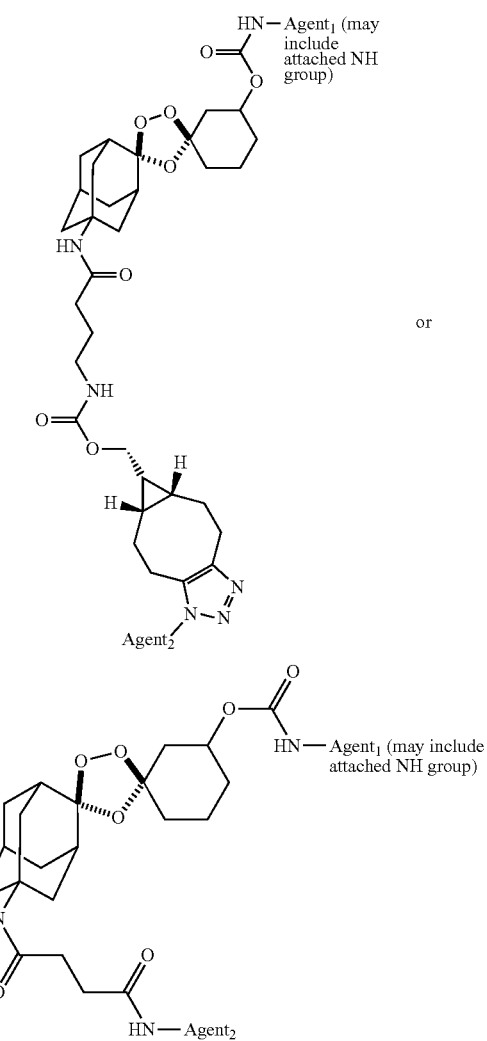

or another compound or formula described herein.

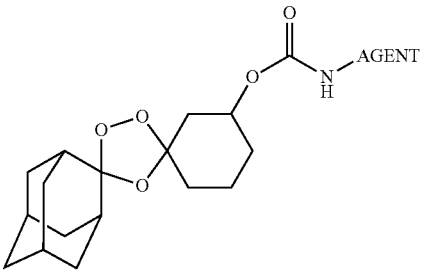

97
-continued
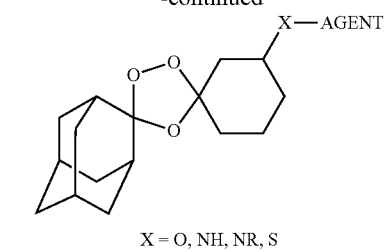
X = O, NH, NR, S
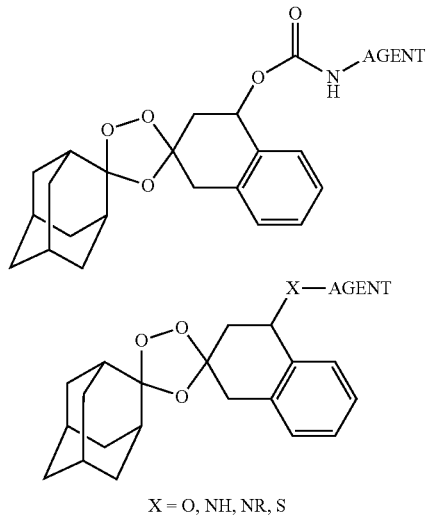
X = O, NH, NR, S
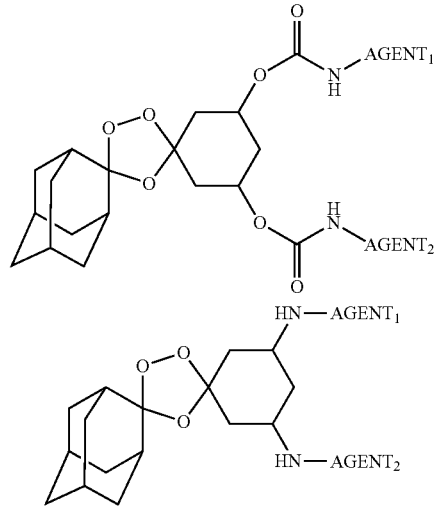
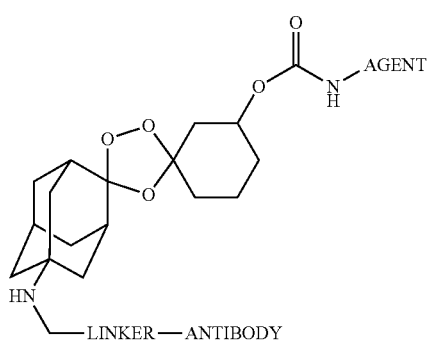
98
-continued
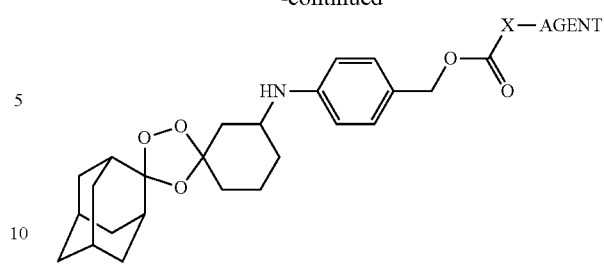
X = NR, O
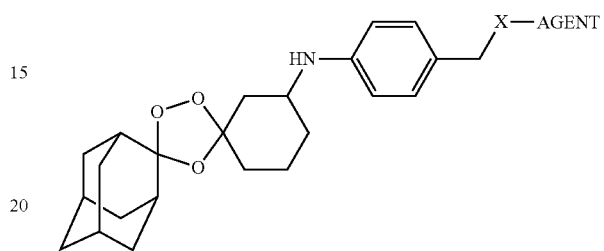
X = O, NR, S,
—O—C(O)—(connects to agent)
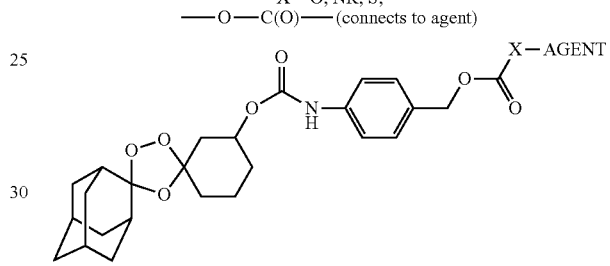
X = NR, O
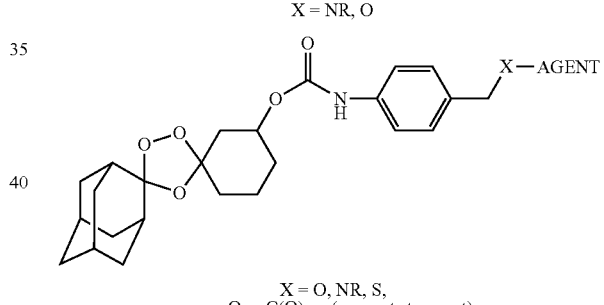
X = O, NR, S,
—O—C(O)—(connects to agent)
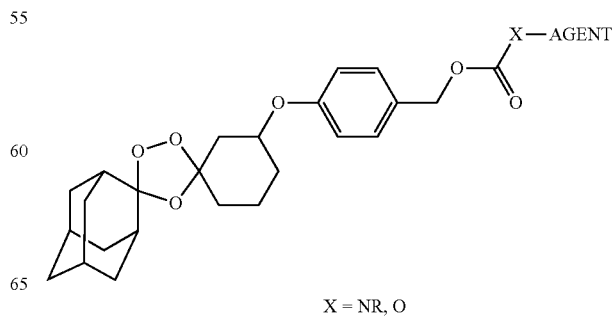
X = NR, O

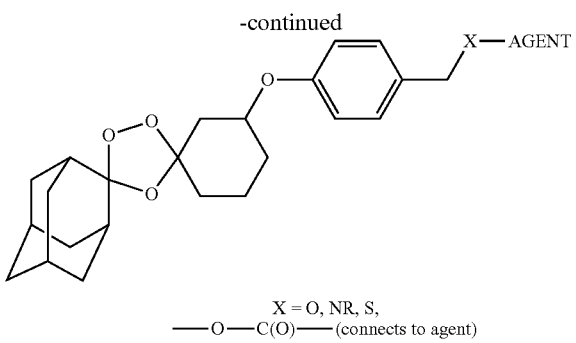

X = O, NR, S,
—O—C(O)— (connects to agent)

An example mechanism of drug delivery via reaction of a prodrug (e.g. as described herein) with ferrous iron:

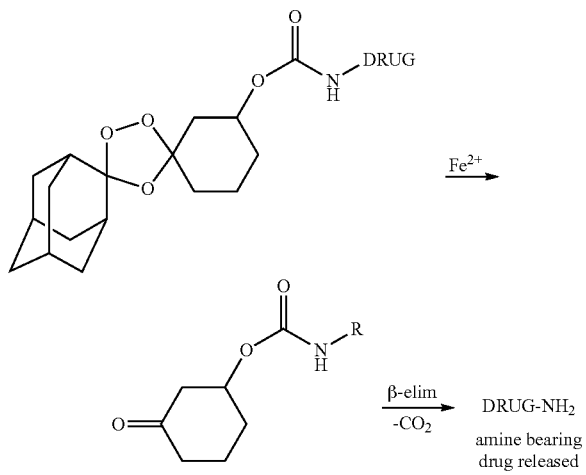

C. Pharmaceutical Compositions

In an aspect is provided a pharmaceutical composition including a pharmaceutically acceptable excipient and a compound described herein (including in an aspect, embodiment, table, example, or claim), or a pharmaceutically acceptable salt thereof.

In embodiments of the pharmaceutical compositions, the pharmaceutical composition includes a compound, or pharmaceutically acceptable salt thereof, as described herein (e.g. compound of formula I, or any embodiment thereof) in a therapeutically effective amount. In embodiments of the pharmaceutical compositions, the pharmaceutical composition includes a second agent (e.g. therapeutic agent). In embodiments of the pharmaceutical compositions, the pharmaceutical composition includes a second agent in a therapeutically effective amount. In embodiments of the pharmaceutical compositions, the second agent is an agent for treating cancer. In embodiments, the second agent is an agent for treating an infectious disease. In embodiments, the second agent is an agent for treating a bacterial disease. In embodiments, the second agent is an agent for treating a parasitic disease. In embodiments, the second agent is an agent for treating malaria. In embodiments, the second agent is an anti-cancer agent. In embodiments, the second agent is an anti-infective agent. In embodiments, the second agent is an anti-parasitic agent. In embodiments, the second agent is an anti-malarial agent. In embodiments, the second agent is an agent for treating solid tumors. In embodiments, the second agent is an agent for treating hematological cancers. In embodiments, the second agent is an agent for treating diseases characterized by an increased level of iron relative to a control (e.g. subject without the disease or sample from a subject without the disease). In embodiments, the second agent is an agent for treating diseases characterized by an increased level of reductant (e.g. biological reductant, $Fe^{II}$) relative to a control (e.g. subject without the disease or sample from a subject without the disease).

D. Methods

In an aspect is provided a method of treating a disease in a patient in need of such treatment, said method including administering a therapeutically effective amount of a compound described herein (including in an aspect, embodiment, table, example, or claim), or a pharmaceutically acceptable salt thereof, to the patient.

In an aspect is provided a compound as described herein (including in an aspect, embodiment, table, example, or claim), or a pharmaceutically acceptable salt thereof, for use in the treatment of a disease in a subject. The use may include administering to the subject a compound described herein. The use may include administering to the subject a therapeutically effective amount of a compound described herein. In an aspect is provided a pharmaceutical composition as described herein (including in an aspect, embodiment, table, example, or claim) for use in the treatment of a disease in a subject.

In an aspect is provided a compound as described herein for use in the manufacture of a medicament for treatment of a disease. In an aspect is provided a pharmaceutical composition as described herein for use in the manufacture of a medicament for treatment of a disease.

In embodiments, the disease is associated with a cell or organism having an increased level of a reductant (e.g. biological reductant, $Fe^{II}$) compared to a standard control (e.g. subject without the disease or sample from a subject without the disease). In embodiments, the disease is associated with a cell or organism having an increased $Fe^{II}$ level compared to a standard control (e.g. subject without the disease or sample from a subject without the disease). In some embodiments, the method of treating is a method of preventing.

Drug moieties that form part of the prodrugs described herein obtain functionality due to chemical changes in the prodrugs that occur under physiological conditions. For example, the trioxane or trioxolane ring moiety of prodrugs described herein (i.e. compounds described herein) may react with $Fe^{II}$, leading to the formation of a ketone species. The ketone then undergoes a beta-elimination reaction to release the agent (e.g. drug, detectable agent, protein, sideropohore, antibody) and a new ketone containing compound. The agent (e.g. drug, detectable agent, protein, sideropohore, antibody) obtained from the prodrug due to chemical changes under physiological conditions may be capable of use in treating or detecting mammalian disease caused by a cell or organism having increased reductant (e.g. biological reductant, $Fe^{II}$) levels compared to reductant (e.g. biological reductant, $Fe^{II}$) levels in mammalian plasma. The agent (e.g. drug, detectable agent, protein, sideropohore, antibody) obtained from the prodrug due to chemical changes under physiological conditions may be capable of use in treating or detecting mammalian disease caused by a cell or organism having increased $Fe^{II}$ levels compared to $Fe^{II}$ levels in mammalian plasma. The mammalian disease may be a human disease. In some embodiments, the human disease may be a parasitic disease or a cancer. In embodiments, the disease may be malaria, schistosomiasis, trypanosomiasis, leukemia, cervical cancer, breast cancer, colon cancer, ovarian cancer, prostate cancer, thyroid cancer, lung cancer, glioblastoma, or melanoma. In embodiments, the disease may be a cancer where transferrin receptors (CD71) are over-expressed as compared to normal cells. In embodiments, the disease may be a bacterial disease. In embodiments, the disease may be an infectious disease.

In another aspect of the present invention, the prodrug compounds (compound described herein, including formula I and embodiments) can be employed in methods to treat a disease that is associated with a cell or organism that has increased reducant (e.g. biological reducant, $Fe^{II}$) levels compared to reducant (e.g. biological reducant, $Fe^{II}$) levels in the same location in a mammal without the disease (e.g. in mammalian plasma).

In an aspect is provided a compound as described herein (including in an aspect, embodiment, table, example, or claim), or a pharmaceutically acceptable salt thereof, for use in the treatment of a disease that is associated with a cell or organism that has increased reducant (e.g. biological reducant, $Fe^{II}$) levels compared to reducant (e.g. biological reducant, $Fe^{II}$) levels in the same location in a mammal without the disease (e.g. in mammalian plasma). The use may include administering to the subject a compound described herein. The use may include administering to the subject a therapeutically effective amount of a compound described herein. In an aspect is provided a pharmaceutical composition as described herein (including in an aspect, embodiment, table, example, or claim) for use in the treatment of a disease that is associated with a cell or organism that has increased reducant (e.g. biological reducant, $Fe^{II}$) levels compared to reducant (e.g. biological reducant, $Fe^{II}$) levels in the same location in a mammal without the disease (e.g. in mammalian plasma).

In an aspect is provided a compound as described herein for use in the manufacture of a medicament for treatment of a disease that is associated with a cell or organism that has increased reducant (e.g. biological reducant, $Fe^{II}$) levels compared to reducant (e.g. biological reducant, $Fe^{II}$) levels in the same location in a mammal without the disease (e.g. in mammalian plasma). In an aspect is provided a pharmaceutical composition as described herein for use in the manufacture of a medicament for treatment of a disease that is associated with a cell or organism that has increased reducant (e.g. biological reducant, $Fe^{II}$) levels compared to reducant (e.g. biological reducant, $Fe^{II}$) levels in the same location in a mammal without the disease (e.g. in mammalian plasma).

The method or use may include administering an effective amount of the prodrug compound (or pharmaceutical formulation thereof) to a patient in need of such treatment. Increased reducant (e.g. biological reducant, $Fe^{II}$) levels are levels (e.g. cellular) of reducant (e.g. biological reducant, $Fe^{II}$) that are sufficiently high to cause disease in a patient and/or are higher than in the plasma of a patient. In some embodiments, the method or use includes administering an effective amount of a prodrug compound and a reducant (e.g. biological reducant, $Fe^{II}$) containing agent to a patient in need of such treatment. The reducant (e.g. biological reducant, $Fe^{II}$) containing agent may be co-administered with the prodrug (compound described herein, including formula I and embodiments). In another embodiment the reducant (e.g. biological reducant, $Fe^{II}$) containing agent may be administered before or after prodrug administration. A disease that is associated with a cell or organism that has increased reducant (e.g. biological reducant, $Fe^{II}$) levels refers to a disease in which reducant (e.g. biological reducant, $Fe^{II}$) levels are elevated relative to reducant (e.g. biological reducant, $Fe^{II}$)$^I$ levels in the cell or organism in the absence of the disease. The disease associated with increased reducant (e.g. biological reducant, $Fe^{II}$) levels is not bound by any particular mechanistic theory, and include those diseases resulting in increased reducant (e.g. biological reducant, $Fe^{II}$) levels and/or caused by increased reducant (e.g. biological reducant, $Fe^{II}$) levels. Thus, in some embodiments, the increased reducant (e.g. biological reducant, $Fe^{II}$) levels are the result of the disease. In some embodiments, the increased reducant (e.g. biological reducant, $Fe^{II}$) levels are the result of the disease, and additionally the increased reducant (e.g. biological reducant, $Fe^{II}$) levels may cause symptoms related to increased reducant (e.g. biological reducant, $Fe^{II}$) levels.

In another aspect of the present invention, the prodrug compounds (compound described herein, including formula I and embodiments) can be employed in methods to treat a disease that is associated with a cell or organism that has increased $Fe^{II}$ levels compared to $Fe^{II}$ levels in mammalian plasma.

In an aspect is provided a compound as described herein (including in an aspect, embodiment, table, example, or claim), or a pharmaceutically acceptable salt thereof, for use in the treatment of a disease that is associated with a cell or organism that has increased $Fe^{II}$ levels compared to $Fe^{II}$ levels in mammalian plasma. The use may include administering to the subject a compound described herein. The use may include administering to the subject a therapeutically effective amount of a compound described herein. In an aspect is provided a pharmaceutical composition as described herein (including in an aspect, embodiment, table, example, or claim) for use in the treatment of a disease that is associated with a cell or organism that has increased $Fe^{II}$ levels compared to $Fe^{II}$ levels in mammalian plasma.

In an aspect is provided a compound as described herein for use in the manufacture of a medicament for treatment of a disease that is associated with a cell or organism that has increased $Fe^{II}$ levels compared to $Fe^{II}$ levels in mammalian plasma. In an aspect is provided a pharmaceutical composition as described herein for use in the manufacture of a medicament for treatment of a disease that is associated with a cell or organism that has increased $Fe^{II}$ levels compared to $Fe^{II}$ levels in mammalian plasma.

The method or use may include administering an effective amount of the prodrug compound (or pharmaceutical formulation thereof) to a patient in need of such treatment. Increased $Fe^{II}$ levels are cellular levels of $Fe^{II}$ that are sufficiently high to cause disease in a patient and are higher than in the plasma of a patient. In some embodiments, the method or use includes administering an effective amount of a prodrug compound and an $Fe^{II}$ containing agent to a patient in need of such treatment. In another embodiment, the $Fe^{II}$ containing agent is ferroglycine sulfate or transferrin. The $Fe^{II}$ containing agent may be co-administered with the prodrug (compound described herein, including formula I and embodiments). In another embodiment the $Fe^{II}$ containing agent may be administered before or after prodrug administration. A disease that is associated with a cell or organism that has increased $Fe^{II}$ levels compared to $Fe^{II}$ levels in mammalian plasma refers to a disease in which $Fe^{II}$ levels are elevated relative to $Fe^{II}$ levels in mammalian plasma in the absence of the disease. The disease associated with increased $Fe^{II}$ levels is not bound by any particular mechanistic theory, and include those diseases resulting in increase $Fe^{II}$ levels and/or caused by $Fe^{II}$ levels. Thus, in some embodiments, the increased $Fe^{II}$ levels are the result of the disease. In some embodiments, the increased $Fe^{II}$ levels are the result of the disease, and additionally the increased $Fe^{II}$ levels cause symptoms related to increased $Fe^{II}$ levels.

In an aspect is provided a method of identifying a patient having a disease associated with a cell or organism having an increased reducant (e.g. biological reducant, $Fe^{II}$) level compared to a standard control, the method including administering an effective amount of a compound described herein (including in an aspect, embodiment, table, example, or claim), or a pharmaceutically acceptable salt thereof, to the patient. The method may include detecting the presence of the compound. The method may include detecting an increased level of the compound or detectable agent compared to the level of compound or detectable agent detected in a patient without the disease.

In an aspect is provided a compound as described herein (including in an aspect, embodiment, table, example, or claim), or a pharmaceutically acceptable salt thereof, for use in identifying a patient having a disease associated with a cell or organism having an increased reducant (e.g. biological reducant, $Fe^{II}$) level compared to a standard control. The use may include administering to the subject a compound described herein. The use may include administering to the subject an effective amount of a compound described herein.

In an aspect is provided a method of identifying a patient having a disease associated with a cell or organism having an increased $Fe^{II}$ level compared to a standard control, the method including administering an effective amount of a compound described herein (including in an aspect, embodiment, table, example, or claim), or a pharmaceutically acceptable salt thereof, to the patient.

In an aspect is provided a compound as described herein (including in an aspect, embodiment, table, example, or claim), or a pharmaceutically acceptable salt thereof, for use in identifying a patient having a disease associated with a cell or organism having an increased $Fe^{II}$ level compared to a standard control. The use may include administering to the subject a compound described herein. The use may include administering to the subject an effective amount of a compound described herein.

The method or use may include detecting the presence of the compound. The method or use may include detecting an increased level of the compound or detectable agent compared to the level of compound or detectable agent detected in a patient without the disease.

In embodiments, the compound includes a detectable moiety. In embodiments, the detectable moiety is a fluorescent moiety. In embodiments, the detectable moiety is a moiety of a fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticle, USPIO nanoparticle aggregate, nanoparticle contrast agent, liposome or other delivery vehicle containing Gadolinium chelate ("Gd-chelate") molecules, Gadolinium, radioisotope (e.g. $^{32}P$), radionuclide (e.g. carbon-11, nitrogen-13, oxygen-15, fluorine-18, rubidium-82), fluorodeoxyglucose (e.g. fluorine-18 labeled), gamma ray emitting radionuclide, positron-emitting radionuclide, iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, fluorescent protein, xanthene derivative (e.g. fluorescein, rhodamine, Oregon green, eosin, or Texas red), cyanine or derivative (e.g. cyanine, indocarbocyanine, oxacarbocyanine, thiacarbocyanine or merocyanine), napththalene derivative (e.g. dansyl or prodan derivative), coumarin or a derivative, oxadiazole derivative (e.g. pyridyloxazole, nitrobenzoxadiazole or benzoxadiazole), anthracene derivative (e.g. anthraquinone, DRAQ5, DRAQ7, or CyTRAK Orange), pyrene derivative (e.g. cascade blue or derivative), oxazine derivative (e.g. Nile red, Nile blue, cresyl violet, oxazine 170), acridine derivative (e.g. proflavin, acridine orange, acridine yellow), arylmethine derivative (e.g. auramine, crystal violet, malachite green), tetrapyrrole derivative (e.g. porphin, phthalocyanine, bilirubin), CF Dye™, DRAQ™, CyTRAK™, BODIPY™, Alexa Fluor™, DyLight Fluor™, Atto™, Tracy™, FluoProbe™, Abberior Dve™. DY™ dyes, MegaStokes Dye™, Sulfo Cy™, Seta™ dyes, SeTau™ dye, Square Dye™, Quasar™ dyes, Cal Fluor™ dyes, SureLight Dye™, PerCP™, Phycobilisome™, APC™, APCXL™, RPE™, or BPE™.

In another aspect, is provided a method of detecting a detectable agent (e.g. fluorescent agent) in an organism, by administering a compound described herein to an organism, allowing the organism to metabolize the compound thereby producing a detectable agent (e.g fluorescent agent), and detecting the detectable agent (e.g. fluorescent agent) in a sample from the organism.

In another aspect, the present invention provides a method of detecting a detectable agent (e.g. fluorescent agent) in a sample from an organism, by administering a compound described herein to the sample from an organism, allowing the sample to metabolize the compound thereby producing a detectable agent (e.g fluorescent agent), and detecting the detectable agent (e.g. fluorescent agent) in the sample.

E. Additional Embodiments

1. A compound having the formula:

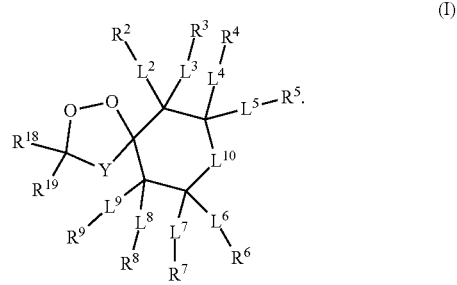

(I)

wherein $L^2$, $L^3$, $L^4$, $L^5$, $L^6$, $L^7$, $L^8$, $L^9$, $L^{11}$, and $L^{12}$ are independently a bond, —N($R^{17}$)-$L^{13}$-$L^{14}$-, —N($R^{17}$)C(O)O-$L^{13}$-$L^{14}$-, —O-$L^{13}$-$L^{14}$-, —S-$L^{13}$-$L^{14}$-, —OC(O)-$L^{13}$-$L^{14}$-, —OC(O)N($R^{17}$)-$L^{13}$-$L^{14}$-, —OC(O)O-$L^{13}$-$L^{14}$-, —OSO$_2$-$L^{13}$-$L^{14}$-, —C(O)N($R^{17}$)-$L^{13}$-$L^{14}$-, —N($R^{17}$)C(O)-$L^{13}$-$L^{14}$-, —S(O)$_2$N($R^{17}$)-$L^{13}$-$L^{14}$-, —N($R^{17}$)S(O)$_2$-$L^{13}$-$L^{14}$-, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{10}$ is —N(-$L^{11}$-$R^{11}$)— or —C((-$L^{11}$-$R^{11}$)(-$L^{12}$-$R^{12}$))—; each $L^{13}$ and $L^{14}$ are independently selected from a bond, —N($R^{17}$)—, —N($R^{17}$)C(O)O—, —O—, —S—, —OC(O)—, —OC(O)N($R^{17}$)—, —OC(O)O—, —OSO$_2$—, —C(O)N($R^{17}$)—, —N($R^{17}$)C(O)—, —S(O)$_2$N (R$^{17}$)—, —N(R$^{17}$)S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; R$^2$, R$^3$, R$^4$, R$^5$, R$^6$, R$^7$, R$^8$, R$^9$, R$^{11}$, and R$^{12}$, are independently hydrogen, oxo, halogen, —CX$_3$, —CN, —SO$_2$Cl, —SO$_n$R$^{16}$, —SO$_v$NR$^{13}$R$^{14}$, —NHNH$_2$, —ONR$^{13}$R$^{14}$, —NHC=(O)NHNH$_2$, —NHC=(O)NR$^{13}$R$^{14}$, —N(O)$_m$, —NR$^{13}$R$^{14}$, —C(O)R$^{15}$, —C(O)—OR$^{15}$, —C(O)NR$^{13}$R$^{14}$, —OR$^{16}$, —NR$^{13}$SO$_2$R$^{16}$, —NR$^{13}$C=(O)R$^{15}$, —NR$^{13}$C(O)—OR$^{15}$, —NR$^{13}$OR$^{15}$, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, a detectable moiety, or a drug moiety; R$^5$ and R$^{11}$ substituents may be joined to form a substituted or unsubstituted cycloalkyl, substituted or unsubstituted heterocycloalkyl, substituted or unsubstituted aryl, or substituted or unsubstituted heteroaryl; R$^6$ and R$^{11}$ substituents may be joined to form a substituted or unsubstituted cycloalkyl, substituted or unsubstituted heterocycloalkyl, substituted or unsubstituted aryl, or substituted or unsubstituted heteroaryl; R$^2$ and R$^3$, R$^4$ and R$^5$, R$^6$ and R$^7$, R$^8$ and R$^9$, or R$^{11}$ and R$^{12}$ may be joined to form a substituted or unsubstituted cycloalkyl, substituted or unsubstituted heterocycloalkyl, substituted or unsubstituted aryl, or substituted or unsubstituted heteroaryl; each R$^{13}$, R$^{14}$, R$^{15}$, R$^{16}$, and R$^{17}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{13}$ and R$^{14}$ substituents bonded to the same atom may be joined to form a substituted or unsubstituted heterocycloalkyl or substituted or unsubstituted heteroaryl; R$^{18}$ and R$^{19}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, detectable moiety, siderophore moiety, or a drug moiety; R$^{18}$ and R$^{19}$ may be joined to form a substituted or unsubstituted cycloalkyl, substituted or unsubstituted heterocycloalkyl, protein moiety, detectable moiety, siderophore moiety, or drug moiety; m and v are independently 1 or 2; n is independently an integer from 0 to 2; Y is —O—, —S—, —OO—, —CH$_2$O—, or —OCH$_2$—; and X is independently —Cl, —Br, —I, or —F.

2. The compound of embodiment 1, wherein the compound is not a compound wherein R$^{11}$ and R$^{12}$ do not comprise a drug moiety, protein moiety, or detectable moiety; L$^2$, L$^3$, L$^4$, L$^5$, L$^6$, L$^7$, L$^8$, and L$^9$ are bonds; and R$^2$, R$^3$, R$^4$, R$^5$, R$^6$, R$^7$, R$^8$, and R$^9$ are hydrogen.

3. The compound of embodiment 1, wherein the compound is not a compound wherein R$^{11}$ and R$^{12}$ do not comprise a drug moiety, protein moiety, or detectable moiety; R$^{18}$ and R$^{19}$ are joined to form a substituted or unsubstituted cycloalkyl, substituted or unsubstituted heterocycloalkyl, protein moiety, detectable moiety, or drug moiety; L$^2$, L$^3$, L$^4$, L$^5$, L$^6$, L$^7$, L$^8$, and L$^9$ are bonds; and R$^2$, R$^3$, R$^4$, R$^5$, R$^6$, R$^7$, R$^8$, and R$^9$ are hydrogen.

4. The compound of embodiment 1, wherein the compound is not a compound wherein: R$^{11}$ and R$^{12}$ do not comprise a drug moiety, protein moiety, or detectable moiety; R$^{18}$ and R$^{19}$ are joined to form an unsubstituted adamantyl; L$^2$, L$^3$, L$^4$, L$^5$, L$^6$, L$^7$, L$^8$, and L$^9$ are bonds; and R$^2$, R$^3$, R$^4$, R$^5$, R$^6$, R$^7$, R$^8$, and R$^9$ are hydrogen.

5. The compound of one of embodiments 1 to 4 having the formula:

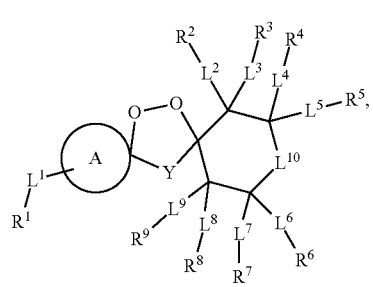

(Ia)

wherein Ring A is a substituted or unsubstituted cycloalkylene or substituted or unsubstituted heterocycloalkylene; R$^1$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a protein moiety, a detectable moiety, a siderophore, moiety, or a drug moiety; L$^1$ is independently a bond, —N(R$^{17}$)-L$^{13}$-L$^{14}$-, —N(R$^{17}$)C(O)O-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R 17)-L$^{13}$-L$^{14}$-, —OC(O)O-L$^{13}$-L$^{14}$-, —OSO$_2$-L$^{13}$-L$^{14}$-, —C(O)N(R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, —N(R$^{17}$)S(O)$_2$-L$^{13}$-L$^{14}$-, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

6. A compound of one of embodiments 1 to 5 having the formula:

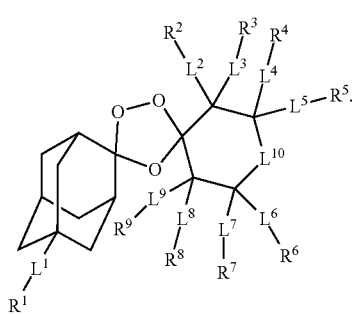

(Ib)

7. The compound of one of embodiments 5 to 6, wherein -L¹-R¹ is —H.
8. The compound of one of embodiments 5 to 6, wherein -L¹ is
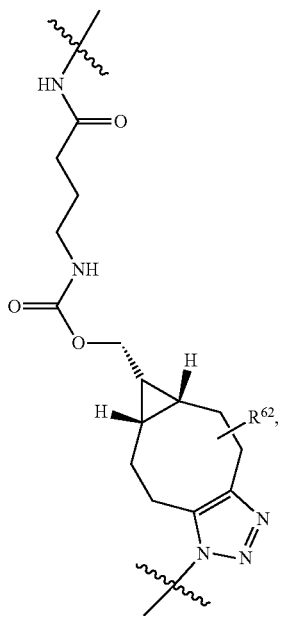
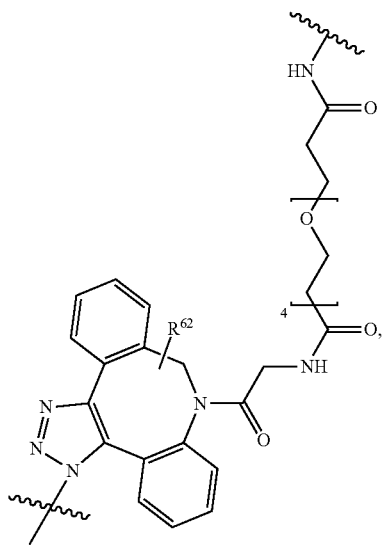
-continued
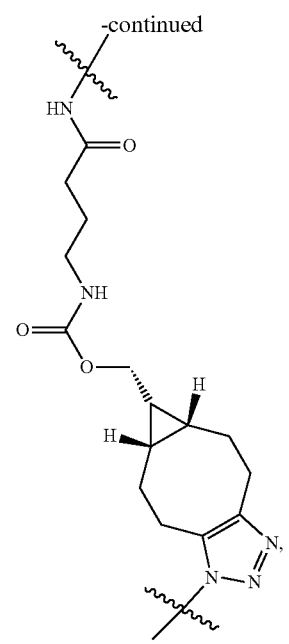
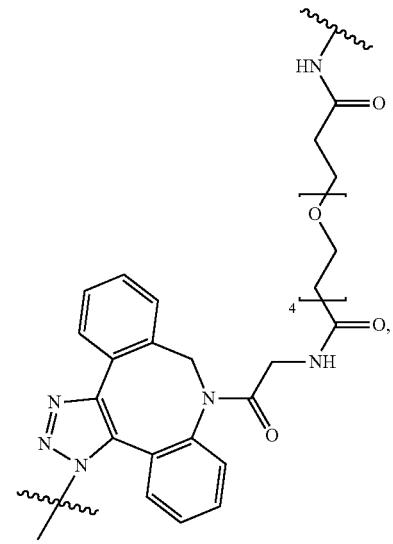
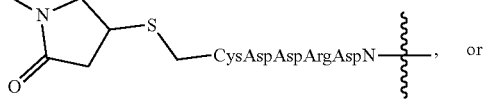
or -continued

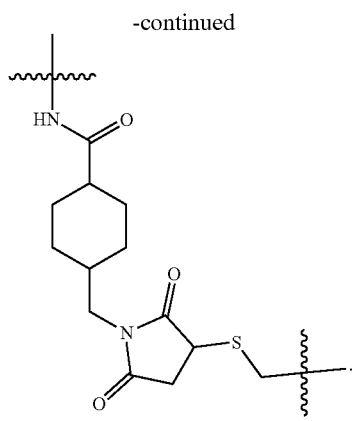

9. The compound of one of embodiments 5 to 6, wherein -L$^1$ is is —NHC(O)—(CH$_2$)$_W$—NHC(O)O—(CH$_2$)$_{Y1}$—, —NHC(O)—(CH$_2$)$_W$—C(O)NH—(CH$_2$)$_{Y1}$—, —NHC(O)—(CH$_2$) w-C(O)—, —NHC(O)—(CH$_2$)$_W$—NH—, —NHC(O)—(CH$_2$)$_W$—NHC(O)—, —NHC(O)—(CH$_2$)$_W$—C(O)NH—, —NHC(O)—(CH$_2$)$_W$—NHC(O)O—, —NHC(O)—(CH$_2$)$_W$—(OCH$_2$CH$_2$)$_{T1}$—C(O)NH—(CH$_2$)$_{Y1}$—, —NHC(O)—(CH$_2$)$_W$—(OCH$_2$CH$_2$)$_{T1}$—C(O)NH—(CH$_2$)$_{Y1}$—C(O)—; W is an integer between 1 and 8; T1 is an integer between 1 and 8, and Y1 is an integer between 1 and 8.

10. The compound of one of embodiments 5 to 6 or 8 to 9, wherein R$^1$ is a protein moiety.

11. The compound of one of embodiments 5 to 6 or 8 to 9, wherein R$^1$ is a siderophore moiety.

12. The compound of embodiment 10, wherein R$^1$ is an antibody moiety.

13. The compound of one of embodiments 1 to 12, wherein L$^2$, L$^3$, L$^4$, L$^6$, L$^7$, L$^8$, L$^9$, L$^{11}$, and L$^{12}$ are a bond; R$^2$, R$^3$, R$^5$, R$^6$, R$^7$, R$^8$, R$^9$, R$^{11}$, and R$^{12}$ are hydrogen; L$^{10}$ is —CH$_2$—; L$^5$ is a bond, —N(R$^{17}$)-L$^{13}$-L$^{14}$-, —N(R$^{17}$)C(O)O-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R$^{17}$)-L$^{13}$-L$^{14}$-, —OC(O)O-L$^{13}$-L$^{14}$-, —OSO$_2$-L$^{13}$-L$^{14}$-, —C(O)N(R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, —N(R$^{17}$)S(O)$_2$-L$^{13}$-L$^{14}$-; and R$^5$ is a protein moiety, drug moiety, or a detectable moiety.

14. The compound of embodiment 13, wherein L$^5$ is a bond, —N(R$^{17}$)-L$^{13}$-L$^{14}$-, —O-L$^{13}$-L$^{14}$-, —OC(O)-L$^{13}$-L$^{14}$-, or —OC(O)N(R$^{17}$)-L$^{13}$-L$^{14}$-.

15. The compound of one of embodiments 1 to 12, wherein L$^2$, L$^3$, L$^4$, L$^6$, L$^8$, L$^9$, L$^{11}$, and L$^{12}$ are a bond; R$^2$, R$^3$, R$^5$, R$^6$, R$^8$, R$^9$, R$^{11}$, and R$^{12}$ are hydrogen; L$^5$ and L$^7$ are independently a bond, —N(R$^{17}$)-L$^{13}$-L$^{14}$-, —N(R$^{17}$)C(O)O-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R$^{17}$)-L$^{13}$-L$^{14}$-, —OC(O)O-L$^{13}$-L$^{14}$-, —OSO$_2$-L$^{13}$-L$^{14}$-, —C(O)N(R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, or —N(R$^{17}$)S(O)$_2$-L$^{13}$-L$^{14}$-; and R$^5$ and R$^7$ are each independently a drug moiety, protein moiety, or detectable moiety.

16. The compound of embodiment 15, wherein L$^5$ and L$^7$ are independently a bond, —N(R$^7$)-L$^{13}$-L$^{14}$-, —O-L$^{13}$-L$^{14}$-, —OC(O)-L$^{13}$-L$^{14}$-, or —OC(O)N(R$^{17}$)-L$^{13}$-L$^{14}$-.

17. The compound of one of embodiments 1 to 12, wherein L$^2$, L$^3$, L$^4$, L$^5$, L$^6$, L$^7$, L$^8$, L$^9$, and L$^{12}$ are a bond; R$^2$, R$^3$, R$^4$, R$^5$, R$^6$, R$^7$, R$^9$, and R$^{12}$ are hydrogen; L$^{10}$ is —N(-L$^{11}$-R$^{11}$)—; L$^{11}$ is a bond, —N(R$^{17}$)-L$^{13}$-L$^{14}$-, —N(R$^{17}$)C(O)O-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R$^{17}$)-L$^{13}$-L$^{14}$-, —OC(O)O-L$^{13}$-L$^{14}$-, —OSO$_2$-L$^{13}$-L$^{14}$-, —C(O)N(R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, —N(R$^{17}$)S(O)$_2$-L$^{13}$-L$^{14}$-; and R$^1$ is a drug moiety, protein moiety, or detectable moiety.

18. The compound of embodiment 17, wherein L$^1$ is independently a bond, —N(R$^7$)-L$^{13}$-L$^{14}$-, —O-L$^{13}$-L$^{14}$-, —OC(O)-L$^{13}$-L$^{14}$-, or —OC(O)N(R$^{17}$)-L$^{13}$-L$^{14}$-.

19. The compound of one of embodiments 17 to 18, wherein R$^{11}$ is an antibody moiety.

20. The compound of one of embodiments 1 to 12, wherein L$^2$, L$^3$, L$^4$, L$^6$, L$^7$, L$^8$, L$^9$, L$^1$, and L$^{12}$ are a bond; R$^2$, R$^3$, R$^4$, R$^6$, R$^8$, R$^9$, and R$^{12}$ are hydrogen; L$^{10}$ is —CH(—R$^{11}$)—; R$^7$ and R$^1$ are joined to form a substituted or unsubstituted cycloalkyl, substituted or unsubstituted heterocycloalkyl, substituted or unsubstituted aryl, or substituted or unsubstituted heteroaryl; L$^5$ is a bond, —N(R$^{17}$)-L$^{13}$-L$^{14}$-, —N(R$^{17}$)C(O)O-L$^{13}$-L$^{14}$-, —O-L$^{13}$-L$^{14}$-, —S-L$^{13}$-L$^{14}$-, —OC(O)-L$^{13}$-L$^{14}$-, —OC(O)N(R 17)-L$^{13}$-L$^{14}$-, —OC(O)O-L$^{13}$-L$^{14}$-, —OSO$_2$-L$^{13}$-L$^{14}$-, —C(O)N(R$^{17}$)-L$^{13}$-L$^{14}$-, —N(R$^{17}$)C(O)-L$^{13}$-L$^{14}$-, —S(O)$_2$N(R$^{17}$)-L$^{13}$-L$^{14}$-, or —N(R$^{17}$)S(O)$_2$-L$^{13}$-L$^{14}$-; and R$^5$ is a drug moiety, protein moiety, or detectable moiety.

21. The compound of embodiment 20, wherein L$^5$ is independently a bond, —N(R$^{17}$)-L$^{13}$-L$^{14}$-, —O-L$^{13}$-L$^{14}$-, —OC(O)-L$^{13}$-L$^{14}$-, or —OC(O)N(R$^{17}$)-L$^{13}$-L$^{14}$-.

22. The compound of embodiment 20, wherein R$^7$ and R$^{11}$ are joined to form an unsubstituted aryl.

23. The compound of one of embodiments 1 to 22, wherein each L$^{13}$ is independently selected from a bond or substituted or unsubstituted arylene.

24. The compound of embodiment 23, wherein each L$^{13}$ is independently selected from a bond or substituted or unsubstituted phenylene.

25. The compound of one of embodiments 1 to 24, wherein each L$^{14}$ is independently selected from a bond, substituted or unsubstituted alkylene, or substituted or unsubstituted heteroalkylene.

26. The compound of embodiment 25, wherein each L$^{14}$ is independently selected from a bond, —(CH$_2$)$_w$—, or —(CH$_2$)$_w$—OC(O)—; w is an integer between 1 and 4.

27. The compound of one of embodiments 1 to 26, wherein each -L$^{13}$-L$^{14}$- is independently selected from a bond, -Ph-(CH$_2$)$_w$—, or -Ph-(CH$_2$)$_w$—OC(O)—; w is an integer between 1 and 4.

28. The compound of one of embodiments 1 to 27, wherein -L$^{13}$-L$^{14}$- is a bond.

29. The compound of one of embodiments 1 to 27, wherein -L$^{13}$-L$^{14}$- is -Ph-(CH$_2$)$_w$—; w is an integer between 1 and 4.

30. The compound of one of embodiments 1 to 27, wherein -L$^{13}$-L$^{14}$- is -Ph-(CH$_2$)$_w$—OC(O)—; w is an integer between 1 and 4.

31. The compound of one of embodiments 26 to 30, wherein w is 1.

32. The compound of one of embodiments 1 to 31, wherein the drug moiety is independently a monovalent radical of an anti-infective agent.

33. The compound of embodiment 32, wherein the anti-infective agent is an anti-parasitic agent.

34. The compound of embodiment 32, wherein the anti-infective agent is an anti-malarial drug.

35. The compound of embodiment 32, wherein the anti-infective agent is an anti-bacterial drug.

36. The compound of one of embodiments 1 to 31, wherein the drug moiety is independently a monovalent radical of an anti-cancer drug.

37. The compound of one of embodiments 1 to 36, wherein the detectable moiety is independently a monovalent radical of a fluorophore.

38. The compound of one of embodiments 1 to 37, wherein the protein moiety is independently a monovalent radical of an antibody.

39. A pharmaceutical composition comprising a pharmaceutically acceptable excipient and a compound of one of embodiments 1 to 38.

40. A method of treating a disease in a patient in need of such treatment, said method comprising administering a therapeutically effective amount of a compound of one of embodiments 1 to 38 to said patient.

41. The method of embodiment 40, wherein the disease is associated with a cell or organism having an increased $Fe^{II}$ level compared to a standard control.

42. The method of embodiment 40, wherein the disease is cancer.

43. The method of embodiment 40, wherein the disease is a hematological cancer.

44. The method of embodiment 40, wherein the disease is a non-hematological cancer.

45. The method of embodiment 40, wherein the disease is malaria.

46. The method of embodiment 40, wherein the disease is a bacterial disease.

47. The method of embodiment 40, wherein the disease is a parasitic disease.

48. A method of identifying a patient having a disease associated with a cell or organism having an increased $Fe^{II}$ level compared to a standard control, said method comprising administering an effective amount of a compound of one of embodiments 1 to 38 to said patient.

49. A method of identifying a patient having a disease associated with an increased reductant level compared to a standard control, said method comprising obtaining a biological sample from said patient, contacting said biological sample with an effective amount of a compound of one of embodiments 1 to 38, wherein said compound comprises a detectable moiety, detecting an increased level of said detectable moiety or a detectable agent resulting from cleavage of said detectable moiety relative the level of said detectable moiety or detectable agent in the standard control.

EXAMPLES

Example 1. Preparation of (Cmpd 1), dispiro[adamantane-2,2'-[1,3,5]trioxolane-4',1"-cyclohexane]-3"-yl N-(2,5-dichlorophenyl)carbamate

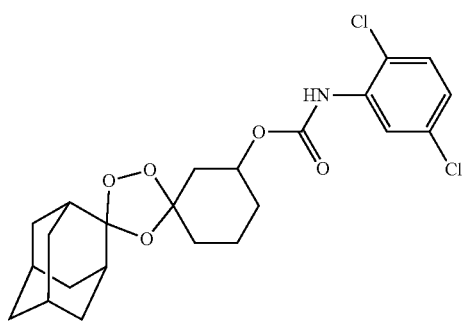 [SMILES: O=C(Nc1cc(Cl)ccc1Cl)OC1CCCC2(C1)OOC1(O2)C2CC3CC(C2)CC1C3]

Step 1: Preparation of Ketone Cmpd 1a, 3-[(tert-butyldiphenylsilyl)oxy]cyclohexan-1-one

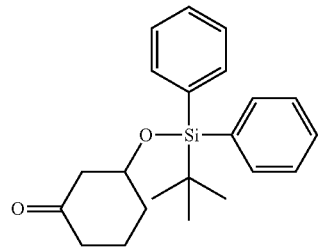 [SMILES: CC(C)(C)[Si](OC1CCCC(=O)C1)(c1ccccc1)c1ccccc1]

A 50-mL, recovery flask equipped with a stirbar, rubber septum, and argon inlet was charged with 3-hydroxycyclohexan-1-one (Karmee, S. K.; van Oosten, R.; Hanefeld, U. *Tetrahedron: Asymm.* 2011, 22, 1736-1739) (0.300 g, 2.63 mmol, 1.0 equiv), N,N-dimethylformamide (10 mL), imidazole (0.358 g, 5.26 mmol, 2.0 equiv), and cooled to 0° C. t-Butyl(chloro)diphenyl silane (0.820 mL, 3.15 mmol, 1.2 equiv) was added rapidly dropwise and the reaction mixture was allowed to warm to slowly warm to rt over ca 1 h and stir at rt overnight. The reaction mixture was diluted with 30 mL of EtOAc and 30 mL of $H_2O$. The aqueous layer was separated and extracted with three 20-mL portions of EtOAc. The combined organic phases were washed with 20 mL of satd aq NaCl solution, dried over $MgSO_4$, filtered, and concentrated to a pale yellow liquid. Purification via column chromatography on 120 g of silica gel (gradient elution with 0-5% EtOAc/hexanes) afforded 0.800 g (82%) of Cmpd 1a as a colorless oil: $^1$H NMR (400 MHz, $CDCl_3$) δ 7.65-7.70 (m, 4H), 7.37-7.48 (m, 6H), 4.21 (app. quin, J=4.9 Hz, 1H), 2.45 (d, J=4.9 Hz, 2H), 2.33-2.41 (m, 1H), 2.22-2.31 (m, J=5.3 Hz, 1H), 2.09-2.21 (m, 1H), 1.76-1.82 (m, 2H), 1.60-1.71 (m, 1H), 1.08 ppm (s, 9H); LRMS (ESI) m/z $[M+H]^+$ calcd for $C_{22}H28OSi$: 353.2; found: 353.1.

Step 2. Preparation of Trioxolane Cmpd 1b, tert-butyl({dispiro[adamantane-2,2'-[1,3,5]trioxolane-4',1"-cyclohexane]-3"-yloxy})diphenylsilane

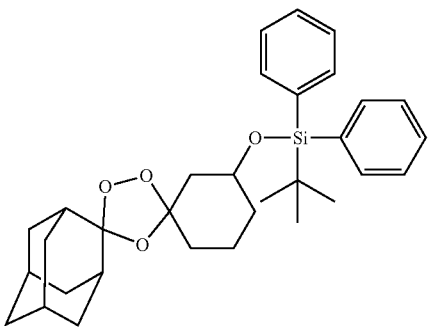 [SMILES: CC(C)(C)[Si](OC1CCCC2(C1)OOC1(O2)C2CC3CC(C2)CC1C3)(c1ccccc1)c1ccccc1]

A 50-mL, recovery flask equipped with a stirbar was charged with adamantanone O-methyloxime (Vennerstrom, J. L.; Dong, Y.; Chollet, J.; Matile, H.; Padmanilayam, M.; Tang, Y.; Charman, W. N. Preparation of spiro and dispiro 1,2,4-trioxolane as antimalarials. U.S. Pat. Appl. Publ., 20040186168, 23 Sep. 2004) (0.270 g, 1.51 mmol, 2 equiv), ketone Cmpd 1a (0.266 g, 0.755 mmol, 1.0 equiv), and $CCl_4$ (15 mL). The mixture was cooled at 0° C. while ozone was bubbled through the solution (0.6 L/min, 30% power). After 10 min of reaction, an additional portion of oxime was added (0.100 g, 0.558 mmol, 0.74 equiv) and bubbling of ozone was continued for an additional 20 min (30 min total reaction time). The reaction mixture was sparged with $O_2$ at 0° C. for 5 min, and with argon while warming to rt over 10 min. The reaction mixture was then concentrated to afford a colorless oil. Purification via column chromatography on 25 g of silica gel (gradient elution with 0-10% EtOAc/hexanes) and then on 40 g of silica gel (gradient elution with 0-10% EtOAc/hexanes) afforded 0.416 g (90%) of Cmpd 1b as a colorless oil: $^1$H NMR (400 MHz, CDCl$_3$) δ 7.68 (td, J=7.7, 1.5 Hz, 4H), 7.35-7.45 (m, 6H), 3.88-3.97 (m, 1H), 3.76-3.85 (m, 1H), 1.44-2.15 (m, 20H), 1.20-1.32 (m, 3H), 1.07 ppm (s, 9H); LRMS (ESI) m/z [M+Na]$^+$ calcd for $C_{32}H_{42}OSi$: 541.3; found: 541.3.

Step 3: Preparation of Alcohol Cmpd 1c, tert-butyl ({dispiro[adamantane-2,2'-[1,3,5]trioxolane-4',1"-cyclohexane]-3"-yloxy})diphenylsilane

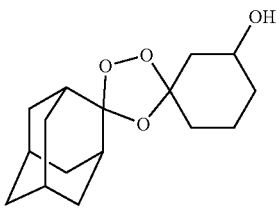 [SMILES: OC1CCCC2(C1)OOC1(O2)C2CC3CC(C2)CC1C3]

A 50-mL, recovery flask equipped with a stirbar and argon inlet adapter was charged with silyl ether Cmpd 1b (0.391 g, 0.754 mmol, 1.0 equiv), THF (10 mL), and cooled to 0° C. A solution of TBAF (1.0 M in THF, 1.13 mL, 1.13 equiv) was added dropwise via syringe and the reaction was stirred at 0° C. for 5 min, allowed to warm to rt for 10 min, and stirred at rt. After 1 h, additional TBAF (1.0 M in THF, 2.0 mL, 2.0 mmol, 2.6 equiv) was added via syringe. The reaction was stirred at rt for another 1 h. Another portion of TBAF (1.0 M in THF, 2.0 mL, 2.0 mmol, 2.6 equiv) added. The reaction was stirred at rt for 1 h. The reaction mixture was concentrated to ca 5 mL and stirring was continued at rt for 1 h. The reaction mixture was diluted with 30 mL of EtOAc and 20 mL of $H_2O$ and 5 mL satd aq NaCl solution. The aqueous layer was separated and extracted with three 20-mL portions of EtOAc. The combined organic phases were washed with 30 mL of satd aq NaCl solution, dried over MgSO$_4$, filtered, and concentrated to afford a colorless oil. Purification via column chromatography on 25 g of silica gel (elution with 15% EtOAc/hexanes) afforded 0.221 g (94%) of Cmpd 1c as a colorless oil: $^1$H NMR (400 MHz, CDCl$_3$) δ 3.98 (app tt, J=7.3, 3.7 Hz, 1H), 1.47-2.09 ppm (m, 23H); LRMS (ESI) m/z [M+Na]$^+$ calcd for $C_{16}H_{24}O_4$: 303.2; found: 303.1.

Step 4: Preparation of Carbamate Cmpd 1

A 20-mL, scintillation vial equipped with a screw cap and stirbar was charged with alcohol Cmpd 1c (0.060 g, 0.210 mmol, 1.0 equiv), toluene (1 mL), pyridine (20 μL, 0.210 mmol, 1 equiv), and 2,5-dichlorophenyl isocyanate (0.080 g, 0.430 mmol, 2 equiv). The reaction mixture was stirred at rt for 18 h. The resulting cloudy reaction mixture was filtered with the aid of 50 mL of EtOAc. The filtrate was washed with 20 mL of $H_2O$. The aqueous layer was extracted with three 20-mL portions of EtOAc. The combined organic phases were washed with 20 mL of satd aq NaCl solution, dried over MgSO$_4$, filtered, and concentrated to a yellow oil. Purification via column chromatography on 50 g of silica gel (elution with 7% EtOAc/hexanes) afforded 0.077 g (79% yield) of Cmpd 1 as a colorless oil: $^1$H NMR (400 MHz, CDCl$_3$) δ 8.28 (m, 1H), 7.28 (dd, J=8.0, 2.0 Hz, 1H), 7.11 (s, 1H), 6.97 (ddd, J=8.0, 2.4, 1.6 Hz, 1H), 4.98-5.05 (m, 1H), 2.26-2.34 (m, 2H), 1.41-2.07 (m, 20H); LRMS (ESI) m/z [M+H]$^+$ calcd for $C_{23}H_{27}C_{12}NO_5$: 468.1; found: 468.6. Some peaks corresponding to the minor isomer were observed: 1H NMR (400 MHz, CDCl$_3$): δ 7.09 (s, 1H), 4.86-4.92 (m, 1H).

Example 2. Preparation of (Cmpd 2), 3"-ethenyldispiro[adamantane-2,2'-[1,3,5]trioxolane-4',1"-cyclohexane]-3"-yl N-(2,5-dichlorophenyl)carbamate

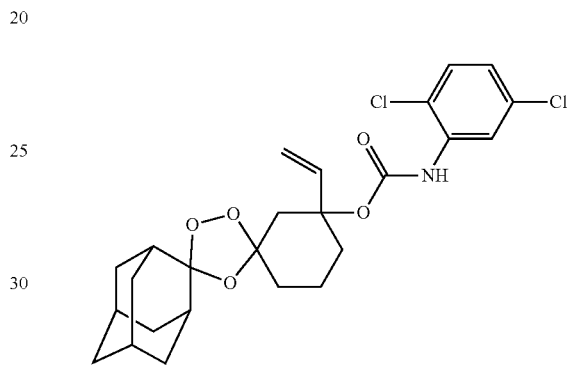

Step 1: Preparation of Trioxolane Cmpd 2a, trispiro [adamantane-2,2'-[1,3,5]trioxolane-4',1"-cyclohexane-3",2'''-[1,3]dioxolane]

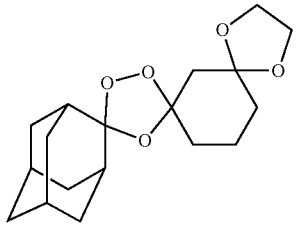 [SMILES: C1CC2(CC3(C1)OOC1(O3)C3CC4CC(C3)CC1C4)OCCO2]

A 500-mL, round-bottomed flask equipped with a stirbar was charged with a solution of 1,4-dioxaspiro[4.5]decan-7-one (Takagi, H.; Hayashi, T.; Mizutani, T.; Masuda, H.; Ogoshi, H. *J. Chem. Soc., Perkin Trans* 1, 1999, 1885-1892) (5.75 g, 36.8 mmol, 2.0 equiv) in CCl$_4$ (180 mL). Adamantanone O-methyloxime (Vennerstrom, J. L.; Dong, Y.; Chollet, J.; Matile, H.; Padmanilayam, M.; Tang, Y.; Charman, W. N. Preparation of spiro and dispiro 1,2,4-trioxolane as antimalarials. U.S. Pat. Appl. Publ., 20040186168, 23 Sep. 2004) (3.30 g, 18.4 mmol, 1.0 equiv) was added and the solution was cooled to 0° C. Ozone (0.6 L/min dial, 30% power) was bubbled through the solution for 2 h. The reaction mixture was sparged with $O_2$ for 10 min, sparged with argon while being allowed to warm to rt over 10 min, and concentrated to afford a colorless oil. Purification via column chromatography on 220 g of silica gel (gradient elution with 5-20% EtOAc/hexanes) afforded 0.265 g of Cmpd 2a as a colorless oil: $^1$H NMR (300 MHz, CDCl$_3$) 3.99-4.04 (m, 1H), 3.87-3.96 (m, 3H), 1.47-2.08 (m, 22H); LRMS (ESI) m/z [M+H]$^+$ calcd for C$_{18}$H$_{26}$O$_3$: 323.2; found 323.1.

Step 2: Preparation of Ketone Cmpd 2b, dispiro [adamantane-2,2'-[1,3,5]trioxolane-4',1"-cyclohexane]-3"-one

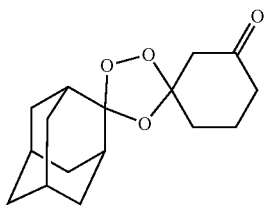 [SMILES: O=C1CCCC2(C1)OOC1(O2)C2CC3CC(C2)CC1C3]

A 100-mL, round-bottomed flask equipped with a stirbar, rubber septum, and argon inlet was charged with the acetal Cmpd 2a (1.0 g, 3.1 mmol, 1.0 equiv), CH$_2$Cl$_2$ (16 mL), acetone (4 mL), and iron(III) chloride hexahydrate (2.80 g, 10.4 mmol, 3.3 equiv). The resulting orange reaction mixture was stirred at rt for 1 h. The reaction mixture was diluted with 30 mL of CH$_2$Cl$_2$ and 20 mL of satd aq NH$_4$Cl. The aqueous layer was separated and extracted with three 30-mL of portions of CH$_2$Cl$_2$. The combined organic phases were washed with 40 mL of satd aq NaCl solution, dried over MgSO$_4$, filtered, and concentrated to afford a yellow oil. Purification via column chromatography on 40 g of silica gel (gradient elution with 0-5% EtOAc/hexanes) afforded 0.517 g of Cmpd 2b as a pale yellow oil: $^1$H NMR (400 MHz, CDCl$_3$) δ 2.72 (s, 2H), 2.35 (t, J=8.0 Hz, 2H), 1.69-2.06 (m, 18H); LRMS (ESI) m/z [M+H]$^+$ calcd for C$_{16}$H$_{22}$O$_4$: 279.1; found: 279.0.

Step 3: Preparation of Alcohol Cmpd 2c, 3"-ethenyldispiro[adamantane-2,2'-[1,3,5]trioxolane-4',1"-cyclohexane]-3"-ol

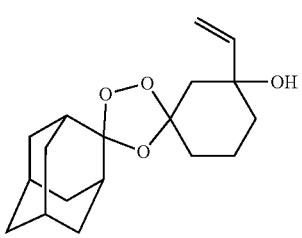 [SMILES: C=CC1(O)CCCC2(C1)OOC1(O2)C2CC3CC(C2)CC1C3]

A 25-mL, recovery flask equipped with a stirbar, rubber septum, and argon inlet needle was charged with Et$_2$O (2 mL) and a solution of vinyl magnesium bromide (1.0 M in THF, 0.89 mL, 0.89 mmol, 3 equiv). The mixture was cooled to −78° C. while a solution of ketone Cmpd 2b (0.083 g, 0.30 mmol, 1 equiv) in Et$_2$O (1.0 mL) was added dropwise via syringe. The reaction was stirred at −78° C. for 1 h. The reaction mixture was quenched by dropwise addition of MeOH (36 μL, 0.89 mmol, 3 equiv) and stirred at −78° C. for 10 min. Another portion of vinyl magnesium bromide (1.0 M in THF, 1.8 mL, 1.8 mmol, 1.8 equiv) was added dropwise via syringe and the reaction mixture was stirred at −78° C. for 1 h. MeOH (84 μL, 2.1 mmol, 7 equiv) was added dropwise via syringe and the reaction mixture was stirred at −78° C. for 10 min. Another portion of vinyl magnesium bromide (1.0 M in THF, 4.0 mL, 4.0 mmol, 14 equiv) was added dropwise via syringe and the reaction mixture was stirred at −78° C. for 45 min. The reaction mixture was then diluted with 20 mL of Et$_2$O and 20 mL of satd aq NH$_4$Cl solution. The aqueous layer was separated and extracted with three 20-mL portions of Et$_2$O. The combined organic phases were washed with 30 mL of satd aq NaCl solution, dried over MgSO$_4$, filtered, and concentrated to afford a cloudy, pale-yellow oil. Purification via column chromatography on 25 g of silica gel (gradient elution with 2-20% EtOAc/hexanes) afforded 0.040 g of Cmpd 2c as a pale yellow oil: $^1$H NMR (CDCl$_3$, 400 MHz) δ 5.90 (dd, J=16.0, 11.2 Hz, 1H), 5.31 (d, J=17.0 Hz, 1H), 5.05 (d, J=10.8 Hz, 1H), 2.70 (s, 1H), 1.57-2.02 (m, 21H), 1.43 (td, J=13.0, 4.8 Hz, 1H); LRMS (ESI) m/z [M+H]$^+$ calcd for C$_{18}$H$_{26}$O$_4$: 307.4; found: 307.1.

Step 4: Preparation of Carbamate Cmpd 2

A 20-mL, scintillation vial equipped with a stirbar and screw cap was charged with alcohol Cmpd 2c (0.030 g, 0.1 mmol, 1 equiv), toluene (0.5 mL), pyridine (8 μL, 0.1 mmol, 1 equiv), and 2,5-dichlorophenyl isocyanate (0.037 g, 0.20 mmol, 2 equiv). The resulting white slurry was stirred at rt for 18 h then heated at 50° C. for 4.5 h. The reaction mixture was then diluted with 2 mL of H$_2$O. The resulting precipitate was removed via filtration through a 1.5"×2" pad of Celite with the aid of 20 mL of Et$_2$O and 10 mL of H$_2$O. The aqueous phase of the filtrate was separated and extracted with three 20-mL portions of Et$_2$O. The combined organic phases were washed with 30 mL of satd aq NaCl solution, dried over MgSO$_4$, filtered and concentrated to afford a cloudy oil. Purification via column chromatography on 12 g of silica gel (gradient elution with 2-20% EtOAc/hexanes) afforded 0.016 g (53% recovered SM) of starting material and 0.006 g (13%) of desired carbamate Cmpd 2 as a colorless oil: $^1$H NMR (400 MHz, CDCl$_3$) δ 8.24 (d, J=2.4 Hz, 1H), 7.24 (m, 1H), 7.11 (br s, 1H), 6.95 (dd, J=9.0, 4.0 Hz, 1H), 6.19 (dd, J=16.8, 11.2 Hz, 1H), 5.25 (d, J=18.4 Hz, 1H), 5.21 (d, J=11.2 Hz, 1H), 2.80 (d, J=14.4 Hz, 1H), 2.22 (d, J=13.6 Hz, 1H), 1.47-2.12 (m, 20H); LRMS (ESI) m/z [M]$^+$ calcd for C$_{25}$H$_{29}$Cl$_2$NO$_5$: 493.1; found: 493.3.

Example 3. Preparation of (Cmpd 3), (3"S,5"S)-5"-tert-butyldispiro[adamantane-2,2'-[1,3,5]trioxolane-4',1"-cyclohexane]-3"-yl N-(2,5-dichlorophenyl) carbamate

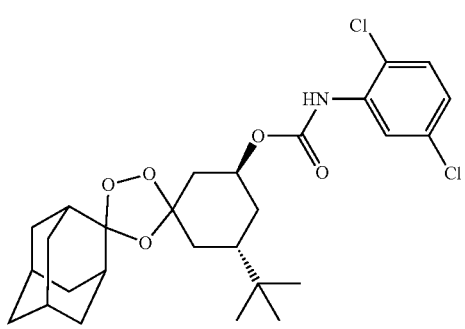 [SMILES: CC(C)(C)[C@H]1C[C@H](OC(=O)Nc2cc(Cl)ccc2Cl)CC2(C1)OOC1(O2)C2CC3CC(C2)CC1C3]

Step 1: Preparation of Trioxolane Cmpd 3a, tert-butyl[(3″S,5″S)-5″-tert-butyldispiro[adamantane-2,2′-[1,3,5]trioxolane-4′,1″-cyclohexane]-3″-yloxy]dimethylsilane

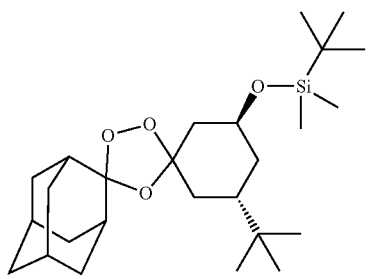 [SMILES: CC(C)(C)[C@H]1C[C@H](O[Si](C)(C)C(C)(C)C)CC2(C1)OOC1(O2)C2CC3CC(C2)CC1C3]

A 25-mL, pear-shaped flask equipped with a stirbar was charged with adamantanone O-methyloxime (Vennerstrom, J. L.; Dong, Y.; Chollet, J.; Matile, H.; Padmanilayam, M.; Tang, Y.; Charman, W. N. Preparation of spiro and dispiro 1,2,4-trioxolane as antimalarials. U.S. Pat. Appl. Publ., 20040186168, 23 Sep. 2004) (0.153 g, 0.854 mmol, 2.1 equiv) and (3S,5S)-3-tert-butyl-5-[(tert-butyldimethylsilyl)oxy]cyclohexan-1-one (Hareau, G. P-J.; Koiwa, M.; Hikichi, S.; Sato, F. *J. Am. Chem. Soc.*, 1999, 121, 3640-3650)(0.116 g, 0.4 mmol, 1.0 equiv), in CCl$_4$ (4 mL). The solution was cooled at 0° C. while ozone (0.6 L/min, 30% power) was bubbled through the solution for 50 min. An addition portion of the oxime (0.155 g, 0.865 mmol, 2.1 equiv) was added in a single portion. Ozone was bubbled through the reaction mixture at 0° C. for an additional 1 h. O$_2$ was bubbled through the solution while stirring at 0° C., then the reaction mixture was allowed to warm to rt while argon was bubbled through the reaction mixture. The reaction solution was concentrated to afford a colorless oil. Purification via column chromatography on 12 g of silica gel (gradient elution with 0-10% EtOAc/hexanes), and purification of mixed fractions on 12 g silica gel (elution with 5% EtOAc/hexanes) and on 25 g silica gel (elution with 5% EtOAc/hexanes) afforded 0.042 g of Cmpd 3a as a colorless oil: $^1$H NMR (CDCl$_3$, 400 MHz) δ 4.28 (m, 1H), 2.39 (s, 1H), 1.56-2.17 (m, 18H), 1.21 (t, J=12.4 Hz, 1H), 1.09 (td, J=12.4, 2.8 Hz, 1H), 0.91 (s, 9H), 0.86 (s, 9H), 0.05 (s, 3H), 0.04 (s, 3H); LRMS (ESI) m/z [M+H+H$_3$COH]$^+$ calcd for C$_{26}$H$_{46}$O$_4$Si: 483.3; found: 483.3.

Step 2: Preparation of Cmpd 3b, (3″S*, 5″S*)-5″-tert-butyldispiro[adamantane-2,2′-[1,3,5]trioxolane-4′,1″-cyclohexane]-3″-ol

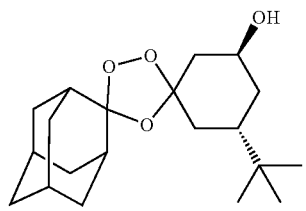 [SMILES: CC(C)(C)[C@H]1C[C@H](O)CC2(C1)OOC1(O2)C2CC3CC(C2)CC1C3]

A 25-mL, recovery flask equipped with a stirbar, rubber septum, and argon inlet needle was charged with a solution of silyl ether Cmpd 3a (0.042 g, 0.093 mmol, 1.0 equiv) in THF (1.5 mL). The solution was cooled at 0° C. while a solution of TBAF (1.0 M in THF, 0.140 mL, 0.140 mmol, 1.5 equiv) was added via syringe. The reaction mixture was allowed to warm to rt and was stirred at rt for 30 min. Another portion of TBAF (1.0 M in THF, 0.230 mL, 0.230 mmol, 2.5 equiv) was added via syringe and the reaction mixture was stirred at rt for 42 h. Additional TBAF was added (1.0 M in THF, 0.190 mL, 0.190 mmol, 2 equiv) and the reaction mixture was heated at 40° C. for 5 h. The reaction mixture was allowed to cool to rt and diluted with 20 mL of Et$_2$O and 20 mL of H$_2$O. The aqueous layer was separated and extracted with three 20-mL portions of Et$_2$O. The combined organic phases were washed with 30 mL of satd aq NaCl solution, dried over MgSO$_4$, filtered, and concentrated to afford a colorless oil. Purification via column chromatography on 12 g of silica gel (gradient elution with 0-10% EtOAc/hexanes) afforded 0.020 g (48%) of the silyl ether starting material and 0.013 g (42%) of Cmpd 3b as a colorless oil: $^1$H NMR (400 MHz, CDCl$_3$) δ 4.27 (dt, J=10.0, 2.8 Hz, 1H), 3.40 (d, J=10.4 Hz, 1H), 1.71-2.11 (m, 19H), 1.29 (t, J=12.4 Hz, 1H), 1.16 (td, J=13.2, 2.8 Hz, 1H), 0.89 (s, 9H); LRMS (ESI) m/z [M+H]$^+$ calcd for C$_{20}$H$_{32}$O$_4$: 337.2; found: 337.1.

Step 3: Preparation of Carbamate Cmpd 3

A 20-mL, scintillation vial equipped with a screw cap and stirbar was charged with a solution of alcohol Cmpd 3b (0.016 g, 0.048 mmol, 1.0 equiv) in toluene (1 mL) and pyridine (4 µL, 0.05 mmol, 1 equiv). 2,5-dichlorophenyl isocyanate (0.018 g, 0.095 mmol, 2 equiv) was added and the reaction mixture was stirred at rt for 20 h. Additional 2,5-dichlorophenyl isocyanate (0.020 g, 0.1 mmol, 2 equiv) and 1 equiv of pyridine (4 µL, 0.05 mmol, 1 equiv) were added and the reaction as stirred at rt for an additional 22 h. At 42 hr total reaction time, additional 2,5-dichlorophenyl isocyanate (0.020 g, 0.1 mmol, 2 equiv) was added and the reaction was stirred at 40° C. for 4 h. The reaction mixture was diluted with 5 mL of H$_2$O and 5 mL of Et$_2$O. The resulting mixture was filtered through a 3″ by 3″ pad of celite with the aid of 50 mL Et$_2$O and 20 mL of H$_2$O. The resulting aqueous layer was separated and extracted with three 20-mL portions of Et$_2$O. The combined organic phases were washed with 20 mL of satd aq NaCl solution, dried over MgSO$_4$, filtered, and concentrated to afford a white slurry. This material was suspended in hexanes and filtered. The resulting filtrate was concentrated to afford a cloudy pale yellow oil. Purification via column chromatography on 12 g of silica gel (gradient elution with 2-20% EtOAc/hexanes) and then on 25 g of silica gel (gradient elution with 5-10% EtOAc/hexanes) afforded 0.013 g (52%) of Cmpd 3 as a colorless solid: $^1$H NMR (400 MHz, CDCl$_3$) δ 8.27 (s, 1H), 7.26 (d, J=8.4 Hz, 1H), 7.11 (br s, 1H), 6.97 (dd, J=8.4, 2.4 Hz, 1H), 5.28 (m, 1H), 2.36 (dd, J=14.0, 1.2 Hz, 1H), 1.54-2.09 (m, 16H), 1.25-1.35 (m, 2H), 0.92 (s, 9H).

Example 4. Preparation of (Cmpd 4), (3"R*,5"S*)-5"-{[(2,5-dichlorophenyl)carbamoyl]oxy}dispiro[adamantane-2,2'-[1,3,5]trioxolane-4',1"-cyclohexane]-3"-yl N-(2,5-dichlorophenyl)carbamate

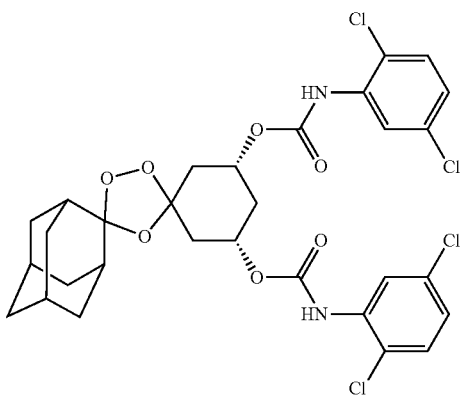 [SMILES: O=C(Nc1cc(Cl)ccc1Cl)O[C@@H]1C[C@H](OC(=O)Nc2cc(Cl)ccc2Cl)CC2(C1)OOC1(O2)C2CC3CC(C2)CC1C3]

Step 1: Preparation of Cmpd 4a, 3"-(acetyloxy)dispiro[adamantane-2,2'-[1,3,5]trioxolane-4',1"-cyclohexane]-5"-yl acetate

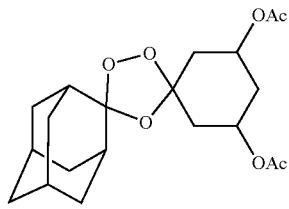 [SMILES: CC(=O)OC1CC(OC(C)=O)CC2(C1)OOC1(O2)C2CC3CC(C2)CC1C3]

A 50-mL, recovery flask was charged with (1S*,3R*)-3-(acetyloxy)-5-oxocyclohexyl acetate (Hilpert, H.; Wirz, B. Tetrahedron, 2001, 57, 681-694)(0.176 g, 0.8 mmol, 1.0 equiv.), CCl$_4$ (6.882 ml), and adamantanone O-methyloxime (Vennerstrom, J. L.; Dong, Y.; Chollet, J.; Matile, H.; Padmanilayam, M.; Tang, Y.; Charman, W. N. Preparation of spiro and dispiro 1,2,4-trioxolane as antimalarials. U.S. Pat. Appl. Publ., 20040186168, 23 Sep. 2004) (0.145 g, 0.809 mmol, 1 equiv). The reaction mixture was cooled at 0° C. while ozone (0.6 L/min, 30% power) was bubbled through solution for 45 min. Additional oxime (0.175 g, 0.976 mmol, 1 equiv) was added as a solid in a single portion and ozone was bubbled through the reaction mixture for an additional 45 min at 0° C. The reaction was sparged with O$_2$ for 5 min, allowed to warm to rt over 10 min while sparging with argon, and concentrated to afford Cmpd 4a as a colorless oil. Purification via column chromatography on 12 g of silica gel (elution with 15% EtOAc/hexanes) afforded 0.258 g (83%) of a viscous oil: $^1$H NMR (400 MHz, CDCl$_3$) δ 4.82 (tt, J=4.5, 11.7 Hz, 2H), 2.30-2.38 (m, 1H), 2.23-2.29 (m, J=1.6 Hz, 2H), 1.97-2.02 (m, 6H), 1.61-1.95 (m, 16H), 1.38 (q, J=11.5 Hz, 1H); LRMS (ESI) m/z [M+Na]$^+$ calcd for C$_{20}$H$_{28}$O$_7$: 403.2; found: 403.1.

Step 2: Preparation of Cmpd 4b, (3"R*,5"S*)-dispiro[adamantane-2,2'-[1,3,5]trioxolane-4',1"-cyclohexane]-3",5"-diol

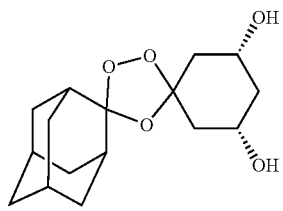 [SMILES: O[C@@H]1C[C@H](O)CC2(C1)OOC1(O2)C2CC3CC(C2)CC1C3]

A 20-mL, scintillation vial equipped with a screw cap and stirbar was charged with bis-acetate Cmpd 4a, methanol (12 mL), and K$_2$CO$_3$ (0.278 g, 2.01 mmol, 5.0 equiv) and the resulting mixture was stirred at 1.5 h. The reaction mixture was diluted with 30 mL of EtOAc and 20 mL of H$_2$O. The aqueous layer was separated and extracted with four 25-mL portions of EtOAc. The combined organic phases were washed with 20 mL of satd aq NaCl solution, dried over MgSO$_4$, filtered, and concentrated to afford a pale yellow oil. A solution of this material in CH$_2$Cl$_2$ was deposited onto 5 g of silica gel. The resulting free flowing powder was transferred to the top of a 25 g column of silica gel. Gradient elution with 50-100% EtOAc/hexanes afforded 0.072 g (60%) of Cmpd 4b as a white solid: $^1$H NMR (400 MHz, CD$_3$OD) δ 3.61 (tt, J=4.4, 11.6 Hz, 2H), 2.21 (ttd, J=1.9, 4.0, 11.5 Hz, 1H), 2.09-2.17 (m, 2H), 2.02 (d, J=12.5 Hz, 2H), 1.87-1.97 (m, 4H), 1.70-1.85 (m, 8H), 1.57 (t, J=12.5 Hz, 2H), 1.22 (q, J=11.5 Hz, 1H); LRMS (ES) m/z [M+Na]$^+$ calcd for C$_{16}$H$_{24}$O$_5$: 319.2; found: 319.0.

Step 3: Preparation of Cmpd 4

A 20-mL, scintillation vial equipped with a stirbar and screw cap was charged with diol Cmpd 4b (0.013 g, 0.044 mmol, 1.0 equiv), pyridine (1.5), and 2,5-dichlorophenyl isocyanate (0.040 g, 0.219 mmol, 5 equiv). The reaction mixture was stirred rt for 2 h. Additional 2,5-dichlorophenyl isocyanate (0.020 g, 0.109 mmol, 2.5 equiv) was added and the reaction mixture was stirred at rt for 22 h. The reaction mixture was treated with an additional 2,5-dichlorophenyl isocyanate (0.040 g, 0.219 mmol, 5 equiv) and heated to 50° C. for 2 h. Additional 2,5-dichlorophenyl isocyanate (0.100 g, 0.532 mmol, 12 equiv) and DMAP (0.020 g, 0.2 mmol, 3.7 equiv) were added and the reaction mixture was stirred at 50° C. for 29 h. The reaction mixture was diluted with 20 mL of EtOAc and 15 mL of H$_2$O and the resulting slurry was filtered through a 2"×2" pad of Celite. The aqueous phase was separated and extracted with three 20-mL portions of EtOAc. The combined organic phases were washed with 35 mL satd aq NaCl solution, dried over Na$_2$SO$_4$, filtered, and concentrated to afford a white solid. A solution of this material in 10 mL of CH$_2$Cl$_2$ was deposited onto 5 g of silica gel. The resulting free flowing powder was loaded on top of a 25 g column of silica gel. Gradient elution with 5-15% EtOAc/hexanes afforded 0.016 g (58%) of Cmpd 4 as a white solid: $^1$H NMR (400 MHz, CDCl$_3$): δ 8.25 (d, J=1.1 Hz, 2H), 7.23-7.27 (m, 4H), 7.09 (s, 2H), 6.97 (dd, J=8.5, 2.5 Hz, 2H), 4.91 (tt, J=11.5, 4.5 Hz, 2H), 2.53-2.61 (m, 1H), 2.40-2.46 (m, 2H), 1.52-2.01 (m, 16H), 1.22-1.28 ppm (m, 1H).

121

Example 5. Preparation of (Cmpd 5), dispiro[adamantane-2,2'-[1,3,5]trioxolane-4',1''-cyclohexane]-3''-yl N-ethylcarbamate

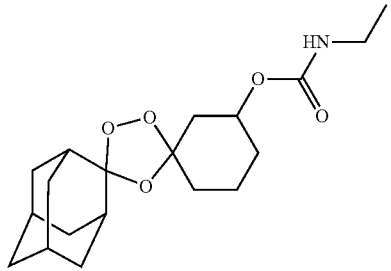 [SMILES: CCNC(=O)OC1CCCC2(C1)OOC1(O2)C2CC3CC(C2)CC1C3]

A 20-mL, scintillation vial equipped with a stirbar and screw cap was charged with alcohol Cmpd 1c, toluene (1 mL), and pyridine (50 μL, 0.62 mmol, 1.5 equiv). Ethyl isocyanate (70 μL, 0.83 mmol, 2.1 equiv) was added via syringe and the resulting mixture was stirred at rt for 17 h. Additional ethyl isocyanate (0.100 mL, 1.26 mmol, 3 equiv) was added and the resulting mixture was heated at 50° C. for 72 h. After 89 h total reaction time, the reaction mixture was diluted with 20 mL of $CH_2Cl_2$ and 20 mL of $H_2O$. The aqueous layer was separated and extracted with three 20-mL portions of $CH_2Cl_2$. The combined organic phases were washed with 30 mL of satd aq NaCl solution, dried over $MgSO_4$, filtered, and concentrated to afford a pale yellow oil. Purification via column chromatography on 25 g of silica gel (gradient elution with 20-25% EtOAc/hexanes) afforded the following: $^1$H NMR (CDCl$_3$, 400 MHz) δ 4.83-4.89 (m, 1H), 4.71 (m, 1H), 4.64 (m, 1H), 3.18-3.22 (m, 4H), 2.15-2.24 (m, 2H), 1.85-2.03 (m, 18H), 1.44-1.81 (m, 22H), 1.09-1.13 (m, 6H); LRMS (ESI) m/z [M+Na]$^+$ calcd for $C_{19}H_{29}NO_5$: 374.2; found: 374.1.

Example 6. Preparation of (Cmpd 6) dispiro[adamantane-2,2'-[1,3,5]trioxolane-4',1''-cyclohexane]-3''-yl 2-[(S)-[2,8-bis(trifluoromethyl)quinolin-4-yl](hydroxy)methyl]piperidine-1-carboxylate

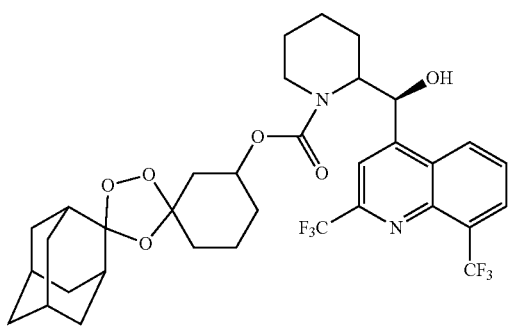 [SMILES: O=C(OC1CCCC2(C1)OOC1(O2)C2CC3CC(C2)CC1C3)N1CCCCC1[C@@H](O)c1cc(C(F)(F)F)nc2c(C(F)(F)F)cccc12]

122

Step 1: Preparation of P-Nitrophenyl Carbonate Cmpd 6a (dispiro[adamantane-2,2'-[1,3,5]trioxolane-4',1''-cyclohexane]-3''-yl 4-nitrophenyl carbonate

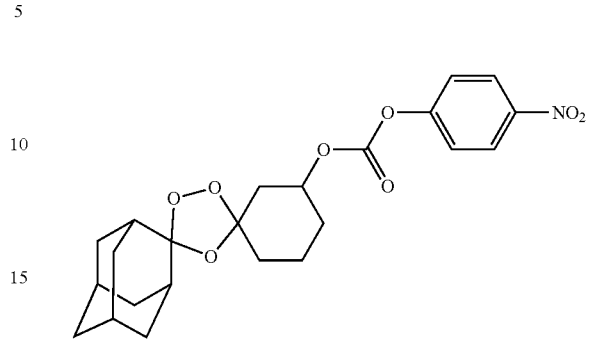

To a solution of alcohol Cmpd 1c (0.085 g, 0.30 mmol, 1.0 equiv) in $CH_2Cl_2$ (5.0 mL) was added triethylamine (71 μL, 0.51 mmol, 1.7 equiv), p-nitrophenyl chloroformate (0.103 g, 0.51 mmol, 1.7 equiv), followed by DMAP (0.037 g, 0.30 mmol, 1 equiv). The reaction mixture was stirred at rt for 22 h, and then diluted with $CH_2Cl_2$ and washed with a three portions of satd aq $NaHCO_3$ solution three times, and one portion of satd aq NaCl solution. The organic layer was dried over $MgSO_4$, filtered, and evaporated. The crude oil was purified by column chromatography on 25 g of silica gel (gradient elution with 0-30% EtOAc/hexanes with 1% $Et_3N$) to obtain 0.130 g of Cmpd 6a (96%) (as a 60:40 mixture of diastereomers) as a colorless oil: $^1$H NMR (400 MHz, CDCl$_3$): δ 8.27 (d, 2H, J=8 Hz), 7.39 (m, 2H), 4.94 (m, 0.6H), 4.83 (m, 0.4H), 2.36 (t, 1H, J=12 Hz), 1.99-1.50 (m, 21H); LRMS (ESI) m/z [2M+Na]$^-$ calcd for $C_{46}H_{54}N_2O_{16}$: 913.34; found 913.4.

Step 2: Preparation of Cmpd 6

A 20-mL, scintillation vial equipped with stirbar and screw cap was charged with a solution of carbonate Cmpd 6a (0.058 g, 0.13 mmol, 1 equiv) in DMF (1 mL) and N,N-diisopropylethylamine (60 μL, 0.33 mmol, 2.5 equiv). Mefloquine hydrochloride (0.081 g, 0.195 mmol, 1.5 equiv) was added as a solid in a single portion and the reaction mixture was stirred at rt for 18 h. The reaction mixture was diluted with 30 mL of EtOAc and washed with three 20-mL portions of satd aq $NaHCO_3$ and 20 mL satd aq NaCl solution. The organic phase was dried over $MgSO_4$, filtered and concentrated to afford a yellow oil. Purification via column chromatography on 25 g of silica gel (elution with 10% EtOAc/hexanes) afforded 0.070 g (89%) of Cmpd 6 as a colorless solid: $^1$H NMR (400 MHz, CDCl$_3$) δ 8.60-8.70 (m, 1H), 8.11-8.17 (m, 1H), 8.05-8.09 (m, 1H), 7.68-7.77 (m, 1H), 5.85-5.94 (m, 1H), 4.81-4.93 (m, 1H), 4.72-4.81 (m, 1H), 4.19-4.31 (m, 1H), 3.85-4.00 (m, 1H), 3.29-3.46 (m, 1H), 2.97-3.26 (m, 1H), 2.08-2.26 (m, 1H), 1.31-2.07 (m, 25H), 0.77-0.92 ppm (m, 1H); LRMS (ESI) m/z [M+H]$^+$ calcd for $C_{34}H_{38}F_6N_2O_6$: 685.3; found: 685.2.

Example 7. Preparation of (Cmpd 7), dispiro[adamantane-2,2'-[1,3,5]trioxolane-4',1''-cyclohexane]-3''-yl N-{4-[(6-methoxyquinolin-8-yl)amino]pentyl}carbamate

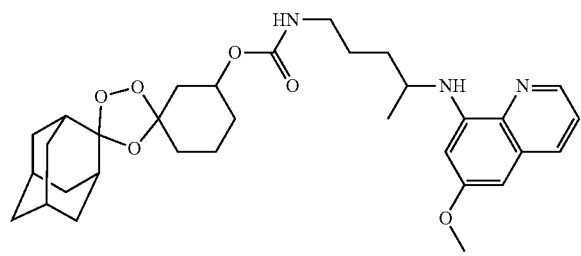 [SMILES: COc1cc(NC(C)CCCNC(=O)OC2CCCC3(C2)OOC2(O3)C3CC4CC(C3)CC2C4)c2ncccc2c1]

A 4-mL, scintillation vial equipped with a stirbar and screw cap was charged with a solution of p-nitrophenyl carbonate Cmpd 6a (0.026 g, 0.061 mmol, 1 equiv) in DMF (0.7 mL) and i-Pr$_2$NEt (37 µL, 0.21 mmol, 3.5 equiv), and primaquine bisphosphate (0.041 g, 0.091 mmol, 1.5 equiv). The reaction mixture as stirred at rt for 18 h then diluted with 20 mL of EtOAc. The organic phase was washed with three 20-mL portions of satd aq NaHCO$_3$ solution and 20 mL of satd aq NaCl solution. The organic phase was dried of MgSO$_4$, filtered, and concentrated to afford a yellow oil. Purification via column chromatography on 12 g of silica gel (elution with 70% EtOAc/hexanes) and purification of mixed fractions on 12 g of silica gel (gradient elution 10-20% EtOAc/hexanes) afforded 0.023 g (68%) of Cmpd 7 as a colorless solid: $^1$H NMR (400 MHz, CD$_3$OD) δ 8.50 (dd, J=4.2, 1.6 Hz, 1H), 8.08 (d, J=8.4 Hz, 1H), 7.39 (dd, J=8.2, 4.2 Hz, 1H), 6.48-6.51 (m, 1H), 6.35-6.38 (m, 1H), 4.72-4.81 (m, 1H), 4.54-4.66 (m, 1H), 3.85-3.90 (m, 3H), 3.61-3.72 (m, 1H), 3.07-3.16 (m, 2H), 2.09-2.19 (m, 1H), 1.54-2.09 (m, 24H), 1.26-1.50 ppm (m, 6H); LRMS (ESI) m/z [M+H]$^+$ calcd for C$_{32}$H$_{43}$N$_3$O$_6$: 566.3; found: 566.3.

Example 8. Preparation of (Cmpd 8), 3-(dibutylamino)-1-[1,3-dichloro-6-(trifluoromethyl)phenanthren-9-yl]propyl dispiro[adamantane-2,2'-[1,3,5]trioxolane-4',1''-cyclohexane]-3''-yl carbonate

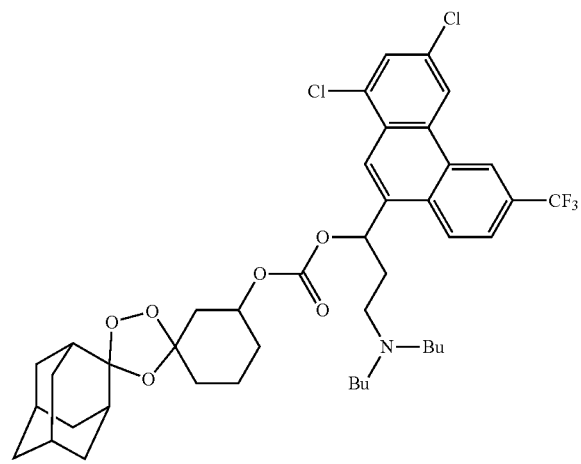

A 4-mL, scintillation vial equipped with a screw cap and stirbar was charged with p-nitrophenyl carbonate Cmpd 6a (0.008 g, 0.02 mmol, 1.0 equiv), DMF (0.250 mL), halofantrine hydrochloride (0.010 g, 0.02 mmol, 1.0 equiv), and i-Pr$_2$NEt (20 ul, 0.12 mmol, 6.4 equiv). The reaction mixture was stirred at rt for 20 h. DMAP (0.002 g, 0.02 mmol, 1.0 equiv) was added and the reaction was heated at 38° C. for 48 h. The reaction mixture was diluted with 20 mL of EtOAc and washed with four 10-mL portions of 1 M aq NaOH solution until the aqueous washes no longer appeared yellow. The organic phase was washed with 20 mL of satd aq NaCl solution, dried over MgSO$_4$, filtered, and concentrated to afford a white residue. A solution of this residue in 10 mL of 10% methanol in CH$_2$Cl$_2$ was deposited onto 5 g of silica gel. The resulting free flowing powder was loaded on top of a 12 g column of silica gel and elution with 10% EtOAc/hexanes afforded 0.013 g (89%) of Cmpd 8 (as a mixture of 4 diastereomers): For the mixture of diastereomers with a higher R$_f$: $^1$H NMR (400 MHz, CDCl$_3$) δ 8.87 (s, 2H), 8.56 (d, J=1.3 Hz, 2H), 8.42 (d, J=8.8 Hz, 2H), 8.33 (d, J=1.3 Hz, 2H), 7.97-7.84 (m, 2H), 7.76-7.68 (m, 2H), 6.53-6.41 (m, 2H), 4.78 (ddd, J=4.2, 9.9, 14.5 Hz, 1H), 4.64 (tt, J=4.3, 10.8 Hz, 1H), 3.05-2.80 (m, 2H), 2.79-2.61 (m, J=5.3 Hz, 2H), 2.53-2.39 (m, J=12.1 Hz, 4H), 2.39-2.30 (m, J=2.7, 8.1 Hz, 4H), 2.26 (d, J=11.0 Hz, 2H), 2.03-1.16 (m, 62H), 0.90 (t, J=6.1 Hz, 12H); LRMS (ESI) m/z [M+H]$^+$ calcd for C$_{43}$H$_{52}$F$_3$NO$_6$: 806.31; found: 806.3. For the mixture of diastereomers with a lower R$_f$: $^1$H NMR (300 MHz, CDCl$_3$): δ 8.90 (s, 2H), 8.59 (s, 2H), 8.44 (d, J=8.9 Hz, 2H), 8.37 (d, J=6.0 Hz, 2H), 7.93 (s, 2H), 7.76 (s, 2H), 6.50 (s, 2H), 4.73-4.87 (m, 1H), 4.57-4.73 (m, 1H), 1.99-2.99 (m, 14H), 1.19-1.98 (m, 62H), 0.91 ppm (m., 12H); LRMS (ESI) m/z calcd for C$_{43}$H$_{52}$F$_3$NO$_6$: 806.31; found: 806.2.

Example 9. Preparation of (Cmpd 9), dispiro[adamantane-2,2'-[1,3,5]trioxolane-4',1''-cyclohexane]-3''-yl N-(1-{1-[2-oxo-1-(2,3,5,6-tetrafluorophenoxy)heptan-3-yl]-1H-1,2,3-triazol-4-yl}cyclohexyl)carbamate)

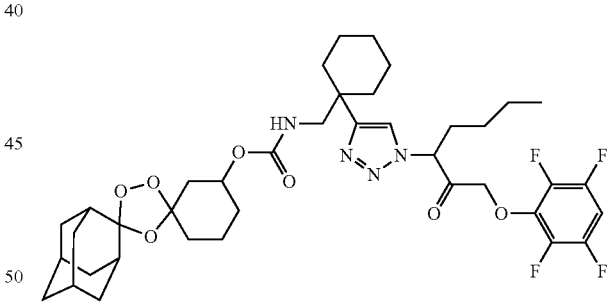

To a solution of HN3019 hydrochloride (Deu, E.; Leyva, M. J.; Albrow, V. E.; Rice, M. J.; Ellman, J. A.; Bogyo, M. Chem. Biol. 2010, 17, 808-819)(0.023 g, 0.048 mmol, 1 equiv) in anhydrous DMF (1 mL) was added i-Pr$_2$NEt (18 µL, 0.11 mmol, 2.3 equiv) followed by p-nitrophenyl carbonate Cmpd 6a (0.021 g, 0.048 mmol, 1 equiv) in DMF (1 mL), and DMAP (0.001 g, 0.010 mmol, 2 equiv). The yellow solution was stirred at rt for 20 h, at which point additional i-Pr$_2$NEt (9.0 µL, 0.005 mmol, 1 equiv) and DMAP (0.001 g, 0.01 mmol, 2 equiv) were added. The reaction mixture was stirred at rt for an additional 24 h. The reaction mixture was diluted with 10 mL of satd aq NaHCO$_3$ solution and 10 mL of EtOAc. The organic phase was separated and washed sequentially with 10 mL of 1 M aq HCl solution, 10 mL of 1 M aq NaOH solution, and 15 mL of satd aq NaCl solution.

The organic phase was dried over MgSO₄, filtered, and concentrated to afford a pale yellow oil. Purification via column chromatography on 12 g of silica gel (gradient elution with 10-25% EtOAc/hexanes) afforded 0.013 g (36%) of Cmpd 9 (as a mixture of isomers) as a viscous/glassy oil: $^1$H NMR (400 MHz, CDCl₃): δ 7.65 (s, 1H), 6.81 (m, 1H), 5.53 (br s, 1H), 4.96 (s, 1H), 4.87 (m, 1H), 4.73 (br s, 0.5H), 4.56 (br s, 0.5H), 2.28 (m, 2H), 2.10-1.58 (m, 16H), 1.38-1.19 (m, 5H), 0.89 (t, J=4 Hz, 3H); LRMS (ESI) m/z [M+H]⁺ calcd for $C_{38}H_{48}F_4N_4O_7$: 749.4; found 749.3.

Example 10: Preparation of (Cmpd 10), 2-{dispiro[adamantane-2,2'-[1,3,5]trioxolane-4',1''-cyclohexane]-4''-yl}-3-hydroxy-1,4-dihydronaphthalene-1,4-dione

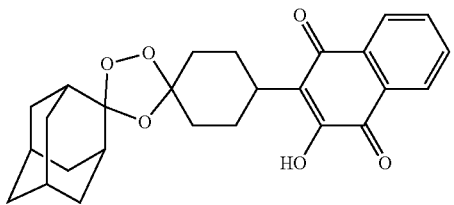 [SMILES: O=C1C(O)=C(C2CCC3(CC2)OOC2(O3)C3CC4CC(C3)CC2C4)C(=O)c2ccccc21]

Step 1. Preparation of Cmpd 10a, 2-chloro-3-{dispiro[adamantane-2,2'-[1,3,5]trioxolane-4',1''-cyclohexane]-4''-yl}-1,4-dihydronaphthalene-1,4-dione

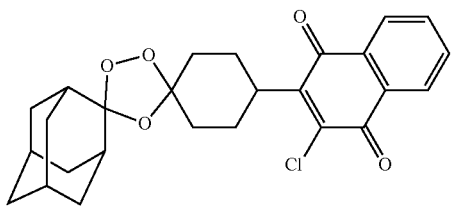 [SMILES: O=C1C(Cl)=C(C2CCC3(CC2)OOC2(O3)C3CC4CC(C3)CC2C4)C(=O)c2ccccc21]

A 20-mL scintillation vial equipped with a stirbar and screw cap was charged with dispiro[adamantane-2,2'-[1,3,5]trioxolane-4',1''-cyclohexane]-4''-carboxylic acid (Tang, Y.; Dong, Y.; Karle, J. M.; DiTusa, C. A.; Vennterstrom, J. L. *J. Org. Chem.* 2004, 69, 6470-6473) (0.096 g, 0.31 mmol, 1.0 equiv), 2,3-dichloro-1,4-naphthoquinone (0.076 g, 0.33 mmol, 1.1 equiv), silver(I) nitrate (0.042 g, 0.25 mmol, 0.8 equiv), and acetonitrile (3 mL). The reaction mixture was heated at 80° C. in a preheated vial block. A solution of ammonium persulfate (0.300 g, 1.32 mmol, 4.2 equiv) in water (2 mL) was added dropwise via syringe and the reaction mixture was stirred at 80° C. for 10 min. The reaction mixture was allowed to cool to rt and was diluted with 25 mL of EtOAc and 20 mL of H₂O. The aqueous phase was separated and extracted with two 25-mL portions of EtOAc and two 25-mL portions of CHCl₃. The combined organic phases were dried over Na₂SO₄, filtered, and concentrated to afford a yellow solid. A solution of this material in 10 mL of 10% MeOH/CH₂Cl₂ was deposited onto 5 g of silica gel. The resulting free flowing powder was loaded atop a column of 12 g of silica gel. Gradient elution with 2-20% EtOAc/hexanes and re-purification of mixed fractions on 25 g of silica gel (elution with 10% EtOAc/hexanes) afforded 0.036 g (24%) of Cmpd 10a (as a mixture of isomers) as a yellow semi solid: $^1$H NMR (400 MHz, CDCl₃) δ 8.07-8.16 (m, 2H), 7.70-7.79 (m, 2H), 3.24-3.37 (m, 1H), 2.38-2.65 (m, 2H), 2.14-2.23 (m, 1H), 1.88-2.12 (m, 8H), 1.59-1.88 ppm (m, 12H); LRMS (ESI) m/z [M+Na]⁺ calcd for $C_{26}H_{27}ClO_5$: 477.2; found: 477.2.

Step 2: Preparation of Cmpd 10

A 10-mL microwave tube equipped with a stirbar and silicon cap was charged with chloroquinone Cmpd 10a (0.041 g, 0.1 mmol, 1.0 equiv) and methanol (4 mL). A solution of potassium hydroxide (0.200 g, 3.56 mmol, 40 equiv) in water (2 mL) was added dropwise via syringe over 2 min. The reaction mixture was heated in the microwave at 65° C. for 4 h. Due to insolubility of the starting material, the reaction mixture was transferred to a 50-mL recovery flask and diluted with 15 mL of THF. Additional potassium hydroxide (0.200 g, 3.56 mmol, 40 equiv) in 1 mL of water was added. The reaction mixture was heated at 60° C. for 1 h. The reaction mixture was diluted with 40 mL of EtOAc, 20 mL of H₂O, and 5 mL of 1M aq HCl. The aqueous layer was separated and extracted with three 30-mL portions of EtOAc. The combined organic phases were washed with 30 mL of satd aq NaCl solution, dried over Na₂SO₄, and concentrated to afford an orange oil. A solution of this material in 10 mL of 10% MeOH/CH₂Cl₂ was deposited onto 5 g of silica gel. The resulting free flowing powder was loaded atop a 25 g column of silica gel and gradient elution with 0-50% EtOAc/hexanes afforded 0.011 g (28%) of Cmpd 10 (as a 60:40 mixture of diastereomers) as a yellow oil: $^1$H NMR (400 MHz: CDCl₃) δ 8.11-8.16 (m, 1H), 8.06-8.10 (m, 1H), 7.74-7.79 (m, 1H), 7.66-7.71 (m, 1H), 7.47 (s, 1H), 3.04-3.20 (m, 1H), 2.22-2.35 (m, 1H), 2.12-2.19 (m, 1H), 1.99-2.10 (m, 4H), 1.91-1.99 (m, 2H), 1.53-1.91 ppm (m, 14H) LRMS (ESI) m/z [M+Na]⁺ calcd for $C_{26}H_{28}O_6$: 459.2; found 459.2. Resonances corresponding to the minor isomer were observed at: $^1$H NMR (400 MHz, CDCl₃) δ 7.51 (s, 1H), 2.35-2.53 (m, 1H).

Example 11. Preparation of (Cmpd 11), dispiro[adamantane-2,2'-[1,3,5]trioxolane-4',1''-cyclohexane]-3''-yl N-{2-methoxy-5-[1-(3,4,5-trimethoxyphenyl)-1H-1,2,3-triazol-5-yl]phenyl}carbamate

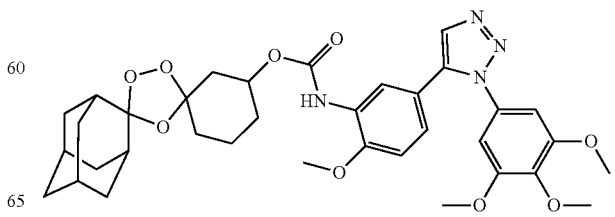

Step 1: Preparation of Isocyanate Cmpd 11a, 5-(3-isocyanato-4-methoxyphenyl)-1-(3,4,5-trimethoxyphenyl)-1H-1,2,3-triazole

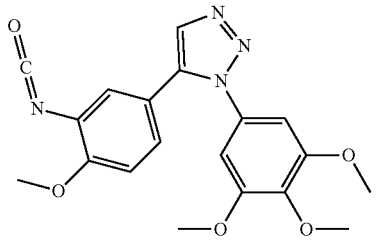 [SMILES: COc1ccc(-c2cnnn2-c2cc(OC)c(OC)c(OC)c2)cc1N=C=O]

A 2-neck, 25-mL, round-bottomed flask equipped with a stirbar, rubber septa, and reflux condenser fitted with an argon inlet adapter was charged with triphosgene (0.020 g, 0.1 mmol, 0.5 equiv) dissolved in 4 mL of toluene. A solution of 2-methoxy-5-[1-(3,4,5-trimethoxyphenyl)-1H-1,2,3-triazol-5-yl]aniline (Odlo, K.; Hentzen, J.; dit Chabert, J. F.; Ducki, S.; Gani, O. a B. S. M.; Sylte, I.; Skrede, M.; Florenes, V. A.; Hansen, T. V. *Bioorg. Med. Chem.* 2008, 16, 4829-4838) (0.046 g, 0.1 mmol, 1.0 equiv) in 4 mL of toluene was added dropwise to this solution at rt. The reaction mixture was heated to reflux for 4 hours then allowed to cool to rt and quenched with 10 mL of $H_2O$ then extracted with three, 15-mL portions of $CH_2Cl_2$. The organic phases were combined, dried over $MgSO_4$, and filtered before concentrating to yield an oil, Cmpd 1a, which was carried forward without further purification. LRMS (ESI) m/z [M+H]$^+$ calcd for $C_{19}H_{18}N_4O_5$: 383.1; found: 383.2.

Step 2: Preparation of Carbamate Cmpd 11

A 25-mL, round-bottomed flask equipped with a stir bar, rubber septa, and an argon inlet needle was charged with a solution of alcohol Cmpd 1c (0.049 g, 0.2 mmol, 1.4 equiv) in 2 mL of dry $CH_2Cl_2$, pyridine (0.050 ml, 0.6 mmol, 4.8 equiv) and 4-dimethylaminopyridine (0.004 g, 0.0 mmol, 0.2 equiv) under argon. The isocyanate (Cmpd 11a) was then added dropwise to this reaction mixture in a solution of $CH_2Cl_2$ (2 mL) and the reaction mixture was heated to 40° C. After 72 hours the reaction mixture was diluted with 10 mL of $CH_2Cl_2$ and washed with 20 mL of $H_2O$. The aqueous fraction was extracted with two, 15-mL portions of $CH_2Cl_2$. The combined organic phases were then washed with 10 mL of satd aq NaCl solution, dried over $MgSO_4$, filtered, and concentrated to a yellow oil. Purification via column chromatography on silica gel (elution with 50% EtOAc/hexanes) afforded 0.029 g (34% over two steps) of Cmpd 11 as a yellow solid: $^1$H NMR (CHLOROFORM-d, 400 MHz): δ 8.19 (br. s., 1H), 7.82-7.85 (m, 1H), 7.17 (s, 1H), 6.78-6.83 (m, 2H), 6.62 (s, 2H), 4.76-4.86 (m, 1H), 3.84-3.90 (m, 5H), 3.71-3.77 (m, 6H), 2.25-2.32 (m, 1H), 1.88-2.00 (m, 7H), 1.74-1.83 (m, 4H), 1.65 (s, 3H), 1.68 (s, 3H), 1.53 (d, J=12.6 Hz, 1H), 1.43 (dd, J=5.7, 0.7 Hz, 1H), 1.32-1.41 ppm (m, 2H); LRMS (ESI) m/z [M+H]$^+$ calcd for $C_{35}H_{42}N_4O_9$: 663.3; found: 663.3.

Example 12. Preparation of (Cmpd 12), dispiro[adamantane-2,4'-[1,3]dioxolane-2',1"-cyclohexane]-3"-yl N-{2-methoxy-5-[1-(3,4,5-trimethoxyphenyl)-1H-1,2,3-triazol-5-yl]phenyl}carbamate

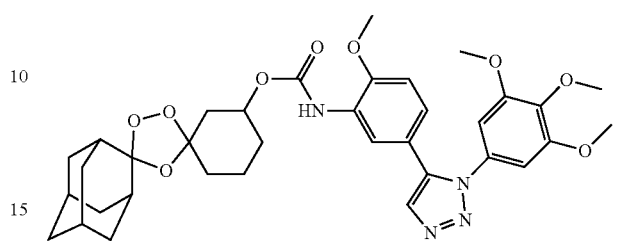

Step 1: Preparation of Alkene Cmpd 12a, 2-Methylideneadamantane

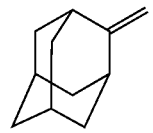

A 200-mL, round-bottomed flask equipped with a stir bar, rubber septa, and an argon inlet needle was charged with a solution of methyltriphenylphosphonium iodide (3.39 g, 8.38 mmol, 1.2 equiv) dissolved in THF (31 mL). A solution of n-BuLi (1.42 M in THF) was added dropwise to this suspension until the starting material dissolved and a bright orange color persisted (ca. 8 mL, 11 mmol, 1.6 equiv). The reaction mixture was stirred at rt for 15 minutes and then a solution of 2-adamantanone (1.049 g, 6.98 mmol, 1 equiv) dissolved in THF (10 mL) was added dropwise to the reaction mixture while stirring under Ar. After stirring for 2 hours the reaction mixture was diluted with $CH_2Cl_2$ and washed with $H_2O$. The aqueous layer was extracted with $CH_2Cl_2$ and the organic phases were combined, washed with satd aq NaCl solution, dried over $MgSO_4$, filtered, and concentrated to a yellow oil which was purified via silica chromatography eluting with 100% hexanes to yield 0.680 g (66%) of Cmpd 12a as a fine white solid. $^1$H NMR (400 MHz, CDCl$_3$) δ 4.51 (s, 2H), 2.49 (br. s., 2H), 1.92-1.97 (m, 2H), 1.85-1.92 (m, 4H), 1.79-1.85 (m, 5H), 1.78 (br. s., 1H), $^{13}$C NMR (100 MHz, CDCl$_3$) δ 158.7, 100.8, 77.5, 77.4, 76.9, 39.9, 39.3, 37.5, 28.5.

Step 2: Preparation of Alkene Cmpd 12b, 2-(hydroxymethyl)adamantan-2-ol

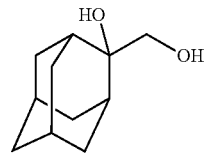 [SMILES: OCC1(O)C2CC3CC(C2)CC1C3]

A 35-mL, round-bottomed flask was charged with Cmpd 12a (0.212 g, 1.4 mmol, 1 equiv) dissolved in 5 mL of tert-butanol, and 5 mL of H₂O. A solution of osmium tetroxide in (2.5% w/v in tert-butanol, 0.25 mL, 0.32 mmol, 0.2 equiv) was added to this solution followed by N-methylmorpholine oxide (0.465 g, 4.0 mmol, 2.8 equiv). This mixture was allowed to stir at rt for 12 hours then diluted with 20 mL of EtOAc and washed with 50 mL of satd aq NaHCO₃ solution. The aqueous phase was extracted with two 50-mL portions of EtOAc. The organic phases were washed with satd aq NaCl solution, dried over MgSO₄, and concentrated to give a light brown solid which was purified via silica chromatography eluting with 40% EtOAc in Hexanes to yield 0.152 g of Cmpd 12b (58%). ¹H NMR (400 MHz, CD₃OD): δ 3.67 (s, 2H), 2.27 (d, J=11.9 Hz, 2H), 1.83-1.91 (m, 2H), 1.77-1.83 (m, 4H), 1.71-1.77 (m, 4H), 1.50-1.58 ppm (m, 2H); LRMS (ESI) m/z [M+Na]⁺ calcd for C₁₁H₁₈O₂: 205.1; found: 204.9.

Step 3: Preparation of Dioxolane Cmpd 12c, tert-butyl({dispiro[adamantane-2,4'-[1,3]dioxolane-2',1"-cyclohexane]-3"-yloxy})diphenylsilane

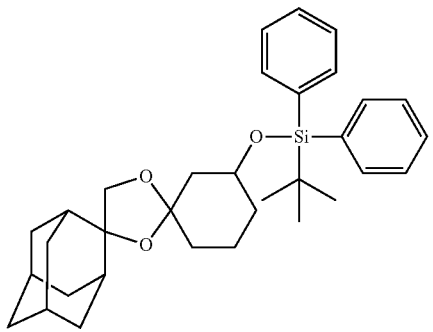 [SMILES: CC(C)(C)[Si](OC1CCCC2(C1)OCC1(O2)C2CC3CC(C2)CC1C3)(c1ccccc1)c1ccccc1]

A 50 mL, 2-neck round-bottomed flask equipped with a stirbar, rubber septa, and reflux condenser fitted with an argon inlet adapter was charged with diol Cmpd 12b (0.126 g, 0.69 mmol, 1 equiv), ketone Cmpd 1a (0.260 g, 0.74 mmol, 1.07 equiv), CH₂Cl₂ (20 mL), and camphor sulfonic acid (0.038 g, 0.016 mmol, 0.24 equiv). The reaction mixture was heated at reflux for 24 h, allowed to cool to rt, diluted with 20 mL of CH₂Cl₂, and washed with 25 mL of H₂O. The aqueous phase was extracted with two, 25-mL portions of CH₂Cl₂. The combined organic phases were washed with satd aq NaCl solution, dried over MgSO₄, filtered, and concentrated to afford a pale yellow oil. Purification via column chromatography on silica gel (elution with 10% EtOAc/Hexanes) to yield 0.295 g (83%) of Cmpd 12c as clear oil. ¹H NMR (400 MHz, CDCl₃) δ 7.69-7.72 (m, 1H), 7.67-7.69 (m, 1H), 7.39-7.46 (m, 1H), 7.38 (d, J=1.5 Hz, 1H), 7.35-7.37 (m, 1H), 3.90-3.99 (m, 1H), 3.77 (dd, J=50.9, 9.5 Hz, 2H), 1.99-2.06 (m, 1H), 1.86-1.94 (m, 1H), 1.82 (d, J=11.5 Hz, 1H), 1.69-1.77 (m, 2H), 1.66 (br. s., 2H), 1.43-1.59 (m, 3H), 1.36-1.43 (m, 2H), 1.27-1.36 (m, 1H), 1.05-1.10 ppm (m, 5H); LRMS (ESI) m/z [M+H]⁺ calcd for C₃₃H₄₄O₃Si: 517.3; found: 517.3.

Step 4: Preparation of Alcohol Cmpd 12d, dispiro[adamantane-2,4'-[1,3]dioxolane-2',1"-cyclohexane]-3"-ol

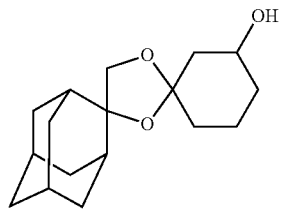 [SMILES: OC1CCCC2(C1)OCC1(O2)C2CC3CC(C2)CC1C3]

A 25-mL, round-bottomed flask equipped with a stir bar, rubber septa, and an argon inlet needle was charged with a solution of dioxolane Cmpd 12c (0.139 g, 0.56 mmol, 1 equiv) in dry THF (6 mL) and cooled to 0° C. A solution of TBAF (1.0 M in THF, 2.8 mL, 2.8 mmol, 5 equiv) was added dropwise to this solution while stirring at 0° C. The reaction was stirred at 0° C. for 30 minutes, allowed to warm to rt, stirred at rt for 19 hours, and then diluted with 20 mL of EtOAc and washed with 50 mL of H₂O. The aqueous layer was extracted with 30 mL of EtOAc. The combined organic phases were washed with satd aq NaCl solution, dried over MgSO₄, filtered, and concentrated to afford a clear oil. Purification via column chromatography on silica gel (elution with 25% EtOAc/hexanes) afforded 0.139 g (89%) of Cmpd 12d as a foamy, white oil: ¹H NMR (400 MHz, CDCl₃): δ 3.98 (br. s., 1H), 3.86-3.92 (m, 2H), 2.67 (br. s., 1H), 2.11-2.19 (m, 2H), 1.88 (d, J=3.8 Hz, 1H), 1.74-1.84 (m, 7H), 1.66-1.72 (m, 3H), 1.54-1.62 (m, 7H), 1.44-1.54 ppm (m, 1H); LRMS (ESI) m/z [M+H]⁺ calcd for C₁₇H₂₆O₃: 279.2; found: 279.1.

Step 5: Preparation of Dioxolane Cmpd 12

Cmpd 12 was prepared in a manner analogous to the preparation of Cmpd 11 (see Example 11) by reacting the requisite alcohol starting material Cmpd 12d (22 mg, 0.08 mmol, 1.16 equiv) with isocyanate (Compound 11a). Affording 0.014 g (31% over two steps) of Cmpd 12 as a yellow solid. ¹H NMR (400 MHz, CDCl₃): δ 7.78-7.87 (m, 1H), 7.19 (s, 1H), 6.73-6.82 (m, 2H), 6.54-6.65 (m, 2H), 3.95 (s, 1H), 3.88 (s, 6H), 3.76 (s, 6H), 2.24 (d, J=14.5 Hz, 2H), 2.14 (s, 1H), 2.06-2.13 (m, 1H), 1.78 (s, 3H), 1.82 (s, 3H), 1.51-1.73 (m, 8H), 1.38 ppm (d, J=5.1 Hz, 2H); LRMS (ESI) m/z [M+H]⁺ calcd for C₃₆H₄₄N₄O₈: 661.3; found: 661.2.

Example 13. Preparation of (Cmpd 13), dispiro[adamantane-2,2'-[1,3]dioxolane-4',1"-cyclohexane]-3"-yl N-{2-methoxy-5-[1-(3,4,5-trimethoxyphenyl)-1H-1,2,3-triazol-5-yl]phenyl}carbamate

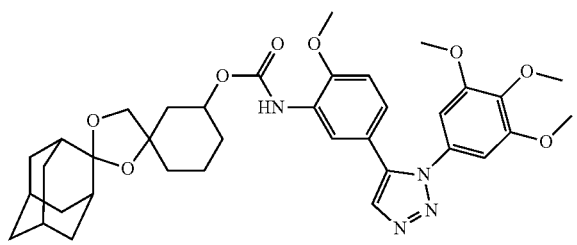 [SMILES: COc1ccc(-c2cnnn2-c2cc(OC)c(OC)c(OC)c2)cc1NC(=O)OC1CCCC2(COC3(O2)C2CC4CC(C2)CC3C4)C1]

Step 1: Preparation of Alkene Cmpd 13a, tert-butyl [(3-methylidenecyclohexyl)oxy]diphenylsilane

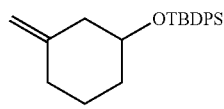

A 25-mL, round-bottomed flask equipped with a stir bar, rubber septa, and an argon inlet needle was charged with a solution of methyltriphenylphosphonium iodide (0.266 g, 0.660 mmol, 2 equiv) in THF (3 mL). A solution of n-BuLi (1.42 M in THF) was added dropwise to this suspension until the starting material dissolved and a bright orange color persisted (ca. 0.43 mL, 0.61 mmol, 1.9 equiv). This solution was stirred at rt for 15 minutes at and then a solution of ketone Cmpd 1a (115 mg, 0.33 mmol, 1 equiv) in THF (2 mL) was added dropwise to the reaction mixture. The reaction mixture was allowed to stir at rt for 5 h then diluted with $CH_2Cl_2$ and washed with $H_2O$. The aqueous layer was extracted with $CH_2Cl_2$ and the combined organic phases were washed with satd aq NaCl solution, dried over $MgSO_4$, filtered, and concentrated to afford an oil. Purification via column chromatography on silica gel (elution with 10% EtOAc/hexanes) afforded 0.050 g (44%) of Cmpd 13a as a white solid: $^1$H NMR (400 MHz, $CDCl_3$): δ 7.65-7.78 (m, 3H), 7.30-7.49 (m, 5H), 4.64 (d, J=1.1 Hz, 1H), 4.52 (d, J=1.1 Hz, 1H), 3.75 (ddd, J=8.7, 5.0, 4.0 Hz, 1H), 2.34 (dd, J=12.8, 4.2 Hz, 1H), 2.05-2.19 (m, 2H), 1.93-2.05 (m, 1H), 1.71-1.84 (m, 2H), 1.46-1.61 (m, 1H), 1.12-1.33 (m, 2H), 1.04-1.12 ppm (m, 9H); $^{13}$C NMR (100 MHz, $CDCl_3$): δ 146.9, 136.0, 136.0, 135.0, 134.9, 134.9, 134.1, 133.9, 129.7, 129.7, 129.0, 128.8, 127.7, 127.6, 109.1, 72.1, 44.5, 35.1, 34.5, 27.2, 24.1, 19.4 ppm.

Step 2: Preparation of Diol Cmpd 13b, 3-[(tert-butyldiphenylsilyl)oxy]-1-(hydroxymethyl)cyclohexan-1-ol

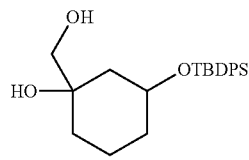

A 35-mL, round-bottomed flask was charged with a solution of alkene Cmpd 13a (0.050 g, 0.14 mmol, 1 equiv) in THF (2 mL). A solution of osmium tetroxide (2.5% w/v in tert-butanol, 6 μL, 0.007 mmol, 0.05 equiv) was then added followed by N-methylmorpholine oxide (0.026 g, 0.2 mmol, 1.6 equiv). This mixture was allowed to stir at rt for 27 hours then diluted with EtOAc and washed with saturated $NaHCO_3$. The aqueous phase was extracted with two portions of EtOAc. The combined organic phases were washed with satd aq NaCl solution, dried over $MgSO_4$, filtered, and concentrated. Purification via column chromatography on silica gel (elution with 40% EtOAc/hexanes) afforded 0.034 g of Cmpd 13b (63%). $^1$H NMR (400 MHz, CDCl3): δ 7.62-7.78 (m, 3H), 7.32-7.51 (m, 5H), 4.21-4.30 (m, 1H), 4.03 (s, 1H), 3.35-3.51 (m, 2H), 3.25-3.35 (m, 1H), 2.02-2.22 (m, 2H), 1.66-1.84 (m, 2H), 1.54-1.66 (m, 1H), 1.44-1.54 (m, 1H), 1.16-1.39 (m, 4H), 1.02-1.16 ppm (m, 9H) $^{13}$C NMR (CHLOROFORM-d, 100 MHz): δ 136.0, 136.0, 136.0, 133.4, 130.2, 130.2, 129.8, 129.7, 128.0, 128.0, 127.7, 127.7, 73.5, 72.7, 71.1, 70.2, 69.1, 43.1, 38.5, 35.4, 34.1, 33.3, 32.5, 27.2, 27.2, 19.5, 19.3, 15.9 ppm. LRMS (ESI) m/z [M+H]$^+$ calcd for $C_{23}H_{32}O_3Si$: 385.2; found: 385.2.

Step 3: Formation of Dioxolane Cmpd 13c, tert-butyl({dispiro[adamantane-2,2'-[1,3]dioxolane-4',1"-cyclohexane]-3"-yloxy})diphenylsilane

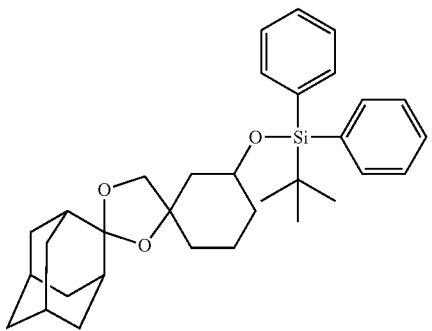 [SMILES: CC(C)(C)[Si](OC1CCCC2(COC3(O2)C2CC4CC(C2)CC3C4)C1)(c1ccccc1)c1ccccc1]

A 35-mL, 2-necked round-bottomed flask equipped with a stir bar, rubber septa, and a reflux condenser fitted with an argon inlet was charged with diol Cmpd 13b (0.035 g, 0.09 mmol, 1 equiv), 2-adamantanone (0.033 g, 0.2 mmol, 2.4 equiv), camphor sulfonic acid (0.038 g, 0.016 mmol, 0.24 equiv), and $CH_2Cl_2$ (4 mL). The reaction mixture was heated to reflux for 45 be allowed to cool to rt, and then diluted with $CH_2Cl_2$ and washed with $H_2O$. The aqueous layer was extracted with two portions of $CH_2Cl_2$. The combined organic phases were washed with satd aq NaCl solution, dried over $MgSO_4$, filtered, and concentrated to a light yellow oil. Purification via column chromatography on silica gel (elution with 5% EtOAc/hexanes) afforded 0.043 g (91%) of Cmpd 13c as clear oil: $^1$H NMR (400 MHz, $CDCl_3$): δ 7.65-7.71 (m, 3H), 7.30-7.49 (m, 5H), 4.09 (s, 1H), 3.75 (dd, J=15.4, 8.2 Hz, 1H), 3.50 (d, J=8.1 Hz, 1H), 3.32-3.43 (m, 1H), 3.17 (dd, J=8.2, 0.9 Hz, 1H), 1.83-2.02 (m, 4H), 1.49-1.79 (m, 14H), 1.19-1.46 (m, 3H), 1.06 (s, 9H), 0.82-1.01 ppm (m, 1H); $^{13}$C NMR (100 MHz, $CDCl_3$): δ 136.0, 136.0, 136.0, 134.7, 134.6, 129.8, 129.8, 129.7, 127.8, 127.7, 127.7, 127.7, 111.2, 80.9, 80.8, 74.3, 71.8, 70.8, 69.9, 47.0, 38.6, 38.5, 38.0, 37.5, 37.5, 36.3, 36.1, 35.2, 35.1, 35.1, 35.0, 34.8, 34.8, 27.3, 27.2, 27.0, 21.1, 19.4, 19.3 ppm.

Step 4: Preparation of Alcohol Cmpd 13d, dispiro[adamantane-2,4'-[1,3]dioxolane-2',1"-cyclohexane]-3"-ol

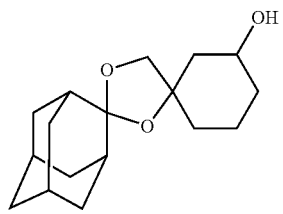 [SMILES: OC1CCCC2(COC3(O2)C2CC4CC(C2)CC3C4)C1]

A 20-mL, scintillation vial equipped with a stir bar, rubber septa, and an argon inlet needle was charged with a solution of dioxolane Cmpd 13c (0.041 g, 0.08 mmol, 1 equiv) in THF (2 mL) and cooled to 0° C. A solution of TBAF (1.0 M in THF, 0.4 mL, 0.4 mmol, 5 equiv) was added dropwise and the reaction mixture was stirred at 0° C. for 30 min, allowed to warm to rt over 1 h, and stirred at rt for 19 h. The reaction mixture was diluted with EtOAc and washed with $H_2O$. The aqueous phase was extracted with EtOAc and the combined organic phases were washed with satd aq NaCl solution, dried over $MgSO_4$, filtered, and concentrated to a clear oil. Purification via column chromatography on silica gel (elution with 25% EtOac/hexanes) afforded 0.020 g of Cmpd 13d (91%) as a foamy, white oil: $^1$H NMR (400 MHz, $CDCl_3$): δ 3.94-4.07 (m, 1H), 3.67-3.81 (m, 2H), 1.84-2.09 (m, 7H), 1.71-1.84 (m, 5H), 1.57-1.71 (m, 6H), 1.39-1.57 (m, 2H), 1.13-1.39 ppm (m, 2H); $^{13}$C NMR (400 MHz, $CDCl_3$): δ 113.1, 81.0, 74.6, 74.5, 68.5, 67.9, 45.5, 41.5, 38.5, 38.2, 37.8, 37.4, 37.3, 36.1, 35.9, 35.2, 35.1, 35.0, 33.0, 27.3, 27.1, 27.0, 26.9, 20.5, 17.4 ppm; LRMS (ESI) m/z [M+H]$^+$ calcd $C_{17}H_{26}O_3$: 279.2; found: 279.1.

Step 5: Preparation of Dioxolane Cmpd 13e, dispiro[adamantane-2,2'-[1,3]dioxolane-4',1''-cyclohexane]-3''-yl 4-nitrophenyl carbonate

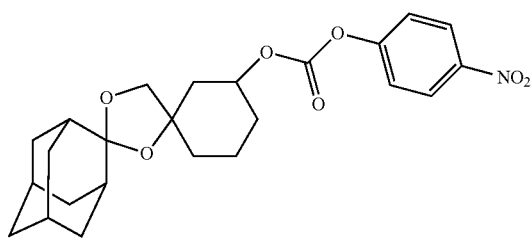 [SMILES: O=C(Oc1ccc([N+](=O)[O-])cc1)OC1CCCC2(COC3(O2)C2CC4CC(C2)CC3C4)C1]

A 20-mL scintillation vial equipped with a stir bar, rubber septa, and an argon inlet needle was charged with a solution of alcohol Cmpd 13d (0.020 g, 0.07 mmol, 1 equiv) in $CH_2Cl_2$ and triethylamine (0.02 mL, 0.29 mmol, 2.95 equiv) and was cooled to 0° C. p-Nitrophenyl chloroformate (0.020 g, 0.10 mmol, 1.38 equiv) and 4-dimethylaminopyridine (0.005 g, 0.04 mmol, 0.57 equiv) were each added as a solid in a single portion. The reaction mixture was stirred at 0° C. for 20 minutes, allowed to warm to rt, and stirred at rt for 49 h. The reaction mixture was diluted with 10 mL of EtOAc and washed with four 15-mL portions of saturated aq $NaHCO_3$ solution and one 20-mL portion of satd aq NaCl solution, then dried over $MgSO_4$, filtered, and concentrated to give a pale yellow oil. Purification via column chromatography on silica gel (elution with 15% EtOAc/hexanes with 1% $Et_3N$) afforded 0.010 g (31%) of Cmpd 13e. $^1$H NMR (400 Mz, $CDCl_3$): δ 8.25-8.32 (m, 1H), 7.36-7.43 (m, 2H), 5.02-5.12 (m, 1H), 4.60-4.70 (m, 1H), 3.74-3.85 (m, 2H), 2.17-2.25 (m, 1H), 2.13 (dd, J=12.5, 4.1 Hz, 1H), 1.90-2.07 (m, 5H), 1.82-1.87 (m, 1H), 1.73-1.82 (m, 4H), 1.60-1.73 (m, 8H), 1.52-1.60 (m, 2H), 1.23-1.32 ppm (m, 2H); LRMS (ESI) m/z [M+H]$^+$ calcd $C_{24}H_{29}NO_7$: 444.2; found: 444.3.

Step 6: Preparation of Dioxolane Cmpd 13

A 4-mL glass vial equipped with a stir bar, rubber septa, and an argon inlet needle containing p-nitrophenyl carbonate Cmpd 13e (0.008 g, 0.02 mmol, 1.0 equiv) was charged sequentially with a solution of 2-methoxy-5-[1-(3,4,5-trimethoxyphenyl)-1H-1,2,3-triazol-5-yl]aniline (Odlo, K.; Hentzen, J.; dit Chabert, J. F.; Ducki, S.; Gani, O. a B. S. M.; Sylte, I.; Skrede, M.; Florenes, V. A.; Hansen, T. V. *Bioorg. Med. Chem.* 2008, 16, 4829-4838)_(0.010 g, 0.03 mmol, 1.6 equiv) in DMF (0.5 mL), DMAP (0.002 g, 0.02 mmol, 1 equiv), and DIPEA (0.02 mL, 0.1 mmol, 6 equiv). The reaction was heated at 90° C. for 73 h while stirring under argon then allowed to cool to rt, diluted with 12 mL of $Et_2O$ and washed with three 15-mL portions of 1 M aq NaOH solution followed by 10 mL of satd aq NaCl solution. The organic phase was dried over $MgSO_4$, filtered, and concentrated. Purification via column chromatography on silica gel (gradient elution with 15-75% EtOAc/hexanes) afforded 0.014 g (31%) of Cmpd 13 as a yellow solid: $^1$H NMR (300 MHz, $CDCl_3$): δ 8.23 (d, J=8.3 Hz, 1H), 7.85 (s, 1H), 7.18 (d, J=13.9 Hz, 1H), 6.80 (s, 1H), 6.62 (s, 2H), 5.01-5.13 (m, 1H), 3.89 (d, J=1.7 Hz, 5H), 3.79-3.85 (m, 2H), 3.73-3.79 (m, 5H), 2.02-2.13 (m, 2H), 1.96 (d, J=10.4 Hz, 3H), 1.76 (br. s., 6H), 1.68 (br. s., 10H), 1.22-1.32 ppm (m, 3H); LRMS (ESI) m/z [M+H]$^+$ calcd for $C_{36}H_{44}N_4O_8$: 661.3; found: 661.2.

Example 14. Preparation of (Cmpd 14), dispiro[adamantane-2,2'-[1,3,5]trioxolane-4',1''-cyclohexane]-3''-yl N-[1-(chloromethyl)-3-[(2E)-3-(4-methoxyphenyl)prop-2-enoyl]-1H,2H,3H-benzo[e]indol-5-yl]carbamate

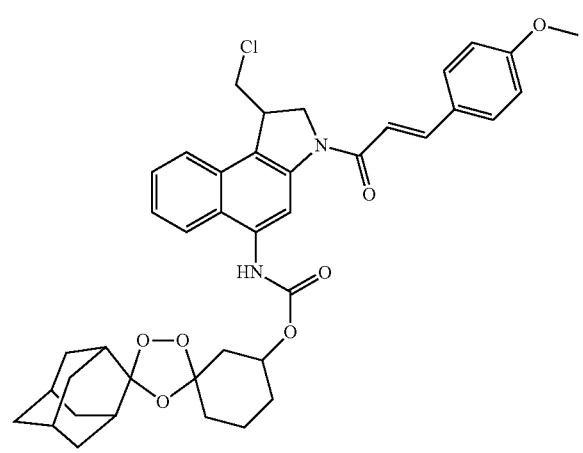

Step 1: Preparation of Isocyanate Cmpd 14a, (2E)-1-[1-(chloromethyl)-5-isocyanato-1H,2H,3H-benzo[e]indol-3-yl]-3-(4-methoxyphenyl)prop-2-en-1-one

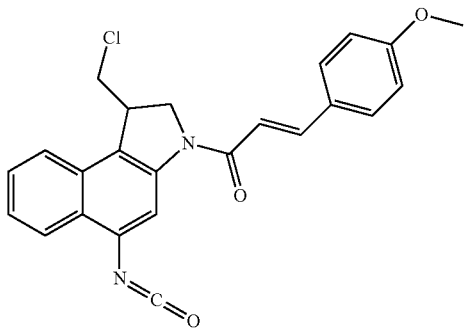 [SMILES: COc1ccc(/C=C/C(=O)N2CC(CCl)c3c2cc(N=C=O)c2ccccc32)cc1]

A 15-mL, re-sealable tube equipped with a stir bar, rubber septa, and an argon inlet needle was charged with a solution of triphosgene (0.021 g, 0.1 mmol, 1.2 equiv.) in anhydrous EtOAc (2 mL). To this solution was added a solution of (2E)-1-[5-amino-1-(chloromethyl)-1H,2H,3H-benzo[e]indol-3-yl]-3-(4-methoxyphenyl)prop-2-en-1-one (Yang, S.; Denny, W. a. *J. Org. Chem.* 2002, 67, 8958-8961) (0.023 g, 0.1 mmol, 1.0 equiv) in CH$_2$Cl$_2$ (4 mL) dropwise over 10 minutes. The rubber septum was then quickly replaced for a threaded Teflon cap. The reaction mixture was heated at 75° C. (behind a blast shield) for 17 h, allowed to cool to rt, and then transferred to a heat-gun dried, 35-mL, round-bottomed flask, and concentrated to afford Cmpd 14a as an orange solid that was further dried on high vacuum for at least 1 hour prior to use in subsequent reactions. This material was used in the next step without further purification.

Step 2: Preparation of Carbamate Cmpd 14

A 35-mL, round-bottomed flask equipped with a stir bar, rubber septa, and an argon inlet needle containing the isocyanate (Cmpd 14a) prepared in the previous step was charged with a solution of alcohol Cmpd 1c (0.036 g, 0.1 mmol, 2.2 equiv.) in DMF (2 mL) (which had been dried on activated molecular sieves while stirring under argon for 30 minutes). This solution was stirred at rt for 45 h. The reaction mixture was diluted with 15 mL of EtOAc and washed with two 20-mL portions of H$_2$O followed by 20 mL of satd aq NaCl solution. The organic phases were dried over MgSO$_4$, filtered, and concentrated to afford a yellow oil. Purification via column chromatography on silica gel (elution with 25% EtOAc/hexanes) afforded 0.012 g (30%) of Cmpd 14 as a yellow solid: $^1$H NMR (400 MHz, CDCl$_3$): δ 7.88-7.94 (m, 1H), 7.76 (d, J=8.1 Hz, 1H), 7.60 (br. s., 1H), 7.51-7.57 (m, 1H), 7.41-7.48 (m, 1H), 6.91-6.98 (m, 1H), 6.79 (br. s., 1H), 5.06 (d, J=2.7 Hz, 1H), 4.92 (br. s., 1H), 4.56 (d, J=9.2 Hz, 1H), 4.46-4.52 (m, 1H), 4.36-4.45 (m, 1H), 3.96 (d, J=11.2 Hz, 1H), 3.85-3.89 (m, 2H), 3.44-3.53 (m, 1H), 3.08 (t, J=5.8 Hz, 1H), 2.25-2.43 (m, 2H), 2.12 (br. s., 2H), 1.89-2.07 (m, 9H), 1.66-1.88 (m, 11H), 0.83-0.95 ppm (m, 1H); $^{13}$C NMR (75 MHz, CDCl$_3$): δ 207.2, 179.2, 161.5, 144.2, 130.1, 127.9, 127.6, 124.9, 114.5, 112.1, 111.8, 108.9, 108.7, 77.7, 77.4, 77.2, 76.8, 73.4, 72.3, 55.6, 46.2, 41.4, 40.3, 40.1, 37.0, 36.6, 36.5, 36.4, 36.0, 35.1, 35.0, 35.0, 34.0, 31.1, 30.8, 27.0, 26.7, 26.0, 22.9, 20.0 ppm; LRMS (ESI) m/z [M+H]$^+$ calcd for C$_{40}$H$_{43}$ClN$_2$O$_7$: 699.3; found: 699.3.

Example 15. Preparation of (Cmpd 15), dispiro[adamantane-2,4'-[1,3]dioxolane-2',1"-cyclohexane]-3"-yl N-[1-(chloromethyl)-3-[(2E)-3-(4-methoxyphenyl)prop-2-enoyl]-1H,2H,3H-benzo[e]indol-5-yl]carbamate

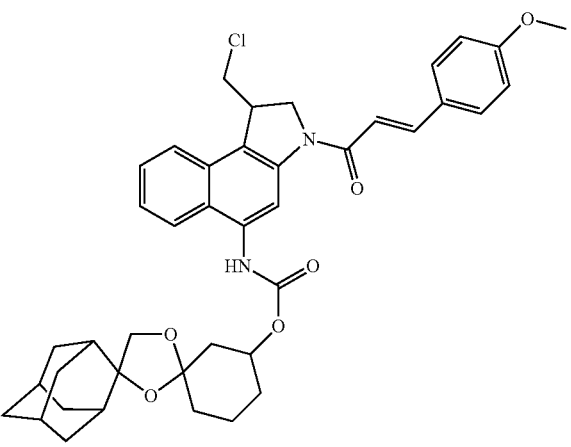 [SMILES: COc1ccc(/C=C/C(=O)N2CC(CCl)c3c2cc(NC(=O)OC2CCCC4(C2)OCC2(O4)C4CC5CC(C4)CC2C5)c2ccccc32)cc1]

This compound (Cmpd 15) was prepared in a manner analogous to trioxolane conjugate Cmpd 14 by reacting the requisite alcohol Cmpd 12d (0.022 g, 0.079 mmol, 1.19 equiv) with isocyanate Cmpd 14a. Affording 0.014 g (0.021 mmol, 31%) of Cmpd 15 as a yellow solid. $^1$H NMR (400 MHz, CDCl$_3$): δ 7.87-7.96 (m, 1H), 7.77 (d, J=8.4 Hz, 1H), 7.50-7.66 (m, 2H), 7.45 (dd, J=8.2, 7.1 Hz, 1H), 6.90-7.00 (m, 2H), 5.03 (d, J=3.3 Hz, 1H), 4.58 (d, J=11.0 Hz, 1H), 4.42 (br. s., 1H), 3.97 (d, J=11.4 Hz, 1H), 3.90-3.95 (m, 1H), 3.87 (s, 2H), 3.49 (t, J=11.0 Hz, 1H), 2.26 (d, J=11.0 Hz, 2H), 2.18 (br. s., 2H), 1.74-1.90 (m, 5H), 1.66-1.74 (m, 3H), 1.61 (br. s., 4H), 1.51 (dd, J=14.9, 5.0 Hz, 2H), 1.13 (dt, J=13.2, 7.3 Hz, 1H), 0.98 (s, 1H), 0.78-0.96 ppm (m, 4H) LRMS (ESI) m/z [M+H]$^+$ calcd for C$_{41}$H$_{45}$ClN$_2$O$_6$: 697.3; found: 697.3.

Example 16. Preparation of (Cmpd 16), dispiro[adamantane-2,4'-[1,3]dioxolane-2',1"-cyclohexane]-3"-yl N-{2-methoxy-5-[1-(3,4,5-trimethoxyphenyl)-1H-1,2,3-triazol-5-yl]phenyl}carbamate

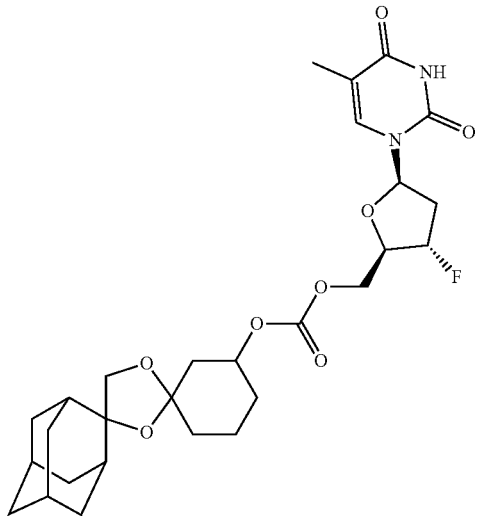 [SMILES: Cc1cn([C@H]2C[C@H](F)[C@@H](COC(=O)OC3CCCC4(C3)OCC3(O4)C4CC5CC(C4)CC3C5)O2)c(=O)[nH]c1=O]

Step 1: Preparation of P-Nitrophenylcarbonate Cmpd 16a, dispiro[adamantane-2,4'-[1,3]dioxolane-2',1"-cyclohexane]-3"-yl 4-nitrophenyl carbonate

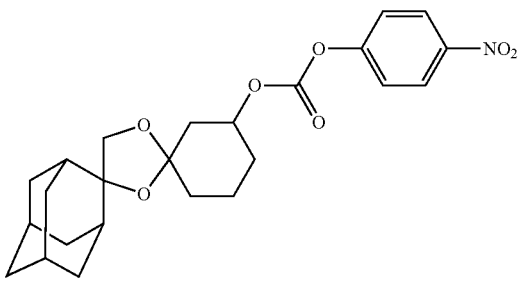 [SMILES: O=C(Oc1ccc([N+](=O)[O-])cc1)OC1CCCC2(C1)OCC1(O2)C2CC3CC(C2)CC1C3]

A solution of alcohol Cmpd 12d (0.027 g, 0.1 mmol, 1 equiv) and N,N-diisopropylethylamine (0.05 mL, 0.29 mmol, 2.95 equiv) in $CH_2Cl_2$ (2 mL) was cooled at 0° C. while p-nitrophenyl chloroformate (0.047 g, 0.23 mmol, 2.4 equiv) and 4-dimethylaminopyridine (0.011 g, 0.09 mmol, 0.92 equiv) were added as solids in a single portion. The reaction mixture was maintained at 0° C. for 20 minutes, allowed to warm to rt, stirred at rt for 48 h, then diluted with 10 mL of EtOAc and washed with four 15-mL portions of satd aq $NaHCO_3$ solution and once with 20 mL of satd aq NaCl solution. The organic phase was dried over $MgSO_4$, filtered, and concentrated to give a pale yellow oil. Purification via column chromatography on silica gel (elution with 15% EtOAc/hexanes with 1% $Et_3N$) afforded 0.026 g (60%) of Cmpd 16a as a white foam: $^1$H NMR (400 MHz, $CDCl_3$) δ 8.28-8.30 (m, 1H), 8.26-8.28 (m, 1H), 7.40-7.42 (m 1H) 7.38-7.40 (m, 1H), 4.91-4.99 (m, 1H), 3.92 (s, 2H), 2.18-2.25 (m, 2H), 2.12-2.18 (m, 2H), 1.74-1.86 (m, 8H), 1.53-1.73 (m, 9H), 1.44-1.52 ppm (m, 2H); LRMS (ESI) m/z $[M+H]^+$ calcd for $C_{24}H_{29}NO_7$: 444.2; found: 444.2.

Step 2: Preparation of Cmpd 16

To a solution of the p-nitrophenyl carbonate Cmpd 16a (0.027 g, 0.06 mmol, 1.13 equiv) in DMF (2 mL) was added sequentially 3'-deoxy-3'-fluorothymidine (0.013 g, 0.05 mmol, 1 equiv), 4-dimethylaminopyridine (0.007 g, 0.06 mmol, 1 equiv), and N,N-diisopropylethylamine (0.06 mL, 0.32 mmol, 6 equiv). The reaction mixture was heated at 50° C. for 48 h, allowed to cool to rt, and diluted with 10 mL of EtOAc and 15 mL of satd aq $NaHCO_3$ solution. The organic phase was separated and washed with three, 15-mL portions of satd aq $NaHCO_3$ and one 15-mL portion of satd aq NaCl solution, dried over $MgSO_4$, filtered, and concentrated. Purification via column chromatography on silica gel (elution with 40-50% EtOAc/hexanes) afforded 0.015 g of Cmpd 16 (51%) as a clear film: $^1$H NMR (400 MHz, $CDCl_3$) δ 8.54 (br. s., 1H), 7.36-7.42 (m, 1H), 6.45 (dd, J=9.1, 5.6 Hz, 1H), 5.19 (d, J=5.1 Hz, 1H), 4.80-4.90 (m, 1H), 4.49 (br. s., 1H), 4.42 (s, 1H), 4.38-4.40 (m, 1H), 4.36 (t, J=2.7 Hz, 1H), 3.89 (d, J=2.4 Hz, 1H), 2.55-2.68 (m, 1H), 2.22-3.13 (m, 2H), 2.09-2.28 (m, 5H), 1.90-1.95 (m, 3H), 1.73-1.84 (m, 7H), 1.54-1.72 ppm (m, 10H); LRMS (ESI) m/z $[M+H]^+$ calcd for $C_{28}H_{37}FN_2O_8$: 549.6; found: 549.3.

Example 17: Preparation of (Cmpd 17), dispiro[adamantane-2,2'-[1,3,5]trioxolane-4',1"-cyclohexane]-3"-yl 2-oxo-2H-chromen-7-yl carbonate

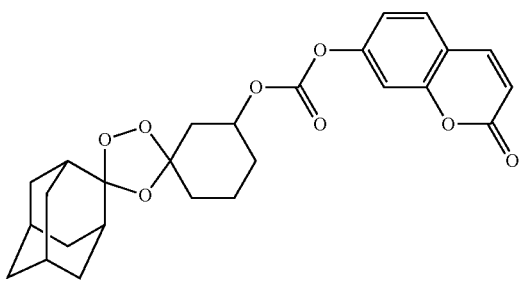 [SMILES: O=C(Oc1ccc2ccc(=O)oc2c1)OC1CCCC2(C1)OOC1(O2)C2CC3CC(C2)CC1C3]

A 20-mL, scintillation vial equipped with a stirbar and screw cap was charged with a solution of p-nitrophenyl carbonate Cmpd 6a (0.043 g, 0.097 mmol, 1.0 equiv) in DMF (1.5 mL). 7-hydroxycoumarin (0.040 g, 0.25 mmol, 2.6 equiv), i-$Pr_2$NEt (0.05 mL, 0.3 mmol, 3 equiv), and DMAP (0.005 g, 0.04 mmol, 0.4 equiv) were added sequentially. The reaction mixture was stirred at rt for 18 h. An additional portion of 7-hydroxycoumarin (0.017 g, 0.10 mmol, 1.1 equiv) and i-$Pr_2$NEt (0.05 mL, 0.3 mmol, 3 equiv) was added and the reaction mixture was stirred at rt for an additional 3 h. After 21 h total reaction time, the reaction mixture was diluted with 50 mL of $Et_2O$. The resulting solution was washed sequentially with 15 mL of 1 M aq HCl solution, five 15-mL portions of 1 M aq NaOH, and 20 mL of satd aq NaCl solution. The organic phase was dried over $MgSO_4$, filtered, and concentrated to afford a colorless oil. Purification via column chromatography on 12 g of silica gel (gradient elution with 2-25% EtOAc/hexanes) afforded 0.037 g (82%) of Cmpd 17 (as a 60:40 mixture of diastereomers) as a colorless oil: $^1$H NMR (400 MHz, $CDCl_3$) δ 7.70 (d, J=9.5 Hz, 1H), 7.50 (d, J=8.6 Hz, 1H), 7.22 (dd, J=9.1, 2.1 Hz, 1H), 7.12-7.18 (m, J=1.9, 1.0, 1.0 Hz, 1H), 6.41 (d, J=9.5 Hz, 1H), 4.91-5.00 (m, 1H), 2.33-2.44 (m, 1H), 1.44-2.15 ppm (m, 21H); LRMS (ESI) m/z $[M+H]^+$ calcd for $C_{26}H_{28}O_8$: 469.2; found: 469.1. A peak corresponding to the minor diastereomer was observed: $^1$H NMR (400 MHz, $CDCl_3$) δ 4.80-4.89 (m, 1H).

Example 18. Preparation of (Cmpd 18), dispiro[adamantane-2,2'-[1,3,5]trioxolane-4',1"-cyclohexane]-7-yl 5-(dimethylamino)naphthalene-1-sulfonate

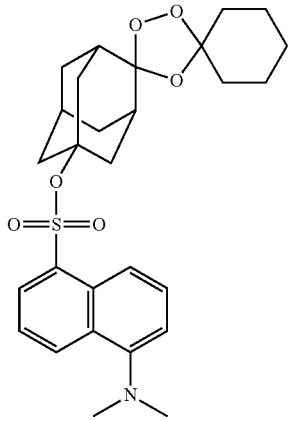 [SMILES: CN(C)c1cccc2c(S(=O)(=O)OC34CC5CC(C3)C3(OOC6(CCCCC6)O3)C(C5)C4)cccc12]

To a solution of adamantyl alcohol (dispiro[adamantane-2,2'-[1,3,5]trioxolane-4',1"-cyclohexane]-7-ol) (Vennerstrom, J. L.; Dong, Y.; Charman, S. A.; Wittlin, S.; Chollet, J.; Wang, X.; Srigraghavan, K.; Zhou, L.; Matile, H.; Charman, W. N. Patent WO/2009/091433, 2009)(0.15 g, 0.54 mmol, 1 equiv) and DMAP (0.065 g, 0.54 mmol, 1 equiv) in pyridine (3 mL) at 0° C. was added dropwise a solution of dansyl chloride (0.29 g, 1.07 mmol, 2 equiv) in CH$_2$Cl$_2$ (0.2 mL). The reaction was warmed slowly to room temperature and stirred overnight, at which time additional dansyl chloride (0.725 g, 1.35 mmol, 5 equiv) was added and the reaction left to stir for an additional 72 h. The reaction mixture was then concentrated in vacuo, and the resulting residue was dissolved with ethyl acetate and water. The aqueous layer was separated and extracted with three 5-mL portions of EtOAc. The combined organic phases were washed with water and satd aq NaCl solution, dried over MgSO$_4$, filtered, and concentrated. Purification via column chromatography on 12 g of silica gel (elution with 7% EtOAc/hexanes) to afford 0.079 g (29%) of Cmpd 18 (as a mixture of stereoisomers) as a foamy, yellow solid: $^1$H NMR (400 MHz, CDCl$_3$) δ 8.56 (dd, J=8.4, 3.6 Hz, 1H), 8.22-8.31 (m, 2H), 7.49-7.60 (m, 2H), 7.19 (dd, J=7.6, 3.2 Hz, 1H), 2.89 (s, 6H), 2.26-2.50 (m, 2H), 2.03-2.21 (m, 7H), 1.79-1.91 (m, 2H), 1.50-1.70 (m, 10H), 1.30-1.45 (m, 2H); LRMS (ESI) m/z [M+H]$^+$ calcd for C$_{28}$H$_{35}$NO$_6$: 514.7; found: 514.7.

Example 19. Preparation of (Cmpd 19), 5-(dimethylamino)-N-[3-({dispiro[adamantane-2,2'-[1,3,5]trioxolane-4',1"-cyclohexane]-4"-yl}amino)propyl]naphthalene-1-sulfonamide

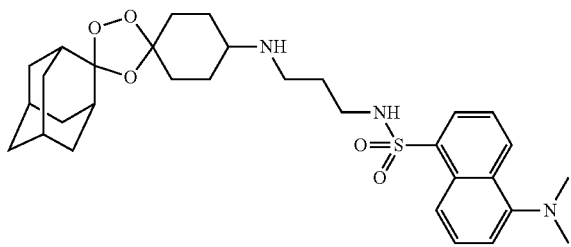 [SMILES: CN(C)c1cccc2c(S(=O)(=O)NCCCNC3CCC4(CC3)OOC3(O4)C4CC5CC(C4)CC3C5)cccc12]

Step 1: Preparation of Diamine Cmpd 19a, tert-butyl N-[3-({dispiro[adamantane-2,2'-[1,3,5]trioxolane-4',1"-cyclohexane]-4"-yl}amino)propyl]carbamate

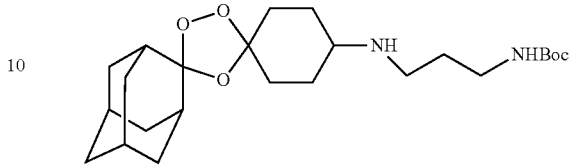

To a solution of (dispiro[adamantane-2,2'-[1,3,5]trioxolane-4',1"-cyclohexane]-4"-one) (Tang, Y.; Dong, Y.; Karle, J. M.; DiTusa, C. A.; Vennerstrom, J. L. J. Org. Chem. 2004, 69, 6470-6473)(0.350 g, 1.26 mmol, 1 equiv) and N-Boc-1,3-propanediamine (0.260 g, 1.5 mmol, 1.2 equiv) in dichloroethane (3 mL) was added sodium triacetoxyborohydride (0.400 g, 1.89 mmol, 1.5 equiv). The reaction mixture was stirred at rt for 1 h. The reaction mixture was then diluted with 10 mL of CH$_2$Cl$_2$, washed with 10 mL of satd aq NaHCO$_3$ solution and 20 mL of satd aq NaCl solution, dried over Na$_2$SO$_4$, filtered, and concentrated. Purification via column chromatography on 25 g of silica gel (elution with 5% MeOH/CH$_2$Cl$_2$) afforded 0.550 g (>95%) of Cmpd 19a (as a mixture of diastereomers) as a colorless oil: $^1$H NMR (400 MHz, CDCl$_3$) δ 5.13-5.17 (m, 0.14H), 3.22-3.23 (m, 2H), 2.70-2.73 (m, 2H), 2.59 (m, 1H), 1.44-2.03 (m, 24H), 1.44 (s, 9H): LRMS (ESI) m/z [M+H]$^+$ calcd for C$_{24}$H$_{40}$N$_2$O$_5$: 437.3; found: 437.3.

Step 2: Preparation of Cmpd 19

Carbamate Cmpd 19a (0.300 g, 0.690 mmol, 1 equiv) was dissolved in a 4 N solution of HCl in dioxane (3.6 mL). The reaction mixture was stirred at rt for 30 min and then concentrated in vacuo. A quarter of the crude product was dissolved in CH$_2$Cl$_2$ (0.5 mL) and treated with dansyl chloride (0.047 g, 0.17 mmol) and triethylamine (0.06 mL, 0.4 mmol). The reaction mixture was stirred overnight protected from light. The reaction mixture was then loaded directly onto a silica gel column (gradient elution 2-5% MeOH/CH$_2$Cl$_2$) to provide 0.008 g (8% over two steps) of Cmpd 19 as a foamy yellow solid: $^1$H NMR (400 MHz, CDCl$_3$) δ 8.49-8.55 (m, 1H), 8.20-8.33 (m, 2H), 7.47-7.59 (m, 2H), 7.15-7.21 (m, 1H), 2.97-3.04 (m, 2H), 2.89 (s, 6H), 2.57-2.64 (m, 2H), 2.35-2.45 (m, 1H), 1.48-2.02 (m, 22H), 1.25-1.34 (m, 2H); LRMS (ESI) m/z [M+H]$^+$ calcd for C$_{31}$H$_{43}$N$_3$O$_5$S: 570.3; found: 570.3.

Example 20. Preparation of (Cmpd 20), 5-(dimethylamino)-N-{dispiro[adamantane-2,2'-[1,3,5]trioxolane-4',1''-cyclohexane]-7-yl}naphthalene-1-sulfonamide

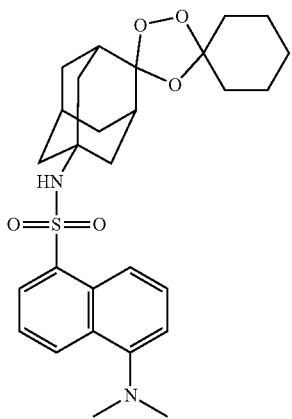 [SMILES: CN(C)c1cccc2c(S(=O)(=O)NC34CC5CC(C3)C3(OOC6(CCCCC6)O3)C(C5)C4)cccc12]

Step 1: Preparation of Carbamate Cmpd 20a, tert-Butyl N-(4-oxoadamantan-1-yl)carbamate

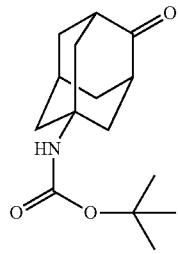 [SMILES: CC(C)(C)OC(=O)NC12CC3CC(C1)C(=O)C(C3)C2]

4-oxoadamantane-1-carboxylic acid (Sengupta, S.; Rajagopalan, S.; Belavagi, N.; Ramachandra, M. Preparation of 2, 4-diaminopyrimidine derivatives as protein kinase inhibitors. WO 201205993 10 May 2012) (0.699 g, 3.59 mmol, 1.0 equiv) was dried twice via azeotrope from 5 mL of toluene in a 25-mL recovery flask. The flask was equipped with a stirbar, rubber septum, and argon inlet needle and was then purged with argon for 5 min. The flask was charged with toluene (15 mL) and triethylamine (1.00 mL, 7.2 mmol, 2.0 equiv). The reaction mixture was cooled at 0° C. while diphenylphosphoryl azide (0.774 mL, 3.6 mmol, 1.0 equiv) was added dropwise via syringe over ca. 4 min. The reaction mixture was stirred at 0° C. for 5 min, allowed to warm to rt over 10 min, and then the rubber septum was quickly exchanged for a reflux condenser fitted with an argon inlet adapter. The reaction mixture was heated at 90° C. for 1.5 h (gas evolution was observed within 5 min of heating and continued for 1 h), allowed to cool to rt over 20 min, and concentrated to afford a pale yellow oil.

The crude isocyanate prepared above was dissolved in tert-butanol (15 mL) and the solution was partitioned equally into three 10-mL microwave reactor tubes each equipped with a stirbar and silicon cap. Each tube was heated in a microwave reactor at 120° C. for 4 h. The reaction mixtures were combined and diluted with 50 mL of EtOAc and 20 mL of 1 M aq $Na_2CO_3$. The aqueous layer was separated and extracted with three 20-mL portions of EtOAc. The organic phases were washed with 30 mL of satd aq NaCl solution, dried over $MgSO_4$, filtered, and concentrated to afford a colorless semi-solid. A solution of this material in 10 mL of $CH_2Cl_2$ was deposited onto silica gel. The resulting free flowing powder was loaded on top of a 25 g silica gel cartridge. Gradient elution with 0-30% EtOAc/hexanes afforded 0.673 g (70%) of Cmpd 20a as a colorless solid with spectral data consistent with that previously reported: (WO 2012059932) $^1$H NMR (400 MHz, $CDCl_3$) δ 4.50 (br. s., 1H), 2.55 (br. s, 2H), 2.23-2.12 (m, 7H), 2.02-1.85 (m, 4H), 1.39 (s, 9H); LRMS (ESI) m/z $[M+Na]^+$ calcd for $C_{15}H_{23}NO_3$: 288.2; found: 288.1.

Step 2: Preparation of Oxime Cmpd 20b, tert-Butyl N-[4-(methoxyimino)adamantan-1-yl]carbamate

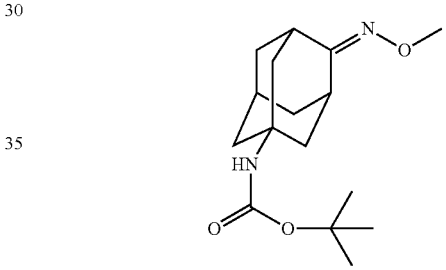

A 25-mL, recovery flask equipped with a stirbar was charged with ketone Cmpd 20a (0.502 g, 1.89 mmol, 1.0 equiv), methanol (6 mL), pyridine (0.305 mL, 3.78 mmol, 2.0 equiv), and methoxylamine hydrochloride (0.237 g, 2.84 mmol, 1.5 equiv) and the reaction mixture was stirred at rt until all reagents dissolved. The reaction mixture was then partitioned equally into three 10-mL microwave tubes each equipped with a stibar and silicon cap. The reaction mixtures were each heated in a microwave reactor at 90° C. for 30 min. The reaction mixtures were then combined and concentrated. The resulting residue was diluted with 30 mL of EtOAc and 30 mL of 0.5 M aq HCl. The aqueous phase was separated and extracted with three 30-mL portions of EtOAc. The combined organic phases were washed with 30 mL of satd aq NaCl solution, dried over $MgSO_4$, filtered, and concentrated to afford a pale yellow oil. Purification via column chromatography on 40 g of silica gel (gradient elution with 10-25% EtOAc/hexanes) afforded 0.474 g (85% yield) of Cmpd 20b as a white solid: $^1$H NMR (400 MHz, $CDCl_3$) δ 4.40 (br s, 1H), 3.78 (s, 3H), 3.55 (br s, 1H), 2.63 (br s, 1H), 2.20-1.67 (m, 11H), 1.41 (s, 9H); LRMS (ESI) m/z $[M+H]^+$ calcd for $C_{16}H_{26}N_2O_3$: 295.2; found: 295.2.

Step 3: Preparation of Trioxolane Cmpd 20c, tert-butyl N-{dispiro[adamantane-2,2'-[1,3,5]trioxolane-4',1''-cyclohexane]-7-yl}carbamate

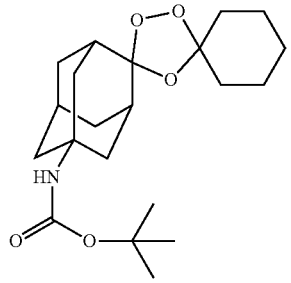 [SMILES: CC(C)(C)OC(=O)NC12CC3CC(C1)C1(OOC4(CCCCC4)O1)C(C3)C2]

A 50-mL, recovery flask equipped with a stirbar was charged with oxime Cmpd 20b (0.237 g, 0.805 mmol, 2.1 equiv), cyclohexanone (0.040 mL, 0.408 mmol, 1.0 equiv), and CCl$_4$ (10 mL). The reaction mixture was cooled at 0° C. while ozone (0.6 L/min, 30% power) was bubbled through the solution for 30 min. The reaction mixture was maintained at 0° C. while being sparged with O$_2$, then was allowed to warm to rt over 10 min while being sparged with argon. The reaction mixture was concentrated to afford a white solid. Purification via column chromatography on 25 g of silica gel (gradient elution with 5-10% EtOAc/hexanes) afforded 0.081 g (55%) of Cmpd 20c as a white solid: $^1$H NMR (CDCl$_3$, 400 MHz) δ 4.43-4.33 (m, 1H), 2.17-2.10 (m, 1H), 2.07 (br. s., 2H), 2.04-1.89 (m, 6H), 1.85 (d, J=12.8 Hz, 2H), 1.79-1.49 (m, 10H), 1.52-1.28 (m, 11H); LRMS (ESI) m/z [M+H]$^+$ calcd for C$_{21}$H$_{33}$NO$_5$: 380.2; found: 380.2.

Step 4: Preparation of Cmpd 20

A 20-mL, scintillation vial equipped with a stirbar and screw cap was charged with carbamate Cmpd 20c (0.073 g, 0.192 mmol, 1.0 equiv) and a solution of hydrochloric acid in dioxane (4 M, 1.80 mL, 7.21 mmol, 37.5 equiv). The resulting mixture was stirred at rt for 30 min. The reaction mixture was diluted with 10 mL toluene and concentrated to a volume of ca 1 mL. The resulting mixture was diluted and concentrated twice from 5 mL of toluene to afford a white solid. This material was used in the next step without further purification.

A 20-mL, scintillation vial equipped with a stirbar and screw cap containing the adamantylamine hydrochloride prepared above was charged with CH$_2$Cl$_2$ (1 mL) and N,N-diisopropylethylamine (0.101 mL, 0.6 mmol, 3.0 equiv) and was stirred at rt for 5 min. Dansyl chloride (0.063 g, 0.2 mmol, 1.2 equiv) was added in a single portion and the reaction was stirred at rt for 2 h. The reaction mixture was diluted with 25 mL of EtOAc and 25 mL of H$_2$O. The aqueous layer was separated and extracted with 3, 20-mL portions of EtOAc. The combined organic phases were washed with 25 mL of satd aq NaCl solution, dried over MgSO$_4$, filtered, and concentrated to afford a yellow oil. A solution of this material in 5 mL of CH$_2$Cl$_2$ was deposited onto silica gel and the free flowing powder was transferred to the top of a 12 g silica gel cartridge. Gradient elution with 0-25% EtOAc/hexanes afforded 0.068 g of Cmpd 20 (as a 67:33 mixture of diastereomers) as a yellow solid: $^1$H NMR (CDCl$_3$, 400 MHz) δ 8.54 (br. d, J=8.4 Hz, 1H), 8.35-8.26 (m, 2H), 7.55 (m, 2H), 7.20 (d, J=7.5 Hz, 1H), 4.82 (br. s, 1H), 2.90 (s, 6H), 2.05 (br. s, 2H), 1.98-1.80 (m, 5H), 1.78-1.48 (m, 13H), 1.47-1.34 (m, 3H); LRMS (ESI) m/z [M+H]f calcd for C$_{28}$H$_{36}$N$_2$O$_5$S: 513.23; found: 513.3; Some resonances corresponding to the minor isomer were observed: $^1$H NMR (CDCl$_3$, 400 MHz) δ 8.26-8.21 (m, 2H), 7.54-7.50 (m, 2H), 7.19 (d, J=7.3 Hz, 1H), 4.80 (br s, 1H).

Example 21. Preparation of (Cmpd 21), 5-({dispiro[adamantane-2,2'-[1,3,5]trioxolane-4',4''-piperidine]-1''-yl}sulfonyl)-N,N-dimethylnaphthalen-1-amine

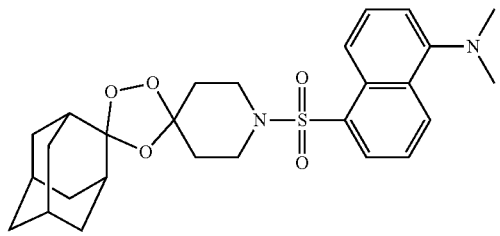 [SMILES: CN(C)c1cccc2c(S(=O)(=O)N3CCC4(CC3)OOC3(O4)C4CC5CC(C4)CC3C5)cccc12]

A 20-mL, scintillation vial equipped with a stirbar and screw cap was charged with tert-butyl dispiro[adamantane-2,2'-[1,3,5]trioxolane-4',4''-piperidine]-1''-carboxylate (Vennerstrom, J. L.; Dong, Y.; Chollet, J.; Matile, H. Spiro and dispiro 1,2,4-trioxolane antimalarials. Preparation of spiro/dispiro-1,2,4-trioxolanes as antimalarial agents. U.S. Pat. No. 6,486,199, 26 Nov. 2002)(0.092 g, 0.25 mmol, 1.0 equiv) and a solution of hydrochloric acid in dioxanes (4 M, 2.0 mL, 8.0 mmol, 32 equiv). The reaction mixture was stirred at rt for 20 min, diluted with 6 mL of toluene, and concentrated to a volume of about 2 mL. The resulting mixture was then diluted with 6 mL of toluene and concentrated to dryness to afford a white solid. This material was used in the next step without further purification.

A 20-mL, scintillation vial containing the hydrochloride salt prepared above (dispiro[adamantane-2,2'-[1,3,5]trioxolane-4',4''-piperidine hydrochloride) was charged with THF (3 mL), and N,N-diisopropylethylamine (0.219 mL, 1.26 mmol, 5 equiv) and was stirred at rt for 5 min. Dansyl chloride (0.068 g, 0.25 mmol, 1.0 equiv) was added as a solid in a single portion and the reaction mixture was stirred at rt for 1 h. The reaction mixture was diluted with 20 mL of EtOAc and 20 mL of H$_2$O. The aqueous layer was separated and extracted with three 20-mL portions of EtOAc. The combined organic phases were washed with 30 mL of satd aq NaCl solution, dried over MgSO$_4$, filtered, and concentrated to afford a yellow foamy solid. Purification via column chromatography on 12 g of silica gel (gradient elution with 0-20% EtOAc/Hex) afforded 0.104 g (83%) of Cmpd 21 as a yellow solid: $^1$H NMR (CDCl$_3$, 400 MHz) δ 8.57 (d, J=8.4 Hz, 1H), 8.35 (d, J=8.6 Hz, 1H), 8.21 (dd, J=0.9, 7.3 Hz, 1H), 7.49-7.59 (m, 2H), 7.19 (d, J=7.5 Hz, 1H), 3.45-3.54 (m, 2H), 3.24 (ddd, J=4.1, 8.1, 12.5 Hz, 2H), 2.89 (s, 6H), 1.62-2.11 (m, 18H); LRMS (ESI) m/z [M+H]$^+$ calcd for C$_{27}$H$_{34}$N$_2$O$_5$S: 499.2; found: 499.2.

Example 22. Preparation of (Cmpd 22), dispiro [adamantane-2,2'-[1,3,5]trioxolane-4',1"-cyclohexane]-3"-yl N-[(1S)-1-{[(2S,3S,4R,5R)-5-[6-(dimethylamino)-9H-purin-9-yl]-4-hydroxy-2-(hydroxymethyl)oxolan-3-yl]carbamoyl}-2-(4-methoxyphenyl)ethyl]carbamate

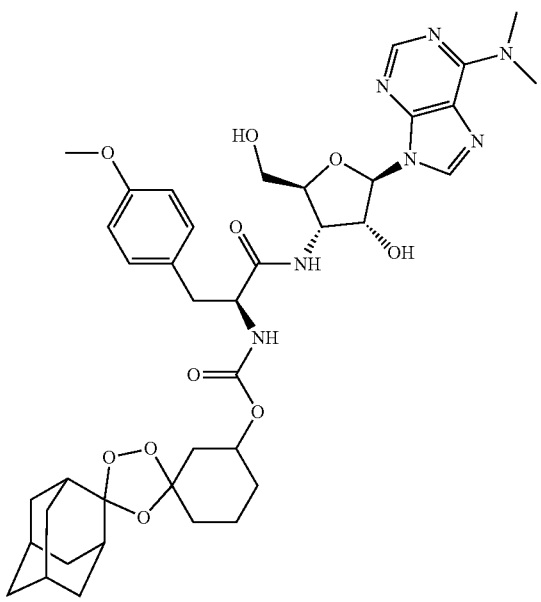 [SMILES: COc1ccc(C[C@H](NC(=O)OC2CCCC3(C2)OOC2(O3)C3CC4CC(C3)CC2C4)C(=O)N[C@H]2[C@@H](O)[C@H](n3cnc4c(N(C)C)ncnc43)O[C@@H]2CO)cc1]

A 20-mL scintillation vial equipped with a stir bar, septa, and argon inlet was charged with Puromycin dihydrochloride from *Streptomyces alboniger* (0.031 g, 0.1 mmol, 1.0 equiv.), 4-dimethylaminopyridine (ca. 0.001 g, 0.0 mmol, 0.1 equiv.), and 4-nitrophenyl carbonate Cmpd 6a (0.025 g, 0.1 mmol, 1.0 equiv.) and the atmosphere was replaced with argon. This material was then dissolved in N,N-dimethylformamide (2.000 ml) and N,N-diisopropylethylamine (0.050 ml, 0.3 mmol, 5.1 equiv.) was added to this solution. The reaction mixture was allowed to stir at room temperature under argon for 4 hours then diluted with 10 mL of EtOAc and washed with three, 15-mL portions of sat. NaHCO$_3$. The aqueous layer was back extracted with 20 mL of EtOAc and the organic layers were combined, washed with 20 mL of satd aq NaCl solution, and then dried over MgSO$_4$, filtered, and concentrated to afford a light yellow oil. Purification via column chromatography on 12 g of silica gel (gradient elution with 10-100% EtOAc/Hex) and re-purification of mixed fractions on 12 g of silica gel (gradient elution with 5-10% MeOH/DCM) afforded 26 mg (61%) of Cmpd 22 as a white solid: $^1$H NMR (CDCl$_3$, 400 MHz) δ: 8.03-8.07 (m, 1H), 7.97 (s, 1H), 7.15 (d, J=8.4 Hz, 2H), 6.87 (d, J=8.4 Hz, 2H), 6.62 (br. s., 1H), 5.52 (d, J=4.4 Hz, 1H), 5.22 (br. s, 1H), 4.84 (br. s., 1H), 4.73-4.79 (m, 1H), 4.35-4.48 (m, 2H), 4.04-4.10 (m, 1H), 3.85-3.94 (m, 1H), 3.78 (s, 3H), 3.70 (d, J=12.6 Hz, 1H), 3.59 (br. s., 1H), 3.35-3.54 (m, 3H), 3.03-3.12 (m, 1H), 2.89-3.00 (m, 2H), 2.13-2.29 (m, 2H), 1.94 (s, 3H), 1.99 (s, 2H), 1.88 (br. s., 2H), 1.80 (d, J=14.8 Hz, 3H), 1.64-1.76 (m, 7H), 1.61 (br. s., 2H); LRMS (ESI) m/z [M+H]$^+$ calcd for C$_{39}$H$_{51}$N$_7$O$_{10}$: 778.4; found: 778.3.

Example 23. Preparation of (Cmpd 23), Dispiro [adamantane-2,2'-[1,3,5]trioxolane-4',1"-cyclohexane]-3"-yl N-(2-amino-2-methylpropyl)carbamate

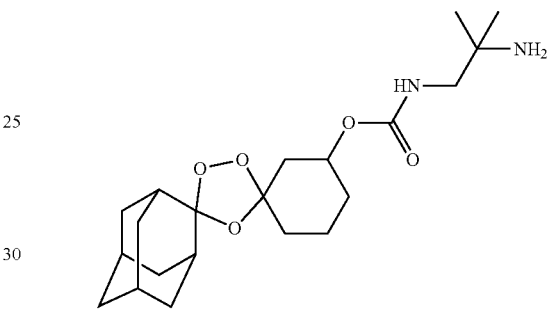

A 20-mL scintillation vial was charged with carbonate 1 (0.300 g, 0.673 mmol, 1.0 equiv), N,N-dimethylformamide (2 mL), N,N-diisopropylethylamine (0.235 mL, 1.35 mmol, 2 equiv). 2-Methylpropane-1,2-diamine (0.105 mL, 1.01 mmol, 1.5 equiv) was added in a single portion via microliter pipettor. The reaction was stirred at rt for 1 h. The reaction mixture was diluted with 30 mL of EtOAc and washed with four 15-mL portions of 1 M aq NaOH solution (until aqueous was no longer bright yellow), washed with 20 mL of satd aq NaCl, dried over MgSO4, filtered, and concentrated to afford a yellow oil. Purification via column chromatography on 25 g of silica gel (75-100% EtOAc/hexanes and then 0-15% MeOH/CH2Cl2) afforded 0.248 g (93%) of carbamate 23 (>95:5 dr) as a yellow foamy/sticky oil: IR (neat) 3343, 2933, 2916, 2859, 1702, 1560, 1542, 1452, 1352, 1298, 1250, 1122, 1146, 1114, 1087, 1067, 142, 1021, 1010, 929, 774 cm-1; 1H NMR (400 MHz, CDCl3) δ=5.10 (br. t, J=5.9 Hz, 1H), 4.68-4.78 (m, 1H), 3.01-3.12 (m, 2H), 2.26 (dt, J=13.0, 2.2 Hz, 1H), 1.44-2.05 (m, 20H), 1.21-1.35 (m, 1H), 1.12 ppm (s, 6H); 13C NMR (100 MHz, CDCl3) δ 156.5, 111.7, 109.0, 71.1, 52.4, 50.6, 40.5, 37.0, 36.5, 35.1, 35.0, 34.9, 34.0, 31.0, 28.3, 28.2, 27.1, 26.7, 20.0; HRMS (ESI) m/z [M+H]$^+$ calcd for C$_{21}$H$_{34}$N$_2$O$_5$: 395.2540; found: 395.2526.

Example 24. Preparation of (Cmpd 24), tert-butyl N-[(3″R,4′R)-3″-[(tert-butyldiphenylsilyl)oxy]dispiro[adamantane-2,2′-[1,3,5]trioxolane-4′,1″-cyclohexane]-7-yl]carbamate

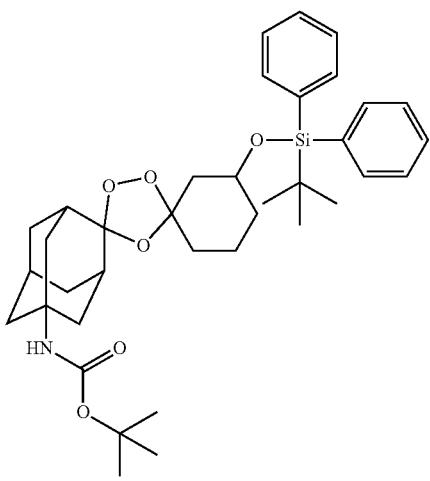 [SMILES: CC(C)(C)OC(=O)NC12CC3CC(C1)C1(OOC4(CCCC(O[Si](c5ccccc5)(c5ccccc5)C(C)(C)C)C4)O1)C(C3)C2]

A 50-mL pear shaped flask equipped with a stirbar was charged with ketone 1a (300 mg, 0.851 mmol, 1 equiv), CCl$_4$ (12 mL), and oxime 20b (500 mg, 1.70, mmol, 2 equiv) and was stirred at rt until solubilized. The reaction mixture was cooled to 0° C. while ozone was bubbled through at 0.6 L/min, 30% power for 1 h. Additional oxime 20b (175 mg, 0.594 mol, 0.7 equiv) was added in a single portion and bubbling of ozone was continued for 40 min. Additional oxime 20b (100 mg, 0.339 mmol, 0.4 equiv) was added in a single portion and ozone was bubbled through the solution at 0 deg C. for an additional 1 h. The reaction mixture was then concentrated to afford a white solid. A solution of this material in 10 mL of DCM was deposited onto 5 g of silica gel. The resulting free flowing powder was loaded atop an 80 g column of silica gel. Gradient elution (1CV 0-10%, 5CV 10%, 5CV 15% EtOAc/hexanes) afforded 306 mg, (57%) of trioxolane 24 as a colorless oil: $^1$H NMR (400 MHz, CDCl$_3$) δ 7.71-7.75 (m, 1H), 7.64-7.70 (m, 3H), 7.34-7.45 (m, 6H), 3.73-3.84 (m, 1H), 2.04-2.16 (m, 1H), 1.84-2.03 (m, 8H), 1.66-1.83 (m, 4H), 1.59 (br. s., 4H), 1.40-1.46 (m, 8H), 1.20-1.30 (m, 1H), 1.08 (s, 2H), 1.05-1.08 (m, 7H); $^{13}$C NMR (100 MHz, CDCl3) δ: 136.0, 135.9, 135.0, 134.6, 134.6, 129.9, 129.8, 129.7, 127.9, 127.8, 127.7, 110.2, 109.7, 109.7, 69.9, 49.8, 49.4, 43.9, 43.8, 39.2, 38.9, 37.3, 37.3, 37.1, 37.0, 34.5, 33.9, 33.7, 33.6, 33.5, 28.7, 28.1, 27.7, 27.2, 26.8, 20.1, 19.3, 19.2. LRMS (ESI) m/z [M+H]$^+$ calcd for C$_{37}$H51NO$_6$Si: 634.9; found: 634.4.

TABLE 1

| | Biological Activity | | |
|---|---|---|---|
| | | | Activity |
| Example # | Structure | EC50 (nM) | Target (Cell Line) |
| Example 1 | 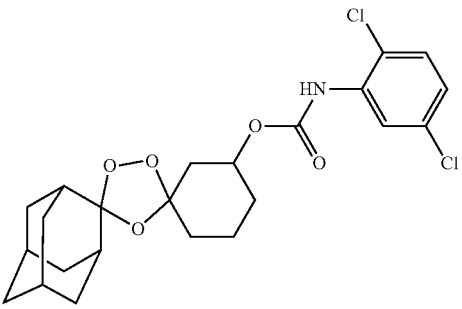 [SMILES: O=C(Nc1cc(Cl)ccc1Cl)OC1CCCC2(C1)OOC1(O2)C2CC3CC(C2)CC1C3] | 14.3 | P. falc |
| Cmpd 2b | 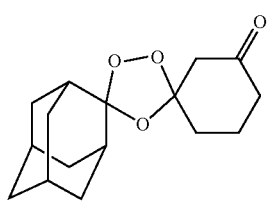 [SMILES: O=C1CCCC2(C1)OOC1(O2)C2CC3CC(C2)CC1C3] | 408 | P. falc |

TABLE 1-continued

| | Biological Activity | | |
|---|---|---|---|
| | | | Activity |
| Example # | Structure | EC50 (nM) | Target (Cell Line) |
| Example 2 | | 10.7 | P. falc |
| Example 3 | | 65.7 | P. falc |
| Example 4 | | 147 | P. falc |
| Example 5 | | 5.9 | P. falc W2 |

TABLE 1-continued

Biological Activity

| Example # | Structure | Activity EC50 (nM) | Target (Cell Line) |
|---|---|---|---|
| Example 6 | | 17.1 | P. falc W2 |
| Example 7 | (in progress) | | P. falc |
| Example 8 | | 8<br>15<br>21 | P. falc HB3<br>P. falc DD2<br>P. falc 3D7 |
| Example 9 | | 29<br>15.7<br>23.3 | P. falc D10<br>P. falc D10<br>P. falc D10 |

TABLE 1-continued

Biological Activity

| Example # | Structure | Activity EC50 (nM) | Target (Cell Line) |
|---|---|---|---|
| Literature Compound A | Deu, E.; Leyva, M. J.; Albrow, V. E.; rice, M. J.; Ellman, J. A.; Bogyo, M. *Chem. Biol.* 2010, 17, 808-819) | 70 | P. falc D10 |
| Example 10 | | 94<br>188<br>188 | P. falc HB3<br>P. falc DD2<br>P. falc 3D7 |
| Literature Compound B | (Odlo, K.; Hentzen, J.; dit Chabert, J. F.; Ducki, S.; Gani, O. a B. S. M.; Sylte, I.; Skrede, M; Flørenes, V. A.; Hansen, T. V. *Bioorg. Med. Chem.* 2008, 16, 4829-4838 | 11<br>9<br>10<br>10<br>>1000 | HeLa<br>PC-3<br>MCF-7<br>MB-MDA-231<br>P. falc W2 |
| Example 11 | | 57<br>26<br>24<br>42<br>34 | HeLa<br>PC-3<br>MCF-7<br>MB-MDA-231<br>P. falc W2 |
| Example 12 | | >1000<br>>1000<br>>1000<br>>1000 | HeLa<br>PC-3<br>MCF-7<br>P. falc W2 |

TABLE 1-continued

Biological Activity

| Example # | Structure | Activity EC50 (nM) | Target (Cell Line) |
|---|---|---|---|
| Example 13 | | >1000<br>>1000<br>>1000<br>>1000<br>>1000<br>>1000 | HeLa<br>U87MG<br>PC-3<br>MCF-7<br>MB-MDA-231<br>P. falc W2 |
| Literature Compound C | (Yang, S.; Denny, W. a. *J. Org. Chem.* 2002, 67, 8958-8961) | 3<br>11<br>5<br>0.45 | IMR90<br>HeLa<br>U87MG<br>P. falc W2 |
| Example 14 | | 100<br>105<br>40<br>2.8 | IMR90<br>HeLa<br>U87MG<br>P. falc W2 |

TABLE 1-continued

| | Biological Activity | | |
|---|---|---|---|
| | | | Activity |
| Example # | Structure | EC50 (nM) | Target (Cell Line) |
| Example 15 | | >1000<br>>1000<br>41 | IMR90<br>HeLa<br>P. falc W2 |
| Example 16 | | | |
| Example 17 | | 25.3 | P. falc D10 |

TABLE 1-continued

| Example # | Structure | Activity EC50 (nM) | Target (Cell Line) |
|---|---|---|---|
| Example 18 | | 17.9 | P. falc FCB |
| Example 19 | | 14.6 | P. falc FCB |
| Example 20 | | 11.4 | P. falc DD2 |
| Example 21 | | 54.2 | P. falc DD2 |

TABLE 1-continued

Biological Activity

| Example # | Structure | Activity EC50 (nM) | Target (Cell Line) |
|---|---|---|---|
| Puromycin dihydrochloride from *Streptomyces alboniger* | | 783<br>1696<br>569<br>25.3 | HeLa<br>IMR90<br>MB-MDA-231<br>P. falc DD2 |
| Example 22 | | 3212<br>6979<br>5272<br>12.7 | HeLa<br>IMR90<br>MB-MDA-231<br>P. falc DD2 |
| Example 23 | | 5 nM | P. falc W2 |

TABLE 1-continued
Biological Activity
| Example # | Structure | EC50 (nM) | Activity Target (Cell Line) |
|---|---|---|---|
| Example 24 | 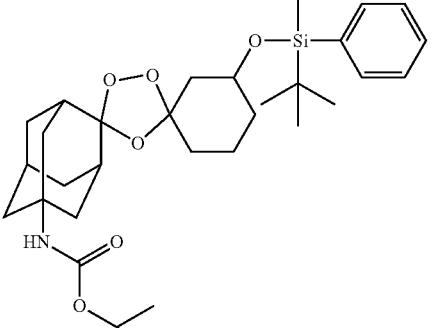 | | |
| Example 25 | 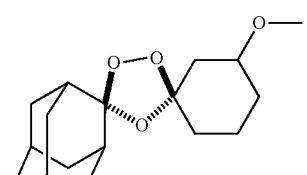<br>Fontaine, S. D., Dipasquale, A. G. & Renslo, A. R. *Org. Lett.* 16, 5776-5779 (2014) | 27 nM | P. falc W2 |
TABLE 2
Additional compounds (prodrugs) being made and tested.
| | Drug/det. Ag./prot | comment |
|---|---|---|
| X = Cl, Br | Phosphoramidate mustard | |

TABLE 2-continued
Additional compounds (prodrugs) being made and tested.
| Structure | Drug/det. Ag./prot | comment |
|---|---|---|
| 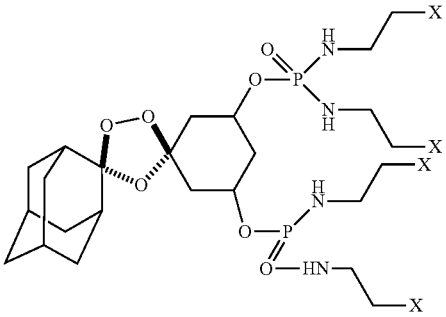 | Phosphoramidate mustard | Double release variant |
| 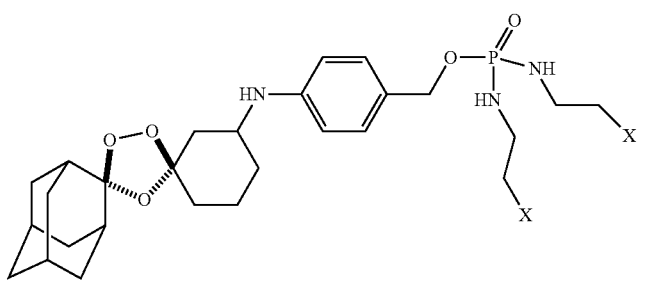<br>X = Cl, Br | Phosphoramidate mustard | Extended linker variant |
| 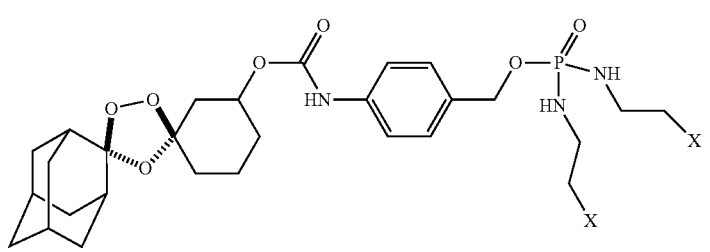<br>X = Cl, Br | Phosphoramidate mustard | Extended linker variant |
| 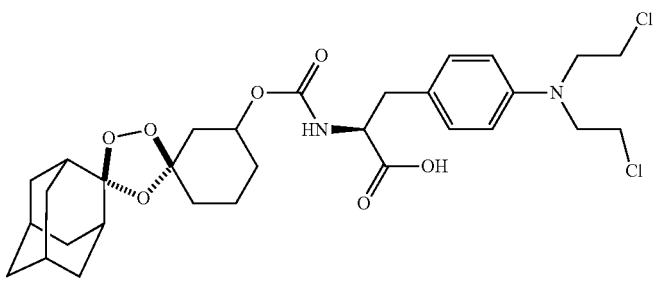 | melphalan | |
| 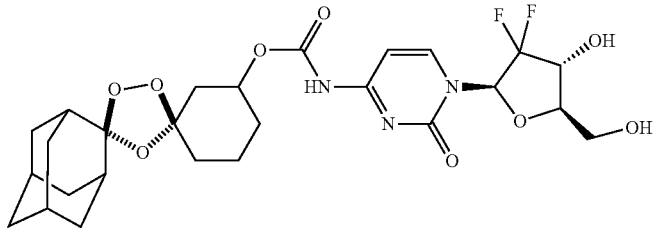 | gemcitabine | |

TABLE 2-continued
Additional compounds (prodrugs) being made and tested.
| Structure | Drug/det. Ag./prot | comment |
|---|---|---|
| 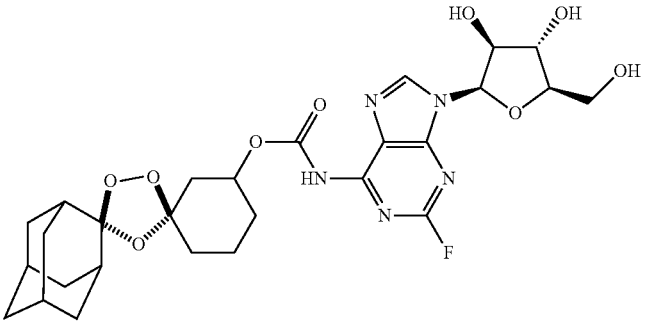 | fludarabine | |
| 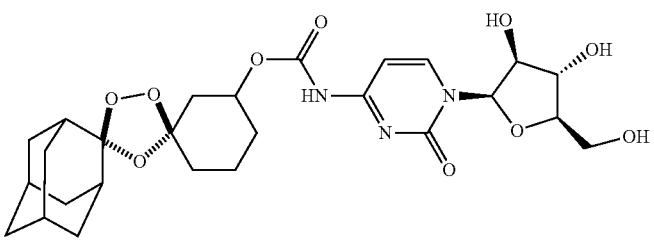 | cytarabine | |
| 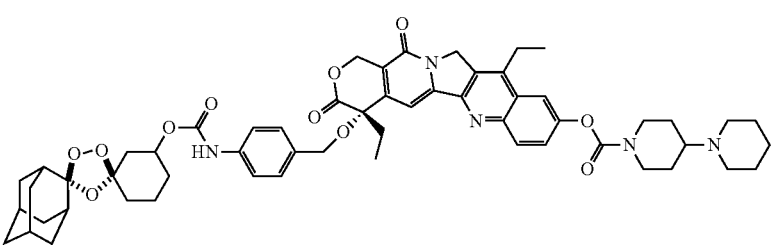 | Irinotecan | Extended linker |
| 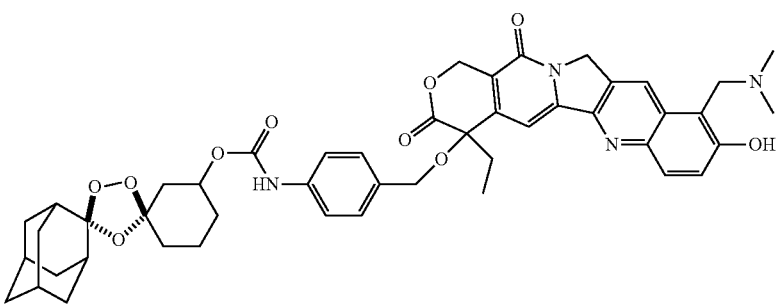 | Topotecan | Extended linker |
| 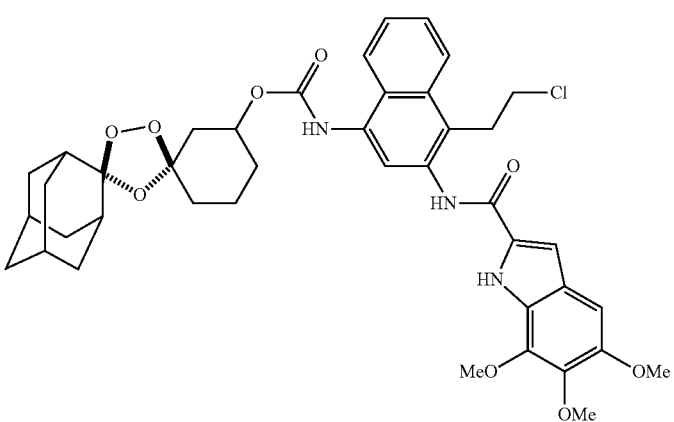 | centanamycin | |

TABLE 2-continued
Additional compounds (prodrugs) being made and tested.
| | Drug/det. Ag./prot | comment |
|---|---|---|
| 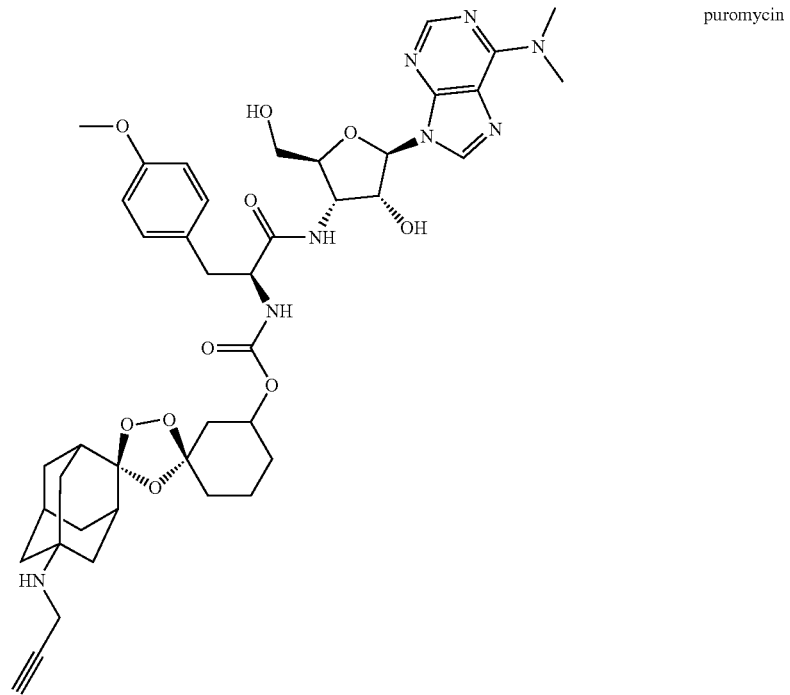 | puromycin | |
| 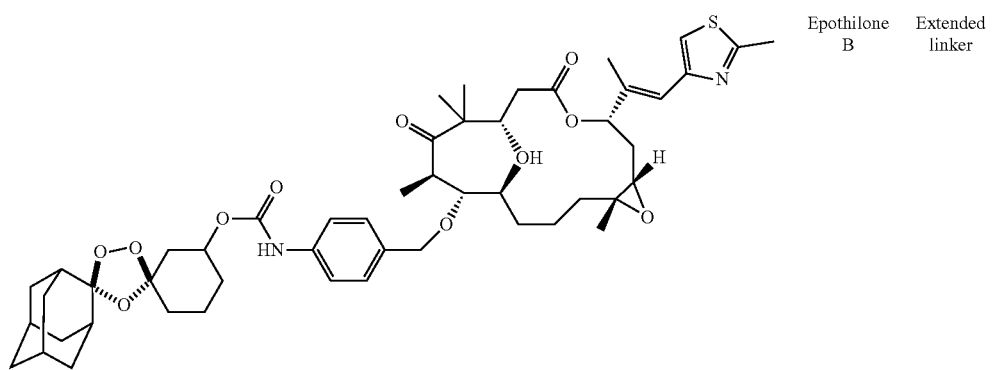 | Epothilone B | Extended linker |

TABLE 2-continued

Additional compounds (prodrugs) being made and tested.

| | Drug/det. Ag./prot | comment |
|---|---|---|
| [structure] | Duocarmycin analog | Folate-receptor targeted conjugate |
| [structure] | Duocarmycin analog | Extended linker type |
| [structure] | Duocarmycin analog | Extended linker type |

TABLE 2-continued

Additional compounds (prodrugs) being made and tested.

| Structure | Drug/det. Ag./prot | comment |
|---|---|---|
| | Combretastatin analog | Folate-receptor targeted conjugate |
| | Duocarmycin analog | Folate-receptor targeted conjugate |
| | vinblastine | Extended linker type |

TABLE 2-continued

Additional compounds (prodrugs) being made and tested.

| Structure | Drug/det. Ag./prot | comment |
|---|---|---|
| [Structure: adamantane-tetraoxaspiro-cyclohexyl carbamate linked to cytotoxic payload, with N-methyl amide-thioether-maleimide-cyclohexyl-amide linker to targeting antibody] | various | |
| [Structure: adamantane-tetraoxaspiro-cyclohexyl carbamate linked via p-aminobenzyloxy to cytotoxic payload, with N-methyl amide-thioether-maleimide-cyclohex TABLE 2-continued Additional compounds (prodrugs) being made and tested.

| Structure | Drug/det. Ag./prot | comment |
|---|---|---|
| | tafenoquine | |
| | antimalarial HDAC inhibitor | |
| | HDAC inhibitor | Extended linker type |
| | Bestatin and analogs | Extended linker type |
| | Bestatin and analogs (metalloprotease inhibitor) | |

TABLE 2-continued

Additional compounds (prodrugs) being made and tested.

| Structure | Drug/det. Ag./prot | comment |
|---|---|---|
| | Metalloprotease inhibitor | |
| | metalloprotease inhibitor | Extended linker |
| | antimalarial (KAF-156) | |
| | antimalarial | |

TABLE 2-continued

Additional compounds (prodrugs) being made and tested.

| Structure | Drug/det. Ag./prot | comment |
|---|---|---|
| [Structure: adamantane-fused 1,2,4-trioxolane spiro cyclohexyl carbamate linked to 2-amino-3-(6-trifluoromethylpyridin-3-yl)-5-(4-methylsulfonylphenyl)pyridine] | antimalarial | |
| [Structure: adamantane-NH-C(O)-CH2CH2-NHBoc with spiro trioxolane cyclohexanol] | | Useful synthetic building block |
| [Structure: adamantane-NH-C(O)-CH2CH2-C(O)OMe with spiro trioxolane cyclohexanol] | | Useful synthetic building block |
| [Structure: adamantane-NH-C(O)-CH2CH2-C(O)OMe with spiro trioxolane piperidine-NBoc] | | Useful synthetic building block |

TABLE 2-continued
Additional compounds (prodrugs) being made and tested.
| | Drug/det. Ag./prot | comment |
|---|---|---|
| 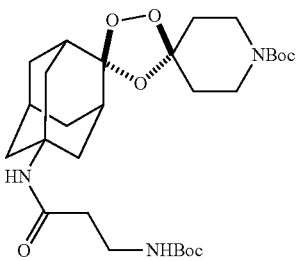 | | Useful synthetic building block |
| 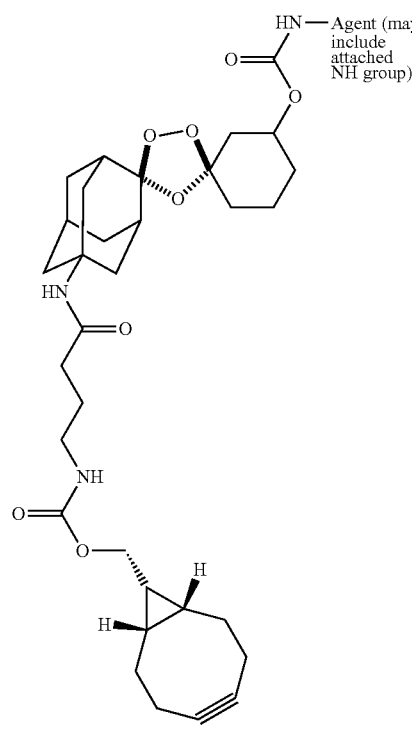 | | Useful reagent for conjugation to targeting moiety |

TABLE 2-continued
Additional compounds (prodrugs) being made and tested.
| Structure | Drug/det. Ag./prot | comment |
|---|---|---|
| 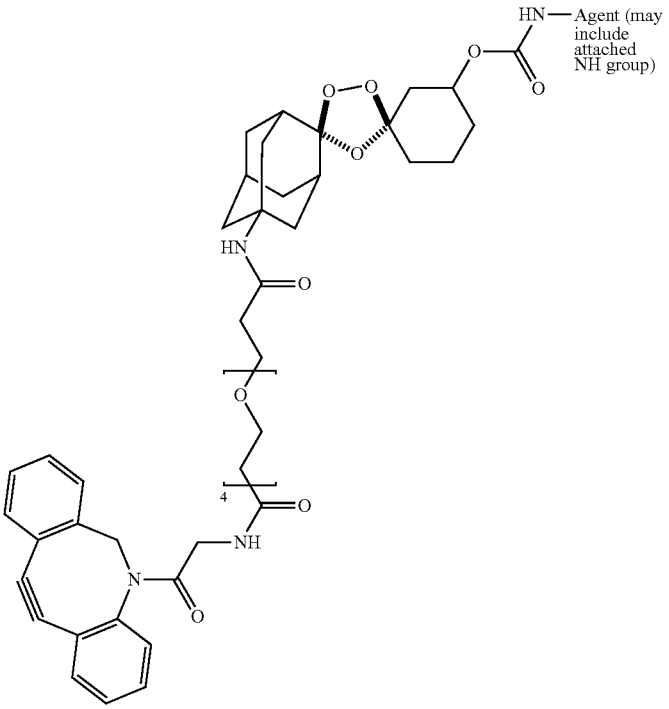 | | Useful reagent for conjugation to targeting moiety |
| 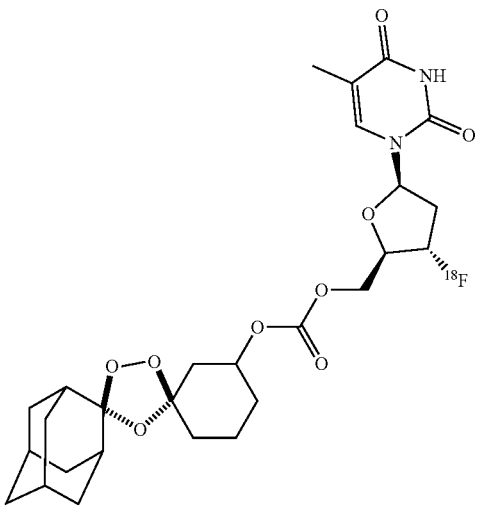 | FLT (PET imaging agent) | |

TABLE 2-continued

Additional compounds (prodrugs) being made and tested.

| Structure | Drug/det. Ag./prot | comment |
|---|---|---|
| (trioxolane-adamantane structure with carbamate-Agent₁ and linker to triazole-Agent₂) | | Antibody drug conjugate based on synthetically accessible trioxolane linker |
| (trioxolane-adamantane structure with carbamate-Agent₁ and PEG linker to DBCO-triazole-Agent₂) | | Antibody drug conjugate based on synthetically accessible trioxolane linker |

TABLE 2-continued
Additional compounds (prodrugs) being made and tested.
| | Drug/det. Ag./prot | comment |
|---|---|---|
| 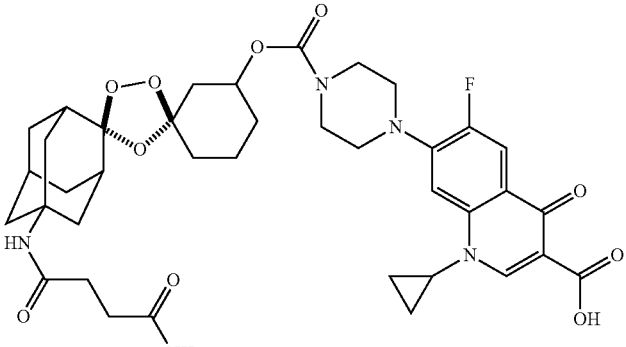 | ciprofloxacin | Targeting moiety is a bacterial siderophore |
| 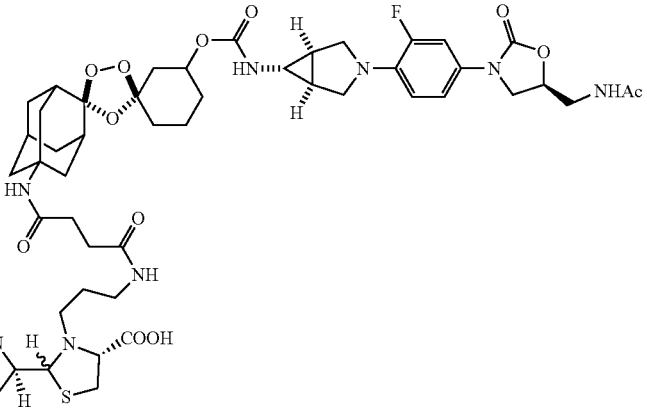 | An oxazolidinone antibacterial | Targeting moiety is a bacterial siderophore |
| 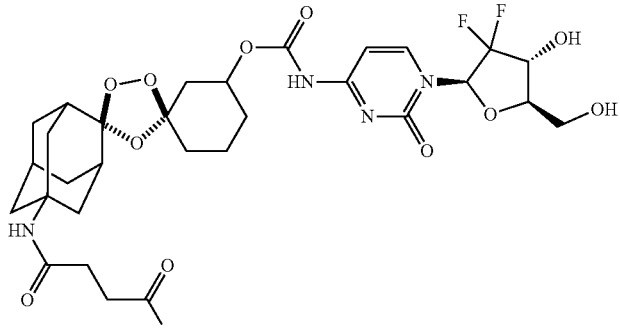 | gemcitabine | Targeting moiety is a bacterial siderophore |

TABLE 2-continued

Additional compounds (prodrugs) being made and tested.

| | Drug/det. Ag./prot | comment |
|---|---|---|
| 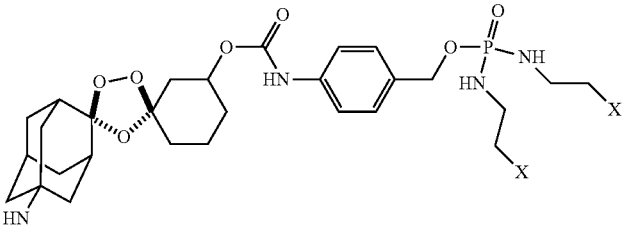 X = Cl, Br | Phosphor-amidate mustard | Targeting moiety is a bacterial sidero-phore |
| 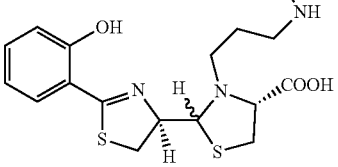 | | Generic targeted drug conjugate employing a syn-thetically accessible trioxolane linker |
| | | Generic targeted drug conjugate employing a syn-thetically accessible trioxolane linker |

TABLE 2-continued

Additional compounds (prodrugs) being made and tested.

| Structure | Drug/det. Ag./prot | comment |
|---|---|---|
| (adamantane-trioxolane-piperidine-carbamate-Agent₁; with HN-succinyl-HN-Agent₂ substituent) | —O—Agent₁ (may include attached O group); HN—Agent₂ | Generic targeted drug conjugate employing a synthetically accessible trioxolane linker |
| (adamantane-trioxolane-piperidine-carbamate-Agent₁; with HN-CO-CH₂CH₂-NH-CO-Agent₂ substituent) | —O—Agent₁ (may include attached O group); —Agent₂ | Generic targeted drug conjugate employing a synthetically accessible trioxolane linker |

Example 25. Fluorescence Microscopy Studies

In order to further study the fate of fragmenting compounds as described herein within cultured parasites, fluorescence microscopy studies can be conducted. For example, the 4-nitrobenzo-2-oxa-1,3,-diazole (NBD) fluorophore has been used previously in studies of artemisinin (Stocks et al., 2007, *Angewandte Chemie International Edition*, 46(33): 6278-6283.) and remains fluorescent over a wide pH range, including the acidic pH (~5) of the *P. falciparum* food vacuole. Microscopes, and techniques thereof, most relevant to the experiments to be conducted include an inverted epifluorescence microscope optimized for time lapse imaging, and a spinning disk confocal microscope. Both microscopes can be equipped with temperature-, humidity-, and $CO_2$-controlled incubators, and both have been used successfully for imaging *P. falciparum*-infected erythrocytes. The epifluorescence microscope can have, for example, a hardware autofocus system (Nikon Perfect Focus) and be optimized for long-term time lapse imaging. The confocal microscope can be optimized, for example, for high detection sensitivity, with a back-thinned EMCCD camera (Photometrics Cascade II) which can be useful for observing the more subtle effects of biological action of compounds on cultured parasites. Additional studies can involve combinations of compounds as described herein and iron chelating reagents. The fluorescence, or lack thereof, of *P. falciparum*-infected cells pre-treated with iron chelating reagents prior to contact with fluorophoric compounds described herein can demonstrate the specific role of iron in the scission of the prodrug.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A compound having the formula:

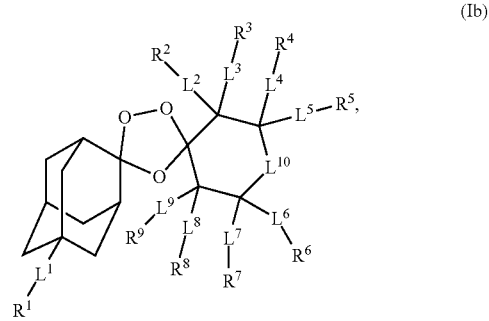

(Ib)

wherein
$L^1$-$R^1$ is —H;
$L^2$, $L^3$, $L^4$, $L^6$, $L^7$, $L^8$, and $L^9$ are each a bond;
$R^2$, $R^3$, $R^4$, $R^6$, $R^7$, $R^8$, and $R^9$ are each hydrogen;
$L^{10}$ is —$CH_2$—;
$L^5$ is independently selected from a bond, —N($R^{17}$)—, —N($R^{17}$)C(O)O—, —O—, —S—, —OC(O)—, —OC(O)N($R^{17}$)—, —OC(O)O—, —OSO$_2$—, —C(O)N($R^{17}$)—, —N($R^{17}$)C(O)—, —S(O)$_2$N($R^{17}$)—, —N($R^{17}$)S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^{17}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^5$ is independently a monovalent form of GDC-0973, a monovalent form of selumetinib, a monovalent form of ARRY-162,

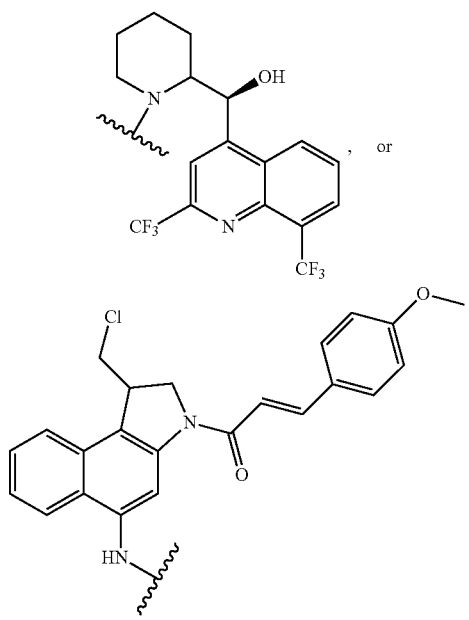

2. The compound of claim 1, wherein $L^5$ is a bond.
3. The compound of claim 1, wherein $L^5$ is —OC(O)—.
4. The compound of claim 1, wherein $R^5$ is a monovalent form of GDC-0973.
5. The compound of claim 1, wherein $R^5$ is a monovalent form of selumetinib.
6. The compound of claim 1, wherein $R^5$ is a monovalent form of ARRY-162.
7. The compound of claim 1, wherein $R^5$ is

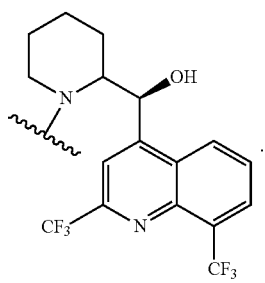 [SMILES: *N1CCCCC1[C@@H](O)c1cc(C(F)(F)F)nc2c(C(F)(F)F)cccc12]

8. The compound of claim 1, wherein $R^5$ is

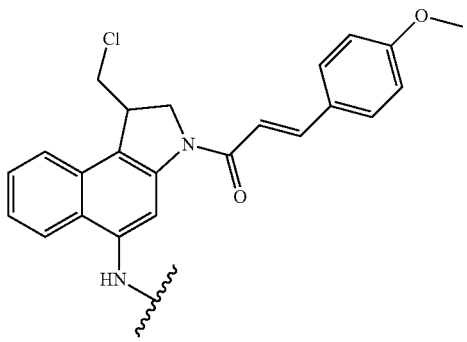

9. The compound of claim 1, wherein the compound has the formula:

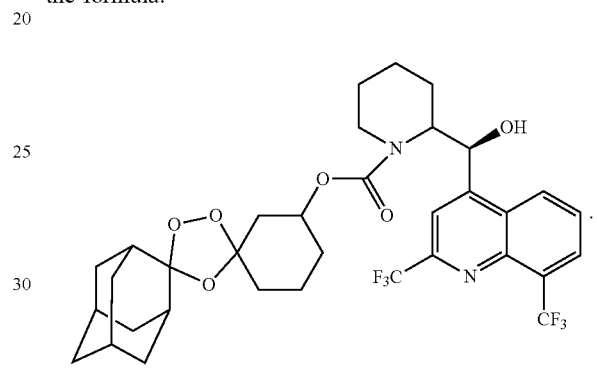

10. The compound of claim 1, wherein the compound has the formula:

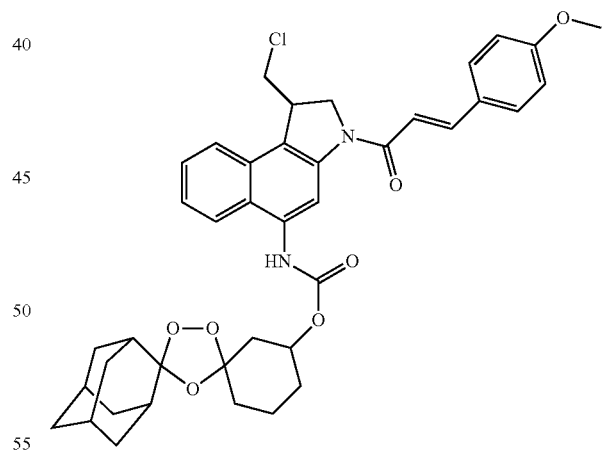

11. A pharmaceutical composition comprising a pharmaceutically acceptable excipient and a compound of claim 1.
12. A pharmaceutical composition comprising a pharmaceutically acceptable excipient and a compound of claim 2.
13. A pharmaceutical composition comprising a pharmaceutically acceptable excipient and a compound of claim 3.
14. A pharmaceutical composition comprising a pharmaceutically acceptable excipient and a compound of claim 4.
15. A pharmaceutical composition comprising a pharmaceutically acceptable excipient and a compound of claim 5.

16. A pharmaceutical composition comprising a pharmaceutically acceptable excipient and a compound of claim 6.

17. A pharmaceutical composition comprising a pharmaceutically acceptable excipient and a compound of claim 7.

18. A pharmaceutical composition comprising a pharmaceutically acceptable excipient and a compound of claim 8.

19. A pharmaceutical composition comprising a pharmaceutically acceptable excipient and a compound of claim 9.

20. A pharmaceutical composition comprising a pharmaceutically acceptable excipient and a compound of claim 10.

* * * * *

UNITED STATES PATENT AND TRADEMARK OFFICE
CERTIFICATE OF CORRECTION

PATENT NO. : 10,662,215 B2  Page 1 of 1
APPLICATION NO. : 16/364577
DATED : May 26, 2020
INVENTOR(S) : Adam R. Renslo et al.

It is certified that error appears in the above-identified patent and that said Letters Patent is hereby corrected as shown below:

In the Claims

In Column 194, Line 59, in Claim 1, delete "each".

In Column 194, Line 60, in Claim 1, delete "each".

In Column 194, Line 62, in Claim 1, delete "independently".

In Column 195, Line 16, in Claim 1, delete "independently".

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*